United States Patent
Dornan et al.

(10) Patent No.: US 9,068,230 B2
(45) Date of Patent: *Jun. 30, 2015

(54) METHODS AND COMPOSITIONS FOR ASSESSING RESPONSIVENESS OF B-CELL LYMPHOMA TO TREATMENT WITH ANTI-CD40 ANTIBODIES

(75) Inventors: David Dornan, San Mateo, CA (US); Bart Burington, Oakland, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/741,814

(22) PCT Filed: Nov. 7, 2008

(86) PCT No.: PCT/US2008/082920
§ 371 (c)(1),
(2), (4) Date: Nov. 9, 2010

(87) PCT Pub. No.: WO2009/062125
PCT Pub. Date: May 14, 2009

(65) Prior Publication Data
US 2011/0104671 A1    May 5, 2011

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,275,149 A | 6/1981 | Litman et al. | |
| 4,318,980 A | 3/1982 | Boguslaki | |
| 4,424,279 A | 1/1984 | Bohn et al. | |
| 4,737,456 A | 4/1988 | Weng et al. | |
| 4,816,567 A | 3/1989 | Cabilly et al. | |
| 5,182,368 A | 1/1993 | Ledbetter et al. | |
| 5,445,934 A | 8/1995 | Fodor et al. | |
| 5,500,362 A | 3/1996 | Robinson et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,591,669 A | 1/1997 | Krimpenfort et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,674,492 A | 10/1997 | Armitage et al. | |
| 5,700,637 A | 12/1997 | Southern | |
| 5,807,522 A | 9/1998 | Brown et al. | |
| 5,821,337 A | 10/1998 | Carter et al. | |
| 6,248,535 B1 | 6/2001 | Danenberg et al. | |
| 6,737,056 B1 | 5/2004 | Presta | |
| 6,838,261 B1 | 1/2005 | Siegall et al. | |
| 6,843,989 B1 | 1/2005 | Siegall et al. | |
| 6,946,129 B1 | 9/2005 | Siegall et al. | |
| 7,288,251 B2 | 10/2007 | Bedian et al. | |
| 2002/0197256 A1 | 12/2002 | Grewal | |
| 2005/0090434 A1* | 4/2005 | Morris et al. | 514/12 |
| 2005/0164231 A1* | 7/2005 | Staudt et al. | 435/6 |
| 2005/0260646 A1 | 11/2005 | Baker et al. | |
| 2007/0110754 A1 | 5/2007 | Long et al. | |
| 2012/0123695 A1 | 5/2012 | Dornan et al. | |

FOREIGN PATENT DOCUMENTS

| | | |
|---|---|---|
| CN | 1582165 A | 2/2005 |
| JP | 2006-342173 A | 12/2006 |
| JP | 2008-539794 A | 11/2008 |
| JP | 2008-544223 A | 12/2008 |
| WO | WO-91/10741 A1 | 7/1991 |
| WO | WO-96/18413 A1 | 6/1996 |
| WO | WO-96/33735 A1 | 10/1996 |
| WO | WO-96/34096 A1 | 10/1996 |
| WO | WO-97/17852 A1 | 5/1997 |
| WO | WO-97/31025 A1 | 8/1997 |
| WO | WO-98/24893 A2 | 6/1998 |
| WO | WO-98/24893 A3 | 6/1998 |
| WO | WO-00/75348 A1 | 12/2000 |
| WO | WO-00/75348 C1 | 12/2000 |
| WO | WO-01/75166 A2 | 10/2001 |
| WO | WO-01/75166 A3 | 10/2001 |
| WO | WO-01/83755 A2 | 11/2001 |
| WO | WO-03/040170 A2 | 5/2003 |
| WO | WO-03/040170 A3 | 5/2003 |
| WO | WO-2004/071572 A2 | 8/2004 |
| WO | WO-2004/071572 A3 | 8/2004 |
| WO | WO-2005/044294 A2 | 5/2005 |
| WO | WO-2005/044294 A3 | 5/2005 |
| WO | WO-2006/125117 A2 | 11/2006 |
| WO | WO-2006/125117 A3 | 11/2006 |
| WO | WO-2006/125143 A2 | 11/2006 |
| WO | WO-2006/125143 A3 | 11/2006 |

(Continued)

OTHER PUBLICATIONS

Dogan et al. American Journal Surgical Pathology. 2000. 24(6): 846-852.*
Tzankov et al. J Clin Pathol. 2003. 56: 747-752.*
GeneCard for UAP1, available via url: <genecards.org/cgi-bin/card-disp.pl?gene=UAP1> printed on Oct. 3, 2012.*
Dermer, G.B. Bio/Technology (1994) 12: 320.*
Smiraglia et al. Human Molecular Genetics. 2001. 10: 1413-1419.*
Singh et al. Proceedings of the New Zealand Society of Animal Production. 2004. 64: 8-10.*
Liu et al . Clinical Immunology. 2004. 112: 225-230.*
Coleman, R. Drug Discovery Today. 2003. 8: 233-235.*
Saetre et al. Molecular Brain Research. 2004. 126: 198-206.*
Haynes et al Electrophoresis. 1998. 19: 1862-1871.*
Gokmen-Polar et al. Cancer Research. 2001. 61: 1375-1381.*
GeneCard for BCL6 (available via url: < genecards.org/cgi-bin/card-disp.pl?gene=BCL6>, printed on Mar. 28, 2013).*

(Continued)

*Primary Examiner* — Carla Myers
(74) *Attorney, Agent, or Firm* — Morrison & Foerster LLP

(57) ABSTRACT

The invention provides methods and kits useful for predicting or assessing responsiveness of B-cell lymphoma to treatment with anti-CD40 antibodies.

16 Claims, 41 Drawing Sheets

(56) References Cited

FOREIGN PATENT DOCUMENTS

| WO | WO-2006/128103 A2 | 11/2006 |
|---|---|---|
| WO | WO-2006/128103 A3 | 11/2006 |
| WO | WO-2006/133420 A2 | 12/2006 |
| WO | WO-2006/133420 A3 | 12/2006 |
| WO | WO-2007/032743 A2 | 3/2007 |
| WO | WO-2007/032743 A3 | 3/2007 |
| WO | WO-2007/066230 A2 | 6/2007 |
| WO | WO-2007/066230 A3 | 6/2007 |
| WO | WO-2007/075348 A1 | 7/2007 |
| WO | WO-2007/082379 A2 | 7/2007 |
| WO | WO-2007/082379 A3 | 7/2007 |
| WO | WO-2007/756326 A2 | 7/2007 |
| WO | WO-2007/756326 A3 | 7/2007 |
| WO | WO-2008/079269 A2 | 7/2008 |
| WO | WO-2008/079269 A3 | 7/2008 |
| WO | WO-2010/121231 A1 | 10/2010 |

OTHER PUBLICATIONS

GeneAnnot for BCL6 (available via url: <genecards.weizmann.ac.il/cgi-bin/geneannot/GA_search.pl?array=HG-U133&array=HG-U133_Plus.2&keyword_type=gene_symbol&keyword=bcl6&target=integrated&.submit=Submit+Query>, printed on Mar. 28, 2013).*

The Free Dictionary definition for "measuring", printed on Mar. 18, 2014, available via url: < thefreedictionary.com/measuring>.*

The Free Dictionary, definition for "determining", printed on Mar. 4, 2014, available via url: < thefreedictionary.com/determining>.*

Definition for "Assay", printed on Dec. 1, 2014, available via url: <https://www.google.com/search?q=assaying+definition>.*

Advani, R. et al. (2009). "Evaluation of a Gene Signature to Predict Single Agent Dactuzumab (SGN-40) Activity in Patients with DLBCL," Abstract No. 11063 presented at 2009 ASCO Annual Meeting, three pages, located at <http://www.asco.org/ASCOv2/Meetings/Abstracts?&vmview=abst_detail_view&confID=65&abstractIDS=32462>, last visited on Aug. 2, 2010, *J Clin Oncol* 27:15S.

Anonoymous. (2011). "The R Project for Statistical Computing," located at <http://www.r-project.org/main.shtml>, last visited on Feb. 18, 2011, one page.

Anonoymous. (Nov. 7, 2003). "Affymetrix GenoChip Human Genome U133 Plus 2.0 Array," *Geo Expression*, two pages.

Ausubel et al. (1995). *Short Protocols in Molecular Biology, Current Protocols in Molecular Biology*, pp. iii-xvii. (Table of Contents Only).

Ausubel, F.M. (1987). *Current Protocols in Molecular Biology*, New York, New York, five pages. (Table of Contents Only.).

Barbas, C.F. et al. (Apr. 26, 1994). "In Vitro Evolution of a Neutralizing Human Antibody to Human Immunodeficiency Virus Type 1 to Enchance Affinity and Broaden Strain cross-Reactivity," *Proc Nat. Acad. Sci USA* 91(9):3809-3813.

Basso, K. et al. (Dec. 15, 2004, e-pub. Aug. 26, 2004). "Tracking CD40 Signaling During Germinal Center Development," *Blood* 104:4088-4096.

Bohen, S.P. et al. (Feb. 18, 2004). "Variation in Gene Expression Patterns in Follicular Lymphoma and the Response to Rituximab," *Proceedings of the National Academy of Sciences of the United States of American* 100(4):1926-1930.

Bruggemann, M. et al. (1993). "Designer Mice:the Production of Human Antibody Repertoires in Transgenic Animals," *Year in Immuno.* 7:33-40.

Canellos G.P. et al. (1998). *The Lymphomas*. W.B.Saunders Company, Philadelphia, Pennsylvania, pp. xi-xiii. (Table of Contents Only.).

Cheung, V.G. et al. (Jan. 1999). "Making and Reading Microarrays," *Nature Genetics* 21(Suppl):15-19.

Clackson, T. et al. (Aug. 15, 1991). "Making Antibody Fragments Using Phage Display Libraries," *Nature* 352(6336):624-628.

Clynes, R. et al. (Jan. 20, 1998). "Fc Receptors are Required in Passive and Active Immunity to Melanoma," *PNAS USA* 95(2):652-656.

Coligen et al. (1991). *Current Protocols in Immunology*, vols. 1 and 2, Ed. Wiley-Interscience, New York, New York, Pubs, one page. (Table of Contents Only.).

Dornan, D. et al. (Nov. 20, 2009). "CD40 Pathway Activation Status Predicts Response to CD40 Targeted Therapy in Diffuse Large b-Cell Lymhoma," 51st Annual Meeting of the American Society of Hematology, New Orleans, Lousiana, Dec. 5 through 8, 2009, four pages, *Blood* 114(22):1065.

Fellouse, F.A. (Aug. 24, 2004, e-pub. Aug. 11, 2004). "Synthetic Antibodies From a Four-Amino-Acid Code: A Dominant Role for Tyrosine in Antigen Recognition," *Proc. Nat. Acad. Sci. USA* 101(34):1246712472.

Fishwild, D.M et al., (Jul. 1996). "High-Avidity Human IgG Kappa Monoclonal Antibodies from a Novel Strain of Minilocus Transgentic Mice," *Nature Biotechnol* 14(7):845-851.

Forero-Torres, A. et al. (Nov. 20, 2009). "A Phase 1b Clinical Trial of Dacetuzumab in Combination with Rituximab and Gemcitabine: Multiple Responses Observed in Patients with Relasped Diffuse Large B-Cell Lymphomia," 51st Annual Meeting of the American Society of Hematology, New Orleans, Lousiana, Dec. 5 though 9, 2009, four pages. *Blood* 114(22):243-244.

Francisco, J.A. et al. (Jun. 15, 2000). "Agonistic Properties and In Vivo Antitumor Activity of the Anti-CD40 Antibody SGN-14," *Cancer Res.* 60(12):3225-3231.

Freshney, R.I. ed. (1987). *Animal Cell Culture*, Oxford, England, pp. ix-xiv. (Table of Contents.).

Friedman J.et al. (2008). "Regularization Paths for Generalized Linear Models via Coordinate Descent." Technical Report, Department of Statistics, Stanford University (World Wide Webstat.stanford.edui-hastie/Papers/glmnet.pdf) R package glmnet; R Development Core Team.

Gait, M.J. ed. (1984). *Oligonucleotide Synthesis*, Oxford, England, pp. vii-xii. (Table of Contents Only.).

GenBank Accession No. AY143166, last updated Dec. 5, 2003, located at <http://www.ncbi.nlm.nih.gov/nuccore/AY143166>, last visited May 15, 2011, two pages.

GenBank Accession No. BC019297, last updated Jul. 15, 2006, located at <http://www.ncbi.nlm.nih.gov/nuccore/BC019297>, last visited May 15, 2011, one page.

GenBank Accession No. BC062723, last updated Sep. 1, 2006, located at <http://www.ncbi.nlm.nih.gov/nuccore/BC062723>, last visited May 15, 2011, three pages.

GenBank Accession No. NM_000344, last updated May 1, 2011, located at <http://www.ncbi.nlm.nih.gov/nuccore/NM_000344>, last visited May 15, 2011, five pages.

GenBank Accession No. NM_000610.3, last updated Aug. 5, 2012, located at <http://www.ncbi.nlm.nih.gov/nuccore/NM-000610>, last visited Aug. 31, 2012, eight pages.

GenBank Accession No. NM_000626, last updated on Jun. 26, 2012, located at <http://www.ncbi.nlm.nih.gov/nuccore/NM_000626>, last visited Aug. 31, 2012, four pages.

GenBank Accession No. NM_000875, last updated May 15, 2011, located at <http://www.ncbi.nlm.nih.gov/nuccore/NM_000875>, last visited May 15, 2011, one page.

GenBank Accession No. NM001250, last updated May 14, 2011, located at <http://www.ncbi.nlm.nih.gov/nuccore/nm_001250>, last visited May 15, 2011, three pages.

GenBank Accession No. NM_001706, last updated Apr. 30, 2011, located at <http://www.ncbi.nlm.nih.gov/nuccore/NM_001706>, last visited May 15, 2011, three pages.

GenBank Accession No. NM_001771, last updated Mar. 13, 2011, located at <http://www.ncbi.nlm.nih.gov/nuccore/NM_001771>, last visited May 15, 2011, four pages.

GenBank Accession No. NM_001814.4, last updated Apr. 6, 2008, located at, NCBI, NLM (Bethesda, MD).

GenBank Accession No. NM_002737, last updated Oct. 7, 2008, located at <http://www.ncbi.nlm.nih.gov/nuccore/NM_002737>, last visited May 15, 2011, seven pages.

GenBank Accession No. NM_002767, last updated Mar. 11, 2011, located at <http://www.ncbi.nlm.nih.gov/nuccore/NM_002767>, last visited May 15, 2011, one page.

(56) References Cited

OTHER PUBLICATIONS

GenBank Accession No. NM_002927, last updated Mar. 20, 2011, located at <http://www.ncbi.nlm.nih.gov/nuccore/NM_002927>, last visited May 15, 2011, four pages.
GenBank Accession No. NM_003115.4, last updated Jun. 27, 2012, located at <http://www.ncbi.nlm.nih.gov/nuccore/NM_003115>, last visited on Aug. 31, 2012, four pages.
GenBank Accession No. NM_003641, last updated May 14, 2011, located at <http://www.ncbi.nlm.nih.gov/nuccore/AJ132100>, last visited May 15, 2011, one page.
GenBank Accession No. NM_004665, last updated Mar. 11, 2011, located at <http://www.ncbi.nlm.nih.gov/nuccore/NM_004665>, last visited May 15, 2011, one page.
GenBank Accession No. NM_005574, last updated Apr. 10, 2011, located at <http://www.ncbi.nlm.nih.gov/nuccore/NM_005574>, last visited May 15, 2011, three pages.
GenBank Accession No. NM_006763 last updated Mar. 13, 2011, located at <http://www.ncbi.nlm.nih.gov/nuccore/NM_006763>, last visited May 15, 2011, three pages.
GenBank Accession No. NM_015883, last updated Oct. 6, 2003, located at <http://www.ncbi.nlm.nih.gov/nuccore/NM_015883.1?report=genbank>, last visited Jun. 13, 2011, one page.
GenBank Accession No. NM_017549, last updated Mar. 11, 2011, located at <http://www.ncbi.nlm.nih.gov/nuccore/NM_017549>, last visited May 15, 2011, three pages.
GenBank Accession No. NM_019042, last updated Feb. 11, 2008, located at <http://www.ncbi.nlm.nih.gov/nuccore/NM_019042>, last visited Aug. 31, 2012, three pages.
Hammerling, G. J. et al. (1981). "Monoclonal Antibodies and T-Cell Hybridomas." Chapter 3 in *Production of Antibody-Producing Hybridomas in the Rodent Systems*, Elsevier/North-Holland Biomedical Press, Amsterdam, Holland, pp. 563-681.
Harlow, E. et al. (1988). *Antibodies: A Laboratory Manual*, Cold Spring Harbor Laboratory Press, pp. iii-ix. (Table of Contents Only.).
Hawkins, R.E. et al. (Aug. 5, 1992). "Selection of Phage Antibodies by Binding Affinity. Mimicking Affinity Maturation," *J Mot Biol.* 226(3):889-896.
International Search Report mailed on Mar. 11, 2009, for PCT Application No. PCT/US2008/082920, filed on Nov. 7, 2008, three pages.
International Search Report mailed on Aug. 24, 2010, for PCT Application No. PCT/US2010/031528, filed on Apr. 17, 2010, four pages.
Jackson, J.R. et al. (Apr. 1995). "In Vitro Antibody Maturation Improvements of High Affinity Neutralizing Antibody Against IL-1 Beta," *J. Immunol.* 154(7):3310-9.
Jakobovits, A. et al. (1993). "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90(6):2551-2555.
Jakobovits, A. et al. (Mar. 18, 1993). "Germ-Line Transmission and Expression of A human-Derived Yeast Artificial Chrmosome," *Nature* 362(6417):255-258.
Jones, P.T. et al. (May 29-Jun. 4, 1986). "Replacing the Complementarity-Determining Regions in a Human Antibody with Those from a Mouse," *Nature* 321(6069):522-525.
Kohler, G. et al. (Aug. 7, 1975). "Continuous Cultures of Fused Cells Secreting Antibody of Predefined Specifcity," *Nature* 256(5517):495-497.
Lee, C.V. et al. (Jan. 2004). "Bivalent Antibody Phage Display Mimics Natural Immunoglbulin," *J. Immunol. Methods* 284(1-2):119-132.
Lee, C.V. et al. (Jul. 23, 2004). "High-Affinity Human Antibodies From Phage-Displayed Synthetic Fab Libraries with a Single Framework Scaffold," *J.Mol.Biol.* 340(5):1073-1093.
Leong, A.S.Y. et al. (1996). "Epitope Retrieval with Microwaves. A Comparison of Citrate Buffer and EDTA with Tree Commercial Retrieval Solutions," *Appl. Immunohistochem.* 4(3):201-207.
Lockhart, D.J. (Dec. 1996). "Expression Monitoring by Hybridization to High-Density Oligonucleotide Arrays," *Nature Biotechnology* 14(13):1675-1680.

Lonberg, N. et al. (Apr. 28, 1994). "Antigen-Specific Human Antibodies From Mice Comprising Distinct Genetic Modifications," *Nature* 368(6474):856-859.
Lonberg, N. et al. (1995). "Human Antibodies From Transgenic Mice," *Intern. Rev. Immunol.* 13:65-93.
Lossos, I.S. et al. (Aug. 15, 2001). "Expression of a Single Gene, BCL-6, Strongly Predicts Survival in Patients With Diffuse Large B-Cell Lymphona," 98(4):945-951.
Luna, L.G. (1960). "Manual of Histological Staining Method of the Armed Forces Institute of Pathology," 3rd edition, The Blakston Division McGraw-Hill Book Company, New York, New York.
Marks, J.D. et al. (Dec. 5, 1991). "By-Passing Immunization. Human Antibodies From V-Gene Libraries Displayed on Phage," *J. Mol. Biol.* 222(3):581-597.
Marks, J.D. et al. (Jul. 1992). "By-Passing Immunization: Building High Affinity Human Antibodies by Chain Shuffling," *Biotechnology* 10(7):779-783.
Mikel, U.V. eds. (1994). "The Armed Forces Institute of Pathology Advanced Laboratory Methods in Histology and Pathology," Armed Forces Institute of Pathology, American Registry of Pathology, Washington, D.C.
Morrison, S.L. et al. (Nov. 1984). "Chimeric Human Antibody Molecules: Mouse Antigen-Binding Domains with Human Constant Region Domains," *Proc. Natl. Acad. Sci. USA* 81(21):6851-6855.
Morrison, S.L. (Apr. 28, 1994). "Immunology. Success in Specification," *Nature* 368:(6474)812-813.
Mullis et al. eds. (1994). "PCR: The Polymerase Chain Reaction" Birkäuser, Boston, MA, pp. xvi-xvii. (Table of Contents Only.).
Neuberger, M. (Jul. 1996). "Generating High-Advidity Human Mabs in Mice," *Nature Biotechnol.* 14(7):826.
O'Sullivan et al. (1981). "Methods for the Preparation of Enzyme-Antibody Conjugates for use in Enzyme Immunoassay," Chap. 73 in *Methods in Enzymology*, J. Langone et al eds., Academic Press, New York, New York, pp. 147-166.
Overbergh, L. et al. (Mar. 2003). "The Use of Real-Time Reverse Transcriptase PCR for the Quantification of Cytokine Gene Expression," *J. Biomolecular Techniques* 14(1):33-43.
Presta, L.G. (Aug. 1992). "Antibody Engineering," *Curr. Op. Struct. Biol.* 2(4):593-596.
Rai, K et al. (2000). "Chronic Lymphocytic Leukemia," Chap. 72 in *Hematology, Basic Principles and Practice*, Hoffman et al. eds., 3rd ed., Churchill Livingstone, Philadelphia, PA, pp. 1350-1362.
Ravetch, J.V. et al. (1991). "FC Receptors," *Annu. Rev. Immunol* 9:457-492.
Reichmann, L. et al. (Mar. 24, 1988). "Reshaping Human Antibodies for Therapy," *Nature* 332(6162):323-329.
Sambrooks, J. (1989). "Molecular Cloning: A Laboratory Manual", second edition. Cold Spring Harbor Laboratory, pp. v-xxxii. (Table of Contents Only.).
Schier, R. et al. (1996). "Identification of Functional and Structural Amino-Acids Residues by Parsimonious Mutagenesis," *Gene* 169(2):147-155.
Shi, X. et al. (Nov. 16, 2008). "Identification of a Diagnostic Gene Signature for SGN-40, Anti-CD40 Monoclonal Antibody, in Pre-Clinical NHL Models and the Role of FAS in SGN-40 Mediated Apoptosis," 50th Annual Meeting of the American Society of Hematology, San Francisco, California, Dec. 6 through 9, 2008, three pages. *Blood* 112(11):565.
Sidhu, S.S. et al. (Apr. 2004). "Phage-Displayed Antibody Libraries of Synthetic Heavy Chain Complementarity Determining Regions," *J. Mol. Biol.* 338(2):299-310.
Singleton et al., (1994). *Dictionary of Microbiology and Molecular Biology*, 2nd ed., J. Wiley & Sons, Chichester, United Kingdom, pp. vii-xiii. (Preface and Notes to the User Only.).
Smith, M.B. et al. (1992). "Advanced Organic Chemistry Reactions, Mechanisms and Structure," 4th ed., John Wiley & Sons, New York, N.Y, pp. xiii, xiv. (Table of Contents Only.).
Thomas, P.S. (Sep. 1980). "Hybridization fo Denatured RNA and Small DNA Fragments Transferred to Nitrocellulose," *Proc. Natl. Acad. Sci. USA* 77(9):5201-5205.

(56) References Cited

OTHER PUBLICATIONS

Turner, J.G. et al. (Jan. 1, 2001). "Anti-CD40 Antibody Induces Antitumor and Antimetasatic Effects: The Role of NK Cells," *Journal of Immunology, American Association of Immunologist* 166(1):89-94.

Van Besien, K. et al. (2000). "Clinical Manifestations, Staging and Treatment of Non-Hodgkin's Lymphoma," Chapter 70 in *Hematology, Basic Principles and Practice*, 3rd ed. Hoffman et al. eds., Churchill Livingstone, Philadelphia, PA, pp. 1293-1338.

Written Opinion mailed on Mar. 11, 2009, for PCT Application No. PCT/US2008/082920, filed on Nov. 7, 2008, five pages.

Written Opinion mailed on Aug. 24, 2010, for PCT Application No. PCT/US2010/031528, filed on Apr. 17, 2010, nine pages.

Yelton, D.E. et al. (Aug. 15, 1995). "Affinity Maturation of the BR96 Anti-Carcinoma Antibody by Codon-Based Mutagenesis," *J Immunol.* 155(4):1994-2004.

Zhou, H. et al. (2005)"Regularization and Variable Selection Via the Elastic Net;" *J. R. Statist. Soc. B.* 67(2):301-320.

Dogan, A. et al. (2000). "CD10 and BCL-6 Expression in Paraffin Sections of Normal Lymphoid Tissue and B-Cell Lymphomas," *Amercian Journal of Surgical Pathology* 24(6):846-852.

Tzankov, A. et al. (2003). "Prognostic Signiicance of CD44 Expression in Diffuse Large B Cell Lymphoma of Activated and Germinal Centre B Cell-Like Types: A Tissue Microarray Analysis of 90 Cases," *J. Clin. Pathol.* 56:747-752.

GenBank Accession No. NM_015388, last updated Jul. 21, 2012, located at <http://www.ncbi.nlm.nih.gov/nuccore/NM_015388 >, last visited Sep. 6, 2012, three pages.

Forero-Torres et al. (2006). "A humanized antibody against CD40 (SGN-40) is well tolerated and active in non-Hodgkin's lymphoma (NHL): Results of phase I Study," *Journal of Clinical Oncology* 24(18S): Abstract No. 7534, one page.

Kimura, H. et al. (Jun. 2005, e-pub. Sep. 8, 2005). "Plasma MIP-1β levels and skin toxicity in Japanese non-small cell lung cancer patients treated with the EGFR-targeted tyrosine kinase inhibitor, gefitinib," *Lung Cancer* 50(3):393-399.

Nutt et al. (Apr. 1, 2003). "Gene expression-based classification of malignant gliomas correlates better with survival than histological classification," *Cancer Research* 63:1602-1607.

Ramaswamy, S. et al. (Dec. 18, 2001, e-pub. Dec. 11, 2001). "Multiclass cancer diagnosis using tumor gene expression signatures," *Proc. Natl. Acad. Sci. U.S.A.* 98(26):15149-15154.

* cited by examiner

VNN2

```
LOCUS       NM_004665               2034 bp    mRNA    linear   PRI 03-SEP-2007
DEFINITION  Homo sapiens vanin 2 (VNN2), transcript variant 1, mRNA.
ACCESSION   NM_004665
VERSION     NM_004665.2  GI:17865813

1 aaaccttggc catggtcact tcctcttttc caatctctgt ggcagttttt gccctaataa
  61 ccctgcaggt tggtactcag gacagtttta tagctgcagt gtatgaacat gctgtcattt
 121 tgccaaataa aacagaaaca ccagtttctc aggaggatgc cttgaatctc atgaacgaga
 181 atatagacat tctggagaca gcgatcaagc aggcagctga gcagggtgct cgaatcattg
 241 tgactccaga agatgcactt tatggatgga aatttaccag ggaaactgtt ttcccttatc
 301 tggaggatat cccagaccct caggtgaact ggattccgtg tcaagacccc cacagatttg
 361 gtcacacacc agtacaagca agactcagct gcctggccaa ggacaactct atctatgtct
 421 tggcaaattt gggggacaaa aagccatgta attcccgtga ctccacatgt cctcctaatg
 481 gctactttca atacaatacc aatgtggtgt ataatacaga aggaaaactc gtggcacgtt
 541 accataagta ccacctgtac tctgagcctc agtttaatgt ccctgaaaag ccggagttgg
 601 tgactttcaa caccgcattt gaaggtttg gcattttcac gtgctttgat atattcttct
 661 atgatcctgg tgttaccctg gtgaaagatt ccatgtgga ccatactg tttcccacag
 721 cttggatgaa cgttttgccc ctttgacag ctattgaatt ccattcagct tgggcaatgg
 781 gaatgggagt taatcttctt gtggccaaca cacatcatgt cagcctaaat atgacaggaa
 841 gtggtattta tgcaccaaat ggtcccaaag tgtatcatta tgacatgaag acagagttgg
 901 gaaaacttct cctttcagag gtggattcac atccccatc ctcgcttgcc tacccaacag
 961 ctgttaattg gaatgcctac gccaccacca tcaaaccatt tccagtacag aaaaacactt
1021 tcagggattt tatttccagg gatggttca acttcacaga acttttgaa aatgcaggaa
1081 accttacagt ctgtcaaaag gagctttgct gtcatttaag ctacagaatg ttacaaaaag
1141 aagagaatga agtatacgtt ctaggagctt ttacaggatt acatggccga aggagaagag
1201 agtactggca ggtctgcaca atgctgaagt gcaaaactac taatttgaca acttgtggac
1261 ggccagtaga aactgcttct acaagatttg aaatgttctc cctcagtggc acatttggaa
1321 cagagtatgt ttttcctgaa gtgctactta ccgaaattca tctgtcacct ggaaaatttg
1381 aggtgctgaa agatgggcgt ttggtaaaca agaatggatc atctgggcct atactaacag
1441 tgtcactctt tgggaggtgg tacacaaagg actcacttta cagctcatgt gggaccagca
1501 attcagcaat aacttacctg ctaatattca tattattaat gatcatagct ttgcaaaata
1561 ttgtaatgtt ataggggcgtc tctttatcac tcagcttctg catcatatgc ttggctgaat
1621 gtgtttatcg gcttcccaag tttactaaga aactttgaag ggctatttca gtagtataga
1681 ccagtgagtc ctaaatattt tttctcatca ataattattt tttaagtatt atgataatgt
1741 tgtccatttt tttggctact ctgaaatgtt gcagtgtgga acaatggaaa gagcctgggt
1801 gtttgggtca gataaatgaa gatcaaactc cagctccagc ctcatttgct tgagactttg
1861 tgtgtatggg ggacttgtat gtatgggagt gaggagtttc agggccattg caaacatagc
1921 tgtgcccttg aagagaatag taatgatggg aatttagagg tttatgactg aattcccttt
1981 gacattaaag actatttgaa ttcaaaaaaa aaaaaaaaaa aaaaaaaaaa aaaa
```

Figure 6-1

RGS13

```
LOCUS       NM_002927               1498 bp    mRNA    linear   PRI 24-AUG-2007
DEFINITION  Homo sapiens regulator of G-protein signaling 13 (RGS13),
            transcript variant 1, mRNA.
ACCESSION   NM_002927
VERSION     NM_002927.3  GI:21464137
KEYWORDS    .
SOURCE      Homo sapiens (human)
ORIGIN
        1 gaggccagag tgccatcgaa ggtaattata gagacagtaa aatcctttta ctctgggaaa
       61 aataaaatgc tgggtgtctc acaaaatttc agaacctgat ttcaaacgga tcataacaaa
      121 gaggagatca aatttagcat ggtggactgc tcgacaggat atatttgtca atggaatgtt
      181 tccacatatt ataccaccaa catgagaaaa aaatgatcat tgtttatttg aagcttgatg
      241 atattctaac gctgcctttt ctcttctcat tttagagaaa aatgagcagg cggaattgtt
      301 ggatttgtaa gatgtgcaga gatgaatcta agaggccccc ttcaaacctt actttggagg
      361 aagtattaca gtgggcccag tcttttgaaa atttaatggc tacaaaatat ggtccagtag
      421 tctatgcagc atatttaaaa atggagcaca gtgacgagaa tattcaattc tggatggcat
      481 gtgaaaccta taagaaaatt gcctcacggt ggagcagaat ttctaggca aagaagcttt
      541 ataagattta catccagcca cagtcccta gagagattaa cattgacagt tcgacaagag
      601 agactatcat caggaacatt caggaaccca ctgaaacatg ttttgaagaa gctcagaaaa
      661 tagtctatat gcatatggaa agggattcct accccagatt tctaaagtca gaatgtacc
      721 aaaaacttt gaaaactatg cagtccaaca acagtttctg actacaactc aaaagtttaa
      781 atagaaaaca gtatattgaa agtggtgggt ttgatctttt tatttagaaa cccacaaaat
      841 cagaaacaca gtacaaataa aacagaaatc aaactataag ttgacttta gttcctaaaa
      901 agaaacatat ttcaaaagca atggaatcta gaattcttat aacatgaata acaaaatgta
      961 cagcaagcct atgtagttca attaatatat aaggaaaagg aaggtctttc ttcatgatac
     1021 aagcattata aagtttttac tgtagtagtc aattaatgga tatttccttg ttaataaaat
     1081 tttgtgtcat aatttacaaa ttagttcttt aaaaattgtt gttatatgaa ttgtgtttct
     1141 agcatgaatg ttctatagag tactctaaat aacttgaatt tatagacaaa tgctactcac
     1201 agtacaatca attgtattat accatgagaa aatcaaaaag gtgttcttca gagacatttt
     1261 atctataaaa ttttcctact attatgttca ttaacaaact tctttatcac atgtatcttc
     1321 tacatgtaaa acatttctga tgatttttta acaaaaaata tatgaatttc ttcatttgct
     1381 cttgcatcta cattgctata aggatataaa atgtggtttc tatatttga gatgtttttt
     1441 ccttacaatg tgaactcatc gtgatcttgg aaatcaataa agtcaaatat caactaaa
```

```
LOCUS       NM_001771               3260 bp    mRNA    linear   PRI 03-SEP-2007
DEFINITION  Homo sapiens CD22 molecule (CD22), mRNA.
ACCESSION   NM_001771
VERSION     NM_001771.1  GI:4502650
KEYWORDS    .
SOURCE      Homo sapiens (human)

ORIGIN
        1 ccatcccata gtgagggaag acacgcggaa acaggcttgc acccagacac gacaccatgc
       61 atctcctcgg cccctggctc ctgctcctgg ttctagaata cttggctttc tctgactcaa
      121 gtaaatgggt ttttgagcac cctgaaaccc tctacgcctg ggaggggcc tgcgtctgga
      181 tccctgcac ctacagagcc ctagatggtg acctggaaag cttcatcctg ttccacaatc
      241 ctgagtataa caagaacacc tcgaagtttg atgggacaag actctatgaa agcacaaagg
      301 atgggaaggt tccttctgag cagaaaaggg tgcaattcct gggagacaag aataagaact
      361 gcacactgag tatccacccg gtgcacctca tgacagtgg tcagctgggg ctgaggatgg
      421 agtccaagac tgagaaatgg atggaacgaa tacacctcaa tgtctctgaa aggccttttc
      481 cacctcatat ccagctccct ccagaaattc aagagtccca ggaagtcact ctgacctgct
      541 tgctgaattt ctcctgctat gggtatccga tccaattgca gtggctccta gaggggttc
      601 caatgaggca ggctgctgtc acctcgacct ccttgaccat caagtctgtc ttcacccgga
      661 gcgagctcaa gttctcccca cagtggagtc accatgggaa gattgtgacc tgccagcttc
      721 aggatgcaga tgggaagttc ctctccaatg acacggtgca gctgaacgtg aagcacaccc
      781 cgaagttgga gatcaaggtc actcccagtg atgccatagt gagggagggg gactctgtga
      841 ccatgacctg cgaggtcagc agcagcaacc cggagtacac gacggtatcc tggctcaagg
      901 atgggacctc gctgaagaag cagaatacat tcacgctaaa cctgcgcgaa gtgaccaagg
      961 accagagtgg gaagtactgc tgtcaggtct ccaatgacgt gggcccggga aggtcggaag
     1021 aagtgttcct gcaagtgcag tatgccccgg aaccttccac ggttcagatc ctccactcac
     1081 cggctgtgga gggaagtcaa gtcgagtttc tttgcatgtc actggccaat cctcttccaa
     1141 caaattacac gtggtaccac aatgggaaag aaatgcaggg aaggacagag gagaaagtcc
     1201 acatcccaaa gatcctcccc tggcacgctg ggacttattc ctgtgtggca gaaaacattc
     1261 ttggtactgg acagaggggc ccgggagctg agctggatgt ccagtatcct cccaagaagg
     1321 tgaccacagt gattcaaaac cccatgccga ttcgagaagg agacacagtg acccttcct
     1381 gtaactacaa ttccagtaac cccagtgtta cccggtatga atggaaaccc catggcgcct
     1441 gggaggagcc atcgcttggg gtgctgaaga tccaaaacgt tggctgggac aacacaacca
     1501 tcgcctgcgc acgttgtaat agttggtgct cgtgggcctc cctgtcgcc ctgaatgtcc
     1561 agtatgcccc ccgagacgtg agggtccgga aaatcaagcc ctttccgag attcactctg
     1621 gaaactcggt cagcctccaa tgtgacttct caagcagcca ccccaaagaa gtccagttct
     1681 tctgggagaa aaatggcagg cttctgggga agaaagcca gctgaatttt gactccatct
     1741 ccccagaaga tgctgggagt tacagctgct gggtgaacaa ctccatagga cagacagcgt
     1801 ccaaggcctg gacacttgaa gtgctgtatg cacccaggag gctgcgtgtg tccatgagcc
     1861 cggggaccca gtgatggag gggaagagtg caaccctgac ctgtgagagt gacgccaacc
     1921 ctcccgtctc ccactacacc tggtttgact ggaataacca aagcctcccc caccacagcc
     1981 agaagctgag attggagccg gtgaaggtcc agcactcggg tgcctactgg tgcaggggg
     2041 ccaacagtgt gggcaaggc cgttcgcctc tcagcaccct tactgtctac tatagcccgg
     2101 agaccatcgg caggcgagtg ctgtgggac tcgggtcctg cctcgccatc ctcatcctgg
     2161 caatctgtgg gctcaagctc cagcgacgtt ggaagaggac acagagccag caggggcttc
     2221 aggagaattc cagcggccag agcttctttg tgaggaataa aaaggttaga agggcccccc
     2281 tctctgaagg cccccactcc ctgggatgct acaatccaat gatggaagat ggcattagct
     2341 acaccaccct gcgctttccc gagatgaaca taccacgaac tggagatgca gagtcctcag
```

Figure 6-3

```
2401 agatgcagag acctccccgg acctgcgatg acacggtcac ttattcagca ttgcacaagc
2461 gccaagtggg cgactatgag aacgtcattc cagattttcc agaagatgag gggattcatt
2521 actcagagct gatccagttt ggggtcgggg agcggcctca ggcacaagaa aatgtggact
2581 atgtgatcct caaacattga cactggatgg gctgcagcag aggcactggg ggcagcgggg
2641 gccagggaag tccccgagtt tccccagaca ccgccacatg gcttcctcct gcgtgcatgt
2701 gcgcacacac acacacacac gcacacacac acacacacac tcactgcgga gaaccttgtg
2761 cctggctcag agccagtctt tttggtgagg gtaaccccaa acctccaaaa ctcctgcccc
2821 tgttctcttc cactctcctt gctacccaga aatcatctaa atacctgccc tgacatgcac
2881 acctcccctg ccccaccagc ccactggcca tctccacccg gagctgctgt gtcctctgga
2941 tctgctcgtc attttccttc ccttctccat ctctctggcc ctctacccct gatctgacat
3001 ccccactcac gaatattatg cccagtttct gcctctgagg gaaagcccag aaaaggacag
3061 aaacgaagta gaaaggggcc cagtcctggc ctggcttctc ctttggaagt gaggcattgc
3121 acggggagac gtacgtatca gcggccccett gactctgggg actccgggtt tgagatggac
3181 acactggtgt ggattaacct gccagggaga cagagctcac aataaaaatg gctcagatgc
3241 cacttcaaag aaaaaaaaaa
```

Figure 6-4

LRRC8A

```
LOCUS       AY143166                2433 bp    mRNA    linear   PRI 05-DEC-2003
DEFINITION  Homo sapiens leucine-rich repeat-containing 8 (LRRC8) mRNA,
            complete cds.
ACCESSION   AY143166
VERSION     AY143166.1  GI:27462053
KEYWORDS    .
SOURCE      Homo sapiens (human)

ORIGIN
        1 atgattccgg tgacagagct ccgctacttt gcggacacgc agccagcata ccggatcctg
       61 aagccgtggt gggatgtgtt cacagactac atctctatcg tcatgctgat gattgccgtc
      121 ttcgggggga cgctgcaggt cacccaagac aagatgatct gcctgccttg taagtgggtc
      181 accaaggact cctgcaatga ttcgttccgg ggctgggcag cccctggccc ggagcccacc
      241 taccccaact ccaccattct gccgacccct gacacgggcc ccacaggcat caagtatgac
      301 ctggaccggc accagtacaa ctacgtggac gctgtgtgct atgagaaccg actgcactgg
      361 tttgccaagt acttccccta cctggtgctt ctgcacacgc tcatcttcct ggcctgcagc
      421 aacttctggt tcaaattccc cgcaccagcc tcgaagctgg agcactttgt gtctatcctg
      481 ctgaagtgct cgactcgcc ctggaccacg agggccctgt cggagacagt ggtggaggag
      541 agcgacccca agccggcctt cagcaagatg aatgggtcca tggacaaaaa gtcatcgacc
      601 gtcagtgagg acgtggaggc caccgtgccc atgctgcagc ggaccaagtc acggatcgag
      661 cagggtatcg tggaccgctc agagacgggc gtgctggaca agaaggaggg ggagcaagcc
      721 aaggcgctgt tgagaaggt gaagaagttc cggacccatg tggaggaggg ggacattgtg
      781 taccgcctct acatgcggca gaccatcatc aaggtgatca agttcatcct catcatctgc
      841 tacaccgtct actacgtgca caacatcaag ttcgacgtgg actgcaccgt ggacattgag
      901 agcctgacgg gctaccgcac ctaccgctgt gcccaccccc tggccacact cttcaagatc
      961 ctggcgtcct tctacatcag cctagtcatc ttctacggcc tcatctgcat gtatactg
     1021 tggtggatgc tacggcgctc cctcaagaag tactcgtttg agtcgatccg tgaggagagc
     1081 agctacagcg acatccccga cgtcaagaac gacttcgcct tcatgctgca cctcattgac
     1141 caatacgacc cgctctactc caagcgcttc gccgtcttcc tgtcggaggt gagtgagaac
     1201 aagctgcggc agctgaacct caacaacgag tggacgctgg acaagctccg gcagcggctc
     1261 accaagaacg cgcaggacaa gctggagctg cacctgttca tgctcagtgg catccctgac
     1321 actgtgttg acctggtgga gctggaggtc ctcaagctgg agctgatccc cgacgtgacc
     1381 atcccgccca gcattgccca gctcacgggc tcaaggagc tgtggctcta ccacacagcg
     1441 gccaagattg aagcgcccgc gctggccttc ctgcgcgaga acctgcgggc gctgcacatc
     1501 aagttcaccg acatcaagga gatcccgctg tggatctata gcctgaagac actggaggag
     1561 ctgcacctga cgggcaacct gagcgcggag aacaaccgct acatcgtcat cgacgggctg
     1621 cgggagctca aacgcctcaa ggtgctgcgg ctcaagagca acctaagcaa gctgccacag
     1681 gtggtcacag atgtgggcgt gcacctgcag aagctgtcca tcaacaatga gggcaccaag
     1741 ctcatcgtcc tcaacagcct caagaagatg cgcgaacctga ctgagctgga gctgatccgc
     1801 tgtgacctgg agcgcatccc ccactccatc ttcagcctcc acaacctgca ggagattgac
     1861 ctcaaggaca caacctcaa gaccatcgag gagatcatca gcttccagca cctgcaccgc
     1921 ctcacctgcc ttaagctgtg gtacaaccac atcgcctaca tcccatcca gatcggcaac
     1981 ctcaccaacc tggagcgcct ctacctgaac gcaacaaga tcgagaagat ccccacccag
     2041 ctcttctact gccgcaagct cgctacctg gacctcagcc acaacaacct gaccttcctc
     2101 cctgccgaca tcggcctcct gcagaacctc agaacctag ccatcacggc caaccggatc
     2161 gagacgctcc ctccggagct cttccagtgc cggaagctgc gggccctgca cctgggcaac
     2221 aacgtgctgc agtcactgcc ctccagggtg ggcgagctga ccaacctgac gcagatcgag
     2281 ctgcggggca accggctgga gtgcctgcct gtggagctgg cgagtgccc actgctcaag
     2341 cgcagcggct tggtggtgga ggaggacctg ttcaacacac tgccacccga ggtgaaggag
     2401 cggctgtgga gggctgacaa ggagcaggcc tga
```

```
LOCUS       NM_001250               1616 bp    mRNA    linear   PRI 30-SEP-2007
DEFINITION  Homo sapiens CD40 molecule, TNF receptor superfamily member 5
            (CD40), transcript variant 1, mRNA.
ACCESSION   NM_001250
VERSION     NM_001250.4  GI:91105420
KEYWORDS    .
SOURCE      Homo sapiens (human)

ORIGIN
        1 gccaaggctg gggcagggga gtcagcagag gcctcgctcg ggcgcccagt ggtcctgccg
       61 cctggtctca cctcgctatg gttcgtctgc ctctgcagtg cgtcctctgg ggctgcttgc
      121 tgaccgctgt ccatccagaa ccacccactg catgcagaga aaaacagtac ctaataaaca
      181 gtcagtgctg ttctttgtgc cagccaggac agaaactggt gagtgactgc acagagttca
      241 ctgaaacgga atgccttcct gcggtgaaa gcgaattcct agacacctgg aacagagaga
      301 cacactgcca ccagcacaaa tactgcgacc caacctagg gcttcgggtc agcagaagg
      361 gcacctcaga aacagacacc atctgcacct gtgaagaagg ctggcactgt acgagtgagg
      421 cctgtgagag ctgtgtcctg caccgctcat gctcgcccgg cttTggggtc aagcagattg
      481 ctacagggt ttctgatacc atctgcgagc cctgccagt cggcttcttc tccaatgtgt
      541 catctgcttt cgaaaaatgt cacccttgga caagctgtga gaccaaagac ctggttgtgc
      601 aacaggcagg cacaaacaag actgatgttg tctgtggtcc ccaggatcgg ctgagagccc
      661 tggtggtgat ccccatcatc ttcgggatcc tgtttgccat cctcttggtg ctggtctTta
      721 tcaaaaaggt ggccaagaag ccaaccaata aggccccca ccccaagcag aaccccagg
      781 agatcaattt tcccgacgat cttcctggct ccaacactgc tgctccagtg caggagactt
      841 tacatggatg ccaaccggtc acccaggagg atggcaaaga gagtcgcatc tcagtgcagg
      901 agagacagtg aggctgcacc cacccaggag tgtggccacg tgggcaaaca ggcagttggc
      961 cagagagcct ggtgctgctg ctgctgtggc gtgagggtga gggctggca ctgactgggc
     1021 atagctcccc gcttctgcct gcacccctgc agtttgagac aggagacctg gcactggatg
     1081 cagaaacagt tcaccttgaa gaacctctca cttcaccctg gagcccatcc agtctcccaa
     1141 cttgtattaa agacagaggc agaagtttgg tggtggtggt gttggggtat ggtttagtaa
     1201 tatccaccag accttccgat ccagcagttt ggtgcccaga gaggcatcat ggtggcttcc
     1261 ctgcgcccag gaagccatat acacagatgc ccattgcagc attgtttgtg atagtgaaca
     1321 actggaagct gcttaactgt ccatcagcag gagactggct aaataaaatt agaatatatt
     1381 tatacaacag aatctcaaaa acactgttga gtaaggaaaa aaaggcatgc tgctgaatga
     1441 tgggtatgga acttttaaa aagtacatg cttttatgta tgtatattgc ctatggatat
     1501 atgtataaat acaatatgca tcatatattg ataaacaag ggttctggaa gggtacacag
     1561 aaaacccaca gctcgaagag tggtgacgtc tggggtgggg aagaagggtc tggggg
```

Figure 6-6

IFITM1

```
LOCUS       NM_003641                733 bp    mRNA    linear   PRI 03-SEP-2007
DEFINITION  Homo sapiens interferon induced transmembrane protein 1 (9-27)
            (IFITM1), mRNA.
ACCESSION   NM_003641
VERSION     NM_003641.3  GI:150010588
KEYWORDS    .
SOURCE      Homo sapiens (human)

ORIGIN
        1 aaacagcagg aaatagaaac ttaagagaaa tacacacttc tgagaaactg aaacgacagg
       61 ggaaaggagg tctcactgag caccgtccca gcatccggac accacagcgg cccttcgctc
      121 cacgcagaaa accacacttc tcaaaccttc actcaacact tccttcccca aagccagaag
      181 atgcacaagg aggaacatga ggtggctgtg ctggggcac ccccagcac catccttcca
      241 aggtccaccg tgatcaacat ccacagcgag acctccgtgc ccgaccatgt cgtctggtcc
      301 ctgttcaaca ccctcttctt gaactggtgc tgtctgggct tcatagcatt cgcctactcc
      361 gtgaagtcta gggacaggaa gatggttggc gacgtgaccg gggcccaggc ctatgcctcc
      421 accgccaagt gcctgaacat ctgggccctg attctgggca tcctcatgac cattggattc
      481 atcctgttac tggtattcgg ctctgtgaca gtctaccata ttatgttaca gataatacag
      541 gaaaacgggg ttactagta gccgcccata gcctgcaacc tttgcactcc actgtgcaat
      601 gctggccctg cacgctgggg ctgttgcccc tgcccccttg gtcctgcccc tagatacagc
      661 agtttatacc cacacacctg tctacagtgt cattcaataa agtgcacgtg cttgtgaaaa
      721 aaaaaaaaa aaa
```

Figure 6-7

PRKCA

```
LOCUS       NM_002737               8787 bp    mRNA    linear   PRI 25-SEP-2007
DEFINITION  Homo sapiens protein kinase C, alpha (PRKCA), mRNA.
ACCESSION   NM_002737
VERSION     NM_002737.2  GI:47157319
KEYWORDS    .
SOURCE      Homo sapiens (human)

ORIGIN
        1 ggccgcagct ccccggcgga ggcaagaggt ggttggggggg gaccatggct gacgttttcc
       61 cgggcaacga ctccacggcg tctcaggacg tggccaaccg cttcgcccgc aaagggggcgc
      121 tgaggcagaa gaacgtgcac gaggtgaagg accacaaatt catcgcgcgc ttcttcaagc
      181 agcccacctt ctgcagccac tgcaccgact tcatctgggg gtttgggaaa caaggcttcc
      241 agtgccaagt ttgctgtttt gtggtccaca gaggtgcca tgaatttgtt acttttcctt
      301 gtccgggtgc ggataaggga cccgacactg atgaccccag gagcaagcac aagttcaaaa
      361 tccacactta cggaagcccc accttctgcg atcactgtgg gtcactgctc tatggactta
      421 tccatcaagg gatgaaatgt gacacctgcg atatgaacgt tcacaagcaa tgcgtcatca
      481 atgtccccag cctctgcgga atggatcaca ctgagaagag ggggcggatt tacctaaagg
      541 ctgaggttgc tgatgaaaag ctccatgtca cagtacgaga tgcaaaaaat ctaatcccta
      601 tggatccaaa cgggctttca gatccttatg tgaagctgaa acttattcct gatcccaaga
      661 atgaaagcaa gcaaaaaacc aaaaccatcc gctccacact aaatccgcag tggaatgagt
      721 cctttacatt caaattgaaa ccttcagaca agaccgacg actgtctgta gaaatctggg
      781 actgggatcg aacaacaagg aatgacttca tgggatccct ttcctttgga gtttcggagc
      841 tgatgaagat gccggccagt ggatggtaca agttgcttaa ccaagaagaa ggtgagtact
      901 acaacgtacc cattccggaa ggggacgagg aaggaaacat ggaactcagg cagaaattcg
      961 agaaagccaa acttggccct gctggcaaca agtcatcag tccctctgaa gacaggaaac
     1021 aaccttccaa caaccttgac cgagtgaaac tcacggactt caatttcctc atggtgttgg
     1081 gaaaggggag ttttggaaag gtgatgcttg ccgacaggaa gggcacagaa gaactgtatg
     1141 caatcaaaat cctgaagaag gatgtggtga ttcaggatga tgacgtggag tgcaccatgg
     1201 tagaaaagcg agtcttggcc tgcttgacaa accccgtt cttgacgcag ctgcactcct
     1261 gcttccagac agtggatcgg ctgtacttcg tcatggaata tgtcaacggt ggggacctca
     1321 tgtaccacat tcagcaagta ggaaaattta aggaaccaca agcagtattc tatgcggcag
     1381 agatttccat cggattgttc tttcttcata aagaggaat catttatagg gatctgaagt
     1441 tagataacgt catgttggat tcagaaggac atatcaaaat gctgactttt gggatgtgca
     1501 aggaacacat gatggatgga gtcacgacca ggaccttctg tgggactcca gattatatcg
     1561 ccccagagat aatcgcttat cagccgtatg gaaaatctgt ggactggtgg gcctatggcg
     1621 tcctgttgta tgaaatgctt gccgggcagc tccatttga tggtgaagat gaagacgagc
     1681 tatttcagtc tatcatggag cacaacgttt cctatccaaa atccttgtcc aaggaggctg
     1741 tttctatctg caaaggactg atgaccaaac cccagccaa gcggctgggc tgtgggcctg
     1801 agggggagag ggacgtgaga gagcatgcct tcttccggag gatcgactgg gaaaaactgg
     1861 agaacaggga gatccagcca ccattcaagc ccaaagtgtg tggcaaagga cagagaact
     1921 tgacaagtt cttcacacga ggacagcccg tcttaacacc acctgatcag ctggttattg
     1981 ctaacataga ccagtctgat tttgaagggg tctcgtatgt caaccccccag tttgtgcacc
     2041 ccatcttaca gagtgcagta tgaaactcac cagcgagaac aaacacctcc ccagccccca
     2101 gccctccccg cagtgggaag tgaatcctta accctaaaat tttaaggcca cggccttgtg
     2161 tctgattcca tatggaggcc tgaaaattgt agggttatta gtccaaatgt gatcaactgt
     2221 tcagggtctc tctcttacaa ccaagaacat tatcttagtg gaagatggta cgtcatgctc
     2281 agtgtccagt ttaattctgt agaagttacg tctggctcta ggttaaccct tcctagaaag
     2341 caagcagact gttgccccat tttgggtaca atttgatata cttttccatac cctccatctg
     2401 tggattttc agcattggaa tccccccaacc agagatgtta aagtgagcct gtcccaggaa
```

Figure 6-8

```
2461 acatctccac ccaagacgtc tttggaatcc aagaacagga agccaagaga gtgagcaggg
2521 agggattggg ggtgggggag gcctcaaaat accgactgcg tccattctct gcctccatgg
2581 aaacagcccc tagaatctga aaggccggga taaacctaat cactgttccc aaacattgac
2641 aaatcctaac ccaaccatgg tccagcagtt accagtttaa acaaaaaaac ctcagatgag
2701 tgttgggtga atctgtcatc tggtaccctc cttggttgat aactgtcttg atacttttca
2761 ttctttgtaa gaggccaaat cgtctaagga cgttgctgaa caagcgtgtg aaatcatttc
2821 agatcaagga taagccagtg tgtacatatg ttcattttaa tctctgggag attattttc
2881 catccagggt gccatcagta atcatgccac tactcaccag tgttgttcgc caacacccac
2941 ccccacacac accaacattt tgctgcctac cttgttatcc ttctcaagaa gctgaagtgt
3001 acgccctctc ccctttttgtg cttatttatt taataggctg cagtgtcgct tatgaaagta
3061 cgatgtacag taacttaatg gaagtgctga ctctagcatc agcctctacc gattgatttt
3121 cctcccttct ctagccctgg atgtccactt agggataaaa agaatatggt tttggttccc
3181 atttctagtt cacgttgaat gacaggcctg gagctgtaga atcaggaaac ccggatgcct
3241 aacagctcaa agatgttttg ttaatagaag gattttaata cgttttgcaa atgcatcatg
3301 caatgaattt tgcatgttta taaaacct taataacaag tgaatctata ttattgatat
3361 aatcgtatca agtataaaga gagtattata ataattttat aagacacaat tgtgctctat
3421 ttgtgcaggt tcttgtttct aatcctcttt tctaattaag ttttagctga atcccttgct
3481 tctgtgcttt ccctccctgc acatgggcac tgtatcagat agattacttt ttaaatgtag
3541 ataaaatttc aaaaatgaat ggctagttta cgtgatagat taggctctta ctacatatgt
3601 gtgtgtatat atatgtattt gattctacct gcaaacaaat ttttattggt gaggactatt
3661 tttgagctga cactccctct tagtttcttc atgtcacctt tcgtcctggt tcctccgcca
3721 ctcttcctct tggggacaac aggaagtgtc tgattccagt ctgcctagta cgttggtaca
3781 cacgtggcat tgccgcagca cctgggctga cctttgtgtg tgcgtgtgtg tgtgtttcct
3841 tcttcccttc agcctgtgac tgttgctgac tccaggggtg ggagggatgg ggagactccc
3901 ctcttgctgt gtgtactgga cacgcaggaa gcatgctgtc ttgctgcctc tgcaacgacc
3961 tgtcgtttgc tccagcatgc acaaacttcg tgagaccaac acagccgtgc cctgcaggca
4021 ccagcacgtg cttttcagag gctgcggact ttcttccagc cattgtggca ttggcctttc
4081 cagtcttggg aggagcgcgc tgctttggtg agacaccccc atgcaaggtc ctcagagtag
4141 ccgggttcta ccacaaacag aaacagaatg aaagtagctg tcagtccttg tagagagccg
4201 ctctgttttcc tcccagaagc atctcccagc taagctcgca ttattttct cctctggctg
4261 tttgcctgaa gttcacagaa cacacaacca tgaaaggctt tttgaggtga gaggcccagg
4321 tggtcctggc aaccctgagt agaaggagag acggggtagg gaacgggccc ggccagaaaa
4381 gaaccatttc ttctgccatc ttttatgcac catagacatc gagactccag ggggtcctgg
4441 ctccccctgtc cctgcagccc tgcaggtcag tgcatgatct gggttcgtgt cctgaccagg
4501 tgctcctcct ttgatccgag gggaaaggga ctggtttata gaaagagcct aggagacaaa
4561 agggccagtc cccctgccca gaatggagca gcagcaggac agaccccac gaggccccc
4621 agagaggagg aagatcccac ggaggaacac atgaggttag ggaccttgt tcagcacccc
4681 aaacagcctg cctgtttaaa gcaggcagca ggcttaggcc ttccctgcaa ccccaacacc
4741 cacaagtttg tttctctagg aaacacattc actgtctcag ctggctgtta ctctctcaga
4801 ccatatggca agttttccca agaaaatgcc ccgacagggg tgcccagcac actgcctgag
4861 ggacaacaga catcagaaca aaccccaga gagaaacagt caaaatcagg gcccggtgca
4921 gtgttgtcat gtggaacctg ctttatccat tgctgagtgt tgaatgtggg taatggttag
4981 ggctttccag atctcagcag ccaaagacag ttattgttgg aagactgtca tgtagataac
5041 catgagcaat ggctcgcctc agaatcagtt cataaaattc tatggtactg gccccttcgt
5101 gggtattgtg tgaaatgaga tggtggcgag gggtgcgctg tggaactgcc gcagccacgc
5161 aggaggtccc tgggggatgc tttgggaagt ccttgcccct gagcactgcc tgattgccag
5221 ggcctgtgga ggtctaggcc gcctggcaga atctagcacc gtccgaatcc ccgcaggacc
5281 catggagcta tgaccacacc aggccattca aatggctctg cattatcttc ccttggaagg
5341 tggccactcc tcggtggcag ggcctttccc tgaggctgca ggccgtgggc tggcagcccg
5401 tctcttggca tttcaattga aggtcaccag gtgctgggtt tgaaaggaag tcactggagt
5461 gctgccaggg gccgccctcc aaggttaatg agaggcccac atccaggcaa gaactaattc
5521 aaaaggcaga tcagaaacca caggagtcaa aattattgct ccggcagtgc ttcccttcct
5581 ttcatccact ggcctcgtgt ggtccatgca gggccactgt ctgcccttc tgatgccacg
```

Figure 6-9

```
5641 tattaggctt tcttactcag aattttgata gaaaaccatg gggccaagag ctctggaagc
5701 ctggccggaa agaccaaggt tcatgcagcc caacaaatga ttgttgagca cctctcggag
5761 ccaaagtcct taggcgagtg tggtgacttc ctggaaggag gatgcagact tccagagagc
5821 ccccccaacg gacgtgctga agggagag ggaggcgggg gctgtagtca ggaaggagcc
5881 agagaagaac agggtttggg tgcatccaga aatatgcctg cagtaggagg gagaggaagg
5941 ggtgccaccg tcaacggctt cccatcggag gtggttggtg cagatggaag tttctgtctg
6001 ctggccctca agagagtgtt ttgccaggga cacagtctgt tcctcctcag aaaacacccc
6061 ccaaatgcta acaacatccc caccagctgc tagaagcccc tttcccctcc ccaccttgaa
6121 gtagctcata gttctctggg cagagccaga ccatccagtg taccccagag gccagtaggt
6181 tcctgcccat tttcctctct ggcttcctgc caagaattat ggcagctgag gatgaatgga
6241 gaagtaaaaa caactaacac cgcacaacta acaactaaca ccgcagttcc cacctgggtt
6301 ccacttagca ggagacattt cggagggttt ttttttgtttt tgttcctgtt ttttttttt
6361 ttgctggaat tgtttttctc agtactgaaa agagaaaaag tgacaatctt gtattttaa
6421 aagcctcgga aaggtgatac catctgacag tcatttctc acgttggtct tctaaagtca
6481 cctatttctt gtgtgtgcac atcacaccat ttcctgtttc tttataaccc gacaagggta
6541 ggagtgcctg tttcccctgc tgggcacacc agacaatcgt aatcacaaaa cagacactga
6601 gccaggggcc caaagggtgt gatcatgaga gttaccggga cagcagtagg catgacagtc
6661 accaggaagg acaagggtgc tctgttgtta gtggccacac accaatttga caaggagtgt
6721 tgcgaaattt ttatttattt atttatttat tttgagatgg agtttcactc ttgttgccca
6781 ggctggagtg cggtggtaca atctcggctc actgcaacct ccacctccca ggttcaagcg
6841 attctcctgc ctcagcctcc caagtacctg gactacagg tgcgtgccac cacacccagc
6901 taaattttgt gtttttagta gagatggggt ttcaccatgt tggccaggat ggtcttgaac
6961 ccctgacctc atgatctgcc tgcctcggcc tcccaaagtg ctgggattac aggcatgagc
7021 caccacgccc agccaaaata ttttttaaa gtcattttcc ttaagctgct tgggctacat
7081 gtgaaataca ctggacggtc aacattcctg tctcctccca tttgggctga tgcagcagat
7141 ccagggaatg ttacctgttt ctgctgctag aagatccagg aaattgggaa ggttacctga
7201 cgcacacatg gatgaaggcc atcatctaga aatggggtca accacaattg tgttaattcc
7261 gtagtgtcag ggattcttcg ggaaggtcaa cagtatgaag gattctgacc cctgtgcctc
7321 ccatttatgt gatcaggtga cagttaataa ccgtggaggt cacactcagc catccaacag
7381 ccttacagtg accctacaca aaagccccca aattccaaag acttttcttt aacctaaagg
7441 aagaaattat tgttaattc cagtagagca actgaatata ctgggctatt tgtactttt
7501 tatagagaac tttaataata attctttaaa aatgagtttt tagaacaaag caactgacga
7561 tttcctaaga ttccaatgcc ctggagcttg taggaggact tagcctgggt cagctggagc
7621 accccgacc tgatctccca ctgccagatt ttcccatgct cctagggtat ggagtccacg
7681 tgggaatgac tgcaagttca ggtggaactt ggccgactga tgctctgcga ttttttaata
7741 gacactgggg acaactgctt aaggtttaga acttccaaa ccacaggaaa gacattttta
7801 gtgtccccca tccagaggca gccctggaat aggattccca ggggtttctg ggaccccttt
7861 ccttgctccg tgaggctctg tggccatctt ttggcaggag gaggatgctt ccttggctct
7921 gtgcccagac ccgcctggtc cccaggtctc tcaccttggg tgaagattca gagatgccct
7981 gtaaggattt tgcccactgg gcaactcaga aatacttcga tctcccaaga tataagaggc
8041 agcagcaaac gtgcctattg acgtctgttt catagttacc acttacgcga gtagacagaa
8101 ctcggctttt cagaaaatag gtgtcaagtc cactttataa gaaccttttt ttctaaaata
8161 agataaaagg tggctttgca ttttctgatt aaacgactgt gtctttgtca cctctgctta
8221 actttaggag tatccattcc tgtgattgta gacttttgtt gatattcttc ctggaagaat
8281 atcattcttt tcttgaaggg ttggtttact agaatattca aaatcaatca tgaaggcagt
8341 tactattttg agtctaaagg ttttctaaaa attaacctca catcccttct gttagggtct
8401 ttcagaatat cttttataaa cagaagcatt tgaagtcatt gcttttgcta catgatttgt
8461 gtgtgtgaag gacataccac gtttaaatca ttaattgaaa acatcatat aagccccaac
8521 tttgtttgga ggaagagacg gaggttgagg tttttccttc tgtataagca cctactgaca
8581 aaatgtagag gccattcaac cgtcaaacac catttggtta tatcgcagag gagacggatg
8641 tgtaaattac tgcattgctt ttttttttcag tttgtataac ctctaatctc cgtttgcatg
8701 atacgctttg ttagaaacat taattgtagt ttggaagcaa gtgtgtatga ataaagataa
8761 tgatcattcc aaaaaaaaaa aaaaaaa
```

Figure 6-10

BCL6

```
LOCUS       NM_001706               3537 bp    mRNA    linear   PRI 30-SEP-2007
DEFINITION  Homo sapiens B-cell CLL/lymphoma 6 (zinc finger protein 51)
            (BCL6), transcript variant 1, mRNA.
ACCESSION   NM_001706
VERSION     NM_001706.2  GI:21040323
KEYWORDS    .
SOURCE      Homo sapiens (human)

ORIGIN
        1 ggcccctcga gcctcgaacc ggaacctcca aatccgagac gctctgctta tgaggacctc
       61 gaaatatgcc ggccagtgaa aaaatcttgt ggctttgagg gcttttggtt ggccagggc
      121 agtaaaaatc tcggagagct gacaccaagt cctcccctgc cacgtagcag tggtaaagtc
      181 cgaagctcaa attccgagaa ttgagctctg ttgattctta aactgggggt tcttagaagt
      241 ggtgatgcaa gaagtttcta ggaaaggccg gacaccaggt tttgagcaaa attttggact
      301 gtgaagcaag gcattggtga agacaaaatg gcctcgccgg ctgacagctg tatccagttc
      361 acccgccatg ccagtgatgt tcttctcaac cttaatcgtc tccggagtcg agacatcttg
      421 actgatgttg tcattgttgt gagccgtgag cagtttagag cccataaaac ggtcctcatg
      481 gcctgcagtg gcctgttcta tagcatcttt acagaccagt tgaaatgcaa ccttagtgtg
      541 atcaatctag atcctgagat caaccctgag ggattctgca tcctcctgga cttcatgtac
      601 acatctcggc tcaatttgcg ggagggcaac atcatggctg tgatggccac ggctatgtac
      661 ctgcagatgg agcatgttgt ggacttgc cggaagttta ttaaggccag tgaagcagag
      721 atggtttctg ccatcaagcc tcctcgtgaa gagttcctca cagccggat gctgatgccc
      781 caagacatca tggcctatcg gggtcgtgag gtggtggaga caacctgcc actgaggagc
      841 gcccctgggt gtgagagcag agcctttgcc ccagcctgt acagtggcct gtccacaccg
      901 ccagcctctt attccatgta cagccacctc cctgtcagca gcctcctctt ctccgatgag
      961 gagtttcggg atgtccggat gctgtggcc aaccccttcc caaggagcg ggcactccca
     1021 tgtgatagtg ccaggccagt ccctggtgag tacagccggc cgactttgga ggtgtccccc
     1081 aatgtgtgcc acagcaatat ctattcaccc aaggaaacaa tcccagaaga ggcacgaagt
     1141 gatatgcact acagtgtggc tgagggcctc aaacctgctg cccccctcagc ccgaaatgcc
     1201 ccctacttcc cttgtgacaa ggccagcaaa gaagaagaga gaccctcctc ggaagatgag
     1261 attgccctgc atttcgagcc cccaatgca ccctgaacc ggaagggtct ggttagtcca
     1321 cagagccccc agaaatctga ctgccagccc aactcgccca cagagtcctg cagcagtaag
     1381 aatgcctgca tcctccaggc ttctggctcc cctccagcca gagccccac tgaccccaaa
     1441 gcctgcaact ggaagaaata caagttcatc gtgctcaaca gcctcaacca gaatgccaaa
     1501 ccagaggggc ctgagcaggc tgagctgggc gcctttccc cacgagccta cggcccca
     1561 cctgcctgcc agccacccat ggagcctgag aaccttgacc tccagtcccc aaccaagctg
     1621 agtgccagcg ggaggactc caccatccca aagccagcc ggctcaataa catcgttaac
     1681 aggtccatga cgggctctcc ccgcagcagc agcgagagcc actcaccact ctacatgcac
     1741 cccccgaagt gcacgtcctg cggctctcag tccccacagc atgcagagat gtgcctccac
     1801 accgctggcc ccacgttccc tgaggagatg ggagagaccc agtctgagta ctcagattct
     1861 agctgtgaga acggggcctt cttctgcaat gagtgtgact gccgcttctc tgaggaggcc
     1921 tcactcaaga ggcacacgct gcagacccac agtgacaaac ctacaagtg tgaccgctgc
     1981 caggcctcct tccgctacaa gggcaacctc gccagccaca gaccgtcca taccggtgag
     2041 aaacccatc gttgcaacat ctgtggggcc agttcaacc ggccagccaa cctgaaaacc
     2101 cacactcgaa ttcactctgg agagaagccc tacaaatgcg aaacctgcgg agcagattt
     2161 gtacaggtgg cccacctccg tgcccatgtg cttatccaca ctggtgagaa gccctatccc
     2221 tgtgaaatct gtggcacccg tttccggcac cttcagactc tgaagagcca cctgcgaatc
     2281 cacacaggag agaaacctta ccattgtgag aagtgtaacc tgcatttccg tcacaaaagc
     2341 cagctgcgac ttcacttgcg ccagaagcat ggcgccatca ccaacaccaa ggtgcaatac
```

Figure 6-11

```
2401 cgcgtgtcag ccactgacct gcctccggag ctccccaaag cctgctgaag catggagtgt
2461 tgatgctttc gtctccagcc ccttctcaga atctacccaa aggatactgt aacactttac
2521 aatgttcatc ccatgatgta gtgcctcttt catccactag tgcaaatcat agctgggggt
2581 tgggggtggt ggggtcggg gcctggggga ctgggagccg cagcagctcc ccctccccca
2641 ctgccataaa acattaagaa aatcatattg cttcttctcc tatgtgtaag gtgaaccatg
2701 tcagcaaaaa gcaaaatcat tttatatgtc aaagcagggg agtatgcaaa agttctgact
2761 tgactttagt ctgcaaaatg aggaatgtat atgttttgtg ggaacagatg tttcttttgt
2821 atgtaaatgt gcattctttt aaaagacaag acttcagtat gttgtcaaag agagggcttt
2881 aatttttta accaaaggtg aaggaatata tggcagagtt gtaaatatat aaatatatat
2941 atatataaaa taaatatata taaacctaac aaagatatat taaaaatata aaactgcgtt
3001 aaaggctcga ttttgtatct gcaggcagac acggatctga aatctttat tgagaaagag
3061 cacttaagag aatattttaa gtattgcatc tgtataagta agaaaatatt ttgtctaaaa
3121 tgcctcagtg tatttgtatt ttttgcaag tgaaggttta caatttacaa agtgtgtatt
3181 aaaaaaaaca aaagaacaa aaaaatctgc agaaggaaaa atgtgtaatt ttgttctagt
3241 tttcagtttg tatatacccg tacaacgtgt cctcacggtg cctttttca cggaagtttt
3301 caatgatggg cgagcgtgca ccatcccttt ttgaagtgta ggcagacaca gggacttgaa
3361 gttgttacta actaaactct ctttgggaat gtttgtctca tcccattctg cgtcatgctt
3421 gtgttataac tactccggag acagggtttg gctgtgtcta aactgcatta ccgcgttgta
3481 aaatatagct gtacaaatat aagaataaaa tgttgaaaag tcaaactgga aaaaaa
```

Figure 6-12

EPDR1

```
LOCUS       NM_017549               2613 bp    mRNA    linear   PRI 26-JUN-2007
DEFINITION  Homo sapiens ependymin related protein 1 (zebrafish) (EPDR1),
            mRNA.
ACCESSION   NM_017549
VERSION     NM_017549.3  GI:116008437
SOURCE      Homo sapiens (human)
ORIGIN
        1 tcccccctct taaaacacga tgcctcccag gatgctagtg gcaccactgc cactgcattt
       61 cctgttggca gcagtgagca gtgaaaaccg aagcggcaga aggcagtggc agcaggcagt
      121 ggcagcaggc agtggcccag gcagaaatag ctcccgcgcg attcactgga gccttccccg
      181 ggccctggtc ccggctaccg ggactcgcgc gtccggatct caaaagcggc agaggccacc
      241 gaagggacag gaagcacttt ggtccagacc acactcccgg cacagtgcgg aaagagccgg
      301 cgggagccac tctgatcccg gacgcctcag cgcccccttg ggcttgggct tgccctcggg
      361 ccggggaagg ctgaccgcga tgccaggacg cgctcccctc cgcaccgtcc cgggcgccct
      421 gggtgcctgg ctgctgggcg gcctctgggc ctggaccctg tgcggcctgt cagcctggg
      481 ggcggtggga gccccgcgcc cgtgccaggc gccgcagcag tgggaggggc gccaggttat
      541 gtaccagcaa agtagcgggc gcaacagccg cgccctgctc tcctacgacg ggctcaacca
      601 gcgcgtgcgg gtgctggacg agaggaaggc gctgatcccc tgcaagagat tatttgaata
      661 tattttgctg tataaggatg gagtgatgtt tcagattgac caagccacca agcagtgctc
      721 aaagatgacc ctgacacagc cctgggatcc tcttgacatt cctcaaaact ccacctttga
      781 agaccagtac tccatcgggg ggcctcagga gcagatcacc gtccaggagt ggtcggacag
      841 aaagtcagct agatcctatg aaacctggat tggcatctat acagtcaagg attgctatcc
      901 tgtccaggaa acctttacca taaactacag tgtgatattg tctacgcggt tttttgacat
      961 ccagctgggt attaaagacc cctcggtgtt tacccctcca agcacgtgcc agatggccca
     1021 actggagaag atgagcgaag actgctcctg gtgagcctgt gcatagggaa gcggcagcat
     1081 cggatgtcag ccccctgcgg ccccagctgg agatggatat gagactagtc aagatgtgaa
     1141 tgctaattgg agagaaatat aattttagga gatgcacat tgatgtgggg ttttgatgtg
     1201 tctgattttg actactcaag ctctgtttac agaagaaaat tgaatggcga gggtgtggcc
     1261 atatgaactg actagatggc taatatggac actttgggta tttctaatgc ctgttcaggg
     1321 ctggttttct gcatgcacgg gtatacacat aatgcagtgc catgcacata gggaagggtc
     1381 agtaagagaa gtttgccttg gcagcaagta tttattgttg acattattca gaattagtga
     1441 taataaaaag cagagtgatt ttggtcaatt ttattattaa ttcttaaatt ccctgcagag
     1501 aatgccccct ttattgctgc caggggttg gcattgctcc cactgagccc tactccaccc
     1561 tgtccctgca ctcccttggt tgccaaaaaa atgataactt aaatcccttc cagacttaag
     1621 aatttatgg catgcccaa ttgatataaa catttagaag gaaatgaaaa gctaaaatag
     1681 gaagtaatta ttcctctaaa gaaacatttt gagcaaggca gtttagagaa tcctaatgtc
     1741 tacactggca tagcacgagc catgtaagct tcttttttt ctatgcaaga gtattgatgt
     1801 atgtgctgaa tcttcacaga cttgtcaata cacaggcagt attctaaaat agcactgaac
     1861 agggagtcag gagactattg tctcctaaac ccaggactag agttccctcg tactgtcact
     1921 ccttggtca ttaaatgcac tgggcttgcc cgcactttgg ccttcctaga acactgcttc
     1981 ataacctctc tgtctgactt ctgcatctcc ttccaggtca gctcattcac aagagttgct
     2041 cccaagcctg gatgagttgc accttgcatc ttgagcatgc atttctcaca ataattatta
     2101 agctgtgtga atttctgc tttcaggaca ctcatccatt atcttggctg tgagctcctt
     2161 gggtacgggt accttgtatg tttacttta tatccctagc acaaagcaag tgcctggcac
     2221 atagtcagtg ccctaagtat tcgtagagtg aagaatgcca gcctcttg tccctggttt
     2281 ccttatgtgt tgaatgtggt tgagtttgtc cattgctagg gagagacttc cagtaataaa
     2341 atttactatt ctagatgctt ctactgttat gttttatctg cccatttatc tttcttagtt
     2401 accaggagaa atgtgtgaca cctatattat aatgaaaaca atctcattac ttatagttta
     2461 tctatattaa acaaatttaa ttgcatttta aagcattctt tgatactgtt gcttttgcaa
     2521 taaatatgga taatcttggt tataagggag ttaaaacaat gctgtaataa ataaagtgct
     2581 tcatgtgatc aaaatcaaaa aaaaaaaaa aaa
```

Figure 6-13

PRPSAP2

```
LOCUS       NM_002767               1890 bp    mRNA    linear   PRI 03-JUN-2007
DEFINITION  Homo sapiens phosphoribosyl pyrophosphate synthetase-associated
            protein 2 (PRPSAP2), mRNA.
ACCESSION   NM_002767
VERSION     NM_002767.2  GI:22538484
KEYWORDS    .
SOURCE      Homo sapiens (human)

ORIGIN
        1 ctagagaggc cgccaggaga cccggcgctt tcttccttct gcagctgagg ctgcggcggg
       61 gccggggctg gggtcgggc caggaggaat tttgttgtca gagaataaaa ggaggttgtc
      121 cataattgac tttaagcagc aatcagtaaa acattgagct cttcagctcc gcctttcttg
      181 ctctgaaaat tggaaaacca agaaggtttt gatgttttgt gtgacgccac ctgaattaga
      241 aaccaagatg aacataacca aaggtggtct ggtgttgttt tcagcaaact cgaattcatc
      301 atgtatggag ctatcaaaga aaattgcaga gcggctaggg gtggagatgg gcaaagtgca
      361 ggtttaccag gaacctaaca gagaaacaag agtacaaatt caagagtctg tgagggaaa
      421 agatgttttc atcatccaaa ctgtttcgaa ggacgtgaac accaccatca tggagctcct
      481 gatcatggtg tatgcatgta agacctcttg tgccaagagc atcattggcg tgataccta
      541 ctttccttac agcaagcagt gcaagatgag aaaaagaggc tccattgtct ctaaattgct
      601 ggcttccatg atgtgcaaag ctggtctaac tcatcttatt actatggatt tacaccagaa
      661 ggaaattcag ggcttcttca atattcctgt tgacaattta agagcatctc ccttcttatt
      721 acagtatatt caagaagaga tcccagatta caggaatgca gtaatcgtgg ccaagtctcc
      781 agcctcggcg aagagggcac agtcttttgc tgagcgcctg cgcctgggaa ttgcagtgat
      841 tcatggagag gcgcaggatg ccgagtcgga cttggtggat ggacggcatt ccccacccat
      901 ggtcagaagt gtggctgcca tccaccccag cctggagatc cccatgctga ttcctaaaga
      961 aaagccccca atcacggttg tgggtgatgt tggaggaagg attgccatca tcgtggatga
     1021 catcattgat gatgttgaca gctttcttgc tgcagcagag accctgaagg aaagaggtgc
     1081 atataagatc tttgtgatgg caactcatgg cttgttgtct tctgacgccc ccggcggat
     1141 tgaagagtct gccattgatg aggtggtggt caccaataca attccacatg aagtccagaa
     1201 gctccagtgc ccaagatta aactgtgga tatcagcatg atcctttcag aggcgatccg
     1261 tcggatccac aatggggagt ccatgtccta ccttttcaga aacataggct tagatgactg
     1321 agttttcctt taggaaaact cccgagggcc aaactggaaa cataagagtg actgctcggt
     1381 gggatggatt tcacaggaac cgtcatgctt gttcctccct ctcccctgta acctcacttc
     1441 ttattgattc ctaagaagat agaccaactt tttatgtcgg tttgggtgtt tgtgagtttg
     1501 gggagcaatt tttataaaag aaaaacttta ttctcctctt ttgaaaaggt aagacctcgt
     1561 tttagttgta actgtttaaa aaataacact tggaataaga tttgtaagct cacaaagcct
     1621 tcttccaaag ttgcttgagc caagtgctta aaaagttaat aaaataaaat gatctgtatg
     1681 atacctgcaa ttgaaaagcc gaaaagatta tactgtcaag tccagtaaat gacattttta
     1741 gagatgcttt tgtagacaag catatggaat atgtgattgt atttattttc tgcaactaaa
     1801 aaaggaataa aaacttgtgt ttgtgtgttt ttctaaaact ttgtgttttg gcaatcgttt
     1861 tataactaaa ataaaatgaa agctaaatct
```

IGF1R

```
LOCUS       NM_000875              11242 bp    mRNA    linear   PRI 22-OCT-2007
DEFINITION  Homo sapiens insulin-like growth factor 1 receptor (IGF1R),
mRNA.
ACCESSION   NM_000875 NM_015883
VERSION     NM_000875.3  GI:119220593
KEYWORDS    .
SOURCE      Homo sapiens (human)

ORIGIN
        1 tttttttttt ttttttttga gaaaggggaa tttcatccca aataaaagga atgaagtctg
       61 gctccggagg agggtccccg acctcgctgt gggggctcct gtttctctcc gccgcgctct
      121 cgctctggcc gacgagtgga gaaatctgcg ggccaggcat cgacatccgc aacgactatc
      181 agcagctgaa gcgcctggag aactgcacgg tgatcgaggg ctacctccac atcctgctca
      241 tctccaaggc cgaggactac cgcagctacc gcttccccaa gctcacggtc attaccgagt
      301 acttgctgct gttccgagtg gctggcctcg agagcctcgg agacctcttc cccaacctca
      361 cggtcatccg cggctggaaa ctcttctaca actacgccct ggtcatcttc gagatgacca
      421 atctcaagga tattgggctt acaacctga ggaacattac tcggggggcc atcaggattg
      481 agaaaaatgc tgacctctgt tacctctcca ctgtggactg gtccctgatc ctggatgcgg
      541 tgtccaataa ctacattgtg gggaataagc ccccaaagga atgtggggac ctgtgtccag
      601 ggaccatgga ggagaagccg atgtgtgaga agaccaccat caacaatgag tacaactacc
      661 gctgctggac cacaaaccgc tgccagaaaa tgtgcccaag cacgtgtggg aagcgggcgt
      721 gcaccgagaa caatgagtgc tgccaccccg agtgcctggg cagctgcagc gcgcctgaca
      781 acgacacggc ctgtgtagct tgccgccact actactatgc cggtgtctgt gtgcctgcct
      841 gcccgcccaa cacctacagg tttgagggct ggcgctgtgt ggaccgtgac ttctgcgcca
      901 acatcctcag cgccgagagc agcgactccg aggggtttgt gatccacgac ggcgagtgca
      961 tgcaggagtg ccccctcggc ttcatccgca acggcagcca gagcatgtac tgcatccctt
     1021 gtgaaggtcc ttgcccgaag gtctgtgagg aagaaaagaa aacaaagacc attgattctg
     1081 ttacttctgc tcagatgctc caaggatgca ccatcttcaa gggcaatttg ctcattaaca
     1141 tccgacgggg gaataacatt gcttcagagc tggagaactt catgggctc atcgaggtgg
     1201 tgacgggcta cgtgaagatc cgccattctc atgccttggt ctccttgtcc ttcctaaaaa
     1261 accttcgcct catcctagga gaggagcagc tagaagggaa ttactccttc tacgtcctcg
     1321 acaaccagaa cttgcagcaa ctgtgggact gggaccaccg caacctgacc atcaaagcag
     1381 ggaaaatgta ctttgctttc aatcccaaat tatgtgtttc cgaaatttac cgcatggagg
     1441 aagtgacggg gactaaaggg cgccaaagca agggggacat aaacaccagg aacaacgggg
     1501 agagagcctc ctgtgaaagt gacgtcctgc atttcacctc accaccacg tcgaagaatc
     1561 gcatcatcat aacctggcac cggtaccggc cccctgacta cagggatctc atcagcttca
     1621 ccgtttacta caaggaagca ccctttaaga tgtcacaga gtatgatggg caggatgcct
     1681 gcggctccaa cagctggaac atggtggacg tggacctccc gcccaacaag gacgtggagc
     1741 ccggcatctt actacatggg ctgaagccct ggactcagta cgccgtttac gtcaaggctg
     1801 tgaccctcac catggtggag aacgaccata tccgtgggc caagagtgag atcttgtaca
     1861 ttcgcaccaa tgcttcagtt ccttccattc ccttggacgt tctttcagca tcgaactcct
     1921 cttctcagtt aatcgtgaag tggaaccctc cctctctgcc aacggcaac ctgagttact
     1981 acattgtgcg ctggcagcgg cagcctcagg acggctacct ttaccggcac aattactgct
     2041 ccaaagacaa atcccatc aggaagtatg ccgacggcac catcgacatt gaggaggtca
     2101 cagagaaccc caagactgag gtgtgtggtg gggagaaagg ccttgctgc cctgccccca
     2161 aaactgaagc cgagaagcag gccgagaagg aggaggctga ataccgcaaa gtctttgaga
     2221 atttcctgca caactccatc ttcgtgccca gacctgaaag gaagcggaga gatgtcatgc
     2281 aagtggccaa caccaccatg tccagccgaa gcaggaacac cacggccgca gacacctaca
     2341 acatcaccga cccggaagag ctggagacag agtaccctt ctttgagagc agagtggata
     2401 acaaggagag aactgtcatt ctaaccttcg gcctttcac attgtaccgc atcgatatcc
```

Figure 6-15

```
2461 acagctgcaa ccacgaggct gagaagctgg gctgcagcgc ctccaacttc gtctttgcaa
2521 ggactatgcc cgcagaagga gcagatgaca ttcctgggcc agtgacctgg gagccaaggc
2581 ctgaaaactc catctttta aagtggccgg aacctgagaa tcccaatgga ttgattctaa
2641 tgtatgaaat aaaatacgga tcacaagttg aggatcagcg agaatgtgtg tccagacagg
2701 aatacaggaa gtatggaggg gccaagctaa accggctaaa cccggggaac tacacagccc
2761 ggattcaggc cacatctctc tctgggaatg ggtcgtggac agatcctgtg ttcttctatg
2821 tccaggccaa aacaggatat gaaaacttca tccatctgat catcgctctg cccgtcgctg
2881 tcctgttgat cgtgggaggg ttggtgatta tgctgtacgt cttccataga aagagaaata
2941 acagcaggct ggggaatgga gtgctgtatg cctctgtgaa cccggagtac ttcagcgctg
3001 ctgatgtgta cgttcctgat gagtgggagg tggctcggga agatcacc atgagccggg
3061 aacttgggca ggggtcgttt gggatggtct atgaaggagt tgccaagggt gtggtgaaag
3121 atgaacctga accagagtg ccattaaaa cagtgaacga ggccgcaagc atgcgtgaga
3181 ggattgagtt tctcaacgaa gcttctgtga tgaaggagtt caattgtcac catgtggtgc
3241 gattgctggg tgtggtgtcc caaggccagc caacactggt catcatggaa ctgatgacac
3301 ggggcgatct caaaagttat ctccggtctc tgaggccaga aatggagaat aatccagtcc
3361 tagcacctcc aagcctgagc aagatgattc agatggccgg agagattgca gacggcatgg
3421 catacctcaa cgccaataag ttcgtccaca gagaccttgc tgcccggaat gcatggtag
3481 ccgaagattt cacagtcaaa atcggagatt ttggtatgac gcagatatc tatgagacag
3541 actattaccg gaaggaggg aagggctgc tgcccgtgcg ctggatgtct cctgagtccc
3601 tcaaggatgg agtcttcacc acttactcgg acgtctggtc cttcggggtc gtcctctggg
3661 agatcgccac actggccgag cagccctacc agggcttgtc caacgagcaa gtccttcgct
3721 tcgtcatgga gggcggcctt ctggacaagc cagacaactg tcctgacatg ctgtttgaac
3781 tgatgcgcat gtgctggcag tataacccca agatgaggcc ttccttcctg gagatcatca
3841 gcagcatcaa agaggagatg gagcctggct tccgggaggt ctccttctac tacagcgagg
3901 agaacaagct gcccgagccg gaggagctgg acctggagcc agagaacatg gagagcgtcc
3961 ccctggaccc ctcggcctcc tcgtcctccc tgccactgcc cgacagacac tcaggacaca
4021 aggccgagaa cggccccggc cctggggtgc tggtcctccg cgccagcttc gacgagagac
4081 agccttacgc ccacatgaac gggggccgca agaacgagcg ggccttgccg ctgccccagt
4141 cttcgacctg ctgatccttg gatcctgaat ctgtgcaaac agtaacgtgt gcgcacgcgc
4201 agcggggtgg ggggggagag agagttttaa caatccattc acaagcctcc tgtacctcag
4261 tggatcttca gaactgccct tgctgcccgc gggagacagc ttctctgcag taaaacacat
4321 ttgggatgtt cctttttca atatgcaagc agcttttat tccctgccca aacccttaac
4381 tgacatggc ctttaagaac cttaatgaca acacttaata gcaacagagc acttgagaac
4441 cagtctcctc actctgtccc tgtccttccc tgttctccct ttctctctcc tctctgcttc
4501 ataacggaaa aataattgcc acaagtccag ctgggaagcc cttttatca gtttgaggaa
4561 gtggctgtcc ctgtggcccc atccaaccac tgtacacacc cgcctgacac cgtgggtcat
4621 tacaaaaaaa cacgtggaga tggaaatttt tacctttatc tttcacctttt ctagggacat
4681 gaaatttaca aagggccatc gttcatccaa ggctgttacc attttaacgc tgcctaattt
4741 tgccaaaatc ctgaactttc tccctcatcg gcccggcgct gattcctcgt gtccggaggc
4801 atgggtgagc atggcagctg gttgctccat ttgagagaca cgctggcgac acactccgtc
4861 catccgactg cccctgctgt gctgctcaag gccacaggca cagggtctc attgcttctg
4921 actagattat tatttggggg aactggacac aataggtctt tctctcagtg aaggtgggga
4981 gaagctgaac cggcttccct gccctgcctc cccagccccc tgcccaaccc ccaagaatct
5041 ggtggccatg ggccccgaag cagcctggcg gacaggcttg gagtcaaggg gccccatgcc
5101 tgcttctctc ccagccccag ctcccccgcc cgccccaag gacacagatg ggaagggtt
5161 tccaggact cagcccact gttgatgcag gtttgcaagg aagaaattc aaacaccaca
5221 acagcagtaa gaagaaaagc agtcaatgga ttcaagcatt ctaagctttg ttgacatttt
5281 ctctgttcct aggacttctt catgggtctt acagttctat gttagaccat gaaacatttg
5341 catacacatc gtctttaatg tcacttttat aacttttta cggttcagat attcatctat
5401 acgtctgtac agaaaaaaaa aagctgctat tttttttgtt cttgatcttt gtggatttaa
5461 tctatgaaaa ccttcaggtc caccctctcc cctttctgct cactccaaga aacttcttat
5521 gctttgtact agagtgcgtg actttcttcc tcttttcccg gtaatggata cttctatcac
5581 ataatttgcc atgaactgtt ggatgccttt ttataaatac atccccccatc cctgctccca
```

Figure 6-16

```
5641 cctgcccctt tagttgtttt ctaacccgta ggctctctgg gcacgaggca gaaagcaggc
5701 cgggcaccca tcctgagagg gccgcgctcc tctccccagc ctgccctcac agcattggag
5761 cctgttacag tgcaagacat gatacaaact caggtcagaa aaacaaaggt taaatatttc
5821 acacgtcttt gttcagtgtt tccactcacc gtggttgaga agcctcaccc tctctttccc
5881 ttgcctttgc ttaggttgtg acacacatat atatatattt ttttaattct tgggtacaac
5941 agcagtgtta accgcagaca ctaggcattt ggattactat ttttcttaat ggctatttaa
6001 tccttccatc ccacgaaaaa cagctgctga gtccaaggga gcagcagagc gtggtccggc
6061 agggcctgtt gtggccctcg ccacccccct caccggaccg actgacctgt ctttggaacc
6121 agaacatccc aagggaactc cttcgcactg gcgttgagtg ggaccccggg atccaggctg
6181 gcccagggcg gcaccctcag ggctgtgccc gctggagtgc taggtggagg cagcacagac
6241 gccacggtgg cccaagagcc cctttgcttc ttgctggggg accagggctg tggtgctggc
6301 ccactttccc tcggccagga atccaggtcc ttggggccca ggggtcttgt cttgtttcat
6361 ttttagcact tctcaccaga gagatgacag cacaagagtt gcttctggga tagaaatgtt
6421 taggagtaag aacaaagctg ggatacggtg attgctagtt gtgactgaag attcaacaca
6481 gaaaagaaag tttatacggc ttttttgctg gtcagcagtt tgtcccactg ctttctctag
6541 tctctatccc atagcgtgtt cccttaaaaa aaaaaaaaaa ggtattatat gtaggagttt
6601 tcttttaatt tattttgtga taaattacca gtttcaatca ctgtagaaaa gccccattat
6661 gaatttaaat ttcaaggaaa gggtgtgtgt gtgtgtatgt gtggggtgtg tgtgtgtgag
6721 agtgatggga cagttcttga ttttttgggt ttttttttcc ccaaacattt atctacctca
6781 ctcttatttt ttatatgtgt atatagacaa aagaatacat ctcacctttc tcagcacctg
6841 acaataggcc gttgatactg gtaacctcat ccacgccaca ggcgccacac ccaggtgatg
6901 caggggggaag ccaggctgta ttccggggtc aaagcaacac taactcacct ctctgctcat
6961 ttcagacagc ttgcctttt ctgagatgtc ctgttttgtg ttgcttttt tgttttgttt
7021 tctatcttgg tttccaccaa ggtgttagat ttctcctcct cctagccagg tggccctgtg
7081 aggccaacga gggcaccaga gcacacctgg gggagccacc aggctgtccc tggctggttg
7141 tctttggaac aaactgcttc tgtgcagatg gaatgaccaa cacatttcgt ccttaagaga
7201 gcagtggttc ctcaggttct gaggagagga aggtgtccag gcagcaccat ctctgtgcga
7261 atccccaggg taaaggcgtg gggcattggg tttgctcccc ttgctgctgc tccatccctg
7321 caggaggctc gcgctgaggc aggaccgtgc ggccatggct gctgcattca ttgagcacaa
7381 aggtgcagct gcagcagcag ctggagagca agagtcaccc agcctgtgcg ccagaatgca
7441 gaggctcctg acctcacagc cagtccctga tagaacacac gcaggagcag agtccctcc
7501 ccctccaggc tgccctctca acttctccct cacctccttc cctagggta gacagagatg
7561 taccaaacct tccggctgga aagcccagtg gccggcgccg aggctcgtgg cgtcacgccc
7621 cccccgccag ggctgtacct ccgtctccct ggtcctgctg ctcacaggac agacggctcg
7681 ctccctctt ccagcagctg ctcttacagg cactgatgat ttcgctggga agtgtggcgg
7741 gcagctttgc ctaagcgtgg atggctcctc ggcaattcca gcctaagtga aggcgctcag
7801 gagcctcctg ctggaacgcg acccatctct cccaggaccc cggggatctt aaggtcattg
7861 agaaatactg ttggatcagg gttttgttct tccacactgt aggtgacccc ttgaataac
7921 ggcctctcct ctcgtgcaca tacctaccgg ttttccacaac tggatttcta cagatcattc
7981 agctggttat aagggttttg tttaaactgt ccgagttact gatgtcattt tgttttgtt
8041 ttatgtaggt agcttttaag tagaaaacac taacagtgta gtgcccatca tagcaaatgc
8101 ttcagaaaca cctcaataaa agagaaaact tggcttgtgt gatggtgcag tcactttact
8161 ggaccaaccc acccaccttg actataccaa ggcatcatct atccacagtt ctagcctaac
8221 ttcatgctga tttctctgcc tcttgattt tctctgtgtg ttccaaataa tcttaagctg
8281 agttgtggca ttttccatgc aacctccttc tgccagcagc tcacactgct tgaagtcata
8341 tgaaccactg aggcacatca tggaattgat gtgagcatta agacgttctc ccacacagcc
8401 cttccctgag gcagcaggag ctggtgtgta ctggagacac tgttgaactt gatcaagacc
8461 cagaccaccc caggtctcct tcgtgggatg tcatgacgtt tgacatacct ttggaacgag
8521 cctcctcctt ggaagatgga agaccgtgtt cgtggccgac ctggcctctc ctggcctgtt
8581 tcttaagatg cggagtcaca tttcaatggt acgaaaagtg gcttcgtaaa atagaagagc
8641 agtcactgtg gaactaccaa atggcagat gctcggtgca cattggggtg ctttgggata
8701 aaagatttat gagccaacta ttctctggca ccagattcta ggccagtttg ttccactgaa
8761 gcttttccca cagcagtcca cctctgcagg ctggcagccg aatggcttgc cagtggctct
```

Figure 6-17

```
8821 gtggcaagat cacactgaga tcgatgggtg agaaggctag gatgcttgtc tagtgttctt
8881 agctgtcacg ttggctcctt ccagggtggc cagacggtgt tggccactcc cttctaaaac
8941 acaggcgccc tcctggtgac agtgacccgc cgtggtatgc cttggcccat tccagcagtc
9001 ccagttatgc atttcaagtt tggggtttgt tcttttcgtt aatgttcctc tgtgttgtca
9061 gctgtcttca tttcctgggc taagcagcat tgggagatgt ggaccagaga tccactcctt
9121 aagaaccagt ggcgaaagac actttctttc ttcactctga agtagctggt ggtacaaatg
9181 agaacttcaa gagaggatgt tatttagact gaacctctgt tgccagagat gctgaagata
9241 cagaccttgg acaggtcaga gggtttcatt tttggccttc atcttagatg actggttgcg
9301 tcatttggag aagtgagtgc tccttgatgg tggaatgacc gggtggtggg tacagaacca
9361 ttgtcacagg gatcctggca cagagaagag ttacgagcag cagggtgcag ggcttggaag
9421 gaatgtgggc aaggttttga acttgattgt tcttgaagct atcagaccac atcgaggctc
9481 agcagtcatc cgtgggcatt tggtttcaac aaagaaacct aacatcctac tctggaaact
9541 gatctcggag ttaaggcgaa ttgttcaaga acacaaacta catcgcactc gtcagttgtc
9601 agttctgggg catgacttta gcgttttgtt tctgcgagaa cataacgatc actcattttt
9661 atgtcccacg tgtgtgtgtc cgcatctttc tggtcaacat tgttttaact agtcactcat
9721 tagcgttttc aatagggctc ttaagtccag tagattacgg gtagtcagtt gacgaagatc
9781 tggtttacaa gaactaatta aatgtttcat tgcatttttg taagaacaga ataatttat
9841 aaaatgtttg tagtttataa ttgccgaaaa taatttaaag cactttttt tttctctgtg
9901 tgtgcaaatg tgtgtttgtg atccattttt ttttttttt tttaggacac ctgtttacta
9961 gctagcttta caatatgcca aaaaaggatt tctccctgac cccatccgtg gttcaccctc
10021 ttttccccc atgctttttg ccctagttta taacaaagga atgatgatga tttaaaagt
10081 agttctgtat cttcagtatc ttggtcttcc agaaccctct ggttgggaag gggatcattt
10141 tttactggtc atttcccttt ggagtgtagc tactttaaca gatggaaaga acctcattgg
10201 ccatggaaac agccgaggtg ttggagccca gcagtgcatg gcaccgttcg gcatctggct
10261 tgattggtct ggctgccgtc attgtcagca cagtgccatg acatgggaa gacttgactg
10321 cacagccaat ggttttcatg atgattacag catacacagt gatcacataa acgatgacag
10381 ctatggggca cacaggccat ttgcttacat gcctcgtatc atgactgatt actgctttgt
10441 tagaacacag aagagaccct atttattta aggcagaacc ccgaagatac gtatttccaa
10501 tacagaaaag aattttaat aaaaactata acatacacaa aaattggttt taaagttgac
10561 tccacttcct ctaactccag tggattgttg gccatgtctc cccaactcca caatatctct
10621 atcatgggaa acacctgggg ttttgcgct acataggaga aagatctgga aactatttgg
10681 gttttgtttt caacttttca tttggatgtt tggcgttgca cacacatc caccggtgga
10741 agagacgccc ggtgaaaaca cctgtctgct tctaagcca gtgaggttga ggtgagaggt
10801 ttgccagagt ttgtctacct ctgggtatcc ctttgtctgg gataaaaaa atcaaaccag
10861 aaggcgggat ggaatggatg caccgcaaat aatgcatttt ctgagttttc ttgttaaaaa
10921 aaaatttttt taagtaagaa aaaaaaggt aataacatgg ccaatttgtt acataaaatg
10981 actttctgtg tataaattat tcctaaaaaa tcctgtttat ataaaaaatc agtagatgaa
11041 aaaatttca aatgttttt gtatattctg ttgtaagaat ttattccgt tattgcgata
11101 tactctggat tctttacata atggaaaaaa gaaactgtct attttgaatg gctgaagcta
11161 aggcaacgtt agtttctctt actctgcttt tttctagtaa agtactacat ggtttaagtt
11221 aaataaaata attctgtatg ca
```

Figure 6-18

BTG2

```
LOCUS       NM_006763               2718 bp    mRNA    linear   PRI 25-SEP-2007
DEFINITION  Homo sapiens BTG family, member 2 (BTG2), mRNA.
ACCESSION   NM_006763
VERSION     NM_006763.2  GI:28872718
KEYWORDS    .
SOURCE      Homo sapiens (human)

ORIGIN
        1 cagggtaacg ctgtcttgtg gacccgcact tcccacccga gacctctcac tgagcccgag
       61 ccgcgcgcga catgagccac gggaagggaa ccgacatgct cccggagatc gccgccgccg
      121 tgggcttcct ctccagcctc ctgaggaccc ggggctgcgt gagcgagcag aggcttaagg
      181 tcttcagcgg ggcgctccag gaggcactca cagagcacta caaacaccac tggtttcccg
      241 aaaagccgtc caagggctcc ggctaccgct gcattcgcat caaccacaag atggacccca
      301 tcatcagcag ggtggccagc cagatcggac tcagccagcc cagctgcac cagctgctgc
      361 ccagcgagct gaccctgtgg gtggacccct atgaggtgtc ctaccgcatt ggggaggacg
      421 gctccatctg cgtcttgtac gaggaggccc cactggccgc ctcctgtggg ctcctcacct
      481 gcaagaacca agtgctgctg ggccggagca gcccctccaa gaactacgtg atggcagtct
      541 ccagctaggc ccttccgccc ccgccctggg cgccgccgtg ctcatgctgc cgtgacaaca
      601 ggccaccaca tacctcaacc tggggaactg tattttaaa tgaagagcta tttatatata
      661 ttatttttt ttaagaaagg aggaaaagaa accaaaagtt tttttaaga aaaaaatcc
      721 ttcaagggag ctgcttggaa gtggcctccc caggtgcctt tggagagaac tgttgcgtgc
      781 ttgagtctgt gagccagtgt ctgcctatag aggggggagc tgttagggg tagacctagc
      841 caaggagaag tgggagacgt ttggctagca ccccaggaag atgtgagagg gagcaagcaa
      901 ggttagcaac tgtgaacaga gaggtcggga tttgccctgg gggaggaaga gaggccaagt
      961 tcagagctct ctgtctcccc cagccagaca cctgcatccc tggctcctct attactcagg
     1021 ggcattcatg cctggactta acaatacta tgttatcttt tctttatt ttctaatgag
     1081 gtcctgggca gagagtgaaa aggcctctcc tgattcctac tgtcctaagc tgcttttctt
     1141 gaaatcatga cttgtttcta attctaccct caggggcctg tagatgttgc tttccagcca
     1201 ggaatctaaa gctttgggtt ttctgagggg ggggaggagg gaactggagg ttattggggt
     1261 taggatggaa gggaactctg cacaaaacct ttgctttgct agtgctgctt tgtgtgtatg
     1321 tgtggcaaat aatttggggg tgatttgcaa tgaaattttg ggacccaaag agtatccact
     1381 ggggatgttt tttggccaaa actcttcctt ttggaaccac atgaaagtct tgatgctgct
     1441 gccatgatcc ctttgagagg tggctcaaaa gctacaggga actccaggtc ctttattact
     1501 gccttctttt caaaagcaca actctcctct aaccctcccc tccccttcc cttctggtcg
     1561 ggtcatagag ctaccgtatt ttctaggaca agagttctca gtcactgtgc aatatgcccc
     1621 ctgggtccca ggagggtctg gaggaaaact ggctatcaga acctcctgat gccctggtgg
     1681 gcttagggaa ccatctctcc tgctctcctt gggatgatgg ctggctagtc agccttgcat
     1741 gtattccttg gctgaatggg agagtgcccc atgttctgca agactacttg gtattcttgt
     1801 agggccgaca ctaaataaaa gccaaacctt gggcactgtt ttttctccct ggtgctcaga
     1861 gcacctgtgg gaaaggttgc tgtctgtctc agtacaatcc aaatttgtcg tagacttgtg
     1921 caatatatac tgttgtgggt tggagaaaag tggaaagcta cactgggaag aaactccctt
     1981 ccttcaattt ctcagtgaca ttgatgaggg tcctcaaaa gacctcgagt tcccaaacc
     2041 gaatcacctt aagaaggaca gggctagggc atttggccag gatggccacc ctcctgctgt
     2101 tgcccccttag tgaggaatct tcaccccact tcctctaccc ccaggttctc ctccccacag
     2161 ccagtccct ttcctggatt tctaaactgc tcaattttga ctcaaaggtg ctatttacca
     2221 aacactctcc ctacccattc ctgccagctc tgcctccttt tcaactctcc acattttgta
     2281 ttgccttccc agacctgctt ccagtcttta ttgctttaaa gttcactttg gcccacaga
     2341 cccaagagct aattttctgg tttgtgggtt gaaacaaagc tgtgaatcac tgcaggctgt
     2401 gttcttgcat cttgtctgca aacaggtccc tgccttttta gaagcagcct catggtctca
```

Figure 6-19

```
2461 tgcttaatct tgtctctctt ctcttcttta tgatgttcac tttaaaaaca acaaaacccc
2521 tgagctggac tgttgagcag gcctgtctct cctattaagt aaaaataaat agtagtagta
2581 tgtttgtaag ctattctgac agaaaagaca aaggttacta attgtatgat agtgttttta
2641 tatggaagaa tgtacagctt atggacaaat gtacaccttt ttgttacttt aataaaaatg
2701 tagtaggata aaaaaaaa
```

Figure 6-20

LMO2

```
LOCUS       NM_005574               2304 bp    mRNA    linear   PRI 30-SEP-
2007
DEFINITION  Homo sapiens LIM domain only 2 (rhombotin-like 1) (LMO2), mRNA.
ACCESSION   NM_005574
VERSION     NM_005574.2  GI:6633806
KEYWORDS    .
SOURCE      Homo sapiens (human)

ORIGIN
        1 gaattcgtcc aaactgagga tcacaagtct ccacattctg agtaggagga tgagggtctg
       61 agttaggatt tgggtcctgc agggcttgct aaggaatccc ctgatggcct aggattccac
      121 gcagagcaca tctggtgtga gagagctcgc tgcaagggtg aaggctccgc cctatcagat
      181 agacaaccag gccaccaaga ggcccagccc tccaaaccct ggatttgcaa catcctcaaa
      241 gaacagcaac gggccttgag cagaattgag aaggaaatac cccacctgc cctcagccgt
      301 taagtgggct ttgctattca caagggcctc tgggtgtcct ggcagagagg ggagatggca
      361 caggcaccag gtgctagggt gccagggcct cccgagaagg aacaggtgca aagcaggcaa
      421 ttagcccaga aggtatccgt ggggcaggca gcctagatct gatggggaa gccaccagga
      481 ttacatcatc tgctgtaaca actgctctga aagaagata ttttcaacc tgaacttgca
      541 gtagctagtg gagaggcagg aaaaaggaaa tgaaacagag acagagggaa gcctgagcca
      601 aaatagacct tcccgagaga ggaggaagcc cggagagaga cgcacggtcc cctccccgcc
      661 cctaggccgc cgcccctct ctgccctcgg cggcgagcag ggcgccgcga cccggggccg
      721 gaaaggtgcc aggggctccg gcggccgggc cggcgcaca ccatccccgc gggcggcgcg
      781 gagccggcga cagcgcgcga gagggaccgg gcggtggcgg cggcgggacc gggatggaag
      841 ggagcgcggt gactgtcctt gagcgcggag gggcgagctc gccggcggag gccgagcaag
      901 cggaggcagg agcggcggcg acggcggcgg cggcggcggc gcccgagcac ccgagggggt
      961 ccgagccccg gcagccggcc agccccgcgc acaaaggga gcgccccgc cgcccggcac
     1021 cccgcctccc tccccaatgt cctcggccat cgaaggaag agcctggacc cttcagagga
     1081 accagtggat gaggtgctgc agatccccc atccctgctg acatgcggcg gctgccagca
     1141 gaacatcggg gaccgctact tcctgaaggc catcgaccag tactggcacg aggactgcct
     1201 gagctgcgac ctctgtggct gccggctggg tgaggtgggg cggcgcctct actacaaact
     1261 gggccggaag ctctgccgga gagactatct caggctttt gggcaagacg gtctctgcgc
     1321 atcctgtgac aagcggattc gtgcctatga tgacaatg cgggtgaaag acaaagtgta
     1381 tcacctggaa tgtttcaagt gcgccgcctg tcagaagcat ttctgtgtag gtgacagata
     1441 cctcctcatc aactctgaca tagtgtgcga acaggacatc tacgagtgga ctaagatcaa
     1501 tgggatgata taggcccgag tccccgggca tctttgggga ggtgttcact gaagacgccg
     1561 tctccatggc atcttcgtct tcactcttag gcactttggg ggtttgaggg tggggtaagg
     1621 gatttcttag gggatggtag acctttattg ggtatcaaga catagcatcc aagtggcata
     1681 attcaggggc tgacacttca aggtgacaga aggaccagcc cttgagggag aacttatggc
     1741 cacagcccat ccatagtaac tgacatgatt agcagaagaa aggaacattt aggggcaagc
     1801 aggcgctgtg ctatcatgat ggaatttcat atctacagat agagagttgt tgtgtacaga
     1861 cttgttgtga ctttgacgct tgcgaactag agatgtgcaa ttgatttctt ttcttcctgg
     1921 cttttttaact cccctgtttc aatcactgtc ctccacacaa gggaaggaca gaaaggagag
     1981 tggccattct tttttcttg gccccttcc caaggcctta agctttggac ccaagggaaa
     2041 actgcatgga gacgcatttc ggttgagaat ggaaaccaca acttttaacc aaacaattat
     2101 ttaaagcaat gctgatgaat cactgttttt agacaccttc attttgaggg gaggagttcc
     2161 acagattgtt tctatacaaa tataaatctt aaaagttgt tcaactattt tattatccta
     2221 gattatatca aagtatttgt cgtgtgtaga aaaaaaaac agctctgcag gcttaataaa
     2281 aatgacagac tgaaaaaaaa aaaa
```

Figure 6-21

YIPF3

```
LOCUS       BC019297                1554 bp    mRNA    linear   PRI 15-JUL-2006
DEFINITION  Homo sapiens Yip1 domain family, member 3, mRNA (cDNA clone
            MGC:4111 IMAGE:2905449), complete cds.
ACCESSION   BC019297
VERSION     BC019297.1  GI:17939493
KEYWORDS    MGC.
SOURCE      Homo sapiens (human)

ORIGIN
        1 gcttctcctt tttgtgttcc ggccgatccc acctctcctc gaccctggac gtctaccttc
       61 cggaggccca catcttgccc actccgcgcg cggggctagc gcgggtttca gcgacgggag
      121 ccctcaaggg acatggcaac tacagcggcg ccggcgggcg gcgcccgaaa tggagctggc
      181 ccggaatggg gagggttcga agaaaacatc cagggcggag gctcagctgt gattgacatg
      241 gagaacatgg atgatacctc aggctctagc ttcgaggata tgggtgagct gcatcagcgc
      301 ctgcgcgagg aagaagtaga cgctgatgca gctgatgcag ctgctgctga agaggaggat
      361 ggagagttcc tgggcatgaa gggctttaag ggacagctga ccggcaggt ggcagatcag
      421 atgtggcagg ctgggaaaag acaagcctcc agggccttca gcttgtacgc caacatcgac
      481 atcctcagac cctactttga tgtggagcct gctcaggtgc gaagcaggct cctggagtcc
      541 atgatcccta tcaagatggt caacttcccc cagaaaattg caggtgaact ctatggacct
      601 ctcatgctgg tcttcactct ggttgctatc ctactccatg ggatgaagac gtctgacact
      661 attatccggg agggcaccct gatgggcaca gccattggca cctgcttcgg ctactggctg
      721 ggagtctcat ccttcattta cttccttgcc tacctgtgca acgcccagat caccatgctg
      781 cagatgttgg cactgctggg ctatggcctc tttgggcatt gcattgtcct gttcatcacc
      841 tataatatcc acctccacgc cctcttctac ctcttctggc tgttggtggg tggactgtcc
      901 acactgcgca tggtagcagt gttggtgtct cggaccgtgg gcccacaca gcggctgctc
      961 ctctgtggca ccctggctgc cctacacatg ctcttcctgc tctatctgca ttttgcctac
     1021 cacaaagtgg tagaggggat cctggacaca ctggagggcc caacatccc gcccatccag
     1081 agggtcccca gagacatccc tgccatgctc cctgctgctc ggcttccac caccgtcctc
     1141 aacgccacag ccaaagctgt tgcggtgacc ctgcagtcac actgacccca cctgaaattc
     1201 ttggccagtc ctctttcccg cagctgcaga gaggaggaag actattaaag gacagtcctg
     1261 atgacatgtt tcgtagatgg ggtttgcagc tgccactgag ctgtagctgc gtaagtacct
     1321 ccttgatgcc tgtcggcact tctgaaaggc acaaggccaa gaactcctgg ccaggactgc
     1381 aaggctctgc agccaatgca gaaaatgggt cagctccttt gagaacccct ccccacctac
     1441 cccttccttc ctctttatct ctcccacatt gtcttgctaa atatagactt ggtaattaaa
     1501 atgttgattg aagtctggaa aaaaaaaaaa aaaaaaaaa aaaaaaaaa aaaa
```

Figure 6-22

SMN1

```
LOCUS       BC062723                1511 bp    mRNA    linear   PRI 01-SEP-2006
DEFINITION  Homo sapiens survival of motor neuron 1, telomeric, mRNA (cDNA
            clone MGC:72037 IMAGE:4250429), complete cds.
ACCESSION   BC062723
VERSION     BC062723.1  GI:38571799
KEYWORDS    MGC.
SOURCE      Homo sapiens (human)

ORIGIN
        1 ggggacccgc gggtttgcta tggcgatgag cagcggcggc agtggtggcg gcgtcccgga
       61 gcaggaggat tccgtgctgt tccggcgcgg cacaggccag agcgatgatt ctgacatttg
      121 ggatgataca gcactgataa aagcatatga taaagctgtg gcttcattta agcatgctct
      181 aaagaatggt gacatttgtg aaacttcggg taaaccaaaa accacaccta aagaaaaacc
      241 tgctaagaag aataaaagcc aaaagaagaa tactgcagct tccttacaac agtggaaagt
      301 tgggacaaa tgttctgcca tttggtcaga agacggttgc atttacccag ctaccattgc
      361 ttcaattgat tttaagagag aaacctgtgt tgtggtttac actggatatg gaaatagaga
      421 ggagcaaaat ctgtccgatc tactttcccc aatctgtgaa gtagctaata atatagaaca
      481 aaatgctcaa gagaatgaaa atgaaagcca gtttcaaca gatgaaagtg agaactccag
      541 gtctcctgga aataaatcag ataacatcaa gcccaaatct gctccatgga actctttct
      601 ccctccacca cccccccatgc cagggccaag actgggacca ggaaagccag gtctaaaatt
      661 caatggccca ccaccgccac cgccaccacc accacccccac ttactatcat gctggctgcc
      721 tccattcct tctggaccac caataattcc cccaccacct cccatatgtc cagattctct
      781 tgatgatgct gatgctttgg gaagtatgtt aatttcatgg tacatgagtg gctatcatac
      841 tggctattat atgggtttca gacaaaatca aaagaagga aggtgctcac attccttaaa
      901 ttaaggagaa atgctggcat agagcagcac taaatgacac cactaaagaa acgatcagac
      961 agatctggaa tgtgaagcgt tatagaagat aactggcctc atttcttcaa aatatcaagt
     1021 gttgggaaag aaaaaaggaa gtggaatggg taactcttct tgattaaaag ttatgtaata
     1081 accaaatgca atgtgaaata ttttactgga ctctattttg aaaaaccatc tgtaaaagac
     1141 tggggtgggg gtgggaggcc agcacggtgg tgaggcagtt gagaaaattt gaatgtggat
     1201 tagattttga atgatattgg ataattattg gtaatttta tgagctgtga aagggtgtt
     1261 gtagtttata aaagactgtc ttaatttgca tacttaagca tttaggaatg aagtgttaga
     1321 gtgtctaaa atgtttcaaa tggtttaaca aaatgtatgt gaggcgtatg tggcaaaatg
     1381 ttacagaatc taactggtgg acatggctgt tcattgtact gttttttct atcttctata
     1441 tgtttaaaag tatataataa aaatatttaa ttttttttta aaaaaaaaa aaaaaaaaca
     1501 aaaaaaaaa a
```

```
LOCUS       NM_000626               1300 bp    mRNA    linear   PRI 21-SEP-2008
DEFINITION  Homo sapiens CD79b molecule, immunoglobulin-associated beta
(CD79B),    transcript variant 1, mRNA.
ACCESSION   NM_000626
VERSION     NM_000626.2  GI:90193589
```

```
   1 ctgcagccgg tgcagttaca cgttttcctc caaggagcct cggacgttgt cacgggtttg
  61 gggtcgggga cagagcggtg accatggcca ggctggcgtt gtctcctgtg cccagccact
 121 ggatggtggc gttgctgctg ctgctctcag ctgagccagt accagcagcc agatcggagg
 181 accggtaccg gaatcccaaa ggtagtgctt gttcgcggat ctggcagagc ccacgtttca
 241 tagccaggaa acggggcttc acgtgaaaaa tgcactgcta catgaacagc gcctccggca
 301 atgtgagctg gctctggaag caggagatgg acgagaatcc ccagcagctg aagctggaaa
 361 agggccgcat ggaagagtcc cagaacgaat ctctcgccac cctcaccatc caaggcatcc
 421 ggtttgagga caatggcatc tacttctgtc agcagaagtg caacaacacc tcggaggtct
 481 accagggctg cggcacagag ctgcgagtca tgggattcag caccttggca cagctgaagc
 541 agaggaacac gctgaaggat ggtatcatca tgatccagac gctgctgatc atcctcttca
 601 tcatcgtgcc tatcttcctg ctgctggaca aggatgacag caaggctggc atggaggaag
 661 atcacaccta cgagggcctg gacattgacc agacagccac ctatgaggac atagtgacgc
 721 tgcggacagg ggaagtgaag tggtctgtag gtgagcaccc aggccaggag tgagagccag
 781 gtcgccccat gacctgggtg caggctccct ggcctcagtg actgcttcgg agctgcctgg
 841 ctcatggccc aaccccttc ctggaccccc cagctggcct ctgaagctgg cccaccagag
 901 ctgccatttg tctccagccc ctggtcccca gctcttgcca aagggcctgg agtagaagga
 961 caacagggca gcaacttgga gggagttctc tggggatgga cgggacccag ccttctgggg
1021 gtgctatgag gtgatccgtc cccacacatg ggatggggga ggcagagact ggtccagagc
1081 ccgcaaatgg actcggagcc gagggcctcc cagcagagct gggaaggc catggaccca
1141 actgggcccc agaagagcca caggaacatc attcctctcc gcaaccact cccaccccag
1201 ggaggccctg gcctccagtg ccttccccg tggaataaac ggtgtgtcct gagaaaccac
1261 aaaaaaaaaa aaaaaaaaaa aaaaaaaaaa aaaaaaaaa
```

LOCUS       NM_000610               5748 bp    mRNA    linear   PRI 23-OCT-2008
DEFINITION  Homo sapiens CD44 molecule (Indian blood group) (CD44),
transcript variant 1, mRNA.
ACCESSION   NM_000610
VERSION     NM_000610.3  GI:48255934

```
   1 gagaagaaag ccagtgcgtc tctgggcgca ggggccagtg gggctcggag gcacaggcac
  61 cccgcgacac tccaggttcc ccgacccacg tccctgcag ccccgattat ttacagcctc
 121 agcagagcac ggggcggggg cagaggggcc cgcccgggag ggctgctact tcttaaaacc
 181 tctgcgggct gcttagtcac agccccctt gcttgggtgt gtccttcgct cgctccctcc
 241 ctccgtctta ggtcactgtt ttcaacctcg aataaaaact gcagccaact tccgaggcag
 301 cctcattgcc cagcggaccc cagcctctgc caggttcggt ccgccatcct cgtccgtcc
 361 tccgccggcc cctgccccgc gcccagggat cctccagctc ctttcgcccg cgcctccgt
 421 tcgctccgga caccatggac aagttttggt ggcacgcagc ctggggactc tgcctcgtgc
 481 cgctgagcct ggcgcagatc gatttgaata taacctgccg ctttgcaggt gtattccacg
 541 tggagaaaaa tggtcgctac agcatctctc gacggaggc cgctgacctc tgcaaggctt
 601 tcaatagcac cttgcccaca atgggccaga tggagaaagc tctgagcatc ggatttgaga
 661 cctgcaggta tgggttcata aagggcacg tggtgattcc ccggatccac cccaactcca
 721 tctgtgcagc aaacaacaca ggggtgtaca tcctcacatc aacacctcc cagtatgaca
 781 catattgctt caatgcttca gctccacctg aagaagattg tacatcagtc acagacctgc
 841 ccaatgcctt tgatggacca attaccataa ctattgttaa ccgtgatggc accgctatg
 901 tccagaaagg agaatacaga acgaatcctg aagacatcta ccccagcaac cctactgatg
 961 atgacgtgag cagcggctcc tccagtgaaa ggagcagcac ttcaggaggt tacatctttt
1021 acacctttc tactgtacac cccatcccag acgaagacag tcctggatc accgacagca
1081 cagacagaat ccctgctacc actttgatga cactagtgc tacagcaact gagacagcaa
1141 ccaagaggca agaaacctgg attggtttt catggttgtt tctaccatca gagtcaaaga
1201 atcatcttca cacaacaaca caaatggctg gtacgtcttc aaataccatc tcagcaggct
1261 gggagccaaa tgaagaaat gaagatgaaa gagacagaca cctcagtttt tctggatcag
1321 gcattgatga tgatgaagat tttatctcca gcaccatttc aaccacacca cgggctttg
1381 accacacaaa acagaaccag gactggaccc agtggaaccc aagccattca atccggaag
1441 tgctacttca gacaaccaca aggatgactg atgtagacag aaatggcacc actgcttatg
1501 aaggaaactg gaacccagaa gcacaccctc cctcattca ccatgagcat catgaggaag
1561 aagagaccc acattctaca agcacaatcc aggcaactcc tagtagtaca acggaagaaa
1621 cagctaccca aaggaacag tggtttggca acagatggca tgggatat cgccaaacac
1681 ccaaagaaga ctcccattcg acaacaggga gctgcagc ctcagctcat accagccatc
1741 caatgcaagg aaggacaaca ccaagcccag ggacagttc ctggactgat tcttcaacc
1801 caatctcaca ccccatggga cgaggtcatc aagcaggaag aaggatggat atggactcca
1861 gtcatagtat aacgcttcag cctactgcaa atccaaacac aggttggtg aagattgg
1921 acaggacagg acctctttca atgacaacgc agcagagtaa ttctcagagc ttctctacat
1981 cacatgaagg cttggaagaa gataaagacc atccaacaac ttctactctg acatcaagca
2041 ataggaatga tgtcacaggt ggaagaagag acccaaatca ttctgaaggc tcaactactt
2101 tactggaagg ttatacctct cattacccac acgaagga agcaggacc ttcatcccag
2161 tgacctcagc taagactggg tcctttggag ttactgcagt tactgttgga gattccaact
2221 ctaatgtcaa tcgttcctta tcaggagacc aagacacatt ccacccagt gggggtccc
2281 ataccactca tggatctgaa tcagatggac actcatgg gagtcaagaa ggtggagcaa
2341 acacaacctc tggtcctata aggacacccc aaattccaga atggctgatc atcttggcat
2401 ccctcttggc cttggctttg attcttgcag tttgcattgc agtcaacagt cgaagaaggt
2461 gtgggcagaa gaaaagcta gtgatcaaca gtggcaatgg agctgtggag acagaaagc
2521 caagtggact caacggagag gccagcaagt ctcaggaaat ggtgcatttg gtgaacaagg
2581 agtcgtcaga aactccagac cagttttatga cagctgatga caaggaac ctgcagaatg
2641 tggacatgaa gattggggtg taacacctac accattatct tggaaagaaa caaccgttgg
```

Figure 6-25

```
2701 aaacataacc attacaggga gctgggacac ttaacagatg caatgtgcta ctgattgttt
2761 cattgcgaat cttttttagc ataaaatttt ctactctttt tgttttttgt gttttgttct
2821 ttaaagtcag gtccaatttg taaaaacagc attgcttttct gaaattaggg cccaattaat
2881 aatcagcaag aatttgatcg ttccagttcc cacttggagg cctttcatcc ctcgggtgtg
2941 ctatggatgg cttctaacaa aaactacaca tatgtattcc tgatcgccaa cctttccccc
3001 accagctaag gacatttccc agggttaata gggcctggtc cctgggagga aatttgaatg
3061 ggtccatttt gcccttccat agcctaatcc ctgggcattg cttccactg aggttggggg
3121 ttggggtgta ctagttacac atcttcaaca gacccctct agaaattttt cagatgcttc
3181 tgggagacac ccaaagggtg aagctattta tctgtagtaa actatttatc tgtgttttg
3241 aaatattaaa ccctggatca gtcctttgat cagtataatt ttttaaagtt actttgtcag
3301 aggcacaaaa gggtttaaac tgattcataa taaatatctg tacttcttcg atcttcacct
3361 tttgtgctgt gattcttcag tttctaaacc agcactgtct gggtccctac aatgtatcag
3421 gaagagctga gaatggtaag gagactcttc taagtcttca tctcagagac cctgagttcc
3481 cactcagacc cactcagcca aatctcatgg aagaccaagg agggcagcac tgtttttgtt
3541 ttttgttttt tgttttttt ttttgacact gtccaaggt tttccatcct gtcctggaat
3601 cagagttgga agctgaggag cttcagcctc ttttatggtt taatggccac ctgttctctc
3661 ctgtgaaagg cttttgcaaag tcacattaag tttgcatgac ctgttatccc tggggcccta
3721 tttcatagag gctggcccta ttagtgattt ccaaaaacaa tatggaagtg cctttgatg
3781 tcttacaata agagaagaag ccaatggaaa tgaaagagat tggcaaaggg gaaggatgat
3841 gccatgtaga tcctgtttga catttttatg gctgtatttg taaacttaaa cacaccagtg
3901 tctgttcttg atgcagttgc tatttaggat gagttaagtg cctggggagt ccctcaaaag
3961 gttaaaggga ttcccatcat tggaatctta tcaccagata ggcaagttta tgaccaaaca
4021 agagagtact ggctttatcc tctaacctca tattttctcc cacttggcaa gtcctttgtg
4081 gcatttattc atcagtcagg gtgtccgatt ggtcctagaa cttccaaagg ctgcttgtca
4141 tagaagccat tgcatctata agcaacggc tcctgttaaa tggtatctcc tttctgaggc
4201 tcctactaaa agtcatttgt tacctaaact tatgtgctta acaggcaatg cttctcagac
4261 cacaaagcag aaagaagaag aaaagctcct gactaaatca gggctgggct tagacagagt
4321 tgatctgtag aatatcttta aaggagagat gtcaactttc tgcactattc ccagcctctg
4381 ctcctccctg tctaccctct ccctccctc tctccctcca cttcacccca caatcttgaa
4441 aaacttcctt tctcttctgt gaacatcatt ggccagatcc attttcagtg gtctggattt
4501 cttttattt tcttttcaac ttgaagaaa ctggacatta ggccactatg tgttgttact
4561 gccactagtg ttcaagtgcc tcttgttttc ccagagattt cctgggtctg ccagaggccc
4621 agacaggctc actcaagctc tttaactgaa aagcaacaag ccactccagg acaaggttca
4681 aaatggttac aacagcctct acctgtcgcc ccagggagaa aggggtagtg atacaagtct
4741 catagccaga gatggttttc cactccttct agatattccc aaaaagaggc tgagacagga
4801 ggttattttc aatttatt tggaattaaa tacttttttc cctttattac tgttgtagtc
4861 cctcacttgg atatacctct gttttcacga tagaaataag ggaggtctag agcttctatt
4921 ccttggccat tgtcaacgga gagctggcca agtcttcaca aacccttgca acattgcctg
4981 aagtttatgg aataagatgt attctcactc ccttgatctc aagggcgtaa ctctggaagc
5041 acagcttgac tacacgtcat ttttaccaat gattttcagg tgacctgggc taagtcattt
5101 aaactgggtc tttataaaag taaaaggcca acatttaatt attttgcaaa gcaacctaag
5161 agctaaagat gtaatttttc ttgcaattgt aaatcttttg tgtctcctga agacttccct
5221 taaaattagc tctgagtgaa aaatcaaaag agacaaaaga catcttcgaa tccatatttc
5281 aagcctggta gaattggctt ttctagcaga acctttccaa aagttttata ttgagattca
5341 taacaacacc aagaattgat tttgtagcca acattcattc aatactgtta tatcagagga
5401 gtaggagaga ggaaacattt gacttatctg gaaaagcaaa atgtacttaa gaataagaat
5461 aacatggtcc attcacctt atgttataga tatgtctttg tgtaaatcat ttgttttgag
5521 ttttcaaaga atagcccatt gttcattctt gtgctgtaca atgaccactg ttattgttac
5581 tttgactttt cagagcacac ccttcctctg gtttttgtat atttattgat ggatcaataa
5641 taatgaggaa agcatgatat gtatattgct gagttgaaag cacttattgg aaaatattaa
5701 aaggctaaca ttaaaagact aaaggaaaca gaaaaaaaaa aaaaaaa
```

Figure 6-26

CTSC

LOCUS       NM_001814               1924 bp    mRNA    linear   PRI 06-APR-2008
DEFINITION  Homo sapiens cathepsin C (CTSC), transcript variant 1, mRNA.
ACCESSION   NM_001814
VERSION     NM_001814.3  GI:167000478

```
   1 cgtagctatt tcaaggcgcg cgcctcgtgg tggactcacc gctagcccgc agcgctcggc
  61 ttcctggtaa ttcttcacct cttttctcag ctccctgcag catgggtgct gggccctcct
 121 tgctgctcgc cgccctcctg ctgcttctct ccggcgacgg cgccgtgcgc tgcgacacac
 181 ctgccaactg cacctatctt gacctgctgg gcacctgggt cttccaggtg ggctccagcg
 241 gttcccagcg cgatgtcaac tgctcggtta tgggaccaca agaaaaaaaa gtagtggtgt
 301 accttcagaa gctggataca gcatatgatg accttggcaa ttctggccat ttccatcatca
 361 tttacaacca aggctttgag attgtgttga atgactacaa gtggtttgcc tttttttaagt
 421 ataaagaaga gggcagcaag gtgaccactt actgcaacga gacaatgact gggtgggtgc
 481 atgatgtgtt gggccggaac tgggcttgtt tcaccggaaa gaaggtggga actgcctctg
 541 agaatgtgta tgtcaacata gcacacctta agaattctca ggaaaagtat tctaataggc
 601 tctacaagta tgatcacaac tttgtgaaag ctatcaatgc cattcagaag tcttggactg
 661 caactacata catggaatat gagactctta ccctgggaga tatgattagg agaagtggtg
 721 gccacagtcg aaaaatccca aggcccaaac ctgcaccact gactgctgaa atacagcaaa
 781 agattttgca tttgccaaca tcttgggact ggagaaatgt tcatggtatc aattttgtca
 841 gtcctgttcg aaaccaagca tcctgtggca gctgctactc atttgcttct atgggtatgc
 901 tagaagcgag aatccgtata ctaaccaaca attctcagac cccaatccta agccctcagg
 961 aggttgtgtc ttgtagccag tatgctcaag gctgtgaagg cggcttccca taccttattg
1021 caggaaagta cgcccaagat tttgggctgg tggaagaagc ttgcttcccc tacacaggca
1081 ctgattctcc atgcaaaatg aaggaagact gctttcgtta ttactcctct gagtaccact
1141 atgtaggagg tttctatgga ggctgcaatg aagccctgat gaagcttgag ttggtccatc
1201 atgggcccat ggcagttgct tttgaagtat atgatgactt cctccactac aaaaagggga
1261 tctaccacca cactggtcta agagacccct tcaaccctt tgagctgact aatcatgctg
1321 ttctgcttgt gggctatgc actgactcag cctctgggat ggattactgg attgttaaaa
1381 acagctgggg caccggctgg ggtgagaatg gctacttccg gatccgcaga ggaactgatg
1441 agtgtgcaat tgagagcata gcagtggcag ccacaccaat tcctaaattg tagggtatgc
1501 cttccagtat ttcataatga tctgcatcag ttgtaaaggg gaattggtat attcacagac
1561 tgtagacttt cagcagcaat ctcagaagct tacaaataga tttccatgaa gatatttgtc
1621 ttcagaatta aaactgccct taattttaat ataccttca atcggccact ggccattttt
1681 ttctaagtat tcaattaagt gggaatttc tggaagatgg tcagctatga agtaatagag
1741 tttgcttaat catttgtaat tcaaacatgc tatattttt aaaatcaatg tgaaaacata
1801 gacttatttt taaattgtac caatcacaag aaaataatgg caataattat caaaactttt
1861 aaaatagatg ctcatatttt taaaataaag ttttaaaaat aactgcaaaa aaaaaaaaa
1921 aaaa
```

Figure 6-27

UAP1

```
LOCUS       NM_003115               2344 bp    mRNA    linear   PRI 22-OCT-
2008
DEFINITION  Homo sapiens UDP-N-acteylglucosamine pyrophosphorylase 1
            (UAP1), mRNA.
ACCESSION   NM_003115
VERSION     NM_003115.4  GI:156627574

1 cggccgcctc cgcgtccgcg tcgtcgtctg tgctcccggc gctgacgtgt ctgggcggtc
   61 ggcttccact ccttcaggcg tcggcagcca ctagtcgtgg cgagaggggc ggggtggccg
  121 gggctggcgc tccacttggc ccccgctccc ggcccgcccc gccgccgcgg cccccggat
  181 gagggtatat attcggagcg agcgcgggac gccgatgagt ggccgcgcgg aaggagctgg
  241 agacggtcgt agctgcggtc gcgccgagaa aggtttacag gtacatacat tacacccta
  301 tttctacaaa gcttggctat tagagcatta tgaacattaa tgacctcaaa ctcacgttgt
  361 ccaaagctgg caagagcac ctactacgtt tctggaatga gcttgaagaa gcccaacagg
  421 tagaactta tgcagagctc caggccatga actttgagga gctgaacttc ttttttccaaa
  481 aggccattga aggttttaac cagtcttctc accaaaagaa tgtggatgca cgaatggaac
  541 ctgtgcctcg agaggtatta ggcagtgcta caagggatca agatcagctc caggcctggg
  601 aaagtgaagg acttttccag atttctcaga ataaagtagc agttcttctt ctagctggtg
  661 ggcaggggac aagactcggc gttgcatatc ctaaggggat gtatgatgtt ggtttgccat
  721 cccgtaagac acttttcag attcaagcag agcgtatcct gaagctacag caggttgctg
  781 aaaaatatta tggcaacaaa tgcattattc catggtatat aatgaccagt ggcagaacaa
  841 tggaatctac aaaggagttc ttcaccaagc acaagtactt tggtttaaaa aaagagaatg
  901 taatctttt tcagcaagga atgctcccg ccatgagttt tgatgggaaa attatttttgg
  961 aagagaagaa caaagtttct atggctccag atgggaatgg tggtctttat cgggcacttg
 1021 cagcccagaa tattgtggag gatatggagc aaagaggcat ttggagcatt catgtctatt
 1081 gtgttgacaa catattagta aaagtggcag acccacggtt cattggattt tgcattcaga
 1141 aaggagcaga ctgtggagca aaggtggtag agaaaacgaa ccctacagaa ccagttggag
 1201 tggtttgccg agtggatgga gtttaccagg tggtagaata tagtgagatt tccctggcaa
 1261 cagctcaaaa acgaagctca gacggacgac tgctgttcaa tgcggggaac attgccaacc
 1321 atttcttcac tgtaccattt ctgagagatg ttgtcaatgt ttatgaacct cagttgcagc
 1381 accatgtggc tcaaaagaag attccttatg tggataccca aggacagtta attaagccag
 1441 acaaacccaa tggaataaag atggaaaaat tgtctttga catcttccag tttgcaaaga
 1501 agtttgtggt atatgaagta ttgcgagaag atgagttttc cccactaaag aatgctgata
 1561 gtcagaatgg gaaagacaac cctactactg caaggcatgc tttgatgtcc cttcatcatt
 1621 gctgggtcct caatgcaggg ggccatttca tagatgaaaa tggctctcgc cttccagcaa
 1681 ttccccgctt gaaggatgcc aatgatgtac caatccaatg tgaaatctct cctcttatct
 1741 cctatgctgg agaaggatta gaaagttatg tggcagataa agaattccat gcacctctaa
 1801 tcatcgatga aatggagtt catgagctgg tgaaaaatgg tatttgaacc agataccaag
 1861 ttttgtttgc cacgatagga atagctttta ttttgatag accaactgtg aacctacaag
 1921 acgtcttgga caactgaagt ttaaatatcc acagggtttt attttgcttg ttgaactctt
 1981 agagctattg caaacttccc aagatccaga tgactgaatt tcagatagca tttttatgat
 2041 tcccaactca ttgaaggtct tatttatata attttttcca agccaaggag accattggcc
 2101 atccaggaaa tttcgtacag ctgaaatata gcaggatgt tcaacatcag tttacttgca
 2161 gctggaagca tttgttttttg aagttgtaca tagtaataat atgtcattgt acatgttgaa
 2221 aggtttctat ggtactaaaa gtttgtttta tttatcaaa cattaagctt ttttaagaaa
 2281 ataattgggc agtgaaataa atgtatcttc ttgtctctgg agtgtcaaaa aaaaaaaaa
 2341 aaaa
```

Figure 6-28

PUS7

LOCUS       NM_019042               3484 bp    mRNA    linear   PRI 11-FEB-2008
DEFINITION  Homo sapiens pseudouridylate synthase 7 homolog (S. cerevisiae)
(PUS7), mRNA.
ACCESSION   NM_019042 XM_496914 XM_499357
VERSION     NM_019042.3  GI:50727001

```
   1 gtgcgagccc ggccgccggt gagtcggctg gagcgcatct ggtcctccgc gcggaaagcg
  61 ctgcttttgc ctggccgccc tagccgctgg ctcatccaag tggccttcgc cgctctcttg
 121 cgtcccaacc agagcgctgg ccacctcgcc gcccagctca cgccgcgccc gcgctcccag
 181 gctccgggtt ttcttaaatg ttttcttgga gccttaaaga tggagatgac agaaatgact
 241 ggtgtgtcgc tgaaacgtgg ggcactggtt gtcgaagata atgacagtgg agtcccagtt
 301 gaagagacaa aaaaacagaa gctgtcggaa tgcagtctaa ccaaaggtca agatgggcta
 361 cagaatgact ttctgtccat cagtgaagac gtgcctcggc ctcctgacac tgtcagtact
 421 gggaaaggtg gaaagaattc tgaggctcag ttggaagatg aggaagaaga ggaggaagat
 481 ggactttcag aggagtgcga ggaggaggaa tcagagagtt ttgcagacat gatgaagcat
 541 ggactcactg aggctgacgt aggcatcacc aagtttgtga gttctcatca agggttctcg
 601 ggaatcttaa agaaagata ctccgacttc gttgttcatg aaataggaaa agatggacgg
 661 atcagccatt gaatgactt gtccattcca gtggatgagg acgaccctc agaagacata
 721 tttacagttt tgacagctga agaaaagcag cgattggaag agctccagct gttcaaaaat
 781 aaggaaacca gtgttgccat tgaggttatc gaggacacca agagaaaag aaccatcatc
 841 catcaggcta tcaaatctct gtttccagga ttagagacaa aaacagagga tagggagggg
 901 aagaaataca ttgtagccta ccacgcagct gggaaaaagg cttttggcaa tccaagaaaa
 961 cattcttggc caaatctag gggaagttac tgccacttcg tactatataa ggaaaacaaa
1021 gacaccatgg atgctattaa tgtactctcc aaatacttaa gagtcaagcc aaatatattc
1081 tcctacatgg gaaccaaaga taaagggct ataacagttc aagaaattgc tgttctcaaa
1141 ataactgcac aaagacttgc ccacctgaat aagtgcttga tcaactttaa gctagggaat
1201 ttcagctatc aaaaaaaccc actgaaattg ggagagcttc aaggaaacca cttcactgtt
1261 gttctcagaa atataacagg aactgatgac caagtacagc aagctatgaa ctctctcaag
1321 gagattggat ttattaacta ctatggaatg caaagatttg gaaccacagc tgtccctacg
1381 tatcaggttg gaagagctat actacaaaat tcctggacag aagtcatgga tttaatattg
1441 aaaccccgct ctggagctga aaagggctac ttggttaaat gcagagaaga atgggcaaag
1501 accaaagacc caactgctgc cctcagaaaa ctacctgtca aaggtgtgt ggaagggcag
1561 ctgcttcgag gactttcaaa atatggaatg aagaatatag tctctgcatt tggcataata
1621 cccagaaaata atcgcttaat gtatattcat agctaccaaa gctatgtgtg gaataacatg
1681 gtaagcaaga ggatagaaga ctatggacta aaacctgttc caggggacct cgttctcaaa
1741 ggagccacag ccacctatat tgaggaagat gatgttaata attactctat ccatgatgtg
1801 gtaatgccct tgcctggttt cgatgttatc tacccaaagc ataaaattca agaagcctac
1861 agggaaatgc tcacagctga caatcttgat attgacaaca tgagacacaa aattcgagat
1921 tattccttgt caggggccta ccgaaagatc attattcgtc ctcagaatgt tagctgggaa
1981 gtcgttgcat atgatgatcc caaaattcca cttttcaaca cagatgtgga caacctagaa
2041 gggaagacac caccagtttt tgcttctgaa ggcaaataca gggctctgaa aatggatttt
2101 tctctacccc cttctactta cgccaccatg gccattcgag aagtgctaaa aatggatacc
2161 agtatcaaga accagacgca gctgaataca acctggcttc gctgagcagt accttgtcca
2221 cagattagaa aacgtacaca agtgtttgct tcctggctcc ctgtgcattt ttgtcttagt
2281 tcagactcat atatggattt caaatctttg taataaaaat tatttgtatt tttaagtttt
2341 tattagctta aagaaataat ttgcaatatt tgtacatgta cacaaatcct gaggttctta
2401 atttttagctc agaatataaa ttagtcaaaa tacacttcag gtgcttaaat cagagtaaaa
2461 tgtcagcttt acaataataa aaaaaggact ttggtttaaa gtagcaggtt taggttttgc
2521 tacattctca aaagacagca ggagtatttg acacatctgt gatggagtat acaacaatgc
2581 attttaagag caaatgcaac aaaacaaatc tggactatgg ataaataatt tgagagctgc
2641 cacccacaaa tataaataca gtactcatgc tgactgaaat aataagacat ctacaaattt
```

```
2701 ataaacaaaa agtgattgtc attatcctgc ttatgtacta gattcaggca agcattatag
2761 acttttttggt tgcggtggct tttgcattta tattatcaat gccttgcagg aacgttgcat
2821 tgataggccc attttatttt tttatttttt tttcgagac aggatctcac tctgtagcac
2881 aggctggatt gcagtgcaat cctgcaattc tcaatcttgc actgcagcct cgacctccca
2941 ggctccagtg actctcccac ctcagcctcc taagtagctg ggagtacagg cgcgcaccac
3001 cacgcctagc tgattttgt attttttgt agagacgggg gtttggccat gttgccgagg
3061 ctaactcctg ggattacagg catgagctgt gctggccggg ttttttttc ttgatgtaaa
3121 cgtgtacagc tgttttatta gttaaggtct aattttact ctaggtgcct tttatgttca
3181 gaactctttc cactggactg gtatttgctc aaaaataaat aatggtagag aagaaaacta
3241 taaaaatgga caaggctttc ttctatcagt agcgtttacc ctttgtcacc agtggctttg
3301 gtatttccat gtctggcatt gcataaactt ctctggtgtg aaaggataaa tatgcctttc
3361 taaagttgta tatcaaaatt gtatcaattt ttattttcta tgatttctag aaacaaatgt
3421 aataaatatt tttaaaatct cctttctact ggttatgtaa ataaatcaaa taaatatatc
3481 aaaa
```

Figure 6-30

RGS 13

```
LOCUS       NM_002927               1498 bp    mRNA    linear   PRI 10-FEB-2008
DEFINITION  Homo sapiens regulator of G-protein signaling 13 (RGS13),
transcript variant 1, mRNA.
ACCESSION   NM_002927
VERSION     NM_002927.3  GI:21464137

1 gaggccagag tgccatcgaa ggtaattata gagacagtaa atccttttta ctctgggaaa
   61 aataaaatgc tgggtgtctc acaaaatttc agaacctgat ttcaaacgga tcataacaaa
  121 gaggagatca aatttagcat ggtggactgc tcgacaggat atatttgtca atggaatgtt
  181 tccacatatt ataccaccaa catgagaaaa aaatgatcat tgtttatttg aagcttgatg
  241 atattctaac gctgcctttt ctcttctcat tttagagaaa aatgagcagg cggaattgtt
  301 ggatttgtaa gatgtgcaga gatgaatcta agaggccccc ttcaaaccct actttggagg
  361 aagtattaca gtgggcccag tcttttgaaa atttaatggc tacaaaatat ggtccagtag
  421 tctatgcagc atatttaaaa atggagcaca gtgacgagaa tattcaattc tggatggcat
  481 gtgaaaccta aagaaaatt gcctcacggt ggagcagaat ttctaggca aagaagcttt
  541 ataagattta catccagcca cagtcccta gagagattaa cattgacagt tcgacaagag
  601 agactatcat caggaacatt caggaaccca ctgaaacatg ttttgaagaa gctcagaaaa
  661 tagtctatat gcatatggaa agggattcct accccagatt tctaaagtca gaatgtacc
  721 aaaaactttt gaaaactatg cagtccaaca acagtttctg actacaactc aaaagtttaa
  781 atagaaaaca gtatattgaa agtggtgggt ttgatctttt tatttagaaa cccacaaaat
  841 cagaaacaca gtacaaataa aacagaaatc aaactataag ttgacttta gttcctaaaa
  901 agaaacatat ttcaaaagca atggaatcta gaattcttat aacatgaata acaaaatgta
  961 cagcaagcct atgtagttca attaatatat aaggaaaagg aaggtctttt ttcatgatac
 1021 aagcattata aagtttttac tgtagtagtc aattaatgga tatttccttg ttaataaaat
 1081 tttgtgtcat aatttacaaa ttagttcttt aaaaattgtt gttatatgaa ttgtgtttct
 1141 agcatgaatg ttctatagag tactctaaat aacttgaatt tatagacaaa tgctactcac
 1201 agtacaatca attgtattat accatgagaa aatcaaaaag gtgttcttca gagacatttt
 1261 atctataaaa ttttcctact attatgttca ttaacaaact tctttatcac atgtatcttc
 1321 tacatgtaaa acatttctga tgattttta acaaaaaata tatgaatttc ttcatttgct
 1381 cttgcatcta cattgctata aggatataaa atgtggtttc tatattttga gatgttttt
 1441 ccttacaatg tgaactcatc gtgatcttgg aaatcaataa agtcaaatat caactaaa
```

```
LOCUS       NM_001771               3293 bp    mRNA    linear   PRI 16-MAR-2008
DEFINITION  Homo sapiens CD22 molecule (CD22), mRNA.
ACCESSION   NM_001771
VERSION     NM_001771.2  GI:157168354
```

```
   1 cttttgctct cagatgctgc cagggtccct gaagagggaa gacacgcgga acaggcttg
  61 cacccagaca cgacaccatg catctcctcg cccctggct cctgctcctg gttctagaat
 121 acttggcttt ctctgactca agtaaatggg ttttgagca ccctgaaacc ctctacgcct
 181 gggaggggc ctgcgtctgg atcccctgca cctacagagc cctagatggt gacctggaaa
 241 gcttcatcct gttccacaat cctgagtata caagaacac ctcgaagttt gatgggacaa
 301 gactctatga agcacaaag gatgggaagg ttccttctga gcagaaaagg gtgcaattcc
 361 tgggagacaa gaataagaac tgcacactga gtatccaccc ggtgcacctc aatgacagtg
 421 gtcagctggg gctgaggatg gagtccaaga ctgagaaatg gatggaacga atacacctca
 481 atgtctctga aaggcctttt ccacctcata tccagctccc tccagaaatt caagagtccc
 541 aggaagtcac tctgacctgc ttgctgaatt ctcctgcta tgggtatccg atccaattgc
 601 agtggctcct agagggggtt ccaatgaggc aggctgctgt cacctcgacc tccttgacca
 661 tcaagtctgt cttcacccgg agcgagctca agttctcccc acagtggagt caccatggga
 721 agattgtgac ctgccagctt caggatgcag atgggaagtt cctctccaat gacacggtgc
 781 agctgaacgt gaagcacacc ccgaagttgg agatcaaggt cactcccagt gatgccatag
 841 tgagggaggg ggactctgtg accatgacct gcgaggtcag cagcagcaac ccggagtaca
 901 cgacggtatc ctggctcaag gatgggaccc gctgaagaa gcagaataca ttcacgctaa
 961 acctgcgcga agtgaccaag gaccagagtg ggaagtactg ctgtcaggtc tccaatgacg
1021 tgggcccggg aaggtcggaa gaagtgttcc tgcaagtgca gtatgccccg gaaccttcca
1081 cggttcagat cctccactca ccggctgtgg agggaagtca agtcgagttt ctttgcatgt
1141 cactggccaa tcctcttcca acaaattaca cgtggtacca atgggaaa gaaatgcagg
1201 gaaggacaga ggagaaagtc cacatcccaa agatcctccc ctggcacgct gggacttatt
1261 cctgtgtggc agaaaacatt cttggtactg gacagagggg cccgggagct gagctggatg
1321 tccagtatcc tcccaagaag gtgaccacag tgattcaaaa ccccatgccg attcgagaag
1381 gagacacagt gacccttttcc tgtaactaca attccagtaa ccccagtgtt acccggtatg
1441 aatggaaacc catggcgcc tgggaggagc atcgcttgg ggtgctgaag atccaaaacg
1501 ttggctggga caacacaacc atcgcctgcg cagcttgtaa tagttggtgc tcgtgggcct
1561 cccctgtcgc cctgaatgtc cagtatgccc ccgagacgt gagggtccgg aaaatcaagc
1621 ccctttccga gattcactct ggaaactcgg tcagcctcca atgtgacttc aagcagcc
1681 accccaaaga gtccagttc ttctgggaga aaatggcag gcttctgggg aaagaaagcc
1741 agctgaattt tgactccatc tccccagaag atgctgggag ttacagctgc tgggtgaaca
1801 actccatagg acagacagcg tccaaggcct ggacacttga agtgctgtat gcacccagga
1861 ggctgcgtgt gtccatgagc ccggggggacc aagtgatgga ggggaagagt gcaaccctga
1921 cctgtgagag cgacgccaac cctcccgtct cccactacac ctggtttgac tggaataacc
1981 aaagcctccc ctaccacagc cagaagctga gattggagcc ggtgaaggtc cagcactcgg
2041 gtgcctactg tgccagggg accaacagtg tgggcaaggg ccgttcgcct ctcagcaccc
2101 tcaccgtcta ctatagccc gagaccatcg gcaggcgagt ggctgtggga ctcgggtcct
2161 gcctcgccat cctcatcctg gcaatctgtg ggctcaagct ccagcgacgt tggaagagga
2221 cacagagcca gcagggctt caggagaatt ccagcggcca gagcttcttt gtgaggaata
2281 aaaaggttag aagggcccc ctctctgaag ccccactc cctgggatgc tacaatccaa
2341 tgatggaaga tgcattagc tacaccaccc tgcgctttcc cgagatgaac ataccacgaa
2401 ctggagatgc agagtcctca gagatgcaga gacctccccc ggactgcgat gacacggtca
2461 cttattcagc attgcacaag cgccaagtgg gcgactatga aacgtcatt ccagattttc
2521 cagaagatga ggggattcat tactcagagc tgatccagtt tggggtcggg gagcggcctc
2581 aggcacaaga aaatgtggac tatgtgatcc tcaaacattg acactggatg ggctgcagca
2641 gaggcactgg gggcagcggg ggccagggaa gtccccgagt ttccccagac accgccacat
```

Figure 6-32

```
2701 ggcttcctcc tgcgcgcatg tgcgcacaca cacacacaca cgcacacaca cacacacaca
2761 ctcactgcgg agaaccttgt gcctggctca gagccagtct ttttggtgag ggtaacccca
2821 aacctccaaa actcctgccc ctgttctctt ccactctcct tgctacccag aaatccatct
2881 aaatacctgc cctgacatgc acacctcccc ctgccccac cacggccact ggccatctcc
2941 accccagct gcttgtgtcc ctcctgggat ctgctcgtca tcatttttcc ttcccttctc
3001 catctctctg gccctctacc cctgatctga catccccact cacgaatatt atgcccagtt
3061 tctgcctctg agggaaagcc cagaaaagga cagaaacgaa gtagaaaggg gcccagtcct
3121 ggcctggctt ctcctttgga agtgaggcat tgcacgggga gacgtacgta tcagcggccc
3181 cttgactctg gggactccgg gtttgagatg gacacactgg tgtggattaa cctgccaggg
3241 agacagagct cacaataaaa atggctcaga tgccacttca aagaaaaaa aaa
```

Figure 6-33

SMN 1

```
LOCUS       NM_000344               1621 bp    mRNA    linear   PRI 10-AUG-2008
DEFINITION  Homo sapiens survival of motor neuron 1, telomeric (SMN1),
            transcript variant d, mRNA.
ACCESSION   NM_000344 XM_001126655
VERSION     NM_000344.2  GI:13259515

1 ccacaaatgt gggagggcga taaccactcg tagaaagcgt gagaagttac tacaagcggt
  61 cctccggcc accgtactgt tccgctccca gagccccgg gcggcggaag tcgtcactct
 121 taagaaggga cgggccccca cgctgcgcac ccgcgggttt gctatggcga tgagcagcgg
 181 cggcagtggt ggcggcgtcc cggagcagga ggattccgtg ctgttccggc gcggcacagg
 241 ccagagcgat gattctgaca tttgggatga tacagcactg ataaaagcat atgataaagc
 301 tgtggcttca tttaagcatg ctctaaagaa tggtgacatt tgtgaaactt cgggtaaacc
 361 aaaaaccaca cctaaaagaa aacctgctaa gaagaataaa agccaaaaga gaatactgc
 421 agcttcctta caacagtgga agttgggga caaatgttct gccatttggt cagaagacgg
 481 ttgcatttac ccagctacca ttgcttcaat tgatttaag agagaaacct gtgttgtggt
 541 ttacactgga tatggaaata gagaggagca aatctgtcc gatctacttt ccccaatctg
 601 tgaagtagct aataatatag aacagaatgc tcaagagaat gaaaatgaaa gccaagtttc
 661 aacagatgaa agtgagaact ccaggtctcc tggaaataaa tcagataaca tcaagcccaa
 721 atctgctcca tggaactctt ttctccctcc accaccccc atgccagggc caagactggg
 781 accaggaaag ccaggtctaa aattcaatgg cccaccaccg ccaccgccac caccaccacc
 841 ccacttacta tcatgctggc tgcctccatt tccttctgga ccaccaataa ttcccccacc
 901 acctcccata tgtccagatt ctcttgatga tgctgatgct ttgggaagta tgttaatttc
 961 atggtacatg agtggctatc atactggcta ttatatgggt ttcagacaaa atcaaaaaga
1021 aggaaggtgc tcacattcct taaattaagg agaaatgctg catagagca gcactaaatg
1081 acaccactaa agaaacgatc agacagatct ggaatgtgaa gcgttataga agataactgg
1141 cctcatttct tcaaaatatc aagtgttggg aagaaaaaaa ggaagtggaa tgggtaactc
1201 ttcttgatta aagttatgt aataaccaaa tgcaatgtga aatattttac tggactcttt
1261 tgaaaaacca tctgtaaaag actggggtgg gggtgggagg ccagcacggt ggtgaggcag
1321 ttgagaaaat ttgaatgtgg attagatttt gaatgatatt ggataattat tggtaatttt
1381 atggcctgtg agaagggtgt tgtagtttat aaaagactgt cttaatttgc atacttaagc
1441 atttaggaat gaagtgttag agtgtcttaa aatgtttcaa atggtttaac aaaatgtatg
1501 tgaggcgtat gtggcaaaat gttacagaat ctaactggtg gacatggctg ttcattgtac
1561 tgttttttc tatcttctat atgtttaaaa gtatataata aaatattta atttttttt
1621 a
```

Figure 6-34

YIPF 3

```
LOCUS       NM_015388              1572 bp    mRNA    linear   PRI 28-SEP-2008
DEFINITION  Homo sapiens Yip1 domain family, member 3 (YIPF3), mRNA.
ACCESSION   NM_015388
VERSION     NM_015388.2  GI:49472827

1 aagttgcttt tgtccaaaca tccgggcttc tccttttgt gttccggccg atcccacctc
   61 tcctcgaccc tggacgtcta ccttccggag gcccacatct tgcccactcc gcgcgcgggg
  121 ctagcgcggg tttcagcgac gggagccctc aagggacatg caactacag cggcgccggc
  181 gggcggcgcc cgaaatggag ctggcccgga atggggaggg ttcgaagaaa acatccaggg
  241 cggaggctca gctgtgattg acatggagaa catggatgat acctcaggct ctagcttcga
  301 ggatatgggt gagctgcatc agcgcctgcg cgaggaagaa gtagacgctg atgcagctga
  361 tgcagctgct gctgaagagg aggatggaga gttcctgggc atgaagggct taagggaca
  421 gctgagccgg caggtggcag atcagatgtg gcaggctggg aaaagacaag cctccaggc
  481 cttcagcttg tacgccaaca tcgacatcct cagaccctac tttgatgtgg agcctgctca
  541 ggtgcgaagc aggctcctgg agtccatgat ccctatcaag atggtcaact cccccagaa
  601 aattgcaggt gaactctatg gacctctcat gctggtcttc actctggttg ctatcctact
  661 ccatgggatg aagacgtctg acactattat ccgggagggc accctgatgg gcacagccat
  721 tggcacctgc ttcggctact ggctgggagt ctcatccttc atttacttcc ttgcctacct
  781 gtgcaacgcc cagatcacca tgctgcagat gttggcactg ctgggctatg gcctctttgg
  841 gcattgcatt gtcctgttca tcacctataa tatccacctc cacgccctct ctacctcttc
  901 ctggctgttg gtgggtggac tgtccacact gcgcatggta gcagtgttgg tgtctcggac
  961 cgtgggcccc acacagcggc tgctcctctg tggcaccctg ctgccctac acatgctctt
 1021 cctgctctat ctgcattttg cctaccacaa agtggtagag gggatcctgg acacactgga
 1081 gggccccaac atcccgccca tccagagggt ccccagagac atccctgcca tgctccctgc
 1141 tgctcggctt ccaccaccg tcctcaacgc cacagccaaa gctgttgcgg tgaccctgca
 1201 gtcacactga ccccacctga aattcttggc cagtcctctt tcccgcagct gcagagagga
 1261 ggaagactat taaggacag tcctgatgac atgtttcgta gatgggtttt gcagctgcca
 1321 ctgagctgta gctgcgtaag tacctccttg atgcctgtcg gcacttctga aaggcacaag
 1381 gccaagaact cctggccagg actgcaaggc tctgcagcca atgcagaaaa tgggtcagct
 1441 cctttgagaa ccccctcccca cctacccctt ccttcctctt tatctctccc acattgtctt
 1501 gctaaatata gacttggtaa ttaaaatgtt gattgaagtc tggaactgca aaaaaaaaa
 1561 aaaccaaaaa aa
```

METHODS AND COMPOSITIONS FOR ASSESSING RESPONSIVENESS OF B-CELL LYMPHOMA TO TREATMENT WITH ANTI-CD40 ANTIBODIES

RELATED APPLICATIONS

This application is a National Phase application under 35 U.S.C. §371 of International Application No. PCT/US2008/082920, filed on Nov. 7, 2008, which is incorporated herein by reference in its entirety.

TECHNICAL FIELD

The present invention relates generally to the fields of predicting, assessing, aiding assessment of responsiveness of B-cell lymphoma to treatment with anti-CD40 antibodies.

BACKGROUND

CD40 is a type I transmembrane protein of the tumor necrosis receptor superfamily. CD40 is an important molecule involved in B-cell proliferation and differentiation, immunoglobulin isotype switching, and cell viability. Receptor signaling is initiated by the binding of CD40 to the CD40 ligand (CD40L or CD154), which is primarily expressed on activated CD4+ T cells.

On normal cells, CD40 is expressed on cells with high proliferative potential, including hematopoietic progenitors, epithelial and endothelial cells, and all antigen-presenting cells (dendritic cells, activated B lymphocytes, and activated monocytes). CD40 is highly expressed on several types of B-cell hematologic malignancies including multiple myeloma, non-Hodgkin's lymphoma (NHL), and chronic lymphocytic leukemia (CLL). The high prevalence of CD40 expression on B-cell malignancies makes it an attractive potential tumor target for antibody-based cancer therapy. CD40 is also expressed on a majority of bladder cancers and a significant percentage of other solid tumors, including head and neck cancers, renal cell carcinomas, ovarian and lung cancer.

Anti-CD40 antibodies and their uses for treating B cell hematologic malignancies have been described. See, e.g., U.S. Pat. Nos. 6,946,129; 6,843,989; 6,838,261; WO 2000/075348; US-2002-0197256; WO 2006/128103; and WO 2007/075326. It has been shown that a humanized anti-CD40 antibody induces growth inhibition and apoptosis of CD40-positive cells in a subset of hematologic tumor cell lines through direct signal transduction. WO 2006/128103; WO 2007/075326. Furthermore, the humanized anti-CD40 antibody kills tumor cells via immune effector functions, including antibody-dependent cellular cytotoxicity (ADCC) and antibody-dependent cellular phagocytosis (ADCP). In vivo, using xenograft models of multiple myeloma (MM) and non-Hodgkin's lymphoma (NHL), the anti-CD40 antibody suppresses tumor growth and improves survival in severe combined immunodeficient (SCID) mice. Comparison of the anti-CD40 antibody to rituximab (Genentech, Inc.) in several models revealed anti-tumor activity of the anti-CD40 antibody was at least as effective as rituximab.

Seattle Genetics initiated Phase I clinical trials in 2004 with the humanized anti-CD40 antibody in a single agent multi-dose trial in patients with relapsed and refractory multiple myeloma (MM). Subsequently, Phase I trials were initiated in patients with relapsed non-Hodgkin's lymphoma (NHL) and chronic lymphocytic lymphoma (CLL). The results from these Phase I trials showed evidence for anti-tumor activity in myeloma patients with stable disease and decreased M-protein, NHL patients with partial and complete responses, and CLL patients with stable disease. A phase II trial of the anti-CD40 antibody in relapsed diffuse large B cell lymphoma (DLBCL) was initiated in December 2006.

Although it has been shown anti-CD40 antibodies can induce growth inhibition and apoptosis of CD40-positive cells and may have anti-tumor activity in various types of B cell lymphoma patients, not all B lymphoma cells are sensitive to anti-CD40 antibody mediated cell death. There remains a need to identify one or more predictive markers for the responsiveness of B-cell lymphoma patients to anti-CD40 antibody therapy.

All references cited herein, including patent applications and publications, are incorporated by reference in their entirety.

SUMMARY OF THE INVENTION

The invention provides methods and compositions for predicting, assessing or aiding assessment of responsiveness of a subject having a type of B-cell lymphoma to treatment with an anti-CD40 antibody.

In one aspect, the invention provides methods for assessing or aiding assessment of responsiveness of a subject having a B-cell lymphoma to treatment with an anti-CD40 antibody, comprising comparing a measured expression level of at least one marker gene in any of Tables 2-4, 6, 7 and 13 in a B-cell lymphoma sample from the subject to a reference level.

In another aspect, the invention provides methods for predicting responsiveness or monitoring treatment/responsiveness to an anti-CD40 antibody treatment in a subject having a B-cell lymphoma, comprising comparing a measured expression level of at least one marker gene in any of Tables 2-4, 6, 7 and 13 in a B-cell lymphoma sample from the subject to a reference level.

In another aspect, the invention provides methods for predicting, assessing or aiding assessment of responsiveness of a subject having a B-cell lymphoma to an anti-CD40 antibody treatment, comprising the steps of: (a) measuring expression level of one or more marker genes in a sample comprising B lymphoma cells obtained from said subject, wherein said one or more marker genes are selected from the group consisting of IFITM1, CD40, RGS13, VNN2, LMO2, CD79B, CD22, BTG2, IGF1R, CD44, CTSC, EPDR1, UAP1, and PUS7; (b) predicting whether the subject is likely to respond to the anti-CD40 antibody treatment based on the measured expression level of said one or more marker genes from step (a). In some embodiments, expression levels of at least two, at least three, at least four, at least five, at least six, at least seven, at least eight, at least nine, at least ten, at least eleven, at least twelve, at least thirteen, or fourteen maker genes from the group are measured and used for the prediction, assessment, or aiding assessment. In some embodiments, the prediction, assessment, or aiding assessment is determined by comparing the measured expression level of one or more marker genes to a reference level. In some embodiments, a reference level is a value or a range determined based on the measured expression level of the corresponding marker gene in samples comprising the B lymphoma cells from subjects having tumor volume increased or decreased after the anti-CD40 antibody treatment.

In another aspect, the invention provides methods preparing a personalized genomics profile for a subject having B-cell lymphoma comprising the steps of: (a) determining expression level of one or more marker genes selected from the group consisting of IFITM1, CD40, RGS13, VNN2, LMO2, CD79B, CD22, BTG2, IGF1R, CD44, CTSC, EPDR1, UAP1, PUS7, and BCL6 in a sample comprising B lymphoma cells obtained from the subject; and (b) generating a report summarizing the expression level of one or more marker genes obtained in step (a). In some embodiments, expression levels of at least two, at least three, at least four, at least five, at least six, at least seven, at least eight, at least nine, at least ten, at least eleven, at least twelve, at least thirteen, at least fourteen, or fifteen maker genes from the group are measured and used for the generating the report for the personalized genomics profile. In some embodiments, the report includes a recommendation for an anti-CD40 antibody treatment for the subject. In some embodiments, the recommendation is determined by comparing the measured expression level of the marker genes to a reference level. In some embodiments, a reference level is a value or a range determined based on the measured expression level of the corresponding marker gene in samples comprising the B lymphoma cells from subjects having tumor volume increased or decreased after the anti-CD40 antibody treatment.

In another aspect, the invention provides methods for predicting, assessing or aiding assessment of responsiveness of a subject having a B-cell lymphoma to an anti-CD40 antibody treatment, comprising the steps of: (a) measuring expression level at least two marker genes selected from the group consisting of IFITM1, CD40, RGS13, VNN2, LMO2, CD79B, CD22, BTG2, IGF1R, CD44, CTSC, EPDR1, UAP1, and PUS7 in a sample comprising B lymphoma cells from the subject; (b) calculating sensitivity index value (SI) based on the measured expression level of the marker genes in step (a) by the following equation:

$$SI = \sum_{j=1}^{p} \beta_j \frac{x_j - \hat{\mu}_j}{\sqrt{\hat{\sigma}_j^2}}$$

wherein expression level of at least one marker gene having a positive correlation value and at least one marker gene having a negative correlation value shown in Table 13 are measured;
wherein (i) $\beta^j$ is the coefficient value for each marker genes measured; (ii) p is the number of marker genes measured; (iii) $x_j$ is transformed, normalized expression level for the sample from the subject for expression level of each marker measured; and (iv) $\mu_j$ and $\sigma_j$ are means and standard deviations for each marker gene measured; wherein $\beta_j$, $\mu_j$ and $\sigma_j$ are determined from patient samples comprising the B lymphoma cells. In some embodiments, a value equals or greater than zero for the sensitivity index indicates that the subject is likely to respond the anti-CD40 antibody treatment, or wherein a value less than zero for the sensitivity index indicates that the subject is less likely to respond the anti-CD40 antibody treatment. In some embodiments, the expression level of at least three, at least four, at least five, at least six, at least seven, at least eight, at least nine, at least ten, at least eleven, at least twelve, at least thirteen, or fourteen marker genes are measured and used for the sensitivity index calculation. In some embodiments, the expression level of IFITM1, RGS13, CD79B, CD22, BTG2, CD44, EPDR1, and UAP1 are measured and used for the sensitivity index calculation.

In another aspect, the invention provides methods for treating a subject having a B-cell lymphoma, comprising administering an effective amount of the an anti-CD40 antibody to the subject, wherein the responsiveness of the B-cell lymphoma in the subject has been assessed by the methods described herein. In another aspect, the invention provides methods for treating a subject having a B-cell lymphoma, comprising a) selecting a subject for an anti-CD40 antibody treatment by comparing a measured expression level of at least one marker gene in any of Tables 2-4, 6, 7 and 13 in a B-cell lymphoma sample from the subject to a reference level to assess if the B-cell lymphoma in the subject is suitable for the anti-CD40 antibody treatment; and administering an effective amount of the anti-CD40 antibody to the subject.

In some embodiments, the reference level is a measured expression level of one or more reference genes in Table 8 or Table 9 in the B-cell lymphoma sample from the subject.

In some embodiments, the reference level is a measured expression level of the marker gene in a different B-cell lymphoma sample. In some embodiments, the different B cell lymphoma sample comprises B lymphoma cells that are resistant to an anti-CD40 antibody induced cell death.

In some embodiments, the measured expression level of the marker gene and/or the reference level are normalized.

In some embodiments, measured expression levels of at least two, at least five, at least ten, at least fifteen, or at least twenty genes in any of Tables 2-4, 6, 7 and 13 in the B-cell lymphoma sample from the subject are compared to one or more reference levels.

In some embodiments, the expression level is measured by detecting mRNA expression (e.g., real time quantitative reverse transcription PCR (qRT-PCR)) and/or by detecting protein expression (e.g., immunohistochemistry (IHC)).

In some embodiments, the marker genes measured comprise one or more CD40 ligand downregulated genes (e.g., VNN2, MEF2C, LTB, KCNN3, NCF1, BCL6, IGJ, ELTI1902, PNOC, CSF2RB, and POU2AF1). In some embodiments, the marker genes measured comprise one or more genes in the B-cell receptor signaling pathway (e.g., CD22, RGS13, and MEF2B).

In some embodiments, expression levels of at least one, at least two, at least three, at least four, at least five, at least six, at least seven, at least eight, at least nine, at least ten, at least eleven, at least twelve, at least thirteen, or fourteen genes selected from the group consisting of VNN2, MEF2C, LTB, KCNN3, NCF1, BCL6, IGJ, ELTI1902, PNOC, CSF2RB, POU2AF1, CD22, RGS13, and MEF2B in the B-cell lymphoma sample from the subject are compared to one or more reference levels.

In some embodiments, expression levels of one or more gene pairs selected from the group consisting of VNN2 and EPDR1, RGS13 and EPDR1, CD22 and EPDR1, LRRC8A and PRPSAP2, CD40 and IGF1R, IFITM1 and BTG2, SMN1 and LMO2, PRKCA and YIPF3 in a the B-cell lymphoma sample are compared. In some embodiments, expression levels are compared between one or more gene pairs VNN2 and EPDR1, RGS13 and EPDR1, CD22 and EPDR1, LRRC8A and PRPSAP2, CD40 and IGF1R, IFITM1 and BTG2, SMN1 and LMO2, PRKCA and YIPF3 in the B-cell lymphoma sample, and sensitivity index calculated as the sum of signed t-scores for log 2-scale expression of the gene pairs is used to assess responsiveness of the B-cell lymphoma to an anti-CD40 antibody treatment.

In some embodiments, the B-cell lymphoma is non-Hodgkin's lymphoma (NHL), including, but is not limited to, follicular lymphoma, relapsed follicular lymphoma, small lymphocytic lymphoma, mantle cell lymphoma, marginal zone lymphoma, lymphoplasmacytic lymphoma, mycosis fungoides/Sezary syndrome, splenic marginal zone lymphoma, and diffuse large B-cell lymphoma. In some embodiments, the B-cell lymphoma is selected from the group consisting of indolent lymphoma, aggressive lymphoma, and highly aggressive lymphoma.

In a further aspect, the invention provides kits comprising reagents for measuring expression levels of at least one marker gene in any of Tables 2-4, 6, 7 and 13. In some embodiments, the kits comprise at least a pair of primers for amplifying by PCR at least one marker gene in any of Tables 2-4, 6, 7 and 13. For example, forward and reverse primers shown in Table 10 may be used. The kits may further comprise a pair of primers for amplifying a reference gene in Table 8. The kits may further comprise a surface having attached thereof probes for detecting the amplified gene products, such as a microarray and the invention contemplates and includes such surfaces. In some embodiments, the kits comprise at least a pair of primers and a probe for detecting expression level of one marker gene in any of Tables 2-4, 6, 7 and 13 by qRT-PCR. The kits may further comprise a pair of primers and a probe for detecting expression level of a reference gene in Table 8 by qRT-PCR. For example, primer and probe sets shown in Table 10 may be used for detection expression level of genes by qRT-PCR. In some embodiments, the kits comprise one or more antibodies that specifically recognize one or more proteins encoded by the marker gene. The kits may further comprise other reagents and/or instructions for carrying out any of the methods described herein.

It is to be understood that one, some, or all of the properties of the various embodiments described herein may be combined to form other embodiments of the present invention. These and other aspects of the invention will become apparent to one of skill in the art.

BRIEF DESCRIPTION OF THE FIGURES

FIGS. 6-1 to 6-35. Gene bank sequences for genes listed in Table 7 and Table 10. Nucleic acid sequences encoding mRNA of VNN2 (FIG. 6-1: SEQ ID NO:258), RGS13 (FIG. 6-2: SEQ ID NO:259), CD22 (FIGS. 6-3 and 6-4: SEQ ID NO:260), LRRC8A (FIG. 6-5: SEQ ID NO:261), CD40 (FIG. 6-6: SEQ ID NO:262), IFITM1 (FIG. 6-7: SEQ ID NO:263), PRKCA (FIGS. 6-8 to 6-10: SEQ ID NO:264), BCL6 (FIGS. 6-11 and 6-12: SEQ ID NO:265), EPDR1 (FIG. 6-13: SEQ ID NO:266), PRPSAP2 (FIG. 6-14: SEQ ID NO:267), IGF1R (FIGS. 6-15 to 6-18: SEQ ID NO:268), BTG2 (FIGS. 6-19 and 6-20: SEQ ID NO:269), LMO2 (FIG. 6-21: SEQ ID NO:270), YIPF3 (FIG. 6-22: SEQ ID NO:271), SMN1 (FIG. 6-23: SEQ ID NO:272), CD79B (FIG. 6-24: SEQ ID NO:273), CD44 (FIGS. 6-25 and 6-26: SEQ ID NO:274), CTSC (FIG. 6-27: SEQ ID NO:275), UAP1 (FIG. 6-28: SEQ ID NO:276), PUS7 (FIGS. 6-29 and 6-30: SEQ ID NO:277), RGS13 (FIG. 6-31: SEQ ID NO:278), CD22 (FIGS. 6-32 and 6-33: SEQ ID NO:279), SMN1 (FIG. 6-34: SEQ ID NO:280), and YIPF3 (FIG. 6-35: SEQ ID NO:281).

FIG. 7. Association of multivariate sensitivity index and percent change in tumor sum of the product of diameters (SPD) measurements for 21 patients in Clinical Trial 001. SPD percent change is determined by comparing the smallest post-baseline SPD to baseline SPD. Positive change indicates tumor volume increases, and negative change indicates tumor volume decreases. Weights (coefficients) used for the sensitivity index calculation are shown in Table 14. Larger multivariate sensitivity index values are associated with SPD decreases post-baseline (Sperman's Rho=−0.58; P=0.006).

FIG. 8. Association of BCL6 expression and percent change in SPD measurements for 26 patients with DLBCL. SPD percent change is determined by comparing the smallest post-baseline SPD to baseline SPD. Positive change indicates tumor volume increases, and negative change indicates tumor volume decreases.

DETAILED DESCRIPTION

Figure 1:
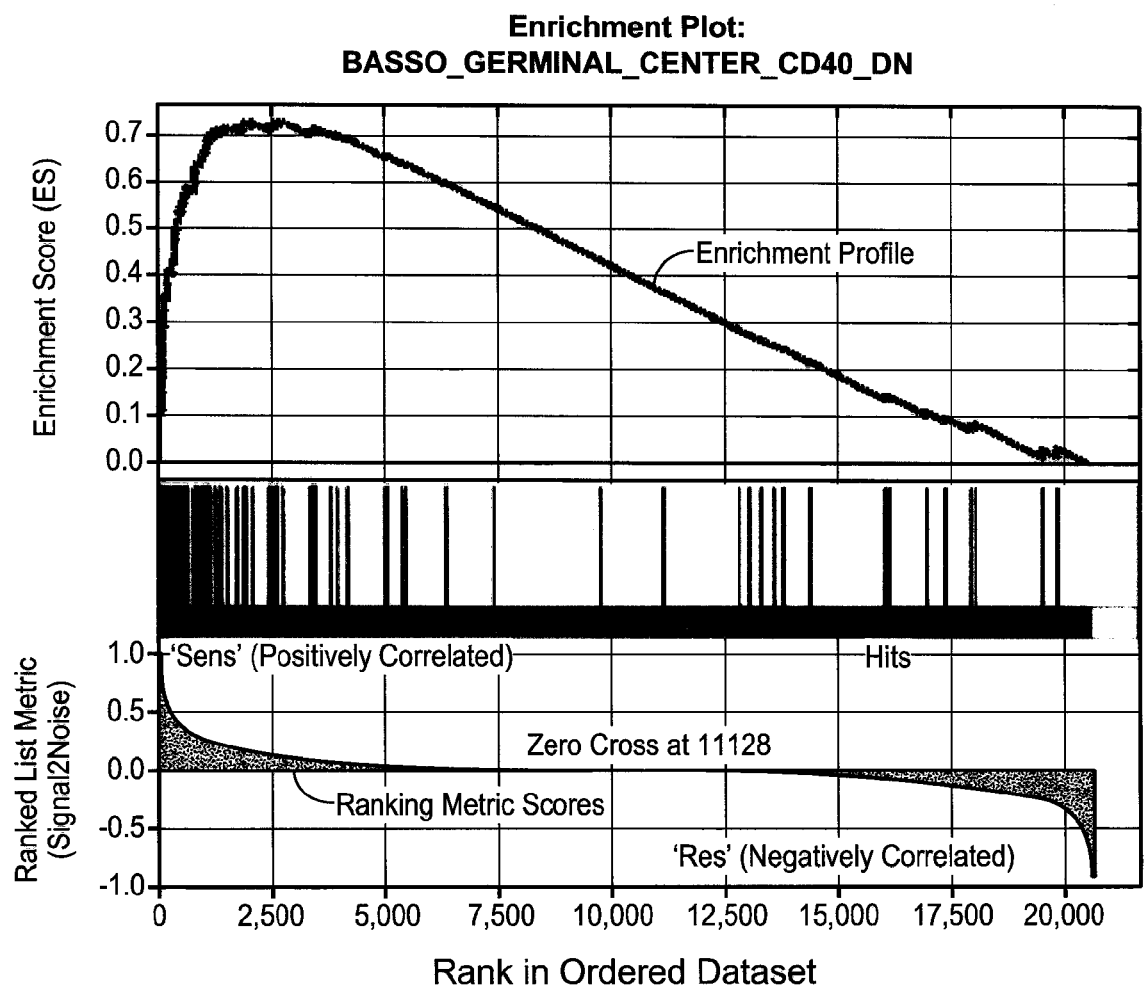
FIG. 1. Enrichment plot of genes within BASSO_GERMINAL_CENTER_CD40_DN gene set. The upper plot represents the enrichment score distribution across the ranked genes from the moderated t-test (Table 2). The lower plot displays the distribution of the enrichment with respect to a ranked list metric known as signal2noice. Overall, these plots clearly show that the gene set is strongly enriched within anti-CD40 Ab.1 sensitive cells.

The present invention is based on the discovery that certain genes (e.g., genes shown in Tables 2-4, 6, 7 and 13) are differentially expressed between B lymphoma cells that are sensitive to anti-CD40 antibody induced cell death and B lymphoma cells that are resistant to anti-CD40 induced cell death. Data from clinical trials described in Example 2 indicate that the expression level of the fourteen genes shown in Table 13 is highly associated with responsiveness to anti-CD40 Ab.1 treatment. Some of the differentially expressed genes between sensitive B lymphoma cells and resistant B lymphoma cells are the CD40 ligand downregulated pathway genes; and some are in the B-cell receptor signaling pathway. Accordingly, expression levels of one or more of these differentially expressed genes can be used for assessing or aiding assessment of responsiveness of a subject having a B-cell lymphoma to treatment with anti-CD40 antibodies, predicting responsiveness of the subject to treatment with anti-CD40 antibodies, and monitoring treatment/responsiveness in the subject.

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

B. Definitions

As used herein, the terms "a subject having a B-cell lymphoma" and "B-cell lymphoma patient" refer to a subject who has been diagnosed with a type of B-cell lymphoma or has been given a probable diagnosis of a type of B-cell lymphoma.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimes based on anti-CD40 antibodies.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

As used herein, a "B-cell lymphoma sample" or a "sample comprising B lymphoma cells" is a tissue or cell sample containing B lymphoma cells from a subject or a patient that have been diagnosed with a type of B-cell lymphoma.

As used herein, method for "aiding assessment" refers to methods that assist in making a clinical determination (e.g., responsiveness of a B-cell lymphoma to treatment with anti-CD40 antibodies), and may or may not be conclusive with respect to the definitive assessment.

A "subject" or an "individual" is a mammal, more preferably a human. Mammals include, but are not limited to, humans, primates, farm animal, sport animals, rodents, and pets (e.g., dogs and cats).

As used herein, a "reference value" can be an absolute value; a relative value; a value that has an upper and/or lower limit; a range of values; an average value; a median value; a mean value; or a value as compared to a particular control or baseline value.

The term "array" or "microarray", as used herein refers to an ordered arrangement of hybridizable array elements, such as polynucleotide probes (e.g., oligonucleotides) and antibodies, on a substrate. The substrate can be a solid substrate, such as a glass slide, or a semi-solid substrate, such as nitrocellulose membrane. The nucleotide sequences can be DNA, RNA, or any permutations thereof.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

Expression/amount of a gene or biomarker in a first sample is at a level "greater than" the level in a second sample if the expression level/amount of the gene or biomarker in the first sample is at least about 1.5×, 1.75×, 2×, 3×, 4×, 5×, 6×, 7×, 8×, 9× or 10× the expression level/amount of the gene or biomarker in the second sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target. A "pair of primers" refer to a 5' primer and a 3' primer that can be used to amplify a portion of a specific target gene.

The term "3'" generally refers to a region or position in a polynucleotide or oligonucleotide 3' (downstream) from another region or position in the same polynucleotide or oligonucleotide. The term "5'" generally refers to a region or position in a polynucleotide or oligonucleotide 5' (upstream) from another region or position in the same polynucleotide or oligonucleotide.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

"Detection" includes any means of detecting, including direct and indirect detection.

The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

The term "long-term" survival is used herein to refer to survival for at least 1 year, 5 years, 8 years, or 10 years following therapeutic treatment.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) relief, to some extent, of one or more symptoms associated with the disorder; (7) increase in the length of disease-free presentation following treatment; and/or (8) decreased mortality at a given point of time following treatment.

The term "antibody" is used in the broadest sense and specifically covers monoclonal antibodies (including full length monoclonal antibodies), multispecific antibodies (e.g., bispecific antibodies), and antibody fragments so long as they exhibit the desired biological activity or function.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816,567), phage display technologies (see, e.g., Clackson et al., *Nature,* 352:624-628 (1991); Marks et al., *J. Mol. Biol.,* 222: 581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806; 5,569,825; 5,591,669 (all of GenPharm); 5,545,807; WO 1997/17852; U.S. Pat. Nos. 5,545,807; 5,545,806; 5,569,825; 5,625,126; 5,633,425; and 5,661,016; Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); and Lonberg and Huszar, *Intern. Rev. Immunol.,* 13: 65-93 (1995).

The monoclonal antibodies herein specifically include "chimeric" antibodies. "Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the known techniques for making human antibodies. This definition of a human antibody specifically excludes a humanized antibody comprising non-human antigen-binding residues.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR/HVR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Treating" or "treatment" or "alleviation" refers to therapeutic treatment wherein the object is to slow down (lessen) if not cure the targeted pathologic condition or disorder or prevent recurrence of the condition. A subject is successfully "treated" for the B cell malignancy if, after receiving a therapeutic amount of a CD40 binding antibody, the subject shows observable and/or measurable reduction in or absence of one or more signs and symptoms of the particular disease. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In one criterion, the antibodies of the invention achieve >95% peripheral blood B cell depletion and the B cells return to 25% of baseline. In some embodiments, treatment with the anti-CD40 antibodies is effective to result in the cancer patients being progression-free in the cancer 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "housekeeping gene" refers to a group of genes that codes for proteins whose activities are essential for the maintenance of cell function. These genes are typically similarly expressed in all cell types.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

As used herein, "a", "an", and "the" can mean singular or plural (i.e., can mean one or more) unless indicated otherwise.

C. Methods of the Invention

The invention provides methods for assessing or aiding assessment of responsiveness of a subject having a B-cell lymphoma to treatment with an anti-CD40 antibody. The invention also provides methods for predicting responsiveness or monitoring treatment/responsiveness to an anti-CD40 antibody treatment in a subject having a B-cell lymphoma. The invention provides methods for selecting a subject having a B-cell lymphoma suitable for treatment with an anti-CD40 antibody and following up with an anti-CD40 antibody treatment. In some embodiments, the methods comprise measuring expression level of one or more marker genes in any of Tables 2-4, 6, 7, and 13 in a sample comprising B lymphoma cells obtained from the subject; and predicting, assessing, or aiding assessment of responsiveness of the subject to an anti-CD40 antibody treatment based on the measure expression level of said one or more marker genes. In some embodiments, the methods comprise comparing a measured expression level of at least one marker gene in any of Tables 2-4, 6, 7, and 13 in a B-cell lymphoma sample from the subject to a reference level for the respective marker gene.

The methods of the present invention are useful for clinicians to identify patients with B-cell lymphoma for treatment with an anti-CD40 antibody, aiding in patient selection during the course of development of anti-CD40 antibody therapy, prediction of likelihood of success when treating an individual patient with a particular treatment regimen, in assessing and monitoring disease progression, in monitoring treatment efficacy, and in determining prognosis for individual patients. Any of these embodiments are included in this invention.

In some embodiments, the B-cell lymphoma is non-Hodgkin's lymphoma (NHL), including, but is not limited to, follicular lymphoma, relapsed follicular lymphoma, small lymphocytic lymphoma, mantle cell lymphoma, marginal zone lymphoma, lymphoplasmacytic lymphoma, mycosis fungoides/Sezary syndrome, splenic marginal zone lymphoma, and diffuse large B-cell lymphoma.

In some embodiments, the B-cell lymphoma is indolent. In some embodiments, the B-cell lymphoma is aggressive. In some embodiments, the B-cell lymphoma is highly aggressive. In some embodiments, the indolent B-cell lymphoma is follicular lymphoma, marginal zone lymphoma, or small lymphocytic lymphoma. In some embodiments, the indolent B-cell lymphoma is follicular lymphoma.

Marker Genes

The expression level of one or more of the marker genes in a B-cell lymphoma sample relative a reference level may be used in the methods of the invention, such as to predict, assess or aid assessment of responsiveness of the B-cell lymphoma to treatment with an anti-CD40 antibody.

Genes that are differentially expressed (statistically significantly increased or decreased) in anti-CD40 antibody sensitive NHL cell lines as compared to resistant NHL cell lines are shown in Tables 2-4, 6 and 7. "Anti-CD40 antibody sensitive cells" are cells having an IC25 value less than 0.4 µg/ml in reduction of cell viability by an anti-CD40 antibody tested as described in Example 1. "Anti-CD40 resistant cells" are cells having an IC25 value greater than 1 µg/ml in reduction in cell viability as tested in Example 1. Some of the genes in Tables 2-4, 6 and 7 are in the CD40 ligand downregulated pathway (for example, VNN2, MEF2C, LTB, KCNN3, NCF1, BCL6, IGJ, ELTI1902, PNOC, CSF2RB, and POU2AF1); and some of the genes in the tables are in the B-cell receptor signaling pathway (for example, CD22, RGS13, and MEF2B). Further, association of the expression level of IFITM1, CD40, RGS13, VNN2, LMO2, CD79B, CD22, BTG2, IGF1R, CD44, CTSC, EPDR1, UAP1, and PUS7 (Table 13) has been confirmed by clinical trials described in Example 2. Expression levels of one or more of these genes are used in the methods of the invention. In some embodiments, expression levels of at least two, at least three, at least four, at least five, at least six, at least seven, at least eight, at least nine, at least ten, at least eleven, at least twelve, at least thirteen, at least fourteen, at least fifteen, at least twenty, at least twenty five, or at least thirty genes are used in the methods of the invention.

In some embodiments, expression levels of one or more of genes selected from the group consisting of VNN2, MEF2C, LTB, KCNN3, NCF1, BCL6, IGJ, ELTI1902, PNOC, CSF2RB, POU2AF1, CD22, RGS13, and MEF2B are measured and/or used. In some embodiments, expression levels of one or more of genes selected from the group consisting of IFITM1, CD40, RGS13, VNN2, LMO2, CD79B, CD22, BTG2, IGF1R, CD44, CTSC, EPDR1, UAP1, and PUS7 are measured and/or used. In some embodiments, expression levels of at least two, at least three, at least four, at least five, at least six, at least seven, at least eight, at least nine, at least ten, at least eleven, at least twelve, at least thirteen, or fourteen of these genes are measured and/or used. In some embodiments, expression levels of CD22, CD40, and BCL6 are measured and/or used. In some embodiments, expression levels of CD40, RGS13, CD22, BTG2, IGF1R, and CD44 are measured and/or used. In some embodiments, expression levels of IFITM1, CD40, RGS13, VNN2, LMO2, CD79B, CD22, BTG2, IGF1R, CD44, CTSC, EPDR1, UAP1, and PUS7 are measured and/or used. In some embodiments, expression levels of at least one, at least two, at least three, at least four, at least five, at least six, at least seven, at least eight, at least nine, at least ten, at least eleven, at least twelve, at least thirteen, at least fourteen, or fifteen of genes in Table 7 or Table 13 are measured and/or used.

Genes (including sequences) identified in Tables 2-4, 6, 7 and 13 are known in the art. For example, the examples of Gene Bank accession numbers for human genes are VNN2 (NM_004665; NM_078488; AJ132100; D89974; BC064641; CR609799; BC126145; BC126147; and AB026705); RGS13 (NM_002927; NM_144766; BT006929; BC056866; AY562947; CR536532; CR610389; CR599001; BC016667; AF493935; BC036950; and AF030107); CD22 (NM_001771; AK026467; BC109306; BC109307; AK225694; AK225625; X52785; and X59350); LRRC8A (AY143166; BC051322; AK123611; AY358286; NM_019594; XM_026998; AK001199; AB037858; CR619692; CR619448; AK024649; BC000775; AK027495; and AK074723); CD40 (NM_001250; NM_152854; BC064518; AY225405; CR619622; CR608994; CR605787; AB209660; AK222896; AJ300189; BT019901; and BC012419); IFITM1 (NM_003641; BC000897; BT007173; BT009859; CR456894; CR541874; CR604902; X57351; X84958; NM_006435; BC009696; X02490; and J04164); SMN1 (NM_000344; BC062723; CR611445; CR593735; BC000908; NM_022874; BC015308; and U18423); PRKCA (NM_002737; AB209475; BC109274; BC109273; AF035594; BC053321; BX648954; AK125425; BC062759; BC071767; BC103691; BC101403; BC107592; AY633609; BC122530; BC015855; AF086287; AF035595; M22199; and X52479); EPDR1 (DQ914439; AY027862; NM_017549; AJ250475; AF202051; CR624676; CR596656; NM_016616; BC000686; BC018299; AF305596; and BC036816); PRPSAP2 (NM_002767; AB007851; BX648850; AK126398; CR457082; BC101672; BC101670; and BC106050); IGF1R(NM_000875; NM_015883; AY429545; CR624013; BC078157; BC088377; BC107089; BC111046; BC113610; BC113612; BC010607; X04434 M24599; and U09023); BTG2 (NM_006763; CR606002; CR604962; CR595352; CR591042; BC105948; BC105949; U72649; and Y09943); LMO2 (BC042426; NM_005574; BC073973; AK127915; CR625714; CR614368; CR604507; AF257211; BC034041; BC035607; and X61118); YIPF3 (AL050274; AK000946; CR533541; CR623137; CR622890; CR622532; CR621993; CR619816; CR619437; CR619054; CR618212; CR616987; CR616384; CR615623; CR615153; CR615118; CR612415; CR611748; CR611260; CR610983; CR610470; CR607768; CR606024; CR603408; CR603202; CR602267; CR601987; CR599615; CR598162; CR597677; CR596581; CR596249; CR595236; CR592266; CR590752; CR590349; NM_015388; AK021433; AK021655; AK022757; BC019297; and AF162672); and BCL6 (NM_001706; NM_138931; BX649185; U00115; BC142705; BC146796; BC150184; AL713713; AK090890; AL832990; and Z21943).

The nucleic acid sequence of some of the genes referenced in Tables 2-4, 6, 7 and 13 are shown in FIG. 6 (6-1 to 6-35).

Reference Levels

The measured expression level of one or more marker genes in a B-cell lymphoma sample is compared to a reference level. In some embodiments, the reference level is the expression level of a gene the expression level of which does not change (does not change significantly) among different type of B-cell lymphomas, for example, between B-cell lymphoma sensitive to anti-CD40 antibody and B-cell lymphoma resistant to anti-CD40 antibody. In some embodiments, expression levels of one or more housekeeping genes shown in Table 8 are used as reference levels. In some embodiments, expression levels of one or more housekeeping genes shown in Table 9 are used as reference levels.

In some embodiments, the measured expression level of the marker gene is normalized using the reference level. In some embodiments, the normalized expression level of the marker gene is calculated as a ratio of or difference between the marker gene and reference expression levels, on the original or on a log scale, respectively.

The reference genes in Table 8 and Table 9 were selected as specific normalizing counterparts to the marker genes in Table 4. Reference genes were selected for high mean expression and low variance in B cell lymphoma samples. In addition, reference genes were selected to have similar variance between replicated expression measurements of individual cell lines relative to variance between expression measurements of biologically distinct cell lines. In addition, reference genes were selected to have low statistical association with one or more markers in Table 4.

In some embodiments, the reference level is a measured expression level of the marker gene in a different B-cell lymphoma sample. In some embodiments, the different B cell lymphoma sample comprises B lymphoma cells that are resistant to an anti-CD40 antibody induced cell death.

In some embodiments, the reference level is determined based on the expression level of the corresponding marker gene in samples comprising B lymphoma cells from subjects having tumor volume increased after the anti-CD40 antibody treatment and/or having tumor volume decreased after the anti-CD40 antibody treatment. In some embodiments, the samples from subjects for reference level determination comprise the same type of B lymphoma cells as the sample from the subject whose responsiveness to the anti-CD40 antibody treatment is predicted or assessed. In some embodiments, the same method (e.g., qRT-PCR) and/or reagents (e.g., primers and probes) are used for measuring expression level of the marker genes in the sample and measuring expression level of the corresponding marker genes in the reference samples.

TABLE 8

| Probe | symb | VarW. VarB | mean | var | vscr | vscr. rank | P. Min | SCR. anti-CD40. Ab.1 | IC25. anti-CD40. Ab.1 | GCB. anti-CD40. Ab.1 | SCR EXT. anti-CD40. Ab.1 |
|---|---|---|---|---|---|---|---|---|---|---|---|
| 202521_at | CTCF | 0.02 | 10.61 | 0.19 | −3.81 | 5079 | 0.020543 | 0.896744 | 0.758931 | 0.927787 | 0.285815 |
| 201949_x_at | CAPZB | 0.04 | 11.78 | 0.33 | 7.92 | 300 | 0.363476 | 0.5627 | 0.9554 | 0.3785 | 0.3635 |
| 201588_at | TXNL1 | 0.01 | 13.00 | 0.29 | −2.39 | 3182 | 2.49E−09 | 0.2422 | 0.5231 | 0.2540 | 0.1104 |
| 201070_x_at | SF3B1 | 0.20 | 9.46 | 0.23 | −3.78 | 5023 | 0.089689 | 0.1715 | 0.1517 | 0.2230 | 0.5294 |
| 209180_at | RABGGTB | 0.23 | 10.80 | 0.40 | −2.89 | 3693 | 0.001233 | 0.9074 | 0.9214 | 0.7339 | 0.1495 |
| AFFX-HSAC07/X00351_5_at | ACTB | 0.03 | 14.02 | 0.53 | 0.48 | 2039 | 0.144577 | 0.6074 | 0.9584 | 0.2415 | 0.4461 |
| 201891_s_at | B2M | 0.13 | 14.67 | 0.22 | 1.98 | 1919 | 0.010118 | 0.2646 | 0.1011 | 0.4501 | 0.0392 |
| FFX-HUMGAPDH/M33197_5_at | GAPDH | 0.59 | 14.78 | 0.04 | 2.95 | 1850 | 0.000944 | 0.7089 | 0.7244 | 0.9014 | 0.3096 |
| 202605_at | GUSB | 0.05 | 10.52 | 0.65 | −3.44 | 4415 | 6.73E−05 | 0.0096 | 0.0104 | 0.0053 | 0.0885 |
| 202854_at | HPRT1 | 0.03 | 12.92 | 0.30 | −1.90 | 2773 | 2.64E−05 | 0.1297 | 0.2069 | 0.0532 | 0.5541 |
| 200737_at | PGK1 | 0.02 | 12.20 | 0.46 | −2.75 | 3533 | 0.000307 | 0.0777 | 0.3535 | 0.0719 | 0.6473 |
| 201293_x_at | PPIA | 0.60 | 14.99 | 0.02 | 3.98 | 1731 | 0.065694 | 0.1406 | 0.3579 | 0.1735 | 0.6190 |
| 201033_x_at | RPLP0 | 0.62 | 15.20 | 0.01 | 4.16 | 1709 | 0.066741 | 0.0667 | 0.1150 | 0.1081 | 0.7451 |
| 203135_at | TBP | 0.06 | 8.29 | 0.19 | −16.66 | 21417 | 0.001289 | 0.6978 | 0.7904 | 0.8630 | 0.2849 |
| 207332_s_at | TFRC | 0.06 | 12.50 | 1.16 | −0.82 | 2311 | 5.66E−06 | 0.1391 | 0.0963 | 0.1051 | 0.1710 |
| 226131_s_at | RPS16 | 0.68 | 15.60 | 0.01 | 15.24 | 1 | 0.4182 | 0.6946 | 0.6783 | 0.9425 | 0.4182 |
| 1553567_s_at | ATP13A5 | 0.53 | 15.77 | 0.04 | 15.10 | 2 | 0.2744 | 0.3205 | 0.5881 | 0.2744 | 0.8039 |
| 213477_x_at | EEF1A1 | 0.80 | 15.71 | 0.02 | 14.94 | 3 | 0.2716 | 0.3490 | 0.5611 | 0.2716 | 0.9425 |
| 229563_s_at | RPL10A | 0.65 | 15.08 | 0.02 | 14.64 | 4 | 0.2266 | 0.3258 | 0.2266 | 0.6668 | 0.7720 |
| 203107_x_at | RPS2 | 0.75 | 15.37 | 0.01 | 14.55 | 5 | 0.2635 | 0.4033 | 0.5834 | 0.2635 | 0.6664 |
| 213614_x_at | EEF1A1 | 0.51 | 16.11 | 0.02 | 14.47 | 6 | 0.2273 | 0.4168 | 0.5721 | 0.2273 | 0.6765 |
| 204892_x_at | EEF1A1 | 0.55 | 15.29 | 0.02 | 14.46 | 7 | 0.3353 | 0.7883 | 0.7755 | 0.5296 | 0.7598 |
| 212391_x_at | RPS3A | 0.78 | 15.00 | 0.01 | 14.34 | 8 | 0.2519 | 0.3159 | 0.6319 | 0.2519 | 0.3350 |
| 211542_x_at | RPS10 | 0.59 | 15.11 | 0.02 | 14.31 | 9 | 0.2000 | 0.8313 | 0.9604 | 0.7117 | 0.7029 |
| 213583_x_at | EEF1A1 | 0.66 | 15.26 | 0.04 | 14.29 | 10 | 0.2172 | 0.4132 | 0.7604 | 0.2172 | 0.8064 |
| 200819_s_at | RPS15 | 0.54 | 15.00 | 0.05 | 13.99 | 11 | 0.3700 | 0.6401 | 0.7339 | 0.8220 | 0.7939 |
| 200095_x_at | FLJ20294 | 0.60 | 15.29 | 0.02 | 13.98 | 12 | 0.3400 | 0.7334 | 0.5003 | 0.4045 | 0.4757 |
| 224585_x_at | ACTG1 | 0.49 | 14.73 | 0.06 | 13.96 | 13 | 0.4788 | 0.9612 | 0.7590 | 0.4788 | 0.5097 |
| 213414_s_at | RPS19 | 0.49 | 15.19 | 0.02 | 13.95 | 14 | 0.3134 | 0.6110 | 0.5909 | 0.3134 | 0.9180 |
| 1553538_s_at | NA | 0.33 | 15.24 | 0.24 | 13.94 | 15 | 0.5473 | 0.6181 | 0.5473 | 0.9966 | 0.9360 |
| 200032_s_at | RPL9 | 0.61 | 15.30 | 0.01 | 13.80 | 16 | 0.2652 | 0.7969 | 0.6658 | 0.8910 | 0.9033 |
| 200063_s_at | NPM1 | 0.68 | 15.34 | 0.02 | 13.78 | 17 | 0.2634 | 0.6557 | 0.7122 | 0.2634 | 0.9201 |
| 213890_x_at | RPS16 | 0.42 | 15.02 | 0.01 | 13.68 | 18 | 0.2333 | 0.2936 | 0.2333 | 0.3297 | 0.2718 |
| 212734_x_at | RPL13 | 0.46 | 14.92 | 0.03 | 13.66 | 19 | 0.2300 | 0.8232 | 0.6720 | 0.4503 | 0.7004 |
| 211983_x_at | ACTG1 | 0.40 | 14.83 | 0.06 | 13.54 | 20 | 0.4100 | 0.9680 | 0.7211 | 0.4205 | 0.7919 |
| 213801_x_at | RPSA | 0.61 | 15.01 | 0.05 | 13.53 | 21 | 0.2661 | 0.4603 | 0.7140 | 0.2661 | 0.4003 |
| 202649_x_at | RPS19 | 0.33 | 15.03 | 0.03 | 13.44 | 22 | 0.3172 | 0.5861 | 0.5086 | 0.3172 | 0.9400 |
| 221607_x_at | ACTG1 | 0.41 | 14.73 | 0.06 | 13.38 | 23 | 0.2715 | 0.9680 | 0.6637 | 0.3927 | 0.6126 |
| 212988_x_at | ACTG1 | 0.45 | 14.53 | 0.06 | 13.31 | 24 | 0.3553 | 0.9075 | 0.6394 | 0.3553 | 0.7217 |
| 208929_x_at | RPL13 | 0.40 | 14.75 | 0.02 | 13.25 | 25 | 0.3500 | 0.3583 | 0.7912 | 0.9760 | 0.6997 |
| 200689_x_at | EEF1G | 0.64 | 14.25 | 0.03 | 13.21 | 26 | 0.2100 | 0.9324 | 0.8163 | 0.8508 | 0.3667 |
| 211345_x_at | EEF1G | 0.54 | 14.23 | 0.03 | 13.21 | 27 | 0.2200 | 0.9444 | 0.8022 | 0.7118 | 0.3901 |
| 211970_x_at | ACTG1 | 0.46 | 14.51 | 0.09 | 13.18 | 28 | 0.3072 | 0.7347 | 0.8427 | 0.7238 | 0.5534 |
| 211995_x_at | ACTG1 | 0.35 | 14.61 | 0.10 | 13.14 | 29 | 0.3981 | 0.5436 | 0.9959 | 0.9161 | 0.3981 |
| 200089_s_at | RPL4 | 0.29 | 15.28 | 0.04 | 13.09 | 30 | 0.2068 | 0.4500 | 0.6581 | 0.5132 | 0.5295 |
| 200024_at | RPS5 | 0.57 | 14.61 | 0.03 | 13.09 | 31 | 0.2000 | 0.7753 | 0.8060 | 0.5846 | 0.9469 |
| 201550_x_at | ACTG1 | 0.33 | 14.50 | 0.10 | 13.04 | 32 | 0.3356 | 0.5966 | 0.9624 | 0.8531 | 0.4378 |

TABLE 8-continued

| Probe | symb | VarW. VarB | mean | var | vscr | vscr. rank | P. Min | SCR. anti-CD40. Ab.1 | IC25. anti-CD40. Ab.1 | GCB. anti-CD40. Ab.1 | SCR EXT. anti-CD40. Ab.1 |
|---|---|---|---|---|---|---|---|---|---|---|---|
| AFFX-r2-P1-cre-3_at | NA | 0.28 | 15.23 | 0.12 | 13.00 | 33 | 0.4500 | 0.9518 | 0.5889 | 0.7244 | 0.8836 |
| 200003_s_at | RPL28 | 0.14 | 15.12 | 0.04 | 12.93 | 34 | 0.5687 | 0.9905 | 0.6582 | 0.9539 | 0.5687 |
| 212363_x_at | ACTG1 | 0.33 | 14.18 | 0.12 | 12.81 | 35 | 0.4219 | 0.6539 | 0.8152 | 0.8079 | 0.4254 |
| 221775_x_at | EVI1 | 0.28 | 14.55 | 0.05 | 12.78 | 36 | 0.2391 | 0.9589 | 0.8109 | 0.4979 | 0.8711 |
| 208768_x_at | RPL22 | 0.30 | 14.56 | 0.05 | 12.78 | 37 | 0.2858 | 0.9577 | 0.8867 | 0.4568 | 0.9964 |
| 212191_x_at | LOC388344 | 0.18 | 14.84 | 0.05 | 12.77 | 38 | 0.2500 | 0.9777 | 0.8542 | 0.3553 | 0.9844 |
| 200021_at | CFL1 | 0.50 | 13.77 | 0.02 | 12.77 | 39 | 0.2775 | 0.8529 | 0.8339 | 0.5283 | 0.2775 |
| 208517_x_at | BTF3 | 0.33 | 14.54 | 0.02 | 12.56 | 40 | 0.2513 | 0.7046 | 0.7417 | 0.9434 | 0.2954 |
| 211956_s_at | EIF1 | 0.16 | 15.12 | 0.08 | 12.50 | 41 | 0.2756 | 0.2756 | 0.3283 | 0.6567 | 0.4596 |
| 214351_x_at | RPL13 | 0.44 | 14.01 | 0.03 | 12.36 | 42 | 0.2703 | 0.4829 | 0.9230 | 0.9173 | 0.4119 |
| 224731_at | HMGB1 | 0.11 | 14.37 | 0.17 | 12.35 | 43 | 0.3496 | 0.4679 | 0.9363 | 0.4219 | 0.3496 |
| 234512_at | LOC388474 | 0.25 | 13.55 | 0.04 | 12.35 | 44 | 0.5910 | 0.9435 | 0.5910 | 0.9578 | 0.6021 |
| 220960_x_at | RPL22 | 0.28 | 14.20 | 0.02 | 12.28 | 45 | 0.5585 | 0.7556 | 0.8571 | 0.7995 | 0.9640 |
| 221791_s_at | CCDC72 | 0.45 | 14.33 | 0.03 | 12.22 | 46 | 0.2692 | 0.5460 | 0.8746 | 0.4059 | 0.2692 |
| 216438_s_at | TMSB4X | 0.04 | 15.34 | 1.15 | 12.02 | 47 | 0.2086 | 0.3130 | 0.2155 | 0.2086 | 0.8821 |
| 201030_at | LDHB | 0.22 | 14.68 | 0.05 | 11.91 | 48 | 0.3032 | 0.4740 | 0.8098 | 0.5684 | 0.3032 |
| AFFX-CreX-3_at | NA | 0.27 | 14.50 | 0.19 | 11.83 | 49 | 0.4700 | 0.9276 | 0.5873 | 0.7234 | 0.9267 |
| 200715_x_at | RPL13A | 0.26 | 13.87 | 0.12 | 11.70 | 50 | 0.3000 | 0.8556 | 0.3818 | 0.6143 | 0.4458 |
| AFFX-CreX-5_at | NA | 0.15 | 14.64 | 0.27 | 11.59 | 51 | 0.3900 | 0.9872 | 0.6546 | 0.5814 | 0.7754 |
| 222976_s_at | TPM3 | 0.04 | 14.13 | 0.09 | 11.54 | 52 | 0.3646 | 0.3786 | 0.7883 | 0.3646 | 0.5240 |
| 210466_s_at | SERBP1 | 0.52 | 13.90 | 0.07 | 11.51 | 53 | 0.2326 | 0.3230 | 0.2326 | 0.2545 | 0.8323 |
| 225413_at | USMG5 | 0.07 | 13.78 | 0.15 | 11.49 | 54 | 0.3239 | 0.9696 | 0.5515 | 0.8338 | 0.3239 |
| 221691_s_at | NPM1 | 0.10 | 15.00 | 0.07 | 11.44 | 55 | 0.5097 | 0.8965 | 0.7627 | 0.5097 | 0.7686 |
| 229353_s_at | NUCKS1 | 0.07 | 13.62 | 0.21 | 11.21 | 56 | 0.6703 | 0.7457 | 0.6703 | 0.7602 | 0.8020 |
| 1555730_a_at | CFL1 | 0.04 | 14.01 | 0.30 | 11.17 | 57 | 0.4996 | 0.9337 | 0.7560 | 0.4996 | 0.5768 |
| 200966_x_at | ALDOA | 0.09 | 14.02 | 0.11 | 11.09 | 58 | 0.2409 | 0.2409 | 0.5526 | 0.4352 | 0.8701 |
| 224654_at | DDX21 | 0.06 | 13.50 | 0.13 | 11.07 | 59 | 0.6759 | 0.8439 | 0.8720 | 0.7694 | 0.6759 |
| 224944_at | TMPO | 0.05 | 13.48 | 0.14 | 10.98 | 60 | 0.2455 | 0.3257 | 0.4478 | 0.3876 | 0.2455 |
| 222985_at | YWHAG | 0.04 | 13.53 | 0.15 | 10.86 | 61 | 0.3506 | 0.7800 | 0.3506 | 0.9581 | 0.9505 |
| 1555837_s_at | POLR2B | 0.07 | 13.18 | 0.16 | 10.85 | 62 | 0.3371 | 0.8399 | 0.3612 | 0.6857 | 0.3371 |
| 209026_x_at | TUBB | 0.07 | 13.60 | 0.24 | 10.73 | 63 | 0.2100 | 0.6957 | 0.4642 | 0.7072 | 0.3910 |
| 238199_x_at | LOC440552 | 0.56 | 11.52 | 0.17 | 10.69 | 64 | 0.2720 | 0.3736 | 0.9156 | 0.2720 | 0.6534 |
| 217807_s_at | GLTSCR2 | 0.07 | 13.62 | 0.19 | 10.61 | 65 | 0.5757 | 0.8314 | 0.7256 | 0.7767 | 0.5757 |
| 242131_at | LOC440552 | 0.53 | 11.20 | 0.10 | 10.42 | 66 | 0.5733 | 0.7746 | 0.5733 | 0.7302 | 0.9388 |
| 222980_at | RAB10 | 0.12 | 12.27 | 0.13 | 10.40 | 67 | 0.2461 | 0.7382 | 0.9132 | 0.2877 | 0.2461 |
| 234339_s_at | GLTSCR2 | 0.58 | 11.32 | 0.29 | 10.39 | 68 | 0.6277 | 0.7136 | 0.9772 | 0.8445 | 0.6277 |
| 1554678_s_at | HNRPDL | 0.04 | 13.21 | 0.22 | 10.39 | 69 | 0.3095 | 0.3381 | 0.3095 | 0.6767 | 0.5390 |
| 200893_at | SFRS10 | 0.12 | 13.68 | 0.06 | 10.38 | 70 | 0.3885 | 0.5944 | 0.8186 | 0.6001 | 0.3885 |
| 223105_s_at | TMEM14C | 0.02 | 13.54 | 0.16 | 10.35 | 71 | 0.6699 | 0.6699 | 0.8055 | 0.8667 | 0.9663 |
| 224579_at | SLC38A1 | 0.02 | 13.49 | 0.20 | 10.21 | 72 | 0.2496 | 0.7799 | 0.3541 | 0.3506 | 0.2496 |
| 1558678_s_at | MALAT1 | 0.16 | 12.46 | 0.89 | 10.21 | 73 | 0.4393 | 0.9362 | 0.8914 | 0.4393 | 0.9347 |
| 223096_at | NOP5/NOP58 | 0.03 | 13.04 | 0.13 | 10.13 | 74 | 0.6162 | 0.6964 | 0.8240 | 0.6162 | 0.6685 |
| 224567_x_at | MALAT1 | 0.11 | 12.50 | 0.69 | 10.10 | 75 | 0.4566 | 0.9218 | 0.9662 | 0.4566 | 0.7071 |
| 226385_s_at | C7orf30 | 0.03 | 12.99 | 0.26 | 10.02 | 76 | 0.6285 | 0.6285 | 0.9109 | 0.7478 | 0.8336 |
| 213011_s_at | TPI1 | 0.04 | 13.56 | 0.18 | 9.96 | 77 | 0.2442 | 0.3471 | 0.6334 | 0.5709 | 0.4333 |
| 225892_at | IREB2 | 0.10 | 12.08 | 0.21 | 9.94 | 78 | 0.4034 | 0.8084 | 0.9066 | 0.6860 | 0.4034 |
| 231896_s_at | DENR | 0.03 | 12.80 | 0.14 | 9.93 | 79 | 0.2977 | 0.6041 | 0.7701 | 0.2977 | 0.4713 |
| 201114_x_at | PSMA7 | 0.12 | 12.78 | 0.15 | 9.87 | 80 | 0.4093 | 0.5862 | 0.5983 | 0.8588 | 0.4093 |
| 208738_x_at | SUMO2 | 0.17 | 14.07 | 0.02 | 9.87 | 81 | 0.2055 | 0.4579 | 0.4606 | 0.3408 | 0.2055 |
| 224592_x_at | HP1BP3 | 0.13 | 11.74 | 0.15 | 9.86 | 82 | 0.6319 | 0.6899 | 0.6319 | 0.8361 | 0.8069 |
| 224935_at | EIF2S3 | 0.03 | 13.01 | 0.35 | 9.86 | 83 | 0.2694 | 0.3291 | 0.6816 | 0.2694 | 0.3207 |
| 224736_at | CCAR1 | 0.10 | 11.79 | 0.09 | 9.86 | 84 | 0.5647 | 0.8733 | 0.9743 | 0.7364 | 0.5647 |
| 224593_at | ZNF664 | 0.20 | 11.63 | 0.37 | 9.85 | 85 | 0.4300 | 0.5453 | 0.8490 | 0.4300 | 0.9881 |
| 224714_at | MKI67IP | 0.07 | 12.26 | 0.23 | 9.83 | 86 | 0.3898 | 0.8170 | 0.7194 | 0.3898 | 0.5026 |
| 223705_s_at | GPBP1 | 0.05 | 12.26 | 0.12 | 9.79 | 87 | 0.6059 | 0.9591 | 0.9834 | 0.6059 | 0.9781 |
| 1553575_at | NA | 0.04 | 12.71 | 0.40 | 9.76 | 88 | 0.2247 | 0.3970 | 0.3953 | 0.2247 | 0.4525 |
| 224591_at | HP1BP3 | 0.04 | 12.57 | 0.24 | 9.72 | 89 | 0.6293 | 0.6293 | 0.6998 | 0.7775 | 0.9947 |
| 202690_s_at | SNRPD1 | 0.07 | 13.90 | 0.13 | 9.70 | 90 | 0.5018 | 0.7715 | 0.5905 | 0.5018 | 0.5865 |
| 223034_s_at | C1orf43 | 0.02 | 13.12 | 0.16 | 9.70 | 91 | 0.4517 | 0.6653 | 0.4517 | 0.7044 | 0.9095 |
| 224376_s_at | C20orf24 | 0.06 | 12.21 | 0.23 | 9.69 | 92 | 0.5630 | 0.9644 | 0.9137 | 0.8592 | 0.5630 |
| AFFX-r2-Ec-bioD-3_at | NA | 0.14 | 14.01 | 0.48 | 9.67 | 93 | 0.3700 | 0.8588 | 0.8057 | 0.4071 | 0.4774 |
| 201277_s_at | HNRPAB | 0.04 | 13.17 | 0.18 | 9.66 | 94 | 0.3203 | 0.8462 | 0.3900 | 0.3789 | 0.3203 |
| 228273_at | NA | 0.03 | 12.65 | 0.19 | 9.66 | 95 | 0.5447 | 0.5447 | 0.6935 | 0.9994 | 0.8749 |
| 202077_at | NDUFAB1 | 0.06 | 13.06 | 0.08 | 9.65 | 96 | 0.2839 | 0.9323 | 0.6388 | 0.6981 | 0.2839 |
| 224561_s_at | MORF4L1 | 0.04 | 12.46 | 0.18 | 9.64 | 97 | 0.6517 | 0.9637 | 0.6517 | 0.8271 | 0.7722 |
| 211623_s_at | FBL | 0.04 | 13.89 | 0.16 | 9.63 | 98 | 0.4800 | 0.5149 | 0.9574 | 0.8996 | 0.9424 |
| 212626_x_at | HNRPC | 0.08 | 13.05 | 0.14 | 9.62 | 99 | 0.2260 | 0.5906 | 0.5146 | 0.3161 | 0.4689 |
| 229128_s_at | ANP32E | 0.03 | 12.72 | 0.39 | 9.61 | 100 | 0.4422 | 0.6538 | 0.8542 | 0.4422 | 0.9196 |

TABLE 9

| Probe | symb.gse | VarW. VarB | mean | var | vscr | vscr. rank | P. Min | SCR. anti-CD40 | IC25. anti-CD40 | GCB. anti-CD40 | SCR EXT. anti-CD40 |
|---|---|---|---|---|---|---|---|---|---|---|---|
| 226131_s_at | RPS16 | 0.68 | 15.60 | 0.01 | 15.24 | 1 | 0.4182 | 0.6946 | 0.6783 | 0.9425 | 0.4182 |
| 1553567_s_at | ATP13A5 | 0.53 | 15.77 | 0.04 | 15.10 | 2 | 0.2744 | 0.3205 | 0.5881 | 0.2744 | 0.8039 |
| 213477_x_at | EEF1A1 | 0.80 | 15.71 | 0.02 | 14.94 | 3 | 0.2716 | 0.3490 | 0.5611 | 0.2716 | 0.9425 |
| 211542_x_at | RPS10 | 0.59 | 15.11 | 0.02 | 14.31 | 9 | 0.2000 | 0.8313 | 0.9604 | 0.7117 | 0.7029 |
| 200095_x_at | FLJ20294 | 0.60 | 15.29 | 0.02 | 13.98 | 12 | 0.3400 | 0.7334 | 0.5003 | 0.4045 | 0.4757 |
| 224585_x_at | ACTG1 | 0.49 | 14.73 | 0.06 | 13.96 | 13 | 0.4788 | 0.9612 | 0.7590 | 0.4788 | 0.5097 |
| 213414_s_at | RPS19 | 0.49 | 15.19 | 0.02 | 13.95 | 14 | 0.3134 | 0.6110 | 0.5909 | 0.3134 | 0.9180 |
| 200032_s_at | RPL9 | 0.61 | 15.30 | 0.01 | 13.80 | 16 | 0.2652 | 0.7969 | 0.6658 | 0.8910 | 0.9033 |
| 200063_s_at | NPM1 | 0.68 | 15.34 | 0.02 | 13.78 | 17 | 0.2634 | 0.6557 | 0.7122 | 0.2634 | 0.9201 |
| 212734_x_at | RPL13 | 0.46 | 14.92 | 0.03 | 13.66 | 19 | 0.2300 | 0.8232 | 0.6720 | 0.4503 | 0.7004 |
| 200689_x_at | EEF1G | 0.64 | 14.25 | 0.03 | 13.21 | 26 | 0.2100 | 0.9324 | 0.8163 | 0.8508 | 0.3667 |
| 200024_at | RPS5 | 0.57 | 14.61 | 0.03 | 13.09 | 31 | 0.2000 | 0.7753 | 0.8060 | 0.5846 | 0.9469 |
| 200003_s_at | RPL28 | 0.14 | 15.12 | 0.04 | 12.93 | 34 | 0.5687 | 0.9905 | 0.6582 | 0.9539 | 0.5687 |
| 221775_x_at | EVI1 | 0.28 | 14.55 | 0.05 | 12.78 | 36 | 0.2391 | 0.9589 | 0.8109 | 0.4979 | 0.8711 |
| 208768_x_at | RPL22 | 0.30 | 14.56 | 0.05 | 12.78 | 37 | 0.2858 | 0.9577 | 0.8867 | 0.4568 | 0.9964 |
| 212191_x_at | LOC388344 | 0.18 | 14.84 | 0.05 | 12.77 | 38 | 0.2500 | 0.9777 | 0.8542 | 0.3553 | 0.9844 |
| 200021_at | CFL1 | 0.50 | 13.77 | 0.02 | 12.77 | 39 | 0.2775 | 0.8529 | 0.8339 | 0.5283 | 0.2775 |
| 208517_x_at | BTF3 | 0.33 | 14.54 | 0.02 | 12.56 | 40 | 0.2513 | 0.7046 | 0.7417 | 0.9434 | 0.2954 |
| 211956_s_at | EIF1 | 0.16 | 15.12 | 0.08 | 12.50 | 41 | 0.2756 | 0.2756 | 0.3283 | 0.6567 | 0.4596 |
| 224731_at | HMGB1 | 0.11 | 14.37 | 0.17 | 12.35 | 43 | 0.3496 | 0.4679 | 0.9363 | 0.4219 | 0.3496 |
| 234512_x_at | LOC388474 | 0.25 | 13.55 | 0.04 | 12.35 | 44 | 0.5910 | 0.9435 | 0.5910 | 0.9578 | 0.6021 |
| 221791_s_at | CCDC72 | 0.45 | 14.33 | 0.03 | 12.22 | 46 | 0.2692 | 0.5460 | 0.8746 | 0.4059 | 0.2692 |
| 216438_s_at | TMSB4X | 0.04 | 15.34 | 1.15 | 12.02 | 47 | 0.2086 | 0.3130 | 0.2155 | 0.2086 | 0.8821 |
| 201030_x_at | LDHB | 0.22 | 14.68 | 0.05 | 11.91 | 48 | 0.3032 | 0.4740 | 0.8098 | 0.5684 | 0.3032 |
| 222976_s_at | TPM3 | 0.04 | 14.13 | 0.09 | 11.54 | 52 | 0.3646 | 0.3786 | 0.7883 | 0.3646 | 0.5240 |
| 210466_s_at | SERBP1 | 0.52 | 13.90 | 0.07 | 11.51 | 53 | 0.2326 | 0.3230 | 0.2326 | 0.2545 | 0.8323 |
| 225413_at | USMG5 | 0.07 | 13.78 | 0.15 | 11.49 | 54 | 0.3239 | 0.9696 | 0.5515 | 0.8338 | 0.3239 |
| 221691_x_at | NPM1 | 0.10 | 15.00 | 0.07 | 11.44 | 55 | 0.5097 | 0.8965 | 0.7627 | 0.5097 | 0.7686 |

Measuring Expression Level

The methods disclosed herein provide methods to examine expression level of one or more of these marker genes in a lymphoma sample (e.g., B-cell lymphoma sample) relative a reference level. The methods and assays include those which examine expression of marker genes such as one or more of those listed in any of Tables 2-4, 6, 7 and 13. Expression levels may be measured at mRNA level and/or protein level.

The invention provides methods for measuring levels of expression from a mammalian tissue or cells sample (such as cells and/or tissues associated with B-cell lymphoma). For example, for obtaining patient samples, H&E staining is carried out and used as a guide for tissue macrodissection to enrich for tumor content. The sample can be obtained by a variety of procedures known in the art including, but is not limited to surgical excision, aspiration or biopsy. The sample may be fresh or frozen. In some embodiments, the sample is fixed and embedded in paraffin or the like. In the methods, a mammalian tissue or cell sample is obtained and examined for expression of one or more biomarkers. The methods may be conducted in a variety of assay formats, including assays detecting mRNA expression, enzymatic assays detecting presence of enzymatic activity, and immunohistochemistry assays. Determination of expression of such biomarkers in said tissues or cells will be predictive that such tissues or cells will be sensitive/responsive to treatment with an anti-CD40 antibody.

As discussed below, expression of various biomarkers in a sample can be analyzed by a number of methodologies, many of which are known in the art and understood by the skilled artisan, including but not limited to, microarray (gene and/or tissue array analysis), in situ hybridization, Northern analysis, PCR analysis of mRNAs, immunochemical and/or Western analysis, quantitative blood based assays (as for example Serum ELISA) (to examine, for example, levels of protein expression), and/or biochemical enzymatic activity assays. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). The protocols below relating to detection of particular biomarkers, such as those listed in Tables 2-4, 6, 7 and 13, in a sample are provided for illustrative purposes.

In some embodiments, the methods of the invention further include protocols which examine the presence and/or expression of mRNAs, such as mRNAs of genes listed in any of Tables 2-4, 6, 7 and 13, in a tissue or cell sample. In some embodiments, expression of various biomarkers in a sample may be analyzed by microarray technologies, which examine or detect mRNAs, such as mRNAs in any of Tables 2-4, 6, 7 and 13, in a tissue or cell sample. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (See, e.g., WO 01/75166 published Oct. 11, 2001; see also, for example, U.S. Pat. Nos. 5,700,637, 5,445,934, and 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps:

1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, expression of various biomarkers in a sample may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. By way of example, these methods may be employed to detect deletion or amplification of genes listed in any of Tables 2-4, 6, 7 and 13.

In some embodiments, expression of various biomarkers in a sample may be assessed by hybridization assays using complementary DNA probes (such as in situ hybridization using labeled riboprobes, Northern blot and related techniques) and various nucleic acid amplification assays (such as RT-PCR using complementary primers, such as primers specific for one or more genes listed in any of Tables 2-4, 6, 7 and 13, and other amplification type detection methods, such as, for example, branched DNA, SISBA, TMA and the like).

Tissue or cell samples from mammals can be conveniently assayed for, e.g., mRNAs of genes listed in any of Tables 2-4, 6, 7 and 13, using Northern, dot blot or PCR analysis. In some embodiments, expression of one or more biomarkers may be assayed by RT-PCR. In some embodiments, the RT-PCR may be quantitative RT-PCR (qRT-PCR). In some embodiments, the RT-PCR is real-time RT-PCR. In some embodiments, the RT-PCR is quantitative real-time RT-PCR. RT-PCR assays such as quantitative PCR assays are well known in the art. In an illustrative embodiment of the invention, a method for detecting a mRNA in a biological sample comprises producing cDNA from the sample by reverse transcription using at least one primer; amplifying the cDNA so produced using a polynucleotide as sense and antisense primers to amplify cDNAs therein; and detecting the presence of the amplified cDNA of interest. In some embodiments, the real-time RT-PCR may be quantitative RT-PCR. In some embodiments, the real-time RT-PCR may be performed using TaqMan® chemistry (Applied Biosystems). In some embodiments, the real-time RT-PCR may be performed using TaqMan® chemistry (Applied Biosystems) and the ABI Prism® 7700 Sequence Detection System (Applied Biosystems). The real-time RT-PCR combines the principles that Taq polymerase has a 5'-3; exonuclease activity and dual-labeled fluorogenic oligonucleotide problems have been created which emit a fluorescent signal only upon cleavage, based on the principle of fluorescence resonance energy transfer. See, e.g., Overbergh, L. et al., *J. Biomolecular Techniques* 14(1): 33-43 (2003). In addition, such methods can include one or more steps that allow one to determine the levels of mRNA, such as a mRNA of genes listed in any of Tables 2-4, 6, 7 and 13, in a biological sample (e.g., by simultaneously examining the levels a comparative control mRNA sequence of a "housekeeping" gene such as an actin family member and/or one or more genes listed in Table 8 or Table 9). Examples of primers and probes that may be used for conducting qRT-PCR are provided in Table 10.

In some embodiments, the expression of proteins encoded by the genes listed in any of Tables 2-4, 6, 7 and 13 in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, tissue biopsy, blood, lung aspirate, sputum, lymph fluid, etc. The sample can be obtained by a variety of procedures known in the art including, but not limited to surgical excision, aspiration or biopsy. The tissue may be fresh or frozen. In some embodiments, the sample is fixed and embedded in paraffin or the like.

The tissue sample may be fixed (i.e. preserved) by conventional methodology (See e.g., "Manual of Histological Staining Method of the Armed Forces Institute of Pathology," 3rd edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

In some embodiments, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., a protein or fragment thereof encoded by one or more genes listed in Tables 1-4, 6 and 7) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-1'-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this.

For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

In some embodiments, the antibodies employed in the IHC analysis to detect expression of one or more biomarkers are antibodies generated to bind primarily to the one or more biomarkers of interest, such as one or more proteins encoded by genes listed in any of Tables 2-4, 6 and 7. In some embodiments, the antibody is a monoclonal antibody. Antibodies are readily available in the art, including from various commercial sources, and can also be generated using routine skills known in the art.

Specimens thus prepared may be mounted and coverslipped. Slide evaluation is then determined, e.g. using a microscope, and staining intensity criteria, routinely used in the art, may be employed. As one example, staining intensity criteria may be evaluated as follows:

TABLE A

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

In some embodiments, the methods involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

In some embodiments, expression of a selected biomarker in a tissue or cell sample may be examined by way of functional or activity-based assays. For instance, if the biomarker is an enzyme, one may conduct assays known in the art to determine or detect the presence of the given enzymatic activity in the tissue or cell sample.

In any of the above methods of assessing level of expression of one or more biomarkers, a sample comprising a target molecule can be obtained by methods well known in the art, and that are appropriate for the particular type and location of the disease of interest. Tissue biopsy is often used to obtain a representative piece of disease tissue. Alternatively, cells can be obtained indirectly in the form of tissues/fluids that are known or thought to contain the disease cells of interest. For instance, samples of disease lesions may be obtained by resection, bronchoscopy, fine needle aspiration, bronchial brushings, or from sputum, pleural fluid or blood. Genes or gene products can be detected from disease tissue or from other body samples such as urine, sputum or serum. The same techniques discussed above for detection of target genes or gene products in disease samples can be applied to other body samples. By screening such body samples, a simple early diagnosis can be achieved for these diseases. In addition, the progress of therapy can be monitored more easily by testing such body samples for target genes or gene products.

Means for enriching a tissue preparation for disease cells are known in the art. For example, the tissue may be isolated from paraffin or cryostat sections. Cells of interest may also be separated from normal cells by flow cytometry or laser capture microdissection. These, as well as other techniques for separating disease from normal cells, are well known in the art. If the disease tissue is highly contaminated with normal cells, detection of signature gene expression profile may be more difficult, although techniques for minimizing contamination and/or false positive/negative results are known, some of which are described herein below. For example, a sample may also be assessed for the presence of a biomarker (including a mutation) known to be associated with a disease cell of interest but not a corresponding normal cell, or vice versa.

Subsequent to the determination that the tissue or cell sample expresses one or more of the biomarkers indicating the tissue or cell sample will be sensitive to treatment with anti-CD40 antibodies, it is contemplated that an effective amount of the anti-CD40 antibody may be administered to the mammal, such as a human to treat a disorder, such as a B-cell lymphoma which is afflicting the mammal. Diagnosis in mammals, such as humans, of the various pathological conditions described herein can be made by the skilled practitioner.

Comparing Expression Levels and Predicting, Assessing or Aiding Assessment of Responsiveness of B-Cell Lymphoma to an Anti-CD40 Antibody Treatment The methods described herein comprise a process of comparing a measured expression level of a marker gene and a reference level. The reference level may be a measured expression level of a reference gene different from the marker gene or a measured expression level of the same marker gene in a different sample.

In some embodiments, a measured expression level of a marker gene in a B cell lymphoma sample from a subject is compared to a measured expression level of a reference gene in the sample. In some embodiments, the expression level of the reference gene does not substantially change among various types of B lymphoma cells, including anti-CD40 antibody sensitive and resistant cells (e.g., genes in Table 8 or Table 9). In some embodiments, the ratio of the measured expression level of the marker gene to the measured expression level of the reference is calculated, and the ratio may be used for assessing or aiding assessment of responsiveness of the B cell lymphoma to an anti-CD antibody treatment.

In some embodiments, a measured expression level of a marker gene in a B cell lymphoma sample from a subject is compared to a measured expression level of the marker gene in a reference sample. In some embodiments, the reference sample comprises B lymphoma cells that are resistant or not responsive to an anti-CD40 antibody. For example, the comparison is performed to determine the magnitude of the difference between the measured expression levels of the marker gene in the sample from the subject and in the reference sample (e.g., comparing the fold or percentage difference between the expression levels of the marker gene in the sample from the subject and the reference sample). An increase or decreased expression of a marker gene in the sample from the subject as compared to the expression of the marker gene in the reference sample comprising B lymphoma cells that are resistant or not responsive to an anti-CD40 antibody suggests or indicates responsiveness of the B-cell lymphoma to treatment with an anti-CD40 antibody. See Table 4 for marker genes having increased and decreased expression in anti-CD40 antibody sensitive cells as compared to resistant cells. For examples, VNN2, MEF2C, LTB, KCNN3, NCF1, BCL6, IGJ, ELTI1902, PNOC, CSF2RB, POU2AF1, CD22, RGS13, and MEF2B are generally overexpressed in anti-CD40 antibody sensitive cells as compared to resistant cells. In some embodiments, a fold of increase in the expression level of the sample from the subject can be at least about any of 1.5×, 1.75×, 2×, 3×, 4×, 5×, 6×, 7×, 8×, 9×, or 10× the expression level of the reference sample. In some embodiments, a fold of decrease in the expression level of the sample from the subject can be less than about any of 0.01, 0.05, 0.1, 0.2, 0.3, 0.4, 0.5, 0.6, 0.7, 0.8 of the expression level of the reference sample.

In some embodiments, expression level of one or more marker genes selected from the group consisting of IFITM1, CD40, RGS13, VNN2, LMO2, CD79B, CD22, BTG2, IGF1R, CD44, CTSC, EPDR1, UAP1, and PUS7 are compared to a reference level.

In some embodiments, an increased expression level of one or more of IFITM1, CD79B, IGF1R, CD44, CTSC, EPDR1, and PUS7 as compared to a reference level indicates that said subject is less likely to respond to an agonist anti-CD40 antibody treatment. In some embodiments, the reference level is a value or a range determined by expression levels of the corresponding marker gene in samples comprising B lymphoma cells from subjects having tumor volume increased after an agonist anti-CD40 antibody treatment.

In some embodiments, an increased expression of one or more of CD40, RGS13, VNN2, LMO2, CD22, BTG2, and UAP1 as compared to a reference level indicates that said subject is likely to respond to the agonist anti-CD40 antibody treatment. In some embodiments, the reference level is a value or a range determined by expression levels of the corresponding marker gene in samples comprising B lymphoma cells from subjects having tumor volume decreased after an agonist anti-CD40 antibody treatment.

In some embodiments, the expression level BCL6 is measured and compared to a reference level. The expression level of BCL6 is used for predicting, assessing, or aiding assessment of responsiveness of the subject to an anti-CD40 antibody treatment. As shown in Example 2, BCL6 expression trends lower in those subjects with tumor increases after an agonist anti-CD40 antibody treatment. In some embodiments, an increased expression of BCL6 as compared to a reference level determined by expression level of BCL6 in samples from subjects having tumor volume decreased after an agonist anti-CD40 antibody treatment may indicate the subject is likely to respond to the agonist anti-CD40 antibody treatment.

In some embodiments, the expression levels of marker genes in Table 7) are measured, and a sensitivity index calculated as the sum of signed t-scores for log 2-scale expression of genes pairs 1-8 in Table 7 is determined, wherein a sensitivity index greater than −4 suggests or indicates the B-cell lymphoma is responsive to an anti-CD40 antibody treatment. In some embodiments, the sensitivity index is greater than −3, greater than −2, greater than −1, or greater than 0. In some embodiments, the sensitivity index is between −4 and 20. In some embodiments, the sensitivity index is between 0 and 20.

In some embodiments, the expression levels of one or more of IFITM1, CD40, RGS13, VNN2, LMO2, CD79B, CD22, BTG2, IGF1R, CD44, CTSC, EPDR1, UAP1, and PUS7 are measured, and a sensitivity index is calculated based on the measured expression level of the marker genes. For example, the following equation may be used for determining sensitivity index (SI):

$$SI = \sum_{j=1}^{p} \beta_j \frac{x_j - \hat{\mu}_j}{\sqrt{\hat{\sigma}_j^2}}$$

wherein expression level of at least one marker gene having a positive correlation value and at least one marker gene having a negative correlation value shown in Table 13 are measured; wherein (i) $\beta_j$ is the coefficient value for each marker genes measured; (ii) p is the number of marker genes measured; (iii) $x_j$ is transformed, normalized expression level for the sample from the subject for expression level of each marker measured; and (iv) $\mu_j$ and $\sigma_j$ are means and standard deviations for each marker gene measured; wherein $\beta_j$, $\mu_j$ and $\sigma_j$ are determined from patient samples comprising B lymphoma cells from a clinical trial. In some embodiments, a value equals or greater than zero for the sensitivity index indicates that the subject is likely to respond the anti-CD40 antibody treatment, or wherein a value less than zero for the sensitivity index indicates that the subject is less likely to respond the anti-CD40 antibody treatment. Example 2 described in detail how to analyze and determine parameters for reference samples and new samples. In some embodiments, the expression level of IFITM1, RGS13, CD79B, CD22, BTG2, CD44, EPDR1, and UAP1 are measured and used for the sensitivity index calculation. In some embodiments, equal number of positive correlated marker genes and negative correlated marker genes are measured and used for the sensitivity index calculation.

Methods for determining sensitivity index are known in the art. See Zhou H. and Hastie T. (2005) *Regularization and variable selection via the elastic net*; J. R. Statist. Soc. B. 67(2). pp. 301-320; Friedman J., Hastie T. and Tibshirani R. 2008. *Regularization Paths for Generalized Linear Models via Coordinate Descent*. Technical Report, Department of Statistics, Stanford University (World Wide Web-stat.stanford.edu/~hastie/Papers/glmnet.pdf) R package glmnet; R Development Core Team (2008). R: A language and environment for statistical computing. R Foundation for Statistical Computing, Vienna, Austria. ISBN 3-900051-07-0, URL World Wide Web at R-project.org.

The comparison can be carried out in any convenient manner appropriate to the type of measured value and reference value for the gene markers at issue. The process of comparing may be manual or it may be automatic. In some embodiments, measured expression levels are normalized values. For example, the expression level may be normalized based on the equation under Transformed, Normalized Assay Values described in Example 2. As will be apparent to those of skill in the art, replicate measurements may be taken for the expression levels of marker genes and/or reference genes. In some embodiments, replicate measurements are taking into account for the measured values. The replicate measurements may be taken into account by using either the mean or median of the measured values as the "measured value". Statistical analysis known in the art may be used to verify the significance of the difference between the two values compared.

Anti-CD40 Antibody Treatment

The marker genes identified in the invention may be used for predicting, assessing, or aiding assessment of responsiveness of B-cell lymphoma to treatment with one or more anti-CD40 antibodies. The anti-CD40 antibodies may be one or more agonist antibodies (i.e., bind and stimulate CD40). Stimulatory antibodies can be of different types, such as: (1) those that deliver a stimulatory signal through CD40 but do not increase the interaction between CD40 and CD40L (e.g., antibody G28-5 and antibodies derived from G28-5 described in U.S. Pat. No. 5,182,368; and PCT WO 96/18413), or decrease the interaction between CD40 and CD40L (e.g., antibodies HuCD40-M2 and HuCD40-M3 and humanized antibodies described in U.S. Pat. No. 5,674,492; and (2) those that deliver a stimulatory signal through CD40 and can increase the interaction between CD40 and CD40L, e.g., S2C6 (Francisco et al., 2000, *Cancer Res.* 60:3225-31) and antibodies derived from S2C6. Agonists antibodies are also described in U.S. Pat. No. 7,288,251. The anti-CD40 antibodies may be one or more antagonist antibodies (i.e., bind CD40 and inhibit activities induced by CD40L). Examples of antagonist anti-CD40 antibodies include human antibody CHIR-12.12 described in U.S. Pub. No. 2007/0110754, and anti-CD40 antibodies described in WO 97/31025.

The methods of the invention may further comprise administering an effective amount of an anti-CD40 antibody to a subject having a B-cell lymphoma after the subject has been identified as a candidate for treatment based on the assays/methods described herein. One or more anti-CD40 antibodies may be administered. In some embodiments, the anti-CD40 antibody is administered in conjunction with one or more of the following therapeutic agents: rituximab, gemzar, and ICE. For example, an anti-CD40 antibody can be administered to the patient in conjunction with rituximab therapy; with rituximal plus gemzar; with rituximal plus ICE (ifosfamide, carboplatin, etoposide) (R-ICE); or with rituximab plus chemotherapy.

As used herein, administration "in conjunction" includes simultaneous administration and/or administration at different times. Administration in conjunction also encompasses administration as a co-formulation (i.e., different drugs are present in the same composition) or administration as separate compositions, administration at different dosing frequencies or intervals, and administration using the same route or different routes.

The anti-CD40 antibodies or functional fragments can be used for the treatment of patients with NHL that are nonresponsive or have an inadequate response to treatment with any one of the following drugs: rituximab (Genentech); ocrelizumab (Genentech, Inc.); ibritumomab tiuxetan (Zevalin™, Biogen Idec); tositumomab (Bexxar™, GlaxoSmithKline); HuMAX-CD20™ (GenMab); IMMU-106 (which is a humanized anti-CD20 a.k.a. hA20 or 90Y-hLL2, Immunomedics); AME-133 (Applied Molecular Evolution/Eli Lilly); gentuzumab ozogamicin (Mylotarg™, a humanized anti-CD33 antibody, Wyeth/PDL); alemtuzumab (Campath™, an anti-CD52 antibody, Schering Plough/Genzyme); epratuzumab (IMMU-103™, a humanized anti-CD22 antibody, Immunomedics), or have relapsed after treatment with these drugs.

The following references describe lymphomas and CLL, their diagnoses, treatment and standard medical procedures for measuring treatment efficacy. Canellos G P, Lister, T A, Sklar J L: *The Lymphomas*. W.B.Saunders Company, Philadelphia, 1998; van Besien K and Cabanillas, F: Clinical Manifestations, Staging and Treatment of Non-Hodgkin's Lymphoma, Chap. 70, pp 1293-1338, in: *Hematology, Basic Principles and Practice,* 3rd ed. Hoffman et al. (editors). Churchill Livingstone, Philadelphia, 2000; and Rai, K and Patel, D: Chronic Lymphocytic Leukemia, Chap. 72, pp 1350-1362, in: *Hematology, Basic Principles and Practice,* 3rd ed. Hoffman et al. (editors). Churchill Livingstone, Philadelphia, 2000.

Anti-CD40 antibodies for use in the treatment include chimeric, humanized and human antibodies. Any agonist or antagonist antibodies described herein or known in the art may be used in the treatment. For example, humanized anti-CD40 antibodies described in WO 2006/128103 may be used for the anti-CD40 antibody treatment, and these antibodies and their amino acid sequences are incorporated herein by reference. In some embodiments, the anti-CD40 antibody for used in the treatment described herein binds to CD40 (such as human CD40) expressed on B lymphoma cells and induces apoptosis of the B lymphoma cells. The anti-CD40 antibody may also have the characteristics of killing B lymphoma cells in vivo via immune effector functions, such as ADCC, CDC, and/or ADCP. In some embodiments, the anti-CD40 antibody binds to CD40 with a $K_d$ value of no higher than about $1 \times 10^{-8}$ or no higher than $1 \times 10^{-9}$. In some embodiments, the anti-CD40 antibody binds to CD40 and stimulates CD40 (i.e., an agonist antibody). In some embodiments, the anti-CD40 antibody increases the binding of CD40 ligand to CD40, for example, by at least 45%, by at least 50%, by at least 60%, or by at least 75%. A method of determining increases in binding of CD40 ligand to CD40 are disclosed in U.S. Pat. No. 6,838, 261 (the disclosure of which is incorporated by reference herein). In some embodiments, the anti-CD40 is a humanized antibody derived from murine monoclonal antibody S2C6 described in WO 00/75348 (including antibodies provided in Tables 3 and 4 of WO 00/75348). In some embodiments, the anti-CD40 antibody comprises the heavy chain amino acid sequence shown in SEQ ID NO:1 and the light chain amino acid sequence shown in SEQ ID NO:2, for example anti-CD40 Ab.1.

D. Kits

For use in the applications described or suggested above, kits or articles of manufacture are also provided by the invention. Such kits may comprise at least one reagent specific for detecting expression level of a marker gene described herein, and may further include instructions for carrying out a method described herein.

In some embodiments, the invention provides compositions and kits comprising primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides, such as the polynucleotides corresponding to genes listed in Table 1-4, 6, 7 and 13, in a sample and as a means for detecting a cell expressing proteins encoded by the polynucleotides corresponding to genes listed in Table 1-4, 6, 7 and 13. As will be understood by the skilled artisan, a great many different primers and probes may be prepared based on the sequences provided in herein and used effectively to amplify, clone and/or determine the presence and/or levels of mRNAs.

In some embodiments, the kits comprise reagents for detecting expression levels of at least two, at least three, at least five, at least ten, at least fifteen, at least twenty marker genes. Kits may also comprise reference samples that are useful as generating reference values. The marker genes include, but are not limited to VNN2, MEF2C, LTB, KCNN3, NCF1, BCL6, IGJ, ELTI1902, PNOC, CSF2RB, POU2AF1, CD22, RGS13, MEF2B, LRRC8A, CD40, IFITM1, SMN1, PRRCA, EPDR1, PRPSAP2, IGF1R, BTG2, LMO2, YIPF3, CD79B, CD44, CTSC, UAP1, and PUS7. The reagents for detecting mRNA expression level of a marker gene may comprise at least one pair of primers specific for amplifying the mRNA products of one marker gene. In some embodiments, the pair of primers may target the 3' end of the mRNA sequence (e.g., targeting mRNA at the 3' UTR which is usually shared in common with all transcript variants). In some embodiments, the kits may further comprise a surface or substrate (such as a microarray) for capture probes for detecting of amplified nucleic acids.

In some embodiments, the kits comprises at least one pair of primers and a probe specific for detecting one marker gene expression level using qRT-PCR. Examples of sets of primers and probes that can be used in qRT-PCR are shown in Table 10. For detecting IFITM1, primer and probe sets shown in SEQ ID NOS:27, 28 and 29, SEQ ID NOS:60, 61, and 62, and SEQ ID NOS:93, 94, and 95 may be used. For detecting CD40, primer and probe sets shown in SEQ ID NOS:24, 25, and 26, SEQ ID NOS:57, 58, and 59, SEQ ID NOS:90, 91 and 92 may be used. For detecting RGS13, primer and probe sets shown in SEQ ID NOS:114, 115, and 116, and SEQ ID NOS:126, 127, and 128 may be used. For detecting VNN2, primer and probe sets shown in SEQ ID NOS:30, 31, and 32, SEQ ID NOS:63, 64, and 65, and SEQ ID NOS:96, 97, and 98. For detecting LMO2, primer and probe sets shown in SEQ ID NOS:12, 13, and 14, SEQ ID NOS:45, 46, and 47, and SEQ ID NOS:78, 79, and 80. For detecting CD79B, primer and probe sets shown in SEQ ID NOS:141, 142, and 143, SEQ ID NOS:150, 151, and 152, and SEQ ID NOS:159, 160, and 161. For detecting CD22, primer and probe sets shown in SEQ ID NOS:15, 16, and 17, SEQ ID NOS:48, 49, and 50, and SEQ ID NOS:81, 82, and 83. For detecting BTG2, primer and probe sets shown in SEQ ID NOS:9, 10, and 11, SEQ ID NOS:42, 43, and 44, and SEQ ID NOS:75, 76, and 77. For detecting IGF1R, primer and probe sets shown in SEQ ID NOS:6, 7, and 8, SEQ ID NOS:39, 40, and 41, and SEQ ID NOS:72, 73, and 74. For detecting CD44, primer and probe sets shown in SEQ ID NOS:174, 175, and 176, SEQ ID NOS:180, 181, and 182, and SEQ ID NOS:186, 187, and 188. For detecting CTSC, primer and probe sets shown in SEQ ID NOS:165, 166, and 167, SEQ ID NOS:168, 169, and 170, and SEQ ID NOS:171, 172, and 173. For detecting EPDR1, primer and probe sets shown in SEQ ID NOS:21, 22, and 23, SEQ ID NOS:54, 55, and 56, SEQ ID NOS:87, 88, and 89, SEQ ID NOS:129, 130, and 131, SEQ ID NOS:132, 133, and 134, SEQ ID NOS:135, 136, and 137. For detecting UAP1, primer and probe sets shown in SEQ ID NOS:138, 139, and 140, SEQ ID NOS:147, 148, and 149, and SEQ ID NOS:156, 157, and 158. For detecting PUS7, primer and probe sets shown in SEQ ID NOS:177, 178, and 179, SEQ ID NOS:183, 184, and 185, and SEQ ID NOS:189, 190, and 191. For detecting BCL6, primer and probe sets shown in SEQ ID NOS:102, 103, and 104, and SEQ ID NOS:108, 109, and 110.

The reagents for detecting protein expression level of a marker gene may comprise an antibody that specifically binds to the protein encoded by the marker gene.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a marker gene. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kit can further comprise a set of instructions and materials for preparing a tissue or cell sample and preparing nucleic acid (such as mRNA) from the sample.

The invention provides a variety of compositions suitable for use in performing methods of the invention, which may be used in kits. For example, the invention provides surfaces, such as arrays that can be used in such methods. In some embodiments, an array of the invention comprises individual or collections of nucleic acid molecules useful for detecting mutations of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of presence or absence of a mutation of the invention.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silican surface chemistry are also known in the art, as disclosed at world wide web at cmt.corning.com and cmgm.stanford.edu/pbrown1.

Attachment of groups to oligonucleotides which could be later converted to reactive groups is also possible using methods known in the art. Any attachment to nucleotides of oligonucleotides will become part of oligonucleotide, which could then be attached to the solid surface of the microarray. Amplified nucleic acids can be further modified, such as through cleavage into fragments or by attachment of detectable labels, prior to or following attachment to the solid substrate, as required and/or permitted by the techniques used.

The following are examples of the methods and compositions of the invention. It is understood that various other embodiments may be practiced, given the general description provided above.

EXAMPLES

Example 1

Identification of Predictive Genetic Markers for Responsiveness of NHL Patients to Anti-CD40 Antibody Treatment Materials and Methods
Cell Viability Assays
NHL Cells were seeded in 384 well plates at 1500-5000 cells/well in 50 ul RPMI 1640 supplemented with 2% FBS and treated with serial concentrations of crosslinked anti- CD40 Ab.1 or control antibody (anti-gD 5B6). For crosslinking, anti-CD40 Ab.1 or anti-gD was incubated with F(ab')2 fragments of a goat anti human IgG Fcγ fragment-specific antibody (Jackson ImmunoResearch, West Grove, Pa.) in a 1:4 ratio in medium for 30 minutes at room temperature before adding to cells. After 96 hours of incubation, cell viability was evaluated using CellTiter-Glo Luminescent Cell Viability Assay (Promega, Madison, Wis.) according to the manufacturer's instructions. Each data point was performed in quadruplicate.

XLfit was used to calculate IC50, IC25 and maximum inhibition. Data are expressed as average of three independent experiments. Sensitivity to anti-CD40 Ab.1 was binned into three categories: Sensitive, Intermediate, and Resistant based on IC25 and IC50 values.

Antibody anti-CD40 Ab.1 is a humanized IgG1 mAb against CD40. It is produced in and secreted by a genetically engineered Chinese Hamster Ovary (CHO) cell line. The anti-CD40 Ab.1 used in the examples and referred to as anti-CD40 Ab.1 has the following amino acid sequence:

Heavy Chain (SEQ ID NO:1). The italicized underlined ASN 294 residue identifies the location of the carbohydrate moiety.

```
EVQLVESGGG LVQPGGSLRL SCAASGYSFT GYYIHWVRQA PGKGLEWVAR    50

VIPNAGGTSY NQKFKGRFTL SVDNSKNTAY LQMNSLRAED TAVYYCAREG   100

IYWWGQGTLV TVSSASTKGP SVFPLAPSSK STSGGTAALG CLVKDYFPEP   150

VTVSWNSGAL TSGVHTFPAV LQSSGLYSLS SVVTVPSSSL GTQTYICNVN   200

HKPSNTKVDK KVEPKSCDKT HTCPPCPAPE LLGGPSVFLF PPKPKDTLMI   250

SRTPEVTCVV VDVSHEDPEV KFNWYVDGVE VHNAKTKPRE EQYNSTYRVV   300

SVLTVLHQDW LNGKEYKCKV SNKALPAPIE KTISKAKGQP REPQVYTLPP   350

SREEMTKNQV SLTCLVKGFY PSDIAVEWES NGQPENNYKT TPPVLDSDGS   400

FFLYSKLTVD KSRWQQGNVF SCSVMHEALH NHYTQKSLSL SPG          443
```

Light Chain (SEQ ID NO:2).

```
DIQMTQSPSS LSASVGDRVT ITCRSSQSLV HSNGNTFLHW YQQKPGKAPK    50

LLIYTVSNRF SGVPSRFSGS GSGTDFTLTI SSLQPEDFAT YFCSQTTHVP   100

WTFGQGTKVE IKRTVAAPSV FIFPPSDEQL KSGTASVVCL LNNFYPREAK   150

VQWKVDNALQ SGNSQESVTE QDSKDSTYSL SSTLTLSKAD YEKHKVYACE   200

VTHQGLSSPV TKSFNRGEC                                     219
```

Generation and Analysis of Gene Expression Profiles

Total RNA was extracted with the mirVana™ miRNA Isolation Kit (Ambion, Austin, Tex.) and was assayed using Affymetrix HGU133P2 whole genome expression microarrays. Raw data was extracted using an Affymetrix scanner and the resulting CEL files were processed using gcRMA with defaults in R Bioconductor Package (world wide web at bioconductor.org). Significantly differentially expressed genes were identified using a moderated t-test for differences across anti-CD40 Ab.1 sensitivity and viability classes. Further parameters were assessed using the LIMA package and t-statistics, p-values, adjusted p-values, and B-statistics were calculated for each gene. Probes were mapped to each gene and a 1:1 probe to gene mapping was selected for downstream analysis using the probe most strongly associated with the measure of sensitivity. For classification into Sensitive or Intermediate versus Resistant groups, quantitative stepwise linear modeling was combined with qualitative analysis of target pathways to identify a parsimonious set of genes to inclusion in the assay. Further details and results are provided in the Results (Table 7).

Gene set enrichment analysis was determined by utilizing the GSEA module within Gene Pattern (world wide web at genepattern.org). The enrichment score awards pre-specified classes of genes when their members are significantly differentially expressed in a concordant manner across phenotypes. The normalized enrichment score is calculated by taking the enrichment score and adjusting for the number of genes within a gene set. The nominal p-value is determined by permutating the sensitive and resistant labels and recomputing the normalized enrichment score to give a null distribution.

Anti-CD40 Ab.1 Sensitivity Index Identified Using Stepwise Linear Modeling

Each Target Gene is shown with its corresponding inversely correlated (anti-correlated) Pair Gene (Table 7), in order of the step at which the Target Gene was chosen for inclusion in the Index. The first 3 Main Genes (VNN2, RGS13, CD22 in Table 7) were selected from Tables 2-4 (Step 1) to model the dominant component of differential overexpression in Sensitive and Intermediate cell lines. The expression of these 3 genes is highly correlated, with correlation coefficients of +0.77 or higher. Due to their similarity, a single pair gene EPDR1 was selected from Tables 2-4 to measure contrasting overexpression in Resistant cell lines. Including such anti-correlated Pair Genes in the assay provides auto-normalization in that both Sensitivity and Resistance are associated with high expression of one arm of the pair. By this mechanism, the assay does not depend upon low overall mRNA assay levels to define any class, but rather describes each by a pattern of relative expression of the Main Genes to their anticorrelated Pairs (i.e. a sum of signed t-scores on the $\log_2$ scale, with signs corresponding to the Fold Change Estimate). In Steps 2-5, additional pairs of genes were chosen based upon mechanism of action from a new list of those with significant associations to IC25 after adjustment for the cumulative sum of signed t-scores for genes identified in previous Steps. This stepwise procedure requires each new pair of genes to add additional predictive power to the Sensitivity Index. After Step 5, no more gene pairs were needed for IC25 prediction. In Step 6, a single additional pair was added for its ability to predict cell viability at maximum inhibition after adjusting for the cumulative Index based upon the previous 7 pairs of genes. BCL6 was added as a singleton without a corresponding pair based upon a mechanism of action rationale: it is not currently incorporated in the final Sensitivity Index, which is given by the sum of signed t-scores for log 2-scale expression of Gene Pairs 1-8. It may be incorporated explicitly into the index based upon clinical experience. For classification into Sensitive or Intermediate versus Resistant groups, a preliminary cutoff was chosen for the Sensitivity Index so as to maximize the overall correct classification rate. Alternate classification rules based upon the selected probes may be optimized later for clinical application.

Results and Analysis

To gain an understanding of the mechanism of action of anti-CD40 antibody, and to identify one or more predictive markers for the responsiveness of NHL patients to anti-CD40 antibody therapy, we tested the activity of anti-CD40 Ab.1 across a panel of 31 NHL cell lines and assessed cell viability in response to a titration of anti-CD40 antibody. The IC25 values highlighted in Table 1 from this experiment reveal that anti-CD40 antibody sensitized 10 cell lines with a reduction in cell viability at a concentration of <0.4 µg/ml, hereon defined as 'sensitive' cell lines, and 13 cell lines that did not achieve a reduction in cell viability even up to concentrations of 1 µg/ml, hereon defined as 'resistant' cell lines. 8 cell lines had an IC25 between >0.4 and <0.8, and will hereon be defined as 'intermediate' cell lines.

Table 1 provides anti-CD40 Ab.1 IC25 sensitivity data across NHL cell lines in vitro. Specific lymphoma subtypes of each cell line, IC25 values and classifier data are given for each cell line. DLBCL (Diffuse Large B-cell Lymphoma), FL (Follicular Lymphoma, MCL (Mantle Cell Lymphoma), ALCL (Anaplastic Large Cell Lymphoma).

TABLE 1

| Cell line | Anti-CD40 Antibody Sensitivity IC25 Classifier | Anti-CD40 Antibody IC25 (µg/ml) | Lymphoma Subtype |
| --- | --- | --- | --- |
| SU-DHL-16 | Sensitive | 0.009817124 | DLBCL |
| SU-DHL-10 | Sensitive | 0.01 | DLBCL |
| SU-DHL-8 | Sensitive | 0.011140955 | DLBCL |
| SU-DHL-5 | Sensitive | 0.015309599 | DLBCL |
| SU-DHL-4 | Sensitive | 0.03 | DLBCL |
| MC116 | Sensitive | 0.03217012 | UBCL |
| HT | Sensitive | 0.123333333 | DLBCL |
| KARPAS-1106P | Sensitive | 0.196666667 | DLBCL |
| BJAB | Sensitive | 0.240995143 | Burkitt's Lymphoma |
| WSU-NHL | Sensitive | 0.348838607 | FL |
| REC-1 | Intermediate | 0.42 | MCL |
| WSU-FSCCL | Intermediate | 0.49 | FL |
| A3/Kawakami | Intermediate | 0.668463355 | DLBCL |
| DB | Intermediate | 0.676933804 | DLBCL |
| Ri-1 | Intermediate | 0.696666667 | DLBCL |
| RL | Intermediate | 0.698508885 | DLBCL |
| Sc-1 | Intermediate | 0.709276746 | FL |
| Farage | Intermediate | 0.796666667 | DLBCL |
| A4/Fukada | Resistant | 1 | DLBCL |
| GRANTA-519 | Resistant | 1 | MCL |
| JeKo-1 | Resistant | 1 | MCL |
| Karpas-422 | Resistant | 1 | DLBCL |
| NU-DHL-1 | Resistant | 1 | DLBCL |
| OCI-Ly19 | Resistant | 1 | DLBCL |
| Pfeiffer | Resistant | 1 | DLBCL |
| RC-K8 | Resistant | 1 | DLBCL |
| SCC-3 | Resistant | 1 | DLBCL |
| SR-786 | Resistant | 1 | ALCL |
| SU-DHL-1 | Resistant | 1 | ALCL |
| TK | Resistant | 1 | DLBCL |
| Toledo | Resistant | 1 | DLBCL |

To identify genes that are predictive of anti-CD40 Ab.1 activity in vitro, RNA was prepared from the cell lines at the log stage of cell division and subjected to gene expression profiling using the Affymetrix HGU133P2 microarray. Differentially expressed genes between Sensitive and Resistant cell lines were determined by a moderated t-test and significance was determined using an adjusted P-value cutoff of ≤0.05 (Table 2). In Table 2, gene list filtered to an adjusted p-value <0.05 (5% FDR) resulting in 110 unique genes. Probe ID, gene symbol and description are indicated. In addition, significant genes that correlated with the IC25 values across all NHL cell lines were determined by the Spearman's Rank Correlation and genes were filtered using a rho value of ≤−0.57 or ≥0.57 (Table 3). In Table 3, gene list filtered with a rho value of ≤−0.57 or ≥0.57 resulting in 130 unique genes. Probe ID, gene symbol and description are also indicated. A combined table of unique genes identified by each or both methodologies is displayed in Table 4. In Table 4, the Log(2) fold change is indicated where a positive fold change represents increased expression in the sensitive class and a negative fold change represents increased expression in the resistant class of NHL cell lines with respect to anti-CD40 Ab.1 sensitivity. Gene represents 195 unique genes. Probe IDs, gene symbol and description are also indicated.

TABLE 2

| Gene Symbol | Probe | Description | adj. P. Val |
| --- | --- | --- | --- |
| RGS13 | 210258_at | regulator of G-protein signalling 13 | 2.57E−05 |
| MGC2463 | 219812_at | | 0.00015799 |
| VNN2 | 205922_at | vanin 2 | 0.000247994 |
| EPDR1 | 223253_at | ependymin related protein 1 (zebrafish) | 0.000434413 |
| MEF2B | 205124_at | MADS box transcription enhancer factor 2, polypeptide B (myocyte enhancer factor 2B) | 0.001352572 |
| SLAMF6 | 1552497_a_at | SLAM family member 6 | 0.00263509 |
| LCK | 204891_s_at | lymphocyte-specific protein tyrosine kinase | 0.00263509 |

TABLE 2-continued

| Gene Symbol | Probe | Description | adj. P. Val |
|---|---|---|---|
| LPP | 202822_at | LIM domain containing preferred translocation partner in lipoma | 0.005668066 |
| SLC30A1 | 212907_at | solute carrier family 30 (zinc transporter), member 1 | 0.00783662 |
| LTB | 207339_s_at | lymphotoxin beta (TNF superfamily, member 3) | 0.008947887 |
| FAM113B | 228298_at | family with sequence similarity 113, member B | 0.008947887 |
| BRDG1 | 220059_at | | 0.011013653 |
| PRPSAP2 | 203537_at | phosphoribosyl pyrophosphate synthetase-associated protein 2 | 0.011342898 |
| 244040_at | 244040_at | | 0.011342898 |
| SEMA4A | 219259_at | sema domain, immunoglobulin domain (Ig), transmembrane domain (TM) and short cytoplasmic domain, (semaphorin) 4A | 0.012794771 |
| CD86 | 210895_s_at | CD86 molecule | 0.013430782 |
| CD22 | 217422_s_at | CD22 molecule | 0.01483858 |
| LIMD1 | 222762_x_at | LIM domains containing 1 | 0.01483858 |
| 236126_at | 236126_at | | 0.01483858 |
| RUNDC2B | 1554411_s_at | RUN domain containing 2B | 0.01483858 |
| LOXL2 | 202998_s_at | lysyl oxidase-like 2 | 0.015908888 |
| GOLPH2 | 217771_at | golgi phosphoprotein 2 | 0.015908888 |
| RASGRP3 | 205801_s_at | RAS guanyl releasing protein 3 (calcium and DAG-regulated) | 0.015908888 |
| C21orf7 | 221211_s_at | chromosome 21 open reading frame 7 | 0.016054465 |
| RAP1A | 202362_at | RAP1A, member of RAS oncogene family | 0.016642805 |
| ANKRD13A | 224810_s_at | ankyrin repeat domain 13A | 0.016798331 |
| ZNF32 | 209538_at | zinc finger protein 32 | 0.017041183 |
| DAAM1 | 216060_s_at | dishevelled associated activator of morphogenesis 1 | 0.017041183 |
| CRTC3 | 218648_at | CREB regulated transcription coactivator 3 | 0.017041183 |
| C13orf31 | 228937_at | chromosome 13 open reading frame 31 | 0.017041183 |
| SMAP1L | 225282_at | stromal membrane-associated protein 1-like | 0.017041183 |
| 224811_at | 224811_at | | 0.017041183 |
| KCNN3 | 205903_s_at | potassium intermediate/small conductance calcium-activated channel, subfamily N, member 3 | 0.017041183 |
| S100Z | 1554876_a_at | S100 calcium binding protein, zeta | 0.017041183 |
| FZD1 | 204451_at | frizzled homolog 1 (Drosophila) | 0.017041183 |
| FLVCR | 222906_at | | 0.017041183 |
| MYBL1 | 213906_at | v-myb myeloblastosis viral oncogene homolog (avian)-like 1 | 0.017041183 |
| EHBP1 | 212653_s_at | EH domain binding protein 1 | 0.017041183 |
| SYNE2 | 242774_at | spectrin repeat containing, nuclear envelope 2 | 0.018508325 |
| FLJ36492 | 1557366_at | | 0.018508325 |
| MAP2K1 | 202670_at | mitogen-activated protein kinase 1 | 0.018508325 |
| NEIL1 | 219396_s_at | nei endonuclease VIII-like 1 (E. coli) | 0.018534278 |
| 228191_at | 228191_at | | 0.018813942 |
| LOC30203 | 225014_at | | 0.02072242 |
| OPN3 | 219032_x_at | opsin 3 (encephalopsin, panopsin) | 0.021965295 |
| 227539_at | 227539_at | | 0.022123902 |
| GCHFR | 204867_at | GTP cyclohydrolase I feedback regulator | 0.024418721 |
| 239287_at | 239287_at | | 0.024681541 |
| B3GALNT2 | 226233_at | beta-1,3-N-acetylgalactosaminyltransferase 2 | 0.024681541 |
| ANUBL1 | 223624_at | AN1, ubiquitin-like, homolog (Xenopus laevis) | 0.024681541 |
| 241879_at | 241879_at | | 0.026428191 |
| HDAC1 | 201209_at | histone deacetylase 1 | 0.027641246 |
| FHL1 | 201540_at | four and a half LIM domains 1 | 0.027802063 |
| PON2 | 201876_at | paraoxonase 2 | 0.028969668 |
| DNMT1 | 227684_at | DNA (cytosine-5-)-methyltransferase 1 | 0.030015625 |
| GABARAPL2 | 209046_s_at | GABA(A) receptor-associated protein-like 2 | 0.031517586 |
| HSP90B1 | 216449_x_at | heat shock protein 90 kDa beta (Grp94), member 1 | 0.031894346 |
| RRAS2 | 212590_at | related RAS viral (r-ras) oncogene homolog 2 | 0.032663885 |
| ARSG | 230748_at | arylsulfatase G | 0.03380232 |
| UGDH | 203343_at | UDP-glucose dehydrogenase | 0.03380232 |
| KCNMB4 | 222857_s_at | potassium large conductance calcium-activated channel, subfamily M, beta member 4 | 0.03380232 |
| SYTL1 | 227134_at | synaptotagmin-like 1 | 0.034025836 |
| CYFIP1 | 208923_at | cytoplasmic FMR1 interacting protein 1 | 0.035718667 |
| HIPK2 | 225368_at | homeodomain interacting protein kinase 2 | 0.035718667 |

TABLE 2-continued

| Gene Symbol | Probe | Description | adj. P. Val |
|---|---|---|---|
| MAN2A2 | 202032_s_at | mannosidase, alpha, class 2A, member 2 | 0.035718667 |
| AAK1 | 225522_at | AP2 associated kinase 1 | 0.035782217 |
| TBPL1 | 208398_s_at | TBP-like 1 | 0.036337106 |
| 1553979_at | 1553979_at | | 0.037283374 |
| CHML | 226350_at | choroideremia-like (Rab escort protein 2) | 0.037979419 |
| VARS | 201796_s_at | valyl-tRNA synthetase | 0.037979419 |
| PTK2 | 208820_at | PTK2 protein tyrosine kinase 2 | 0.037979419 |
| IGF1R | 203627_at | insulin-like growth factor 1 receptor | 0.037979419 |
| GRB2 | 215075_s_at | growth factor receptor-bound protein 2 | 0.039960264 |
| ATP8A1 | 213106_at | ATPase, aminophospholipid transporter (APLT), Class I, type 8A, member 1 | 0.039960264 |
| FZD3 | 219683_at | frizzled homolog 3 (*Drosophila*) | 0.041405941 |
| KIF1B | 225878_at | kinesin family member 1B | 0.041405941 |
| UBXD2 | 212008_at | UBX domain containing 2 | 0.041405941 |
| TMEM87A | 212202_s_at | transmembrane protein 87A | 0.041888206 |
| PARVB | 37965_at | parvin, beta | 0.042377536 |
| SLC26A2 | 205097_at | solute carrier family 26 (sulfate transporter), member 2 | 0.042377536 |
| FCRLM1 | 235400_at | Fc receptor-like and mucin-like 1 | 0.042377536 |
| PDGFD | 219304_s_at | platelet derived growth factor D | 0.043219716 |
| PRDX4 | 201923_at | peroxiredoxin 4 | 0.043219716 |
| SERPINA9 | 1553499_s_at | serpin peptidase inhibitor, clade A (alpha-1 antiproteinase, antitrypsin), member 9 | 0.043248911 |
| C6orf62 | 222309_at | chromosome 6 open reading frame 62 | 0.043554388 |
| 226525_at | 226525_at | | 0.043554388 |
| TOB1 | 228834_at | transducer of ERBB2, 1 | 0.043554388 |
| 228242_at | 228242_at | | 0.043742426 |
| PKHD1L1 | 230673_at | polycystic kidney and hepatic disease 1 (autosomal recessive)-like 1 | 0.04395172 |
| KLHL6 | 1560396_at | kelch-like 6 (*Drosophila*) | 0.04395172 |
| ASB2 | 227915_at | ankyrin repeat and SOCS box-containing 2 | 0.044799524 |
| PLEKHF2 | 222699_s_at | pleckstrin homology domain containing, family F (with FYVE domain) member 2 | 0.046489788 |
| KLHL23 | 213610_s_at | kelch-like 23 (*Drosophila*) | 0.046489788 |
| CPNE2 | 225129_at | copine II | 0.046489788 |
| LOC642236 | 215160_x_at | | 0.047687714 |
| GALNT2 | 217787_s_at | UDP-N-acetyl-alpha-D-galactosamine:polypeptide N-acetylgalactosaminyltransferase 2 (GalNAc-T2) | 0.047687714 |
| CD180 | 206206_at | CD180 molecule | 0.047687714 |
| CPNE5 | 227189_at | copine V | 0.047687714 |
| FH | 203032_s_at | fumarate hydratase | 0.047687714 |
| KIF14 | 206364_at | kinesin family member 14 | 0.047687714 |
| PEA15 | 200787_s_at | phosphoprotein enriched in astrocytes 15 | 0.047687714 |
| TOX | 204529_s_at | | 0.047687714 |
| MRPS31 | 212604_at | mitochondrial ribosomal protein S31 | 0.047687714 |
| SEC23A | 204344_s_at | Sec23 homolog A (*S. cerevisiae*) | 0.047687714 |
| DPYD | 204646_at | dihydropyrimidine dehydrogenase | 0.047864579 |
| 227107_at | 227107_at | | 0.047864579 |
| RAB11FIP1 | 219681_s_at | RAB11 family interacting protein 1 (class I) | 0.047864579 |
| C1orf107 | 214193_s_at | chromosome 1 open reading frame 107 | 0.047864579 |
| ATXN10 | 208833_s_at | ataxin 10 | 0.048252462 |
| CPEB4 | 224831_at | cytoplasmic polyadenylation element binding protein 4 | 0.048504075 |

TABLE 3

| Symbol | Probe | Description | rho |
|---|---|---|---|
| SLC30A1 | 228181_at | solute carrier family 30 (zinc transporter), member 1 | 0.754838311 |
| EPDR1 | 223253_at | ependymin related protein 1 (zebrafish) | 0.733893852 |
| FZD1 | 204451_at | frizzled homolog 1 (*Drosophila*) | 0.732218295 |
| MAN2A2 | 202032_s_at | mannosidase, alpha, class 2A, member 2 | 0.721327176 |
| PVRIG | 219812_at | | −0.715881617 |
| EHBP1 | 212653_s_at | EH domain binding protein 1 | 0.706666055 |
| DAAM1 | 226666_at | G protein-coupled receptor 135 | −0.705409387 |
| SMAP1L | 225282_at | stromal membrane-associated protein 1-like | −0.704990498 |
| PRPSAP2 | 203537_at | phosphoribosyl pyrophosphate synthetase-associated protein 2 | −0.702896052 |
| HSP90B1 | 216449_x_at | heat shock protein 90 kDa beta (Grp94), member 1 | 0.691586044 |

TABLE 3-continued

| Symbol | Probe | Description | rho |
|---|---|---|---|
| ZNF322A | 219376_at | zinc finger protein 322A | 0.690748265 |
| TMEM87A | 212202_s_at | transmembrane protein 87A | 0.68823493 |
| RABGAP1L | 213982_s_at | RAB GTPase activating protein 1-like | −0.681951593 |
| EAF2 | 219551_at | ELL associated factor 2 | −0.681532703 |
| KCNMB4 | 234034_at | potassium large conductance calcium-activated channel, subfamily M, beta member 4 | −0.673992698 |
| LCK | 204891_s_at | lymphocyte-specific protein tyrosine kinase | −0.668547139 |
| RGS13 | 1568752_s_at | regulator of G-protein signalling 13 | −0.666452693 |
| TOB1 | 228834_at | transducer of ERBB2, 1 | −0.663520468 |
| PLEKHF2 | 218640_s_at | pleckstrin homology domain containing, family F (with FYVE domain) member 2 | −0.66268269 |
| TBPL1 | 208398_s_at | TBP-like 1 | −0.658912687 |
| KLHL23 | 230434_at | kelch-like 23 (Drosophila) | 0.658493798 |
| SEMA4C | 46665_at | sema domain, immunoglobulin domain (Ig), transmembrane domain (TM) and short cytoplasmic domain, (semaphorin) 4C | 0.658074909 |
| CRTC3 | 218648_at | CREB regulated transcription coactivator 3 | 0.657237131 |
| 237075_at | 237075_at | | −0.657237131 |
| GCS1 | 210627_s_at | | 0.650534904 |
| CPNE2 | 225129_at | copine II | 0.642576009 |
| PIGL | 205873_at | phosphatidylinositol glycan anchor biosynthesis, class L | −0.64215712 |
| MTHFR | 239035_at | 5,10-methylenetetrahydrofolate reductase (NADPH) | −0.64215712 |
| ENTPD6 | 201704_at | ectonucleoside triphosphate diphosphohydrolase 6 (putative function) | 0.641319342 |
| CD22 | 204581_at | CD22 molecule | −0.640062674 |
| TPD52 | 201691_s_at | tumor protein D52 | −0.637549339 |
| GPSM1 | 226043_at | G-protein signalling modulator 1 (AGS3-like, C. elegans) | 0.633360447 |
| 239467_at | 239467_at | | −0.632941558 |
| ROCK1 | 213044_at | Rho-associated, coiled-coil containing protein kinase 1 | −0.632522669 |
| CENTB2 | 212476_at | centaurin, beta 2 | −0.630847112 |
| WIPF1 | 231182_at | Wiskott-Aldrich syndrome protein interacting protein | −0.629590445 |
| RAB11FIP1 | 219681_s_at | RAB11 family interacting protein 1 (class I) | −0.628333777 |
| LPP | 202822_at | LIM domain containing preferred translocation partner in lipoma | −0.627077109 |
| FLJ22814 | 220674_at | | −0.62665822 |
| TRAP1 | 228929_at | TNF receptor-associated protein 1 | −0.62665822 |
| MRPS31 | 212603_at | mitochondrial ribosomal protein S31 | −0.625401553 |
| ANKRD13A | 224810_s_at | ankyrin repeat domain 13A | −0.625401553 |
| GALNT2 | 217788_s_at | UDP-N-acetyl-alpha-D-galactosamine:polypeptide N-acetylgalactosaminyltransferase 2 (GalNAc-T2) | 0.624982664 |
| ACVR2B | 236126_at | | 0.623160484 |
| CD180 | 206206_at | CD180 molecule | −0.62163155 |
| IXL | 225708_at | intersex-like (Drosophila) | 0.62163155 |
| FAM113B | 228298_at | family with sequence similarity 113, member B | −0.621212661 |
| MEF2B | 205124_at | MADS box transcription enhancer factor 2, polypeptide B (myocyte enhancer factor 2B) | −0.620793772 |
| 224811_at | 224811_at | | −0.620374882 |
| ATP6V1A | 201972_at | ATPase, H+ transporting, lysosomal 70 kDa, V1 subunit A | −0.619955993 |
| SLC15A2 | 205316_at | solute carrier family 15 (H+/peptide transporter), member 2 | −0.618280437 |
| RTN4IP1 | 224509_s_at | reticulon 4 interacting protein 1 | −0.618280437 |
| TTC9 | 213174_at | tetratricopeptide repeat domain 9 | −0.615767101 |
| PTPRC | 212587_s_at | protein tyrosine phosphatase, receptor type, C | −0.615348212 |
| FLJ43663 | 228702_at | | −0.615348212 |
| MARCH6 | 201736_s_at | membrane-associated ring finger (C3HC4) 6 | 0.615348212 |
| C13orf31 | 228937_at | chromosome 13 open reading frame 31 | −0.614929323 |
| CNOT6L | 226153_s_at | CCR4-NOT transcription complex, subunit 6-like | −0.614091545 |
| PIGW | 1558292_s_at | phosphatidylinositol glycan anchor biosynthesis, class W | 0.61115932 |

TABLE 3-continued

| Symbol | Probe | Description | rho |
|---|---|---|---|
| ARTS-1 | 210385_s_at | | 0.610740431 |
| RYK | 216976_s_at | RYK receptor-like tyrosine kinase | 0.609483764 |
| VNN2 | 205922_at | vanin 2 | −0.609483764 |
| FNTB | 204764_at | farnesyltransferase, CAAX box, beta | 0.608645985 |
| BICD1 | 242052_at | bicaudal D homolog 1 (*Drosophila*) | −0.607808207 |
| SEPT8 | 209000_s_at | septin 8 | 0.606970429 |
| WDR6 | 233573_s_at | WD repeat domain 6 | 0.606551539 |
| HDAC1 | 201209_at | histone deacetylase 1 | −0.604038204 |
| ATP2B4 | 212135_s_at | ATPase, Ca++ transporting, plasma membrane 4 | 0.604038204 |
| BRDG1 | 220059_at | | −0.602781537 |
| SERPINA9 | 1553499_s_at | serpin peptidase inhibitor, clade A (alpha-1 antiproteinase, antitrypsin), member 9 | −0.602362648 |
| CRSP6 | 221517_s_at | cofactor required for Sp1 transcriptional activation, subunit 6, 77 kDa | 0.602362648 |
| TMEM17 | 1557137_at | transmembrane protein 17 | 0.602362648 |
| BPNT1 | 232103_at | 3'(2'), 5'-bisphosphate nucleotidase 1 | −0.601943758 |
| 242826_at | 242826_at | | −0.601524869 |
| NCOA3 | 207700_s_at | nuclear receptor coactivator 3 | −0.598592645 |
| LRMP | 35974_at | lymphoid-restricted membrane protein | −0.598592645 |
| PTK2 | 208820_at | PTK2 protein tyrosine kinase 2 | −0.598173756 |
| C21orf7 | 221211_s_at | chromosome 21 open reading frame 7 | −0.598173756 |
| FCRL3 | 231093_at | Fc receptor-like 3 | −0.598173756 |
| FDFT1 | 208647_at | farnesyl-diphosphate farnesyltransferase 1 | −0.597335977 |
| DHX38 | 209178_at | DEAH (Asp-Glu-Ala-His) box polypeptide 38 | 0.596917088 |
| C1orf57 | 223272_s_at | chromosome 1 open reading frame 57 | 0.596917088 |
| ARSG | 230748_at | arylsulfatase G | −0.595660421 |
| MS4A7 | 223343_at | membrane-spanning 4-domains, subfamily A, member 7 | −0.595241531 |
| CYP39A1 | 244407_at | cytochrome P450, family 39, subfamily A, polypeptide 1 | −0.594403753 |
| DCK | 203302_at | deoxycytidine kinase | −0.593565975 |
| CTNNA1 | 1558214_s_at | catenin (cadherin-associated protein), alpha 1, 102 kDa | 0.593565975 |
| SLC27A2 | 205769_at | solute carrier family 27 (fatty acid transporter), member 2 | 0.592728196 |
| SLC35B2 | 224716_at | solute carrier family 35, member B2 | 0.592309307 |
| 243185_at | 243185_at | | −0.592309307 |
| FAM89B | 32209_at | family with sequence similarity 89, member B | 0.591890418 |
| GSG2 | 223759_s_at | germ cell associated 2 (haspin) | −0.591471529 |
| USP6NL | 204761_at | USP6 N-terminal like | −0.591105264 |
| ATPIF1 | 218671_s_at | ATPase inhibitory factor 1 | −0.590214861 |
| SLAMF6 | 1552497_a_at | SLAM family member 6 | −0.590214861 |
| TARSL2 | 227611_at | threonyl-tRNA synthetase-like 2 | 0.590214861 |
| XKR6 | 236047_at | XK, Kell blood group complex subunit-related family, member 6 | −0.589377083 |
| 228242_at | 228242_at | | 0.588958194 |
| EYA3 | 1552314_a_at | eyes absent homolog 3 (*Drosophila*) | −0.586863748 |
| RUNDC2B | 1554413_s_at | RUN domain containing 2B | −0.584530413 |
| BXDC5 | 218462_at | brix domain containing 5 | −0.583512634 |
| SLC26A2 | 205097_at | solute carrier family 26 (sulfate transporter), member 2 | 0.583512634 |
| PNMA1 | 218224_at | paraneoplastic antigen MA1 | 0.583512634 |
| LOC401504 | 226635_at | | −0.583093745 |
| GPR82 | 1553316_at | G protein-coupled receptor 82 | −0.582674856 |
| ZBTB9 | 226163_at | zinc finger and BTB domain containing 9 | 0.582255967 |
| BFSP2 | 207399_at | beaded filament structural protein 2, phakinin | −0.580999299 |
| SLC6A16 | 219820_at | solute carrier family 6, member 16 | −0.580999299 |
| SBNO2 | 204166_at | KIAA0963 | 0.580161521 |
| CTSC | 201487_at | cathepsin C | 0.579323742 |
| EID1 | 208669_s_at | CREBBP/EP300 inhibitor 1 | 0.579323742 |
| RRAS2 | 212589_at | related RAS viral (r-ras) oncogene homolog 2 | −0.578904853 |
| NLK | 238624_at | nemo-like kinase | −0.578904853 |
| FLJ36492 | 1557366_at | | −0.578904853 |
| RALGDS | 209051_s_at | ral guanine nucleotide dissociation stimulator | 0.578485964 |
| CIRBP | 225191_at | cold inducible RNA binding protein | 0.578067075 |
| P4HB | 1564494_s_at | procollagen-proline, 2-oxoglutarate 4-dioxygenase (proline 4-hydroxylase), beta polypeptide | 0.578067075 |
| ATG3 | 221492_s_at | ATG3 autophagy related 3 homolog (*S. cerevisiae*) | −0.578067075 |
| 227539_at | 227539_at | | −0.577648186 |
| FLJ10815 | 56821_at | | 0.577648186 |

TABLE 3-continued

| Symbol | Probe | Description | rho |
|---|---|---|---|
| C19orf54 | 222052_at | chromosome 19 open reading frame 54 | −0.577229296 |
| PORCN | 219483_s_at | porcupine homolog (*Drosophila*) | 0.576810407 |
| PDE6D | 204091_at | phosphodiesterase 6D, cGMP-specific, rod, delta | −0.576391518 |
| LOC389203 | 225014_at |  | −0.576391518 |
| 235018_at | 235018_at |  | −0.575134851 |
| CDK10 | 210622_x_at | cyclin-dependent kinase (CDC2-like) 10 | 0.575134851 |
| KYNU | 210662_at | kynureninase (L-kynurenine hydrolase) | −0.573878183 |
| PIGG | 218652_s_at | phosphatidylinositol glycan anchor biosynthesis, class G | 0.573878183 |
| TMEM64 | 225972_at | transmembrane protein 64 | −0.573878183 |
| NEDD9 | 240019_at | neural precursor cell expressed, developmentally down-regulated 9 | −0.573878183 |

TABLE 4

| Symbol | Probes | Description | logFC | Adj. P. value | rho |
|---|---|---|---|---|---|
| EPDR1 | 223253_at | ependymin related protein 1 (zebrafish) | −6.71079565 | 4.3441E−04 | 0.734 |
| HIPK2 | 225368_at | NA | −5.568390135 | 3.5719E−02 | NA |
| CYFIP1 | 208923_at | NA | −5.507430049 | 3.5719E−02 | NA |
| GOLPH2 | 217771_at | NA | −5.149533123 | 1.5909E−02 | NA |
| PON2 | 201876_at | NA | −5.02937768 | 2.8970E−02 | NA |
| OPN3 | 219032_x_at | NA | −4.868576042 | 2.1965E−02 | NA |
| FHL1 | 201540_at | NA | −4.849936383 | 2.7802E−02 | NA |
| DPYD | 204646_at | NA | −4.601899147 | 4.7865E−02 | NA |
| CRTC3 | 218648_at | CREB regulated transcription coactivator 3 | −4.447380308 | 1.7041E−02 | 0.657 |
| LIMD1 | 222762_x_at | NA | −4.385468009 | 1.4839E−02 | NA |
| IGF1R | 203627_at | NA | −3.780119703 | 3.7979E−02 | NA |
| PARVB | 37965_at | NA | −3.705700946 | 4.2378E−02 | NA |
| 236126_at | 236126_at | NA | −3.694482091 | 1.4839E−02 | NA |
| CHML | 226350_at | NA | −3.643899135 | 3.7979E−02 | NA |
| FZD1 | 204451_at | frizzled homolog 1 (*Drosophila*) | −3.531407505 | 1.7041E−02 | 0.732 |
| AAK1 | 225522_at | NA | −3.502784982 | 3.5782E−02 | NA |
| CPNE2 | 225129_at | copine II | −3.432724459 | 4.6490E−02 | 0.643 |
| KLHL23 | 213610_s_at, 230434_at | kelch-like 23 (*Drosophila*) | −3.407601857 | 4.6490E−02 | 0.658 |
| ZNF32 | 209538_at | NA | −3.37444837 | 1.7041E−02 | NA |
| GALNT2 | 217787_s_at, 217788_s_at | UDP-N-acetyl-alpha-D-galactosamine:polypeptide N-acetylgalactosaminyltransferase 2 (GalNAc-T2) | −3.068993195 | 4.7688E−02 | 0.625 |
| SLC30A1 | 212907_at, 228181_at | solute carrier family 30 (zinc transporter), member 1 | −2.897034114 | 7.8366E−03 | 0.755 |
| KIF1B | 225878_at | NA | −2.893360476 | 4.1406E−02 | NA |
| FZD3 | 219683_at | NA | −2.888266087 | 4.1406E−02 | NA |
| SLC26A2 | 205097_at | solute carrier family 26 (sulfate transporter), member 2 | −2.592191782 | 4.2378E−02 | 0.584 |
| VARS | 201796_s_at | NA | −2.146698292 | 3.7979E−02 | NA |
| MAN2A2 | 202032_s_at | mannosidase, alpha, class 2A, member 2 | −2.05163539 | 3.5719E−02 | 0.721 |
| C6orf62 | 222309_at | NA | −1.970715812 | 4.3554E−02 | NA |
| UGDH | 203343_at | NA | −1.915040205 | 3.3802E−02 | NA |
| HSP90B1 | 216449_x_at | heat shock protein 90 kDa beta (Grp94), member 1 | −1.779135947 | 3.1894E−02 | 0.692 |
| B3GALNT2 | 226233_at | NA | −1.591532059 | 2.4682E−02 | NA |
| FLVCR | 222906_at | NA | −1.528203803 | 1.7041E−02 | NA |
| 227107_at | 227107_at | NA | −1.436834856 | 4.7865E−02 | NA |
| SEC23A | 204344_s_at | NA | −1.377564142 | 4.7688E−02 | NA |
| 228242_at | 228242_at | NA | −1.314847732 | 4.3742E−02 | 0.589 |
| TMEM87A | 212202_s_at | transmembrane protein 87A | −1.267840163 | 4.1888E−02 | 0.688 |
| 228191_at | 228191_at | NA | −1.196685963 | 1.8814E−02 | NA |
| KIF14 | 206364_at | NA | −1.150921894 | 4.7688E−02 | NA |
| EHBP1 | 212653_s_at | EH domain binding protein 1 | −1.110923792 | 1.7041E−02 | 0.707 |
| C1orf107 | 214193_s_at | NA | −1.102968299 | 4.7865E−02 | NA |
| UBXD2 | 212008_at | NA | −1.062833934 | 4.1406E−02 | NA |
| FH | 203032_s_at | NA | −1.047497846 | 4.7688E−02 | NA |
| PRDX4 | 201923_at | NA | −0.976330782 | 4.3220E−02 | NA |
| 1553979_at | 1553979_at | NA | −0.95937263 | 3.7283E−02 | NA |
| ATXN10 | 208833_s_at | NA | 0.717153159 | 4.8252E−02 | NA |
| GABARAPL2 | 209046_s_at | NA | 0.928831609 | 3.1518E−02 | NA |
| MAP2K1 | 202670_at | NA | 1.062284638 | 1.8508E−02 | NA |

TABLE 4-continued

| Symbol | Probes | Description | logFC | Adj. P. value | rho |
|---|---|---|---|---|---|
| LOC642236 | 215160_x_at | NA | 1.091751999 | 4.7688E−02 | NA |
| MRPS31 | 212604_at, 212603_at | mitochondrial ribosomal protein S31 | 1.140136013 | 4.7688E−02 | −0.625 |
| HDAC1 | 201209_at | histone deacetylase 1 | 1.189759283 | 2.7641E−02 | −0.604 |
| RAP1A | 202362_at | NA | 1.235628621 | 1.6643E−02 | NA |
| 226525_at | 226525_at | NA | 1.46297442 | 4.3554E−02 | NA |
| TBPL1 | 208398_s_at | TBP-like 1 | 1.50757518 | 3.6337E−02 | −0.659 |
| TOB1 | 228834_at | transducer of ERBB2, 1 | 1.580519874 | 4.3554E−02 | −0.664 |
| SMAP1L | 225282_at | stromal membrane-associated protein 1-like | 1.582665273 | 1.7041E−02 | −0.705 |
| PEA15 | 200787_s_at | NA | 1.636511829 | 4.7688E−02 | NA |
| LOC389203 | 225014_at | NA | 1.653219861 | 2.0722E−02 | −0.576 |
| 227539_at | 227539_at | NA | 1.706768556 | 2.2124E−02 | −0.578 |
| GRB2 | 215075_s_at | NA | 1.719009368 | 3.9960E−02 | NA |
| PRPSAP2 | 203537_at | phosphoribosyl pyrophosphate synthetase-associated protein 2 | 1.937200364 | 1.1343E−02 | −0.703 |
| ANKRD13A | 224810_s_at | ankyrin repeat domain 13A | 2.096260555 | 1.6798E−02 | −0.625 |
| DAAM1 | 216060_s_at, 226666_at | G protein-coupled receptor 135 | 2.205266761 | 1.7041E−02 | −0.705 |
| SYNE2 | 242774_at | NA | 2.326279517 | 1.8508E−02 | NA |
| ATP8A1 | 213106_at | NA | 2.351268406 | 3.9960E−02 | NA |
| PLEKHF2 | 222699_s_at, 218640_s_at | pleckstrin homology domain containing, family F (with FYVE domain) member 2 | 3.004500438 | 4.6490E−02 | −0.663 |
| S100Z | 1554876_a_at | NA | 3.144995156 | 1.7041E−02 | NA |
| FLJ36492 | 1557366_at | NA | 3.222537991 | 1.8508E−02 | −0.579 |
| SLAMF6 | 1552497_a_at | SLAM family member 6 | 3.363017096 | 2.6351E−03 | −0.590 |
| CPEB4 | 224831_at | NA | 3.444268629 | 4.8504E−02 | NA |
| NEIL1 | 219396_s_at | NA | 3.470614786 | 1.8534E−02 | NA |
| KLHL6 | 1560396_at | NA | 3.592234269 | 4.3952E−02 | NA |
| ANUBL1 | 223624_at | NA | 3.597608491 | 2.4682E−02 | NA |
| SYTL1 | 227134_at | NA | 3.601625514 | 3.4026E−02 | NA |
| LPP | 202822_at | LIM domain containing preferred translocation partner in lipoma | 3.65635503 | 5.6681E−03 | −0.627 |
| ARSG | 230748_at | arylsulfatase G | 3.772680821 | 3.3802E−02 | −0.596 |
| DNMT1 | 227684_at | NA | 3.787896364 | 3.0016E−02 | NA |
| RAB11FIP1 | 219681_s_at | RAB11 family interacting protein 1 (class I) | 3.877841023 | 4.7865E−02 | −0.628 |
| 224811_at | 224811_at | NA | 3.884011816 | 1.7041E−02 | −0.620 |
| 241879_at | 241879_at | NA | 3.897073844 | 2.6428E−02 | NA |
| MYBL1 | 213906_at | NA | 3.964686033 | 1.7041E−02 | NA |
| KCNN3 | 244040_at | potassium large conductance calcium-activated channel, subfamily M, beta member 3 | 4.14713855 | 1.1343E−02 | NA |
| RUNDC2B | 1554413_s_at | RUN domain containing 2B | 4.249552511 | 1.4839E−02 | −0.584 |
| GCHFR | 204867_at | NA | 4.314659424 | 2.4419E−02 | NA |
| C13orf31 | 228937_at | chromosome 13 open reading frame 31 | 4.342634637 | 1.7041E−02 | −0.615 |
| KCNN3 | 205903_s_at | NA | 4.348558398 | 1.7041E−02 | NA |
| SERPINA9 | 1553499_s_at | serpin peptidase inhibitor, clade A (alpha-1 antiproteinase, antitrypsin), member 9 | 4.362716185 | 4.3249E−02 | −0.602 |
| ASB2 | 227915_at | NA | 4.393168852 | 4.4800E−02 | NA |
| CD180 | 206206_at | CD180 molecule | 4.400474176 | 4.7688E−02 | −0.622 |
| SEMA4A | 219259_at | NA | 4.461977712 | 1.2795E−02 | NA |
| PKHD1L1 | 230673_at | NA | 4.462674523 | 4.3952E−02 | NA |
| FAM113B | 228298_at | family with sequence similarity 113, member B | 4.725746806 | 8.9479E−03 | −0.621 |
| MGC2463 | 219812_at | NA | 4.747120819 | 1.5799E−04 | NA |
| PTK2 | 208820_at | PTK2 protein tyrosine kinase 2 | 4.830737904 | 3.7979E−02 | −0.598 |
| LTB | 207339_s_at | NA | 4.861032521 | 8.9479E−03 | NA |
| LOXL2 | 202998_s_at | NA | 4.936851624 | 1.5909E−02 | NA |
| KCNMB4 | 222857_s_at, 234034_at | potassium large conductance calcium-activated channel, subfamily M, beta member 4 | 5.103201059 | 3.3802E−02 | −0.674 |
| PDGFD | 219304_s_at | NA | 5.13661915 | 4.3220E−02 | NA |
| CD22 | 217422_s_at, 204581_at | CD22 molecule | 5.283886004 | 1.4839E−02 | −0.640 |
| CPNE5 | 227189_at | NA | 5.346723772 | 4.7688E−02 | NA |
| C21orf7 | 221211_s_at | chromosome 21 open reading frame 7 | 5.407994478 | 1.6054E−02 | −0.598 |
| CD86 | 210895_s_at | NA | 5.574519784 | 1.3431E−02 | NA |
| VNN2 | 205922_at | vanin 2 | 5.634272247 | 2.4799E−04 | −0.609 |
| TOX | 204529_s_at | NA | 5.647082288 | 4.7688E−02 | NA |
| RASGRP3 | 205801_s_at | NA | 5.676809838 | 1.5909E−02 | NA |

TABLE 4-continued

| Symbol | Probes | Description | logFC | Adj. P. value | rho |
|---|---|---|---|---|---|
| RRAS2 | 212590_at, 212589_at | related RAS viral (r-ras) oncogene homolog 2 | 5.694136051 | 3.2664E−02 | −0.579 |
| 239287_at | 239287_at | NA | 5.91276116 | 2.4682E−02 | NA |
| MEF2B | 205124_at | MADS box transcription enhancer factor 2, polypeptide B (myocyte enhancer factor 2B) | 6.009095593 | 1.3526E−03 | −0.621 |
| BRDG1 | 220059_at | NA | 6.358345958 | 1.1014E−02 | −0.603 |
| FCRLM1 | 235400_at | NA | 6.390558096 | 4.2378E−02 | NA |
| LCK | 204891_s_at | lymphocyte-specific protein tyrosine kinase | 7.315280882 | 2.6351E−03 | −0.669 |
| RGS13 | 210258_at, 1568752_s_at | regulator of G-protein signalling 13 | 10.29738517 | 2.5700E−05 | −0.666 |
| PVRIG | 219812_at | NA | NA | NA | −0.716 |
| RABGAP1L | 213982_s_at | RAB GTPase activating protein 1-like | NA | NA | −0.682 |
| EAF2 | 219551_at | ELL associated factor 2 | NA | NA | −0.682 |
| 237075_at | 237075_at | NA | NA | NA | −0.657 |
| MTHFR | 239035_at | 5,10-methylenetetrahydrofolate reductase (NADPH) | NA | NA | −0.642 |
| PIGL | 205873_at | phosphatidylinositol glycan anchor biosynthesis, class L | NA | NA | −0.642 |
| TPD52 | 201691_s_at | tumor protein D52 | NA | NA | −0.638 |
| 239467_at | 239467_at | NA | NA | NA | −0.633 |
| ROCK1 | 213044_at | Rho-associated, coiled-coil containing protein kinase 1 | NA | NA | −0.633 |
| CENTB2 | 212476_at | centaurin, beta 2 | NA | NA | −0.631 |
| WIPF1 | 231182_at | Wiskott-Aldrich syndrome protein interacting protein | NA | NA | −0.630 |
| FLJ22814 | 220674_at | NA | NA | NA | −0.627 |
| TRAP1 | 228929_at | TNF receptor-associated protein 1 | NA | NA | −0.627 |
| ATP6V1A | 201972_at | ATPase, H+ transporting, lysosomal 70 kDa, V1 subunit A | NA | NA | −0.620 |
| RTN4IP1 | 224509_s_at | reticulon 4 interacting protein 1 | NA | NA | −0.618 |
| SLC15A2 | 205316_at | solute carrier family 15 (H+/peptide transporter), member 2 | NA | NA | −0.618 |
| TTC9 | 213174_at | tetratricopeptide repeat domain 9 | NA | NA | −0.616 |
| FLJ43663 | 228702_at | NA | NA | NA | −0.615 |
| PTPRC | 212587_s_at | protein tyrosine phosphatase, receptor type, C | NA | NA | −0.615 |
| CNOT6L | 226153_s_at | CCR4-NOT transcription complex, subunit 6-like | NA | NA | −0.614 |
| BICD1 | 242052_at | bicaudal D homolog 1 (Drosophila) | NA | NA | −0.608 |
| BPNT1 | 232103_at | 3'(2'),5'-bisphosphate nucleotidase 1 | NA | NA | −0.602 |
| KAR | 242826_at | 3-ketoacyl-CoA reductase | NA | NA | −0.602 |
| LRMP | 35974_at | lymphoid-restricted membrane protein | NA | NA | −0.599 |
| NCOA3 | 207700_s_at | nuclear receptor coactivator 3 | NA | NA | −0.599 |
| FCRL3 | 231093_at | Fc receptor-like 3 | NA | NA | −0.598 |
| FDFT1 | 208647_at | farnesyl-diphosphate farnesyltransferase 1 | NA | NA | −0.597 |
| MS4A7 | 223343_at | membrane-spanning 4-domains, subfamily A, member 7 | NA | NA | −0.595 |
| CYP39A1 | 244407_at | cytochrome P450, family 39, subfamily A, polypeptide 1 | NA | NA | −0.594 |
| DCK | 203302_at | deoxycytidine kinase | NA | NA | −0.594 |
| 243185_at | 243185_at | NA | NA | NA | −0.592 |
| GSG2 | 223759_s_at | germ cell associated 2 (haspin) | NA | NA | −0.591 |
| USP6NL | 204761_at | USP6 N-terminal like | NA | NA | −0.591 |
| ATPIF1 | 218671_s_at | ATPase inhibitory factor 1 | NA | NA | −0.590 |
| XKR6 | 236047_at | XK, Kell blood group complex subunit-related family, member 6 | NA | NA | −0.589 |
| EYA3 | 1552314_a_at | eyes absent homolog 3 (Drosophila) | NA | NA | −0.587 |
| BXDC5 | 218462_at | brix domain containing 5 | NA | NA | −0.584 |
| LOC401504 | 226635_at | NA | NA | NA | −0.583 |

TABLE 4-continued

| Symbol | Probes | Description | logFC | Adj. P. value | rho |
|---|---|---|---|---|---|
| GPR82 | 1553316_at | G protein-coupled receptor 82 | NA | NA | −0.583 |
| BFSP2 | 207399_at | beaded filament structural protein 2, phakinin | NA | NA | −0.581 |
| SLC6A16 | 219820_at | solute carrier family 6, member 16 | NA | NA | −0.581 |
| NLK | 238624_at | nemo-like kinase | NA | NA | −0.579 |
| ATG3 | 221492_s_at | ATG3 autophagy related 3 homolog (*S. cerevisiae*) | NA | NA | −0.578 |
| C19orf54 | 222052_at | chromosome 19 open reading frame 54 | NA | NA | −0.577 |
| PDE6D | 204091_at | phosphodiesterase 6D, cGMP-specific, rod, delta | NA | NA | −0.576 |
| 235018_at | 235018_at | NA | NA | NA | −0.575 |
| KYNU | 210662_at | kynureninase (L-kynurenine hydrolase) | NA | NA | −0.574 |
| NEDD9 | 240019_at | neural precursor cell expressed, developmentally down-regulated 9 | NA | NA | −0.574 |
| TMEM64 | 225972_at | transmembrane protein 64 | NA | NA | −0.574 |
| PIGG | 218652_s_at | phosphatidylinositol glycan anchor biosynthesis, class G | NA | NA | 0.574 |
| CDK10 | 210622_x_at | cyclin-dependent kinase (CDC2-like) 10 | NA | NA | 0.575 |
| PORCN | 219483_s_at | porcupine homolog (*Drosophila*) | NA | NA | 0.577 |
| FLJ10815 | 56821_at | NA | NA | NA | 0.578 |
| CIRBP | 225191_at | cold inducible RNA binding protein | NA | NA | 0.578 |
| P4HB | 1564494_s_at | procollagen-proline, 2-oxoglutarate 4-dioxygenase (proline 4-hydroxylase), beta polypeptide | NA | NA | 0.578 |
| RALGDS | 209051_s_at | ral guanine nucleotide dissociation stimulator | NA | NA | 0.578 |
| CTSC | 201487_at | cathepsin C | NA | NA | 0.579 |
| EID1 | 208669_s_at | CREBBP/EP300 inhibitor 1 | NA | NA | 0.579 |
| SBNO2 | 204166_at | KIAA0963 | NA | NA | 0.580 |
| ZBTB9 | 226163_at | zinc finger and BTB domain containing 9 | NA | NA | 0.582 |
| PNMA1 | 218224_at | paraneoplastic antigen MA1 | NA | NA | 0.584 |
| TARSL2 | 227611_at | threonyl-tRNA synthetase-like 2 | NA | NA | 0.590 |
| FAM89B | 32209_at | family with sequence similarity 89, member B | NA | NA | 0.592 |
| SLC35B2 | 224716_at | solute carrier family 35, member B2 | NA | NA | 0.592 |
| SLC27A2 | 205769_at | solute carrier family 27 (fatty acid transporter), member 2 | NA | NA | 0.593 |
| CTNNA1 | 1558214_s_at | catenin (cadherin-associated protein), alpha 1, 102 kDa | NA | NA | 0.594 |
| C1orf57 | 223272_s_at | chromosome 1 open reading frame 57 | NA | NA | 0.597 |
| DHX38 | 209178_at | DEAH (Asp-Glu-Ala-His) box polypeptide 38 | NA | NA | 0.597 |
| CRSP6 | 221517_s_at | cofactor required for Sp1 transcriptional activation, subunit 6, 77 kDa | NA | NA | 0.602 |
| TMEM17 | 1557137_at | transmembrane protein 17 | NA | NA | 0.602 |
| ATP2B4 | 212135_s_at | ATPase, Ca++ transporting, plasma membrane 4 | NA | NA | 0.604 |
| WDR6 | 233573_s_at | WD repeat domain 6 | NA | NA | 0.607 |
| SEPT8 | 209000_s_at | septin 8 | NA | NA | 0.607 |
| FNTB | 204764_at | farnesyltransferase, CAAX box, beta | NA | NA | 0.609 |
| RYK | 216976_s_at | RYK receptor-like tyrosine kinase | NA | NA | 0.609 |
| ARTS-1 | 210385_s_at | NA | NA | NA | 0.611 |
| PIGW | 1558292_s_at | phosphatidylinositol glycan anchor biosynthesis, class W | NA | NA | 0.611 |
| MARCH6 | 201736_s_at | membrane-associated ring finger (C3HC4) 6 | NA | NA | 0.615 |
| IXL | 225708_at | intersex-like (*Drosophila*) | NA | NA | 0.622 |
| ACVR2B | 236126_at | NA | NA | NA | 0.623 |
| GPSM1 | 226043_at | G-protein signalling modulator 1 (AGS3-like, *C. elegans*) | NA | NA | 0.633 |

TABLE 4-continued

| Symbol | Probes | Description | logFC | Adj. P. value | rho |
|---|---|---|---|---|---|
| ENTPD6 | 201704_at | ectonucleoside triphosphate diphosphohydrolase 6 (putative function) | NA | NA | 0.641 |
| GCS1 | 210627_s_at | NA | NA | NA | 0.651 |
| SEMA4C | 46665_at | sema domain, immunoglobulin domain (Ig), transmembrane domain (TM) and short cytoplasmic domain, (semaphorin) 4C | NA | NA | 0.658 |
| ZNF322A | 219376_at | zinc finger protein 322A | NA | NA | 0.691 |

The genes that are highly expressed in Table 4 may be co-regulated genes that may not be related to the biology of anti-CD40 activity. Therefore to comprehend the biological function of the genes that are differentially expressed between sensitive and resistant cells, we carried out Gene Set Enrichment Analysis (GSEA). In this analysis, we address the question by calculating the mean t-statistic for genes in the set, and then comparing that mean t-statistic to the mean statistics calculated for random sets of genes of the same size. A low p-value may indicate that there is some correlation between the set of genes and the sample classification used to generate the statistics. Gene Set Analysis can thus be interpreted as a summary of the properties of the genes that are highly differentially expressed. Table 5 provides gene set enrichment analysis of anti-CD40 Ab.1 Sensitive vs. Resistant NHL cell lines. Enriched gene sets, number of genes per gene set, normalized enrichment score (NES), and nominal p-value (NOM p-val) are displayed. The higher the NES and the lower the NOM p-val, the more likely the findings are significant.

TABLE 5

| Gene Set Name | Number of Genes | NES | NOM p-val |
|---|---|---|---|
| BCRPATHWAY | 35 | 1.5387669 | 0.018181818 |
| BASSO_GERMINAL_CENTER-CD40_DN | 70 | 1.5124674 | 0.016949153 |

Figure 2:
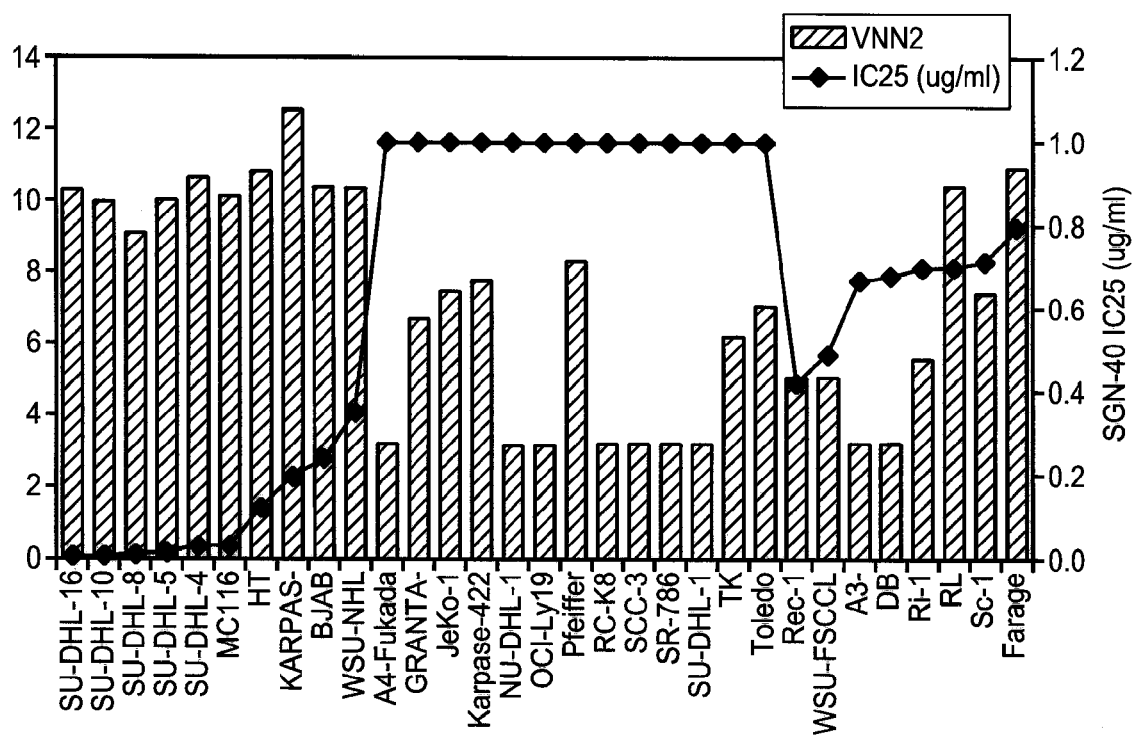
FIG. 2. VNN2, a CD40L-downregulated gene, is overexpressed in sensitive NHL cells to anti-CD40 Ab.1 and discriminates between the two classes of sensitive and resistant. The bar graph represents the mRNA expression level and the line graph represents the IC25 values.

Of the GSEA identified gene sets that were biologically relevant, gene sets involved in B-cell Receptor Signaling (BCR) and genes that are of germinal center origin (Table 5) were enriched. Of primary interest is the observation of genes involved in CD40 signaling as determined by the BASSO_GERMINAL_CENTER_CD40DN gene set (FIG. 1). Basso et al., Blood 104:4088-96, 2004. This gene set refers to genes that have been reported to be repressed by CD40L in a Ramos cell line. The rank and adjusted p-value from the differentially expressed gene list is displayed in Table 6 with respect to this gene set. In Table 6, differentially expressed genes between sensitive and resistant cell lines are enriched for genes that are known to be CD40L downregulated. Ranked genes are derived from the moderated t-test (Table 2). 70 genes in total were part of this gene set with the top 11 being displayed in this table. Genes shown in table 6 were overexpressed in anti-CD40 Ab.1 sensitive cell lines. The partial overlap of genes with the BCR and CD40L genes is expected since the two signal transduction pathways converge at the axis of NF-κB transcription and both pathways can synergize to activate B-cells. We next ascertained if any of the CD40L-induced genes are capable of discriminating between sensitive and resistant NHL cell lines to anti-CD40 Ab.1. Of the CD40L genes within the differentially expressed gene list on Tables 2 and 3, VNN2 gave the most accurate discrimination for sensitive and resistant cell lines (FIG. 2).

TABLE 6

| Rank | Gene Symbol | ProbeID | Description | t-statistic | pvalue | adj. P. Val. |
|---|---|---|---|---|---|---|
| 3 | VNN2 | 205922_at | vanin 2 | 7.2679 | 0 | 0.000248 |
| 5 | MEF2C | 205124_at | MADS box transcription enhancer factor 2, polypeptide B (myocyte enhancer factor 2B) | 6.7125 | 0 | 0.001353 |
| 10 | LTB | 207339_s_at | lymphotoxin beta (TNF superfamily, member 3) | 4.8723 | 1.00E−04 | 0.008948 |
| 14 | KCNN3 | 244040_at | potassium intermediate/small conductance calcium-activated channel, subfamily N, member 3 | 5.4914 | 0 | 0.011343 |
| 252 | NCF1 | 204961_s_at | NCF1 | 4.0453 | 6.00E−04 | 0.094030 |
| 278 | BCL6 | 203140_at | B-cell CLL/lymphoma 6 (zinc finger protein 51) | 4.3355 | 3.00E−04 | 0.098016 |
| 349 | IGJ | 212592_at | immunoglobulin J polypeptide, linker protein for immunoglobulin alpha and mu polypeptides | 3.6952 | 0.0013 | 0.109865 |
| 475 | ELTI1902 | 207761_s_at | methyltransferase like 7A | 3.3433 | 0.0031 | 0.130104 |
| 498 | PNOC | 205901_at | prepronociceptin | 3.7812 | 0.0011 | 0.134773 |

TABLE 6-continued

| Rank | Gene Symbol | ProbeID | Description | t-statistic | pvalue | adj. P. Val. |
|---|---|---|---|---|---|---|
| 548 | CSF2RB | 205159_at | colony stimulating factor 2 receptor, beta, low-affinity (granulocyte-macrophage) | 3.3371 | 0.0031 | 0.146260 |
| 707 | POU2AF1 | 205267_at | POU domain, class 2, associating factor 1 | 3.3788 | 0.0028 | 0.171312 |

Figure 3A:
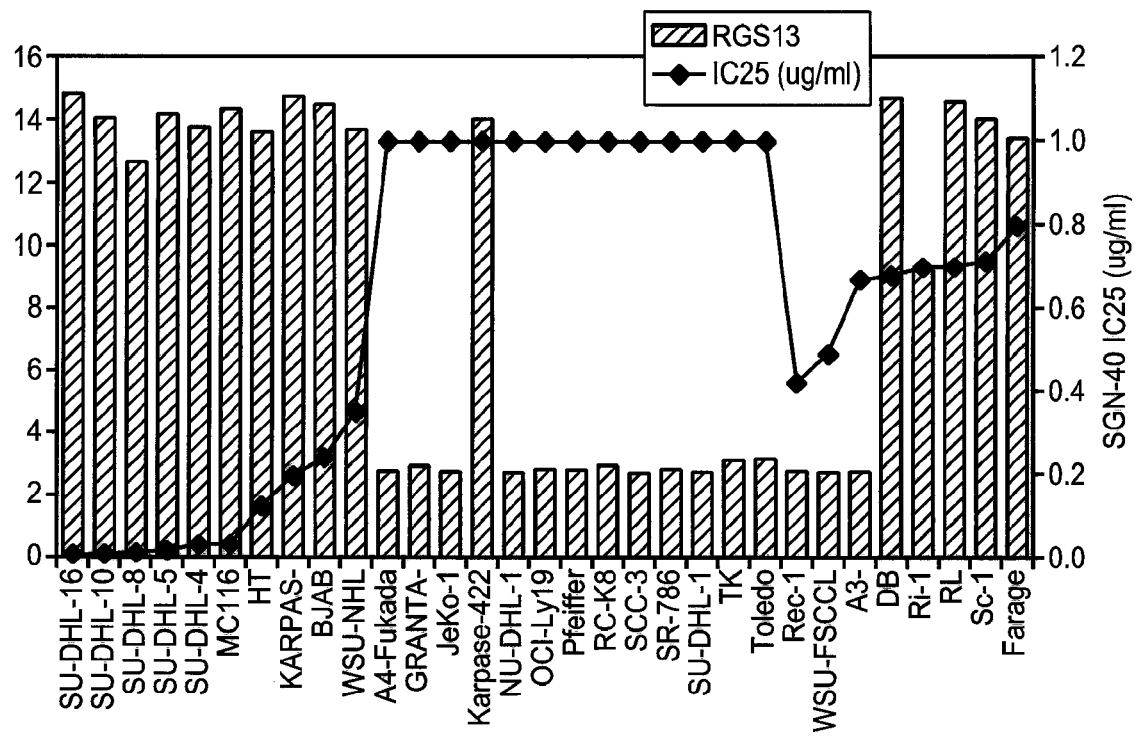
FIG. 3A-3C. RGS13, CD22, and MEF2B germinal center B markers, are overexpressed in sensitive and intermediate NHL cells to anti-CD40 Ab.1 and can discriminate with reasonable accuracy between the two classes of sensitive and resistant. The bar graph represents the mRNA expression level and the line graph represents the IC25 values.
Figure 3B:
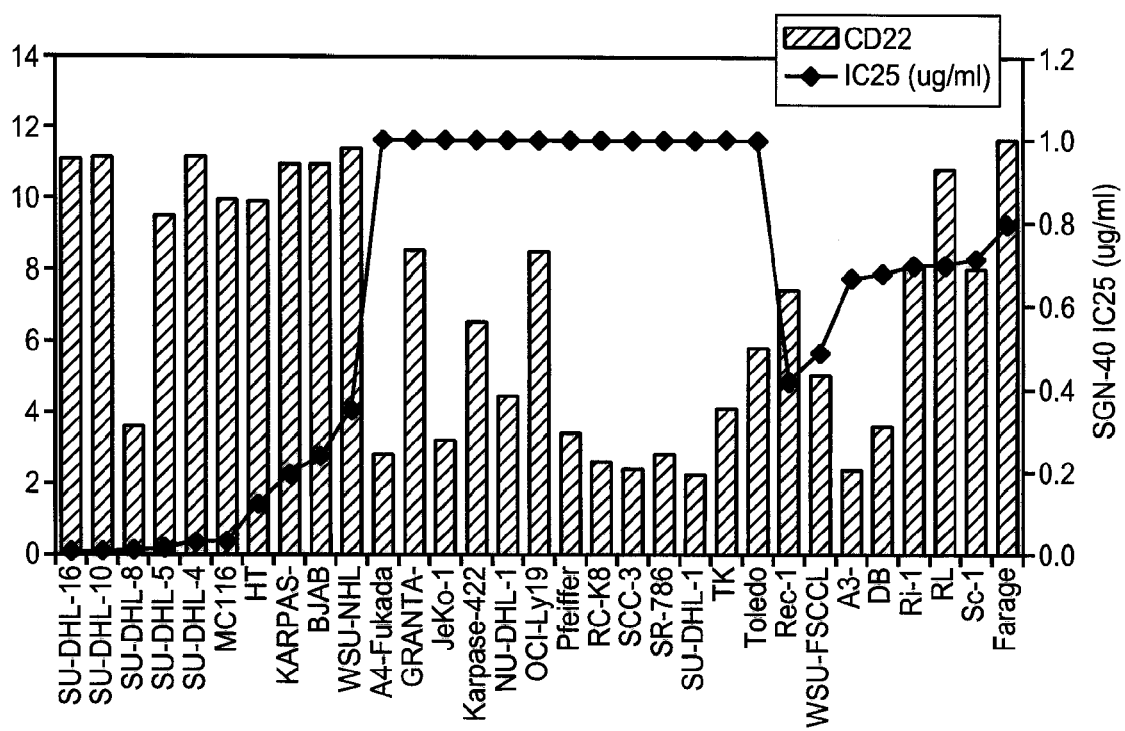
Figure 3C:
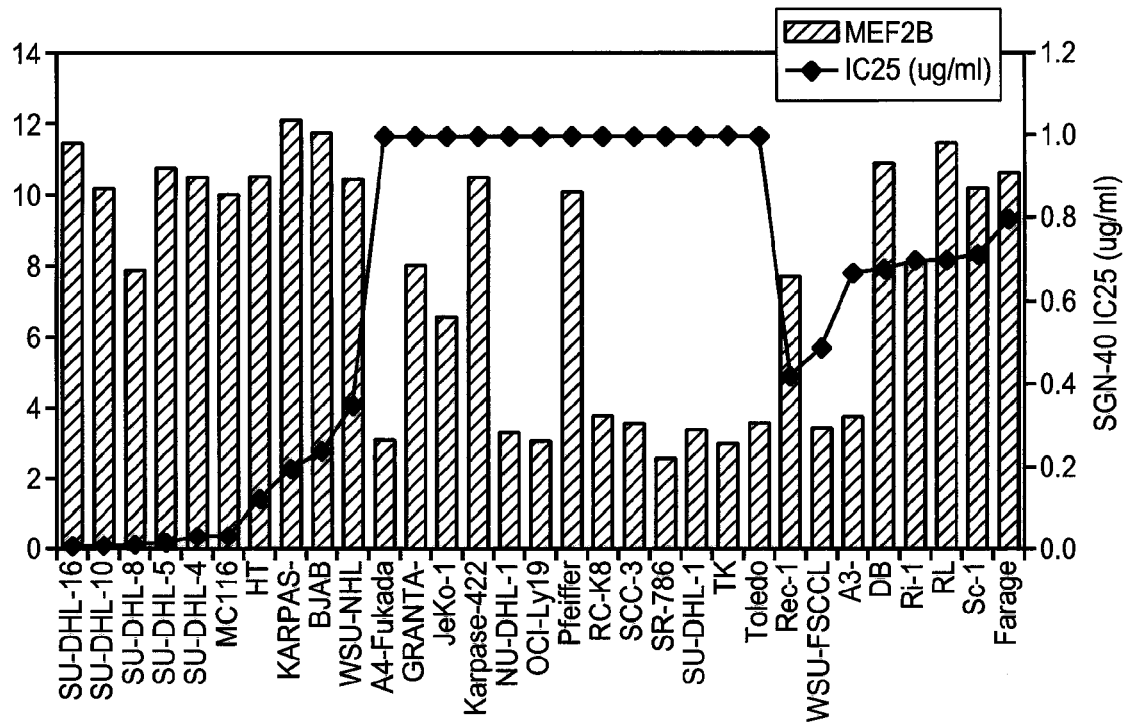
Figure 4:
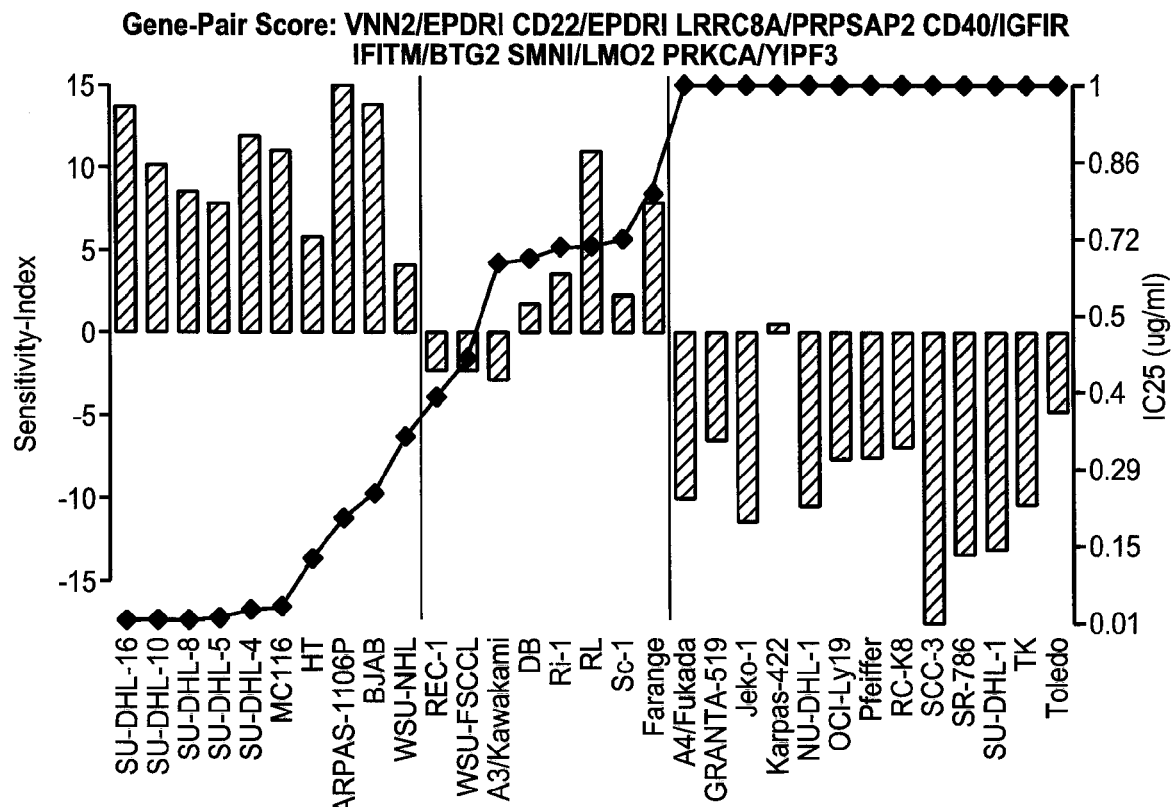
FIG. 4. Anti-CD40Ab.1 Sensitivity Index Scoring Across NHL Cell Lines. Stepwise Linear Modeling and gene-pair scoring was applied to each cell line based on mRNA expression data. The primary y-axis displays the anti-CD40 Ab.1 Sensitivity Index and the secondary y-axis displays the anti-CD40 Ab.1 IC25 values plotted against the NHL cell lines on the x-axis. A high anti-CD40 Ab.1 Sensitivity Index (>-4) represents an increased probability of a cell line being sensitive.
Figure 5:
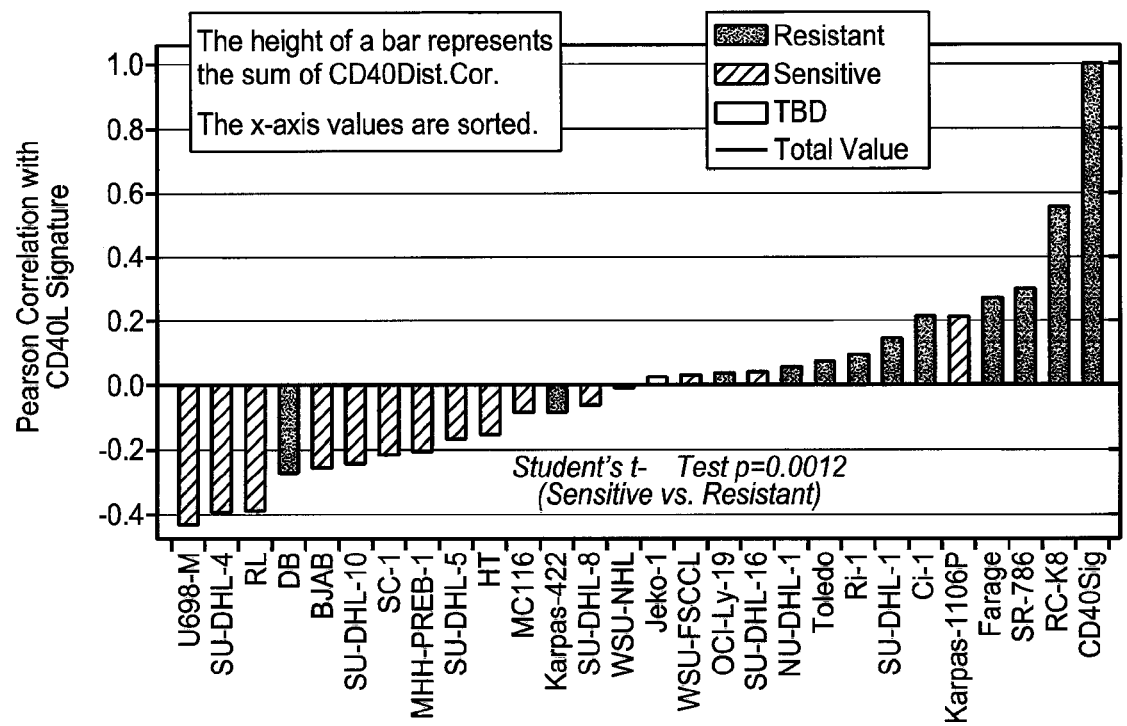
FIG. 5. Correlation of CD40 signature genes with anti-CD40.Ab.1 sensitivity.

Further inspection of the differentially expressed genes list also revealed genes such as CD22, RGS13, and MEF2B (Table 2 and FIGS. 3, 4, 6), that were indicative of germinal center B (GCB) cells were overexpressed in anti-CD40 Ab.1 sensitive cell lines. CD40 signature genes correlated with anti-CD40.Ab.1 sensitivity as shown in FIG. 5. Notably, RGS13 was one of the highest-ranking genes by moderated t-test (Table 2) and Spearman's rank correlation (Table 3) across the cell lines and as a single gene can discriminate between sensitive and resistant as well intermediate and resistant classes with high accuracy: 96% accuracy for sensitive vs. resistant. 81% for intermediate vs. resistant, and 87% for sensitive/intermediate vs. resistant.

To gain optimal classification accuracy it will likely require a gene signature, or metagene, classifier. Therefore, to identify genes that may contribute to the most accurate classifier we generated an algorithm to identify pairs of genes that when combined would give the best possible classification across the cell lines with respect to anti-CD40 Ab.1 sensitivity. We therefore carried out a Stepwise Linear Modeling to achieve this aim and the final gene selection is shown in Table 7. In Table 7, each target gene is shown with its corresponding inversely correlated (anti-correlated) Pair Gene, in order of the step at which the Target Gene was chosen for inclusion in the Index, as described earlier. This selection of gene pairs revealed a robust classification of Sensitive, Intermediate and Resistant classes to anti-CD40 Ab.1 (FIG. 4) when a Sensitivity Index was calculated, which is essentially the sum of signed t-scores for log 2-scale expression of Gene Pairs 1-8.

To further confirm predictive classifier, xenograft models are used to explore in therapy (such as combination therapy). Real time quantitative RT-PCR (qRT-PCR) is used for measuring gene expression levels. After confirming the predictive classifier, immunohistochemistry (IHC) assays are developed for a small group of markers selected (e.g., VNN2 and RGS13). Selected marker genes are further tested in clinical trial samples.

qRT-PCR and IHC are performed to measure expression levels of selected marker genes in clinical trial samples. Expression levels in samples from patients having relapsed diffuse large B-cell lymphoma that are responsive to the anti-CD40 treatment are compared the expression levels in samples from patients that are not responsive to the treatment.

Example 2

Identification of Markers Associated with Responsiveness to Treatment with Anti-CD40 Ab.1 in Clinical Trials Clinical Trial 001 (Phase II)

A multicenter, phase II, open-label study to determine the overall response rate and toxicity profile of anti-CD40 Ab.1 in patients with relapsed DLBCL. Tumor samples were assessed by a central lab for pathology confirmation and CD40 expression. Eligible patients had de novo or a transformed DLBCL at diagnosis and were excluded if there was a prior history of indolent lymphoma. Required prior therapy

TABLE 7

Anti-CD40 Ab.1 Sensitivity Index Identified Using Stepwise Linear Modeling.

| Gene Pair # | Step # | Main Gene Symbol | Main Gene Probe | Fold Change Estimate | Pair Gene Symbol | Pair Gene Probe | Correlation with Main Gene |
|---|---|---|---|---|---|---|---|
| 1 | 1 | VNN2 | 205922_at | +2.63 | EPDR1 | 223253_at | −0.72 |
| 2 | 1 | RGS13 | 210258_at | +5.18 | EPDR1 | 223253_at | −0.88 |
| 3 | 1 | CD22 | 204581_at | +2.70 | EPDR1 | 223253_at | −0.68 |
| 4 | 2 | LRRC8A | 233487_s_at | −0.50 | PRPSAP2 | 203537_at | −0.61 |
| 5 | 3 | CD40 | 205153_s_at | +1.47 | IGF1R | 203627_at | −0.76 |
| 6 | 4 | IFITM1 | 214022_s_at | −2.01 | BTG2 | 201236_s_at | −0.56 |
| 7 | 5 | SMN1 | 203852_s_at | +0.36 | LMO2 | 204249_s_at | −0.49 |
| 8 | 6 | PRKCA | 213093_at | −1.34 | YIPF3 | 216338_s_at | −0.72 |
| 9 | 7 | BCL6 | 203140_at | NA | NA | NA | NA |

Overall, CD40L plays a critical role in activating B-cells and results in the expansion and proliferation of B-cells as well as Ig class switching and the CD40L signaling pathway is also active within pre- and post-GCB-cells including naïve and memory B-cells. Therefore, it is striking to note that NHL cells that are displaying sensitivity to anti-CD40 Ab.1 are similar to GCB-cells in origin by gene expression profiling and have CD40L downregulated genes highly expressed, in contrast to resistant cells, indicative of a relationship between GCB and CD40 pathway activation status determining sensitivity to anti-CD40 Ab. 1.

consisted of combination chemotherapy with rituximab and, if eligible, autologous stem cell transplantation. Patients received 6 IV infusions of anti-CD40 Ab.1 over 5 weeks (Cycle 1) with intra-patient dose loading (1 mg/kg on Day 1; 2 mg/kg on Day 4; 4 mg/kg on Day 8) and 8 mg/kg/wk thereafter. Responding patients and those with SD (stable disease) were eligible to continue therapy until disease progression or up to a maximum of 12 cycles. Tumor tissues were taken from patients before they received treatment with anti-CD40 Ab.1. For example, samples were taken as part of routine lymphoma diagnosis.

Clinical Trial 002 (Phase I)

Multi-institutional, multi-dose phase I study was conducted to test the safety, pharmacokinetic properties, immunogenicity, and antitumor activity of intravenous anti-CD40 Ab.1 in patients with relapsed NHL. Patients with multiple histologic subtypes of NHL were enrolled on this study, including diffuse large B-cell (DLBCL; 14), follicular (FCL; 9), mantle cell (MCL; 9), marginal zone (MZL; 2) and small lymphocytic (SLL; 1). Patients were treated with a dose-loading schedule: 1 mg/kg of anti-CD40 Ab.1 on day 1 and day 4 and subsequent intra-patient dose-escalation during weeks 2-5 to a maximum dose of 3, 4, 6, or 8 mg/kg over four cohorts. Subsequently, a rapid dose-loading schedule was tested in one cohort (40% increase in total anti-CD40 Ab.1 administered during cycle 1). Responding patients or those with stable disease were eligible for a second cycle, consisting of four consecutive weekly infusions at the cohort-specific maximum dose of anti-CD40 Ab.1. Eight patients with DLBCL completed cycle 1 and received a maximum dose of at least 3 mg/kg anti-CD40 Ab.1 with an objective response rate of 37.5% (i.e. 1 CR and 2 PR) and 2 SD. Additional objective responses were seen in one patient with MCL (CR) and one patient with MZL (PR). The median duration of response for these 5 patients has not yet been reached (range 8-37 weeks). Tumor tissues were taken from patients before they received treatment with anti-Cd40 Ab.1. For example, samples were taken as part of routine lymphoma diagnosis.

Clinical Sample Preparation and qRT-PCR

Formalin Fixed Paraffin Embedded (FFPE) archival tumor tissue from the Phase I and Phase II clinical trials described above was obtained from the clinical investigation sites with appropriate IRB approval and patient consent. 4-6 micron sections derived from the tumor tissue were mounted on glass slides and one slide for each case was subject to H&E staining using standard pathology laboratory protocol. A board certified Pathologist marked the H&E slide for tumor content and was used as a guide to macrodissect the remaining tumor-containing region for RNA extraction using the Ambion RecoverAll™ Total Nucleic Acid Isolation Kit for FFPE Tissues (Cat. No. AM1975; Applied Biosystems/Ambion, Austin, Tex.).

450 ng total RNA per sample was reverse transcribed in a total reaction volume of 20 uL using Applied Biosystems' High Capacity Reverse Transcription cDNA Synthesis kit (Cat. No. 4368814; Applied Biosystems, Foster City, Calif.). Manufacturer's recommendations were followed with the exception of a shortened 60 min RT reaction at 37 degrees. 5 ng total RNA equivalent cDNA (assuming 100% cDNA synthesis efficiency) product was mixed with Applied Biosystems' 2× Universal Master Mix (no UNG) in a volume of 15 uL for each PCR assay well. All amplifications were performed in triplicate in 384-well plates using a 2-step (95 degrees 15 sec, 60 degrees 1 min) PCR amplification procedure. Reactions were carried out to 40 cycles on a validated ABI 7900 real-time PCR system. Sequences of the primers and probes used are shown in Table 10.

TABLE 10

Primers and Probes

| Gene Locus | GenBank Accession No. | Probe Overlap | Forward Primer | Reverse Primer | Probe |
|---|---|---|---|---|---|
| PRKCA | NM_002737.2 | 1 | TGACAAAATGTAGAGGCCATTCA (SEQ ID NO: 3) | CATCCGTCTCCTCTGCGATATAA (SEQ ID NO: 4) | CCGTCAAACACCATTT (SEQ ID NO: 5) |
| IGF1R | NM_000875.3 | 1 | TTGCAAGGAAAGAAATTCAAACAC (SEQ ID NO: 6) | TGCTTGAATCCATTGACTGCTT (SEQ ID NO: 7) | ACAACAGCAGTAAGAAGA (SEQ ID NO: 8) |
| BTG2 | NM_006763.2 | 1 | CAGGTCCCTGCCTTTTTAGAAG (SEQ ID NO: 9) | ATCATAAAGAAGAGAAGAGAGACAGAATTAAG (SEQ ID NO: 10) | AGCCTCATGGTCTCAT (SEQ ID NO: 11) |
| LMO2 | NM_005574.2 | 1 | GGCCACAGCCCATCCA (SEQ ID NO: 12) | CTTGCCCCTAAATGTTCCTTTCT (SEQ ID NO: 13) | AGTAACTGACATGATTAGC (SEQ ID NO: 14) |
| CD22 | NM_001771.2 | 1 | TTTGGAAGTGAGGCATTGCA (SEQ ID NO: 15) | CCGGAGTCCCCAGAGTCAA (SEQ ID NO: 16) | AGACGTACGTATCAGCG (SEQ ID NO: 17) |
| SMN1 | NM_000344.2 | 1 | CTGGAATGTGAAGCGTTATAGAAGAT (SEQ ID NO: 18) | CCTTTTTCTTTCCCAACACTTGA (SEQ ID NO: 19) | CTGGCCTCATTTCT (SEQ ID NO: 20) |
| EPDR1 | NM_017549.3 | 1 | CAGCCTCTCTTGTCCCTGGTT (SEQ ID NO: 21) | TCCCTAGCAATGGACAAACTCA (SEQ ID NO: 22) | CCTTATGTGTTGAATGTGG (SEQ ID NO: 23) |
| CD40 | NM_001250.4 | 1 | GGGATCCTGTTTGCCATCCT (SEQ ID NO: 24) | GCTTCTTGGCCACCTTTTTG (SEQ ID NO: 25) | TTGGTGCTGGTCTTT (SEQ ID NO: 26) |
| IFITM1 | NM_003641.3 | 1 | GGCTTCATAGCATTCGCCTACT (SEQ ID NO: 27) | TCACGTCGCCAACCATCTT (SEQ ID NO: 28) | CGTGAAGTCTAGGGACAG (SEQ ID NO: 29) |
| VNN2 | NM_004665.2 | 1 | GACTTGTATGTATGGGAGTGAGGAGTT (SEQ ID NO: 30) | TCTCTTCAAGGGCACAGCTATG (SEQ ID NO: 31) | CAGGGCCATTGCAA (SEQ ID NO: 32) |
| PRPSAP2 | NM_002767.2 | 1 | GCCAAACTGGAAACATAAGAGTGA (SEQ ID NO: 33) | GCATGACGGTTCCTGTGAAA (SEQ ID NO: 34) | TGCTCGGTGGGATGG (SEQ ID NO: 35) |
| PRKCA | NM_002737.2 | 1 | CGGAGGTTGAGGTTTTTCCTT (SEQ ID NO: 36) | GACGGTTGAATGGCCTCTACA (SEQ ID NO: 37) | TGTATAAGCACCTACTGACAAA (SEQ ID NO: 38) |

TABLE 10-continued

Primers and Probes

| Gene Locus | GenBank Accession No. | Probe Over-lap | Forward Primer | Reverse Primer | Probe |
|---|---|---|---|---|---|
| IGF1R | NM_000875.3 | 1 | AGGACTTCTTCATGGGTCTTACAGTT (SEQ ID NO: 39) | AAGTGACATTAAAGACGATGTGTATGC (SEQ ID NO: 40) | TGTTAGACCATGAAACATT (SEQ ID NO: 41) |
| BTG2 | NM_006763.2 | 1 | CAGGCTGTGTTCTTGCATCTTG (SEQ ID NO: 42) | GACCATGAGGCTGCTTCTAAAAA (SEQ ID NO: 43) | CTGCAAACAGGTCCCT (SEQ ID NO: 44) |
| LMO2 | NM_005574.2 | 1 | TTGGACCCAAGGGAAAACTG (SEQ ID NO: 45) | GGTTAAAAGTTGTGGTTTCCATTCTC (SEQ ID NO: 46) | TGGAGACGCATTTCG (SEQ ID NO: 47) |
| CD22 | NM_001771.2 | 1 | GACATCCCCACTCACGAATATTATG (SEQ ID NO: 48) | CTGTCCTTTTCTGGGCTTTCC (SEQ ID NO: 49) | CCAGTTTCTGCCTCTGA (SEQ ID NO: 50) |
| SMN1 | NM_000344.2 | 1 | GGCATAGAGCAGCACTAAATGACA (SEQ ID NO: 51) | TTCTATAACGCTTCACATTCCAGATC (SEQ ID NO: 52) | CACTAAAGAAACGATCAGAC (SEQ ID NO: 53) |
| EPDR1 | NM_017549.3 | 0 | CGCACTTTGGCCTTCCTAGA (SEQ ID NO: 54) | TGGAAGGAGATGCAGAAGTCAGA (SEQ ID NO: 55) | CACTGCTTCATAACCTC (SEQ ID NO: 56) |
| CD40 | NM_001250.4 | 1 | CCTGCCCAGTCGGCTTCT (SEQ ID NO: 57) | GTCCAAGGGTGACATTTTTCG (SEQ ID NO: 58) | CTCCAATGTGTCATCTG (SEQ ID NO: 59) |
| IFITM1 | NM_003641.3 | 1 | GGGTTACTAGTAGCCGCCCATA (SEQ ID NO: 60) | GCAGGGCCAGCATTGC (SEQ ID NO: 61) | CAACCTTTGCACTCCAC (SEQ ID NO: 62) |
| VNN2 | NM_004665.2 | 1 | TGTCCATTTTTTTGGCTACTCTGA (SEQ ID NO: 63) | CCCAAACACCCAGGCTCTT (SEQ ID NO: 64) | CAGTGTGGAACAATG (SEQ ID NO: 65) |
| PRPSAP2 | NM_002767.2 | 0 | GCTCCAGTGCCCCAAGATT (SEQ ID NO: 66) | CGACGGATCGCCTCTGAA (SEQ ID NO: 67) | AAACTGTGGATATCAGCATGA (SEQ ID NO: 68) |
| PRKCA | NM_002737.2 | 0 | TGGGCAACTCAGAAATACTTCGA (SEQ ID NO: 69) | ACGTCAATAGGCACGTTTGCT (SEQ ID NO: 70) | CTCCCAAGATATAAGAGGC (SEQ ID NO: 71) |
| IGF1R | NM_000875.3 | 0 | GTCCACCCTCTCCCCTTTCT (SEQ ID NO: 72) | CACGCACTCTAGTACAAAGCATAAGA (SEQ ID NO: 73) | CTCACTCCAAGAAAC (SEQ ID NO: 74) |
| BTG2 | NM_006763.2 | 0 | CCCAAACCGAATCACCTTAAGA (SEQ ID NO: 75) | CAGGAGGGTGGCCATCCT (SEQ ID NO: 76) | ACAGGGCTAGGGCAT (SEQ ID NO: 77) |
| LMO2 | NM_005574.2 | 0 | TCTCCATGGCATCTTCGTCTT (SEQ ID NO: 78) | ATCCCTTACCCCACCCTCAA (SEQ ID NO: 79) | ACTCTTAGGCACTTTGG (SEQ ID NO: 80) |
| CD22 | NM_001771.2 | 0 | CGGCCTCAGGCACAAGAA (SEQ ID NO: 81) | GCAGCCCATCCAGTGTCAAT (SEQ ID NO: 82) | ATGTGGACTATGTGATCCT (SEQ ID NO: 83) |
| SMN1 | NM_000344.2 | 0 | CATGGTACATGAGTGGCTATCATACTG (SEQ ID NO: 84) | GTGAGCACCTTCCTTCTTTTTGA (SEQ ID NO: 85) | CTATTATATGGGTTTCAGACAAA (SEQ ID NO: 86) |
| EPDR1 | NM_017549.3 | 0 | GACTATTGTCTCCTAAACCCAGGACTA (SEQ ID NO: 87) | CCCAGTGCATTTAATGACCAAA (SEQ ID NO: 88) | AGTTCCCTCGTACTGTC (SEQ ID NO: 89) |
| CD40 | NM_001250.4 | 1 | ATCAATTTTCCCGACGATCTTC (SEQ ID NO: 90) | CGGTTGGCATCCATGTAAAGT (SEQ ID NO: 91) | TGGCTCCAACACTG (SEQ ID NO: 92) |
| IFITM1 | NM_003641.3 | 0 | AGGTCCACCGTGATCAACATC (SEQ ID NO: 93) | CAGGGACCAGACGACATGGT (SEQ ID NO: 94) | ACAGCGAGACCTCCGT (SEQ ID NO: 95) |
| VNN2 | NM_004665.2 | 0 | CAACTTGTGGACGGCCAGTA (SEQ ID NO: 96) | GTGCCACTGAGGGAGAACATTT (SEQ ID NO: 97) | AAACTGCTTCTACAAGATT (SEQ ID NO: 98) |
| PRPSAP2 | NM_002767.2 | 0 | CAGCAGAGACCCTGAAGGAAA (SEQ ID NO: 99) | CAAGCCATGAGTTGCCATCA (SEQ ID NO: 100) | AGGTGCATATAAGATCTT (SEQ ID NO: 101) |
| BCL6 | NM_001706.2 | 1 | CCCATTCTGCGTCATGCTT (SEQ ID NO: 102) | AATGCAGTTTAGACACAGCCAAAC (SEQ ID NO: 103) | TGTTATAACTACTCCGGAGACAG (SEQ ID NO: 104) |

TABLE 10-continued

Primers and Probes

| Gene Locus | GenBank Accession No. | Probe Over- lap | Forward Primer | Reverse Primer | Probe |
|---|---|---|---|---|---|
| LRRC8A | NM_019594.2 | 1 | AGTTCAGCCCAGATGGAAGGT (SEQ ID NO: 105) | GCGGCATCGCTAAATAAGGA (SEQ ID NO: 106) | TTCAGGGAAAGGTGGGC (SEQ ID NO: 107) |
| BCL6 | NM_001706.2 | 1 | CACAGGGACTTGAAGTTGTTACTAACTAA (SEQ ID NO: 108) | TGACGCAGAATGGGATGAGA (SEQ ID NO: 109) | CTCTCTTTGGGAATGTT (SEQ ID NO: 110) |
| LRRC8A | NM_019594.2 | 0 | CAAAGCAGCCAGACGTTGAAC (SEQ ID NO: 111) | CACACCAGATCCGGAAGACA (SEQ ID NO: 112) | TTTCCCTGGGCGCAGG (SEQ ID NO: 113) |
| RGS13 | NM_144766.1 | 0 | GGGATTCCTACCCCAGATTTCTA (SEQ ID NO: 114) | CAGAAACTGTTGTTGGACTGCATAGAGT (SEQ ID NO: 115) | CAGAAATGTACCAAAAA (SEQ ID NO: 116) |
| YIPF3 | NM_015388.2 | 1 | TGAGCTGTAGCTGCGTAAGTACCT (SEQ ID NO: 117) | GGCCTTGTGCCTTTCAGAAG (SEQ ID NO: 118) | CTTGATGCCTGTCGGC (SEQ ID NO: 119) |
| YIPF3 | NM_015388.2 | 1 | TGGCTGCCCTACACATGCT (SEQ ID NO: 120) | CAGGATCCCCTCTACCACTTTG (SEQ ID NO: 121) | CCTGCTCTATCTGCATTT (SEQ ID NO: 122) |
| YIPF3 | NM_015388.2 | 0 | GAGGCTCAGCTGTGATTGACAT (SEQ ID NO: 123) | CACCCATATCCTCGAAGCTAGAG (SEQ ID NO: 124) | AGAACATGGATGATACCTC (SEQ ID NO: 125) |
| RGS13 | NM_44766.1 | 0 | TCCAGCCACAGTCCCCTAGA (SEQ ID NO: 126) | TCCTGAATGTTCCTGATGATAGTCTAGATTAACATTGACAGTTCGCT (SEQ ID NO: 127) | ACA(SEQ ID NO: 128) |
| EPDR1 | NM_017549.3 | 0 | CGAGAGGAAGGCGCTGATC (SEQ ID NO: 129) | ACATCACTCCATCCTTATACAGCAACCTGCAAGAGATTATTA (SEQ ID NO: 130) | (SEQ ID NO: 131) |
| EPDR1 | NM_017549.3 | 0 | GGATCCTCTTGACATTCCTCAAA (SEQ ID NO: 132) | GGCCCCCCGATGGA (SEQ ID NO: 133) | CTCCACCTTTGAAGACC (SEQ ID NO: 134) |
| EPDR1 | NM_017549.3 | 0 | CGAGGGTGTGGCCATATGA (SEQ ID NO: 135) | GAACAGGCATTAGAAATACCCAAAGTGACTAGATGGCTAATATG (SEQ ID NO: 136) | (SEQ ID NO: 137) |
| UAP1 | NM_003115.4 | 0 | CTACTGCAAGGCATGCTTTGAT (SEQ ID NO: 138) | TGGCCCCTGCATTGA (SEQ ID NO: 139) | TCCCTTCATCATTGCTG (SEQ ID NO: 140) |
| CD79B | NM_000626.2 | 0 | GCCGGTGCAGTTACACGTT (SEQ ID NO: 141) | CCCCAAACCCGTGACAAC (SEQ ID NO: 142) | CCTCCAAGGAGCCTC (SEQ ID NO: 143) |
| CLPTM1 | NM_001294.1 | 1 | CAAGGCCCTCAACACATTCA (SEQ ID NO: 144) | GGTACATAACGGGCATCTTGATG (SEQ ID NO: 145) | ACCTGTTCGCCTTTG (SEQ ID NO: 146) |
| UAP1 | NM_003115.4 | 1 | CCTATGCTGGAGAAGGATTAGAAAGT (SEQ ID NO: 147) | CGATGATTAGAGGTGCATGAA (SEQ ID NO: 148) | ATGTGGCAGATAAAG (SEQ ID NO: 149) |
| CD79B | NM_000626.2 | 0 | TCTCGCCACCCTCACCAT (SEQ ID NO: 150) | GCTGACAGAAGTAGATGCCATTGT (SEQ ID NO: 151) | CAAGGCATCCGGTTTG (SEQ ID NO: 152) |
| CLPTM1 | NM_001294.1 | 0 | AAGTCGCCCTGGAACTTCCT (SEQ ID NO: 153) | CACCGAGTCCTGCTCCTCAT (SEQ ID NO: 154) | ATGAGTTGTACGAGCAGTC (SEQ ID NO: 155) |
| UAP1 | NM_003115.4 | 1 | CATGAGCTGGTGAAAAATGGTATTT (SEQ ID NO: 156) | AAAGCTATTCCTATCGTGGCAAA (SEQ ID NO: 157) | AACCAGATACCAAGTTTT (SEQ ID NO: 158) |
| CD79B | NM_000626.2 | 1 | TCCCCAGCTCTTGCCAAAG (SEQ ID NO: 159) | CAGAGAACTCCCTCCAAGTTGCT (SEQ ID NO: 160) | CTGGAGTAGAAGGACAACAG (SEQ ID NO: 161) |
| CLPTM1 | NM_001294.1 | 0 | GGCAGGCCAGGGTTTGT (SEQ ID NO: 162) | CGAGATGGCTGGAAACACAGA (SEQ ID NO: 163) | AGGCGCTGTCTGTC (SEQ ID NO: 164) |
| CTSC | NM_001814.3 | 1 | GACTCAGCCTCTGGGATGAA (SEQ ID NO: 165) | GGATCCGGAAGTAGCCATTCT (SEQ ID NO: 166) | TGGATTGTTAAAAACAGCTGG (SEQ ID NO: 167) |
| CTSC | NM_001814.3 | 0 | AGGCGGCTTCCCATACCT (SEQ ID NO: 168) | CTTCTTCCACCAGCCCAAAA (SEQ ID NO: 169) | ATTGCAGGAAAGTACGCC (SEQ ID NO: 170) |
| CTSC | NM_001814.3 | 0 | CCCAAACCTGCACCACTGA (SEQ ID NO: 171) | CAAGATGTTGGCAAATGCAAA (SEQ ID NO: 172) | CTGAAATACAGCAAAAGA (SEQ ID NO: 173) |

TABLE 10-continued

Primers and Probes

| Gene Locus | GenBank Accession No. | Probe Over-lap | Forward Primer | Reverse Primer | Probe |
|---|---|---|---|---|---|
| CD44 | NM_000610.3 | 0 | CCTTTGTGGCATTTATTCATCAGT (SEQ ID NO: 174) | GCTTCTATGACAAGCAGCCTTTG (SEQ ID NO: 175) | AGGGTGTCCGATTGG (SEQ ID NO: 176) |
| PUS7 | NM_019042.3 | 0 | CTCTGTAGCACAGGCTGGATTG (SEQ ID NO: 177) | AGGCTGCAGTGCAAGATTGA (SEQ ID NO: 178) | AGTGCAATCCTGCAATT (SEQ ID NO: 179) |
| CD44 | NM_000610.3 | 0 | CCACTTGGAGGCCTTTCATC (SEQ ID NO: 180) | AGGTTGGCGATCAGGAATACA (SEQ ID NO: 181) | TCGGGTGTGCTATGGA (SEQ ID NO: 182) |
| PUS7 | NM_019042.3 | 0 | CCTTGCCTGGTTTCGATGTT (SEQ ID NO: 183) | GAGCATTTCCCTGTAGGCTTCTT (SEQ ID NO: 184) | CCCAAAGCATAAAATT (SEQ ID NO: 185) |
| CD44 | NM_000610.3 | 0 | CAACCGTTGGAAACATAACCATT (SEQ ID NO: 186) | AACAATCAGTAGCACATTGCATCTGAGGGAGCTGGGACACT (SEQ ID NO: 187) | (SEQ ID NO: 188) |
| PUS7 | NM_019042.3 | 0 | TGGACTCACTGAGGCTGACGTA (SEQ ID NO: 189) | GATTCCCGAGAACCCTTGATG (SEQ ID NO: 190) | TCACCAAGTTTGTGAGTTC (SEQ ID NO: 191) |
| RPL22 | NM_000983.3 | 1 | GCTGCCAATTTTGAGCAGTTT (SEQ ID NO: 192) | GTTCCCAGCTTTTCCGTTCA (SEQ ID NO: 193) | TGCAAGAAAGGATCAAA (SEQ ID NO: 194) |
| LOC728179 | XR_015348.1 | 1 | TCTTGCCTGCCCTGTGTTG (SEQ ID NO: 195) | TGCCTTCCCCTTAATAATGCA (SEQ ID NO: 196) | AAAATGCGGGTCCCTT (SEQ ID NO: 197) |
| SERBP1 | NM_001018067.1 | 1 | CTCCCGCTACACAGAAGTAACAAA (SEQ ID NO: 198) | AAAACATCCCTGCTACCAATACA (SEQ ID NO: 199) | CATTATGGTAGTCAGTTTTGTATTTAG (SEQ ID NO: 200) |
| RPL9 | NM_000661.4 | 1 | TCCGTTACAAGATGAGGTCTGTGT (SEQ ID NO: 201) | CATTCTCCTGGATAACAACGTTGA (SEQ ID NO: 202) | TGCTCACTTCCCC (SEQ ID NO: 203) |
| CFL1 | NM_005507.2 | 1 | TCCATCCCTTGACGGTTCTG (SEQ ID NO: 204) | AGCCCAAGAGGAATCAAAAGATC (SEQ ID NO: 205) | CCTTCCCAAACTGCTTT (SEQ ID NO: 206) |
| RPL13 | NM_000977.2 | 1 | GAGTCATCACTGAGGAAGAGAAGAATT (SEQ ID NO: 207) | TGGCACGGGCCATACG (SEQ ID NO: 208) | CAAAGCCTTCGCTAGTC (SEQ ID NO: 209) |
| FLJ16025 | NM_198505.1 | 1 | CCTACACCCCTTATCCCCATACT (SEQ ID NO: 210) | CCAGGGCTATTGGTTGAATGA (SEQ ID NO: 211) | TTATTATCGAAACCATCAGCC (SEQ ID NO: 212) |
| RPS10 | NM_001014.3 | 1 | CGACCTGCGAGACTCACAAG (SEQ ID NO: 213) | GGCACAGCACTCCGTCTGT (SEQ ID NO: 214) | AAGCTGACAGAGATACC (SEQ ID NO: 215) |
| NPM1 | NM_002520.5 | 1 | TCTGGCTGTCCTTTTTATAATGCA (SEQ ID NO: 216) | CTTGGCAATAGAACCTGGACAAC (SEQ ID NO: 217) | AGTGAGAACTTTCCC (SEQ ID NO: 218) |
| CCDC72 | NM_015933.3 | 1 | GCAAGAAGAAGCCACTGAAACA (SEQ ID NO: 219) | GAAAGCCTTATCTTCCTCGTCCAT (SEQ ID NO: 220) | CCCAAGAAGCAGGCCA (SEQ ID NO: 221) |
| RPS19 | NM_001022.3 | 1 | GGCTGAAAATGGTGGAAAAGG (SEQ ID NO: 222) | CTTTGTCCCTGAGGTGTCAGTTT (SEQ ID NO: 223) | CCAAGATGGCGGCCG (SEQ ID NO: 224) |
| RPS16 | NM_001020.4 | 1 | TGTGGATGAGGCTTCCAAGAA (SEQ ID NO: 225) | CAGCAGGGTCCGGTCATACT (SEQ ID NO: 226) | AGATCAAAGACATCCTCATC (SEQ ID NO: 227) |
| EEF1G | NM_001404.4 | 1 | GGCAGGTGGACTACGAGTCATAC (SEQ ID NO: 228) | GTCTCCTCGCTGCCAGGAT (SEQ ID NO: 229) | CATGGCGGAAACTG (SEQ ID NO: 230) |
| RPS5 | NM_001009.3 | 1 | CCGGAACATTAAGACCATTGC (SEQ ID NO: 231) | CCCTTGGCAGCATTGATGA (SEQ ID NO: 232) | AGTGCCTGGCAGATG (SEQ ID NO: 233) |
| EEF1A1 | NM_001402.5 | 1 | CTGCCACCCCACTCTTAATCA (SEQ ID NO: 234) | GGCCAATTGAAACAAACAGTTCT (SEQ ID NO: 235) | TGGTGGAAGAACGGTC (SEQ ID NO: 236) |
| RPL28 | NM_000991.3 | 1 | GGAAGCCTGCCACCTCCTAT (SEQ ID NO: 237) | TGGCGCGAGCATTCTTG (SEQ ID NO: 238) | TGCGGACCACCATC (SEQ ID NO: 239) |
| ACTG1 | NM_001614.2 | 1 | TGTCCTTGAAGCTTGTATCTGATATCA (SEQ ID NO: 240) | TTCAATACAAGGTCAAAATCAGCAACACTGGATTGTAGAACTT (SEQ ID NO: 241) | (SEQ ID NO: 242) |

TABLE 10-continued

Primers and Probes

| Gene Locus | GenBank Accession No. | Probe Over-lap | Forward Primer | Reverse Primer | Probe |
|---|---|---|---|---|---|
| BTF3 | NM_001037637.1 | 1 | AGCCTCAGATGAAAGAAACAATCA (SEQ ID NO: 243) | CACTTGTGCCTGCAGTTTGG (SEQ ID NO: 244) | AACCAGGAAAAACTC (SEQ ID NO: 245) |
| TMSB4X | NM_021109.2 | 1 | AAGCAGGCGAATCGTAATGAG (SEQ ID NO: 246) | TGCTTGTGGAATGTACAGTGCAT (SEQ ID NO: 247) | CGTGCGCCGCCAA (SEQ ID NO: 248) |
| TPM3 | NM_153649.3 | 1 | CCCTTTTCTGGGTTTGAAGCT (SEQ ID NO: 249) | CTGACTGATACAAAGCACAATTGAGCTGTCTCTAGAAGTGCCA (SEQ ID NO: 250) | (SEQ ID NO: 251) |
| USMG5 | NM_032747.2 | 1 | GCTGTGAAAGCAACATAAATGGAT (SEQ ID NO: 252) | GGCATGGGAACTTAACAGATGAG (SEQ ID NO: 253) | TTAAACTGTCTACGGTTCTT (SEQ ID NO: 254) |
| EIF1 | NM_005801.3 | 1 | CGCTATCCAGAACCTCCACTCT (SEQ ID NO: 255) | CAGGTCATCACCCTTACTTGCA (SEQ ID NO: 256) | TCGACCCCTTTGCTG (SEQ ID NO: 257) |

Data Processing

The raw qRT-PCR as results were pre-processed according to the description below under Normalization, Transformation, and Imputation and the Sensitivity Index was computed as described under Sensitivity Index and Classifier. Spearman's rank correlations were used for correlation estimates and corresponding P-values. For the Multivariate Sensitivity Index, probes were selected and coefficients estimated using the elastic net blend of lasso (L1) and ridge (L2) penalized regression, as described by Zhou et al., Statist. Soc. B. 67:301-320, 2005 and implemented by Friedman, Hastie and Tibshirani, Regularization Paths for Generalized Linear Models via Coordinate Descent. Technical Report, Dept. of Statistics, Stanford University at www-stat.stanford.edu/~hastie/Papers/glmnet.pdf. $X^2$ tests were used to test for associations among categorical variables.

Normalization, Transformation and Imputation

The following are definitions for assay data and model parameters:

Definitions
Assay Data
l=a reference set of samples (e.g. NHL cell lines)
$N_l$=sample size
p=number of probes (not including normalizers)
$N_{lj}^{(Obs)}$=detected sample size for probe j
$N_{lj}^{(ND)}$=not detected sample size for probe j
$y_{ij}^{(Obs)}$=detected raw assay value for sample i, probe j
$p_i^{(nrm.Obs)}$=number of detected normalizer values for sample i
$y_{ij}^{(nrm.Obs)}$=detected normalizer value for sample i, probe j
Model Parameters
$\hat{\mu}_{lj}^{(Obs.raw)}$=set l mean of detected $\log_2$ assay values for probe j (un-normalized)
$\hat{\sigma}_{lj}^{(Obs)}$=set l standard deviation of detected $\log_2$ assay values for probe j
$\gamma_l^{(ND)}$=set l number of standard deviations above the mean For a reference set of samples, such as that used to fit index coefficients and classifier cutoffs, mean and standard deviation model parameters are computed using the reference set data (refer to the formulas for Reference Set Model Parameters below). For new samples, for example a single new sample for which the index and class are to be computed, model parameters must be taken from a reference set, l, which is chosen to be the most representative of the population from which the new sample is drawn. For example, a clinical reference set for each indication and line of therapy in which the assay is used may be maintained. The formulas for calculating reference set model parameters and transformed, normalized assay values are shown below.

Formulas
Reference Set Model Parameters
Intermediate Values $$\hat{\mu}_i^{(nrm,Obs)} = \frac{1}{p_i^{(nrm,Obs)}} \sum_{j=1}^{p_i^{(nrm,Obs)}} y_{ij}^{(nrm,Obs)} \text{ (sample normalization factor)}$$

$$\hat{\mu}_{lj}^{(Obs)} = \frac{1}{N_{lj}^{(Obs)}} \sum_{i=1}^{N_{lj}^{(Obs)}} [\log_2(y_{ij}^{(Obs)}) - \log_2(\hat{\mu}_i^{(nrm,Obs)})] \text{ (normalized mean)}$$

Model Parameters $$\hat{\sigma}_{lj}^{(Obs)} = \sqrt{\frac{1}{N_{lj}^{(Obs)}} \sum_{i=1}^{N_{lj}^{(Obs)}} (\log_2(y_{ij}^{(Obs)}) - \log_2(\hat{\mu}_i^{(nrm,Obs)}) - \hat{\mu}_{lj}^{(Obs)})^2}$$

$$\hat{\mu}_{lj}^{(Obs,raw)} = \frac{1}{N_{lj}^{(Obs)}} \sum_{i=1}^{N_{lj}^{(Obs)}} \log_2(y_{ij}^{(Obs)})$$

Transformed, Normalized Assay Values
Intermediate Values $$\hat{\mu}_i^{(nrm,Obs)} = \frac{1}{p_i^{(nrm,Obs)}} \sum_{j=1}^{p_i^{(nrm,Obs)}} y_{ij}^{(nrm,Obs)} \text{ (sample normalization factor)}$$

Transformed, Normalized, Imputed Assay Values $$x_{ij}^{(Obs)} = -[\log_2(y_{ij}^{(Obs)}) - \log_2(\hat{\mu}_i^{(nrm.Obs)})], i=1, \ldots, N_{lj}^{(ND)}$$

$$x_{ij}^{(ND)} = -[\hat{\mu}_{lj}^{(Obs.raw)} - \log_2(\hat{\mu}_i^{(nrm,Obs)}) + \gamma_l^{(ND)}\hat{\sigma}_{lj}^{(Obs)}], i=1, \ldots, N_{lj}^{(ND)}$$

The completed $N_l \times p$ matrix of values, $$\begin{bmatrix} x_1^{(Obs)} & \cdots & x_p^{(Obs)} \\ x_1^{(ND)} & \cdots & x_p^{(ND)} \end{bmatrix},$$

is input to the sensitivity index and classifier calculations.

Sensitivity Index and Classifier

The following are definitions for assay data and model parameters:

Definitions
Assay Data
l=a reference set of samples (e.g. NHL cell lines)
$N_l$=sample size
p=number of probe pairs
$x_{ij}$=transformed, normalized assay value for sample i, probe j
$x_{ij}'$=as above with j' the anti-correlated pair probe to probe j Model Parameters
$\beta_{lj}$=set l coefficient for probe j
$\hat{\mu}_{lj}$=set l mean of transformed normalized assay values for probe j
$\hat{\sigma}_{lj}^2$=set l mean of transformed normalized assay values for probe j
$L_l$=classification cutpoint The formulas for calculating reference set model parameters and sensitivity index and classifier are shown below.

Formulas
Reference Set Model Parameters

Probe Means and Standard Deviations $$\hat{\mu}_{lj} = \frac{1}{N_l}\sum_{i=1}^{N_l} x_{ij}$$

$$\hat{\sigma}_{lj}^2 = \frac{1}{N_l}\sum_{i=1}^{N_l} (x_{ij} - \hat{\mu}_{lj})^2$$

Index and Classifier

Sensitivity Index $$S_{li} = \sum_{j=1}^{p} \beta_{lj}\frac{x_{ij} - \hat{\mu}_{lj}}{\sqrt{\hat{\sigma}_{lj}^2}} - \beta_{lj'}\frac{x_{ij'} - \hat{\mu}_{lj'}}{\sqrt{\hat{\sigma}_{lj'}^2}}$$

Sensitivity Class $$T_{li} = \begin{cases} 1 \equiv \text{sensitive} & \text{if} \quad S_{li} \geq C_l \\ 0 \equiv \text{resistant} & \text{otherwise} \end{cases}$$

Clinical Trial 001 Results

Table 11 below provides a sample accounting of assayed specimens and clinical samples from Clinical Trial 001. Twenty nine archival FFPE tumor specimens from 24 patients with DLBCL were submitted for qRT-PCR processing. Three patients had multiple specimens and all 24 patients had usable qRT-PCR results for at least one specimen. Of these 24, 21 had tumor sum of the product of diameters (SPD) measurements reported both at baseline and at least one post-baseline visit.

TABLE 11

Clinical Trial 001 Sample Accounting

| Diagnostic Assay | | | Clinical Database | |
|---|---|---|---|---|
| Archival FFPE specimens | 29 | Analysis sample size | | |
| # of patients (3 with multiple specimens) | 24 | (both qRT-PCR and SPD available) | | |

TABLE 11-continued

Clinical Trial 001 Sample Accounting

| Diagnostic Assay | | | Clinical Database | |
|---|---|---|---|---|
| Specimens qRT-PCR Reported | 27 | | | |
| Usable qRT-PCR results (1 insufficient) | 26 | | 46 | Patients in clinical database |
| qRT-PCR for unique patients (2 patient specimen pairs averaged together) | 24 | 21 | 39 | SPD Change from Baseline Reported |

Table 12 summarizes the pairwise Spearman's rank correlations between the Main and Pair genes that contribute to the sensitivity index. Based on the cell line development samples, genes with low expression in particular groups of patient should be expected to have relatively high expression of the corresponding pair, on average, providing for self-normalization and the interpretation of the Sensitivity Index as a ratio of up- to down-regulated expression pathways (i.e. on a log base 2 scale). The magnitude of the correlations between pairs in this first clinical sample are statistically significant and notable high throughout, with the lower correlation estimate being −0.67 (P=0.0004). These tests alone constitute an independent confirmation that the assay target sequences are expressed in tumor samples from this clinical population in-vitro and that the assay is detecting expression in the archived FFPE tissue samples.

TABLE 12

Main and Pair Gene Anti-correlations (N = 21)

| Main Gene* | Locus Link | Correlation Gene | Pair |
|---|---|---|---|
| IFITM1 | 8519 | −.85 | BTG2 |
| CD40 | 958 | −.84 | IGF1R |
| RGS13 | 6003 | −.70 | CD44 |
| VNN2 | 8875 | −.87 | CTSC |
| LMO2 | 4005 | −.67 | EPDR1 |
| CD79B | 974 | −.75 | UAP1 |
| CD22 | 933 | −.83 | PUS7 |

*CD40, RGS13, VNN2, LMO2, CD22, BTG2, and UAP1 are genes with higher expression in sensitive cell lines.

Table 13 summarizes the associations between the measurements for each probe individually and the largest reduction (or smallest increase) in tumor SPD post-baseline. Since rank correlations are based upon the difference (or ratio) of post-baseline to baseline measurements, positive correlations mean that higher expression of the probe is associated with tumor increases, on average; and the negative correlations mean that higher expression of the probe is associated with tumor decreases on average. Notably, all Main-Pair probe pairs have opposite-direction associations with SPD. The P-values are consistent with a promising trend in this sample. All P-values are below 0.5 (50% expected when there is no true association). All ranges are calculated as bootstrap 95th percentile confidence intervals, based upon 5,000 replicates sampled with replacement from the DLBCL patient sample, N=21. Narrower ranges will become available as the sample size increases. Since no model-building or checking was required to produce these results, they comprise a robust trend, which confirms that these qRT-PCR probe measurements are associated, overall, with reduction in tumor SPD in patients treated with anti-CD40 Ab. 1.

TABLE 13

Associations between SPD and Individual Probe Measurements (N = 21)

| Main Gene | Rho. | P | Range | Pair Gene | Rho. | P | Range |
|---|---|---|---|---|---|---|---|
| IFITM1 | +0.29 | 0.20 | (−0.13, 0.68) | BTG2 | −0.27 | 0.23 | (−0.70, 0.19) |
| CD40 | −0.16 | 0.49 | (−0.58, 0.30) | IGF1R | +0.33 | 0.15 | (−0.17, 0.73) |
| RGS13 | −0.32 | 0.16 | (−0.66, 0.13) | CD44 | +0.34 | 0.14 | (−0.11, 0.70) |
| VNN2 | −0.26 | 0.26 | (−0.67, 0.21) | CTSC | +0.31 | 0.17 | (−0.17, 0.68) |
| LMO2 | −0.25 | 0.27 | (−0.69, 0.25) | EPDR1 | +0.27 | 0.23 | (−0.22, 0.67) |
| CD79B | +0.22 | 0.34 | (−0.22, 0.61) | UAP1 | −0.22 | 0.35 | (−0.59, 0.22) |
| CD22 | −0.25 | 0.28 | (−0.66, 0.21) | PUS7 | +0.20 | 0.39 | (−0.26, 0.66) |

Figure 7:
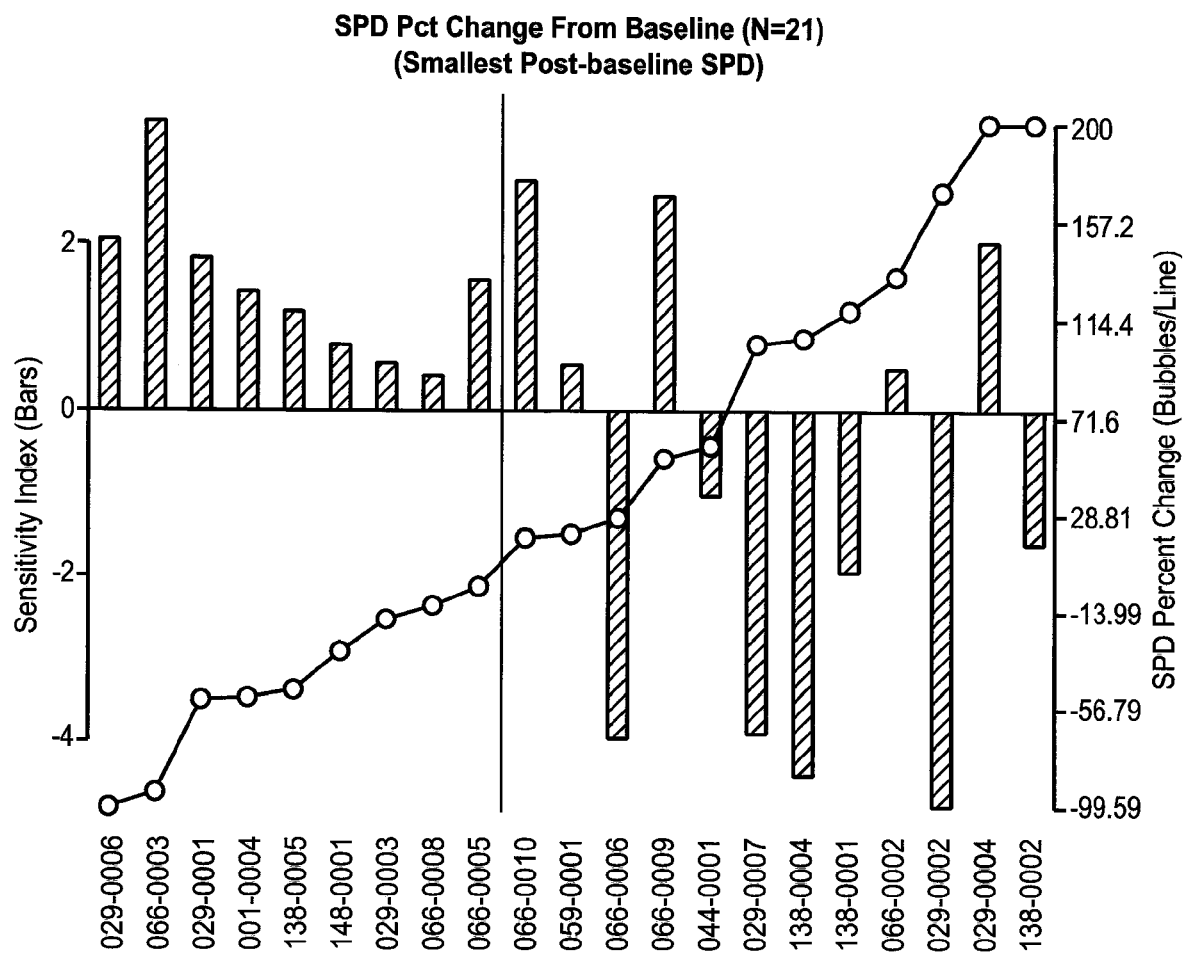

The multivariate sensitivity index is a weighted average of the probes in Tables 12 and 13. Since weights in cell lines were not expected to reflect optimal weights in patient tumor specimens, the weights in cell lines were restricted to 1 and −1, corresponding to the signed, equal-weighted average, where the signs matched the association between each probe and resistance to anti-CD40 Ab.1 by IC25 in the cell lines. For clinical populations, new weights are required. As a preliminary analysis based upon 21 samples only, we chose to use a penalized, multivariate regression procedure to select and estimate weights for the best 8 of the 14 probes. Those weights (coefficient) are shown in Table 14, and the association between the resulting Sensitivity Index and SPD change from baseline is depicted in FIG. 7. Larger multivariate Sensitivity Index values are associated with SPD decreases post-baseline (Spearman's Rho=−0.58, P=0.006). All ranges in Tables 13, 14, and 15 were calculated as bootstrap 95th percentile confidence intervals, based upon 5,000 replicates sampled with replacement from the DLBCL patient sample, N=21. Narrower ranges will become available as the sample size increases.

TABLE 14

Weights for the Multivariate Sensitivity Index (N = 21)

| Main Gene | Coeff. | Range | Pair Gene | Coeff. | Range |
|---|---|---|---|---|---|
| IFITM1 | −0.08 | (−11.7, 3.7) | BTG2 | −0.62 | (−11.6, 0.0) |
| CD40 | 0 | (−9.5, 8.2) | IGF1R | 0 | (−9.0, 5.6) |
| RGS13 | +1.13 | (−1.9, 8.0) | CD44 | −3.39 | (−11.9, 0.0) |
| VNN2 | 0 | (−4.1, 4.1) | CTSC | 0 | (−8.8, 2.1) |
| LMO2 | 0 | (−8.5, 2.1) | EPDR1 | −0.74 | (−4.7, 3.6) |
| CD79B | +0.04 | (−3.2, 9.0) | UAP1 | −2.45 | (−15.1, 0.0) |
| CD22 | +0.63 | (−0.0, 12.7) | PUS7 | 0 | (−7.7, 7.3) |

Using 26 samples from Clinical Trail 001, ranges for $\mu_j$ and $\sigma_j$ values obtained are as shown in Table 15.

TABLE 15

$\mu_j$ and $\sigma_j$ ranges based on data from Clinical Trail 001

| $\mu_j$ | IFITM1 | LMO2 | CD40 | VNN2 | IGF1R | BTG2 | CD22 | BCL6 |
|---|---|---|---|---|---|---|---|---|
| lower | −4.89 | −5.09 | −5.09 | −5.10 | −5.12 | −5.02 | −5.03 | −5.07 |
| upper | −4.79 | −5.00 | −5.02 | −5.02 | −5.06 | −4.92 | −4.93 | −4.99 |

| $\mu_j$ | RGS13 | EPDR1 | CD79B | UAP1 | CTSC | CD44 | PUS7 |
|---|---|---|---|---|---|---|---|
| lower | −5.14 | −5.19 | −5.10 | −5.26 | −5.04 | −4.97 | −5.24 |
| upper | −5.00 | −5.12 | −5.04 | −5.18 | −4.95 | −4.87 | −5.16 |

| $\sigma_j$ | IFITM1 | LMO2 | CD40 | VNN2 | IGF1R | BTG2 | CD22 | BCL6 |
|---|---|---|---|---|---|---|---|---|
| lower | 0.10 | 0.09 | 0.07 | 0.08 | 0.06 | 0.09 | 0.09 | 0.08 |
| upper | 0.17 | 0.14 | 0.12 | 0.13 | 0.10 | 0.15 | 0.14 | 0.12 |

| $\sigma_j$ | RGS13 | EPDR1 | CD79B | UAP1 | CTSC | CD44 | PUS7 |
|---|---|---|---|---|---|---|---|
| lower | 0.14 | 0.07 | 0.06 | 0.08 | 0.09 | 0.09 | 0.08 |
| upper | 0.22 | 0.11 | 0.10 | 0.12 | 0.14 | 0.16 | 0.12 |

Clinical Trial 002 Results

Raw qRT-PCR results were successfully generated for 10 patients with archival specimens. For those 10 patients, diagnosis, treatment group, multivariate sensitivity index, clinical response and SPD change from baseline are shown in Table 16. The multivariate sensitivity index weights were taken from the 21 Clinical Trial 001 patients (Table 14), so that these patients constitute a very small validation set. 2 of 4 patients with Sensitivity Index ≥0 exhibited some tumor shrinkage after anti-CD40 Ab.1 exposure and 4 of 6 patients with Sensitivity Index <0 exhibited either tumor increase or a best response of PD (SPD was unavailable for 2 patients, but a best clinical response outcome was available for this patient).

TABLE 16

Summary of diagnosis, treatment group, multivariate sensitivity index, clinical response and SPD change for 6 patients in Clinical Trial 002.

| Samples | Dx. | Treatment Group | Sensitivity Index | Best Response | SPD Percent Change |
|---|---|---|---|---|---|
| 066-0001 | MCL | Pre-2 | +0.01 | PD | +72.48 |
| 066-0015 | MCL | V | −0.87 | PD | +64.07 |
| 066-0009 | DLBCL | III | +1.06 | PR | −78.02 |
| 066-0006 | DLBCL | I | −2.31 | PR | −66.44 |
| 066-0011 | T-Cell-LBCL | IV | −0.46 | SD (PR) | −10.34 |
| 066-0005 | DLBCL | I | −2.99 | PD | +1,208.94 |
| 066-0013 | MCL | IV | −3.67 | PD | +94.59 |
| 066-0019 | DLBCL | V | +0.15 | SD | −32.64 |

TABLE 16-continued

Summary of diagnosis, treatment group, multivariate sensitivity index, clinical response and SPD change for 6 patients in Clinical Trial 002.

| Samples | Dx. | Treatment Group | Sensitivity Index | Best Response | SPD Percent Change |
|---|---|---|---|---|---|
| 066-0004 | DLBCL | I | −0.46 | PD | ? |
| 066-0002 | DLBCL | Pre-2 | +0.99 | PD | ? |

Figure 8:
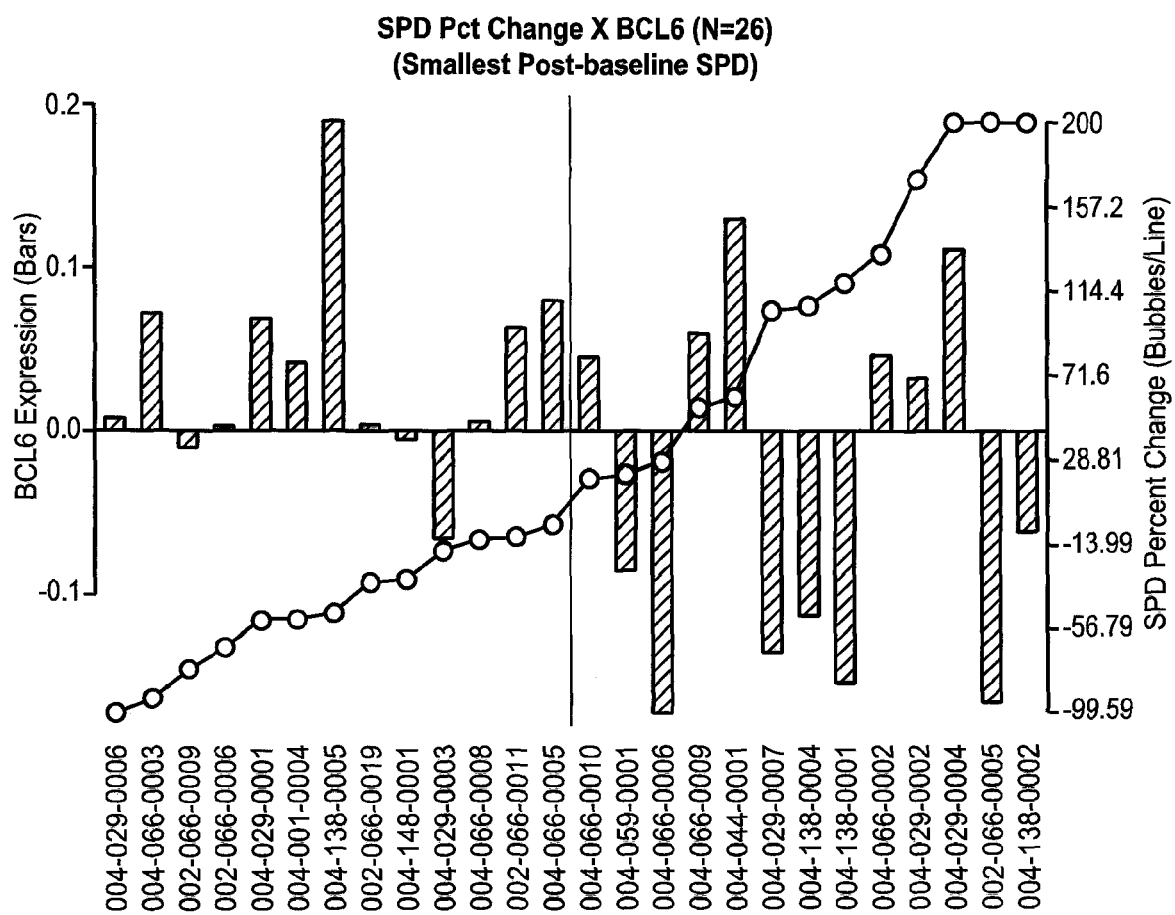

BCL6. The qRT-PCR assay contains a 15th probe for the BCL6 gene. Though not currently used in the multivariate Sensitivity Index, it was a previously identified potential predictor of response to anti-CD40 Ab.1. As shown in FIG. 8, while not significantly associated with SPD change in the combined DLBCL patient sample (P=0.25, N=26), BCL6 trends lower in those with tumor increases (rho=−0.23).

Although the foregoing invention has been described in some detail by way of illustration and example for purposes of clarity of understanding, the descriptions and examples should not be construed as limiting the scope of the invention.

What is claimed is:

1. A method for treating a human subject having a B-cell lymphoma, comprising the steps of:
   (a) performing a nucleic acid-based detection assay to detect the expression level of the UAP1 RNA transcript in a sample comprising B lymphoma cells obtained from the human subject;
   (b) determining that the B lymphoma cells from the human subject express the UAP1 RNA transcript at an increased level compared to a reference level;
   (c) determining that the human subject is responsive to an anti-CD40 antibody treatment based on the increased level of the UAP1 RNA transcript in the B lymphoma cells as compared to the reference level; and
   (d) administering an effective amount of an anti-CD40 antibody to the human subject expressing the increased level of the UAP1 RNA transcript in the B lymphoma cells, thereby treating B-cell lymphoma in the human subject.

2. The method of claim 1, wherein the expression level of the UAP1 RNA transcript is normalized.

3. The method of claim 1, wherein the reference level is determined based on the expression level of the UAP1 RNA transcript in samples comprising B lymphoma cells from subjects having tumor volume decreased after the anti-CD40 antibody treatment.

4. The method of claim 3, wherein the samples from subjects for reference level determination comprise the same type of B lymphoma cells as the sample from the subject whose responsiveness to the anti-CD40 antibody treatment is determined.

5. The method of claim 1, wherein the anti-CD40 antibody stimulates CD40 and enhances the interaction between CD40 and CD40 ligand.

6. The method of claim 5, wherein the anti-CD40 antibody comprises the heavy chain amino acid sequence shown in SEQ ID NO:1 and the light chain amino acid sequence shown in SEQ ID NO:2.

7. The method of claim 1, wherein the anti-CD40 antibody stimulates CD40 and does not enhance or inhibits the interaction between CD40 and CD40 ligand.

8. The method of claim 1, further comprising performing a nucleic acid-based detection assay to detect the expression levels of at least one, at least two, at least three, at least four, at least five, at least six, at least seven, at least eight, at least nine, at least ten, at least eleven, at least twelve, or at least thirteen marker genes in addition to UAP1, wherein the marker genes are selected from the group consisting of IFITM1, CD40, RGS13, VNN2, LMO2, CD79B, CD22, BTG2, IGF1R, CD44, CTSC, EPDR1, and PUS7.

9. The method of claim 8, wherein the expression levels of IFITM1, RGS13, CD79B, CD22, BTG2, CD44, EPDR1, and UAP1 are detected.

10. The method of claim 1, wherein the B cell lymphoma is diffuse large B-cell lymphoma (DLBCL).

11. The method of claim 1, wherein the B cell lymphoma is non-Hodgkin's lymphoma.

12. The method of claim 11, wherein the non-Hodgkin's lymphoma is follicular lymphoma, mantle cell lymphoma, marginal zone lymphoma, or small lymphocytic lymphoma.

13. The method of claim 1, wherein the sample comprising the B lymphoma cells is a formalin fixed paraffin embedded biopsy sample.

14. The method of claim 1, wherein the RNA transcript is measured by qRT-PCR.

15. The method of claim 1, further comprising assaying the expression level of BCL6, wherein an increased expression of BCL6 as compared to a reference level determines that the subject is responsive to the anti-CD40 antibody treatment.

16. The method of claim 15, wherein the reference level is determined based on the expression level of BCL6 in samples comprising B lymphoma cells from subjects having tumor volume decreased after the anti-CD40 antibody treatment.

* * * * *

SEQUENCE LISTING

```
<160> NUMBER OF SEQ ID NOS: 281

<210> SEQ ID NO 1
<211> LENGTH: 443
<212> TYPE: PRT
<213> ORGANISM: Artificial Sequence
<220> FEATURE:
<223> OTHER INFORMATION: Synthetic construct

<400> SEQUENCE: 1

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Phe Thr Gly Tyr
                 20                  25                  30

Tyr Ile His Trp Val Arg Gln Ala Pro Gly Lys Gly Leu Glu Trp Val
             35                  40                  45

Ala Arg Val Ile Pro Asn Ala Gly Gly Thr Ser Tyr Asn Gln Lys Phe
         50                  55                  60

Lys Gly Arg Phe Thr Leu Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
```

```
                210                 215                 220
Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly
            435                 440

<210> SEQ ID NO 2
<211> LENGTH: 219
<212> TYPE: PRT
<213> ORGANISM: Artificial Sequence
<220> FEATURE:
<223> OTHER INFORMATION: Synthetic construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

```
            130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
tgacaaaatg tagaggccat tca                                         23

<210> SEQ ID NO 4
<211> LENGTH: 23
<212> TYPE: DNA
<213> ORGANISM: Artificial Sequence
<220> FEATURE:
<223> OTHER INFORMATION: Synthetic construct

<400> SEQUENCE: 4
catccgtctc tctgcgata taa                                          23

<210> SEQ ID NO 5
<211> LENGTH: 16
<212> TYPE: DNA
<213> ORGANISM: Artificial Sequence
<220> FEATURE:
<223> OTHER INFORMATION: Synthetic construct

<400> SEQUENCE: 5
ccgtcaaaca ccattt                                                 16

<210> SEQ ID NO 6
<211> LENGTH: 24
<212> TYPE: DNA
<213> ORGANISM: Artificial Sequence
<220> FEATURE:
<223> OTHER INFORMATION: Synthetic construct

<400> SEQUENCE: 6
ttgcaaggaa agaaattcaa acac                                        24

<210> SEQ ID NO 7
<211> LENGTH: 22
<212> TYPE: DNA
<213> ORGANISM: Artificial Sequence
<220> FEATURE:
<223> OTHER INFORMATION: Synthetic construct

<400> SEQUENCE: 7
tgcttgaatc cattgactgc tt                                          22

<210> SEQ ID NO 8
```

```
<211> LENGTH: 18
<212> TYPE: DNA
<213> ORGANISM: Artificial Sequence
<220> FEATURE:
<223> OTHER INFORMATION: Synthetic construct

<400> SEQUENCE: 8
acaacagcag taagaaga                                                       18

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
caggtccctg ccttttaga ag                                                   22

<210> SEQ ID NO 10
<211> LENGTH: 32
<212> TYPE: DNA
<213> ORGANISM: Artificial Sequence
<220> FEATURE:
<223> OTHER INFORMATION: Synthetic construct

<400> SEQUENCE: 10
atcataaaga agagaagaga gacaagatta ag                                       32

<210> SEQ ID NO 11
<211> LENGTH: 16
<212> TYPE: DNA
<213> ORGANISM: Artificial Sequence
<220> FEATURE:
<223> OTHER INFORMATION: Synthetic construct

<400> SEQUENCE: 11
agcctcatgg tctcat                                                         16

<210> SEQ ID NO 12
<211> LENGTH: 16
<212> TYPE: DNA
<213> ORGANISM: Artificial Sequence
<220> FEATURE:
<223> OTHER INFORMATION: Synthetic construct

<400> SEQUENCE: 12
ggccacagcc catcca                                                         16

<210> SEQ ID NO 13
<211> LENGTH: 23
<212> TYPE: DNA
<213> ORGANISM: Artificial Sequence
<220> FEATURE:
<223> OTHER INFORMATION: Synthetic construct

<400> SEQUENCE: 13 cttgcccta aatgttcctt tct                                                  23

<210> SEQ ID NO 14
<211> LENGTH: 19
<212> TYPE: DNA
<213> ORGANISM: Artificial Sequence
<220> FEATURE:
<223> OTHER INFORMATION: Synthetic construct

<400> SEQUENCE: 14
```
agtaactgac atgattagc                                                19

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tttggaagtg aggcattgca                                               20

<210> SEQ ID NO 16
<211> LENGTH: 19
<212> TYPE: DNA
<213> ORGANISM: Artificial Sequence
<220> FEATURE:
<223> OTHER INFORMATION: Synthetic construct

<400> SEQUENCE: 16
ccggagtccc cagagtcaa                                                19

<210> SEQ ID NO 17
<211> LENGTH: 17
<212> TYPE: DNA
<213> ORGANISM: Artificial Sequence
<220> FEATURE:
<223> OTHER INFORMATION: Synthetic construct

<400> SEQUENCE: 17
agacgtacgt atcagcg                                                  17

<210> SEQ ID NO 18
<211> LENGTH: 26
<212> TYPE: DNA
<213> ORGANISM: Artificial Sequence
<220> FEATURE:
<223> OTHER INFORMATION: Synthetic construct

<400> SEQUENCE: 18
ctggaatgtg aagcgttata gaagat                                        26

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
ccttttttct ttcccaacac ttga                                          24

<210> SEQ ID NO 20
<211> LENGTH: 14
<212> TYPE: DNA
<213> ORGANISM: Artificial Sequence
<220> FEATURE:
<223> OTHER INFORMATION: Synthetic construct

<400> SEQUENCE: 20
ctggcctcat ttct                                                     14

<210> SEQ ID NO 21
<211> LENGTH: 21
<212> TYPE: DNA

<213> ORGANISM: Artificial Sequence
<220> FEATURE:
<223> OTHER INFORMATION: Synthetic construct

<400> SEQUENCE: 21
cagcctctct tgtccctggt t     21

<210> SEQ ID NO 22
<211> LENGTH: 22
<212> TYPE: DNA
<213> ORGANISM: Artificial Sequence
<220> FEATURE:
<223> OTHER INFORMATION: Synthetic construct

<400> SEQUENCE: 22
tccctagcaa tggacaaact ca    22

<210> SEQ ID NO 23
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
ccttatgtgt tgaatgtgg        19

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
gggatcctgt ttgccatcct       20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gcttcttggc cacctttttg       20

<210> SEQ ID NO 26
<211> LENGTH: 15
<212> TYPE: DNA
<213> ORGANISM: Artificial Sequence
<220> FEATURE:
<223> OTHER INFORMATION: Synthetic construct

<400> SEQUENCE: 26
ttggtgctgg tcttt            15

<210> SEQ ID NO 27
<211> LENGTH: 22
<212> TYPE: DNA
<213> ORGANISM: Artificial Sequence
<220> FEATURE:
<223> OTHER INFORMATION: Synthetic construct

<400> SEQUENCE: 27
ggcttcatag cattcgccta ct    22

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
tcacgtcgcc aaccatctt                                                    19

<210> SEQ ID NO 29
<211> LENGTH: 18
<212> TYPE: DNA
<213> ORGANISM: Artificial Sequence
<220> FEATURE:
<223> OTHER INFORMATION: Synthetic construct

<400> SEQUENCE: 29
cgtgaagtct agggacag                                                     18

<210> SEQ ID NO 30
<211> LENGTH: 27
<212> TYPE: DNA
<213> ORGANISM: Artificial Sequence
<220> FEATURE:
<223> OTHER INFORMATION: Synthetic construct

<400> SEQUENCE: 30
gacttgtatg tatgggagtg aggagtt                                           27

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
tctcttcaag ggcacagcta tg                                                22

<210> SEQ ID NO 32
<211> LENGTH: 14
<212> TYPE: DNA
<213> ORGANISM: Artificial Sequence
<220> FEATURE:
<223> OTHER INFORMATION: Synthetic construct

<400> SEQUENCE: 32
cagggccatt gcaa                                                         14

<210> SEQ ID NO 33
<211> LENGTH: 24
<212> TYPE: DNA
<213> ORGANISM: Artificial Sequence
<220> FEATURE:
<223> OTHER INFORMATION: Synthetic construct

<400> SEQUENCE: 33
gccaaactgg aaacataaga gtga                                              24

<210> SEQ ID NO 34
<211> LENGTH: 20
<212> TYPE: DNA
<213> ORGANISM: Artificial Sequence
<220> FEATURE:

```
<223> OTHER INFORMATION: Synthetic construct

<400> SEQUENCE: 34
gcatgacggt tcctgtgaaa                                              20

<210> SEQ ID NO 35
<211> LENGTH: 15
<212> TYPE: DNA
<213> ORGANISM: Artificial Sequence
<220> FEATURE:
<223> OTHER INFORMATION: Synthetic construct

<400> SEQUENCE: 35
tgctcggtgg gatgg                                                   15

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
cggaggttga ggtttttcct t                                            21

<210> SEQ ID NO 37
<211> LENGTH: 21
<212> TYPE: DNA
<213> ORGANISM: Artificial Sequence
<220> FEATURE:
<223> OTHER INFORMATION: Synthetic construct

<400> SEQUENCE: 37
gacggttgaa tggcctctac a                                            21

<210> SEQ ID NO 38
<211> LENGTH: 22
<212> TYPE: DNA
<213> ORGANISM: Artificial Sequence
<220> FEATURE:
<223> OTHER INFORMATION: Synthetic construct

<400> SEQUENCE: 38
tgtataagca cctactgaca aa                                           22

<210> SEQ ID NO 39
<211> LENGTH: 26
<212> TYPE: DNA
<213> ORGANISM: Artificial Sequence
<220> FEATURE:
<223> OTHER INFORMATION: Synthetic construct

<400> SEQUENCE: 39
aggacttctt catgggtctt acagtt                                       26

<210> SEQ ID NO 40
<211> LENGTH: 27
<212> TYPE: DNA
<213> ORGANISM: Artificial Sequence
<220> FEATURE:
<223> OTHER INFORMATION: Synthetic construct

<400> SEQUENCE: 40
aagtgacatt aaagacgatg tgtatgc                                      27
```

```
<210> SEQ ID NO 41
<211> LENGTH: 19
<212> TYPE: DNA
<213> ORGANISM: Artificial Sequence
<220> FEATURE:
<223> OTHER INFORMATION: Synthetic construct

<400> SEQUENCE: 41
tgttagacca tgaaacatt                                                   19

<210> SEQ ID NO 42
<211> LENGTH: 22
<212> TYPE: DNA
<213> ORGANISM: Artificial Sequence
<220> FEATURE:
<223> OTHER INFORMATION: Synthetic construct

<400> SEQUENCE: 42
caggctgtgt tcttgcatct tg                                               22

<210> SEQ ID NO 43
<211> LENGTH: 23
<212> TYPE: DNA
<213> ORGANISM: Artificial Sequence
<220> FEATURE:
<223> OTHER INFORMATION: Synthetic construct

<400> SEQUENCE: 43
gaccatgagg ctgcttctaa aaa                                              23

<210> SEQ ID NO 44
<211> LENGTH: 16
<212> TYPE: DNA
<213> ORGANISM: Artificial Sequence
<220> FEATURE:
<223> OTHER INFORMATION: Synthetic construct

<400> SEQUENCE: 44
ctgcaaacag gtccct                                                      16

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
ttggacccaa gggaaaactg                                                  20

<210> SEQ ID NO 46
<211> LENGTH: 26
<212> TYPE: DNA
<213> ORGANISM: Artificial Sequence
<220> FEATURE:
<223> OTHER INFORMATION: Synthetic construct

<400> SEQUENCE: 46
ggttaaaagt tgtggtttcc attctc                                           26

<210> SEQ ID NO 47
<211> LENGTH: 15
<212> TYPE: DNA
<213> ORGANISM: Artificial Sequence
<220> FEATURE:
<223> OTHER INFORMATION: Synthetic construct
```

```
<400> SEQUENCE: 47
tggagacgca tttcg                                                    15

<210> SEQ ID NO 48
<211> LENGTH: 25
<212> TYPE: DNA
<213> ORGANISM: Artificial Sequence
<220> FEATURE:
<223> OTHER INFORMATION: Synthetic construct

<400> SEQUENCE: 48
gacatcccca ctcacgaata ttatg                                         25

<210> SEQ ID NO 49
<211> LENGTH: 21
<212> TYPE: DNA
<213> ORGANISM: Artificial Sequence
<220> FEATURE:
<223> OTHER INFORMATION: Synthetic construct

<400> SEQUENCE: 49 ctgtccttt ctgggctttc c                                              21

<210> SEQ ID NO 50
<211> LENGTH: 17
<212> TYPE: DNA
<213> ORGANISM: Artificial Sequence
<220> FEATURE:
<223> OTHER INFORMATION: Synthetic construct

<400> SEQUENCE: 50
ccagtttctg cctctga                                                  17

<210> SEQ ID NO 51
<211> LENGTH: 24
<212> TYPE: DNA
<213> ORGANISM: Artificial Sequence
<220> FEATURE:
<223> OTHER INFORMATION: Synthetic construct

<400> SEQUENCE: 51
ggcatagagc agcactaaat gaca                                          24

<210> SEQ ID NO 52
<211> LENGTH: 26
<212> TYPE: DNA
<213> ORGANISM: Artificial Sequence
<220> FEATURE:
<223> OTHER INFORMATION: Synthetic construct

<400> SEQUENCE: 52
ttctataacg cttcacattc cagatc                                        26

<210> SEQ ID NO 53
<211> LENGTH: 20
<212> TYPE: DNA
<213> ORGANISM: Artificial Sequence
<220> FEATURE:
<223> OTHER INFORMATION: Synthetic construct

<400> SEQUENCE: 53
cactaaagaa acgatcagac                                               20

<210> SEQ ID NO 54
<211> LENGTH: 20
```

```
<212> TYPE: DNA
<213> ORGANISM: Artificial Sequence
<220> FEATURE:
<223> OTHER INFORMATION: Synthetic construct

<400> SEQUENCE: 54
cgcactttgg ccttcctaga                                           20

<210> SEQ ID NO 55
<211> LENGTH: 23
<212> TYPE: DNA
<213> ORGANISM: Artificial Sequence
<220> FEATURE:
<223> OTHER INFORMATION: Synthetic construct

<400> SEQUENCE: 55
tggaaggaga tgcagaagtc aga                                       23

<210> SEQ ID NO 56
<211> LENGTH: 17
<212> TYPE: DNA
<213> ORGANISM: Artificial Sequence
<220> FEATURE:
<223> OTHER INFORMATION: Synthetic construct

<400> SEQUENCE: 56
cactgcttca taacctc                                              17

<210> SEQ ID NO 57
<211> LENGTH: 18
<212> TYPE: DNA
<213> ORGANISM: Artificial Sequence
<220> FEATURE:
<223> OTHER INFORMATION: Synthetic construct

<400> SEQUENCE: 57
cctgcccagt cggcttct                                             18

<210> SEQ ID NO 58
<211> LENGTH: 21
<212> TYPE: DNA
<213> ORGANISM: Artificial Sequence
<220> FEATURE:
<223> OTHER INFORMATION: Synthetic construct

<400> SEQUENCE: 58
gtccaagggt gacatttttc g                                         21

<210> SEQ ID NO 59
<211> LENGTH: 17
<212> TYPE: DNA
<213> ORGANISM: Artificial Sequence
<220> FEATURE:
<223> OTHER INFORMATION: Synthetic construct

<400> SEQUENCE: 59
ctccaatgtg tcatctg                                              17

<210> SEQ ID NO 60
<211> LENGTH: 22
<212> TYPE: DNA
<213> ORGANISM: Artificial Sequence
<220> FEATURE:
<223> OTHER INFORMATION: Synthetic construct

<400> SEQUENCE: 60
```
gggttactag tagccgccca ta                                          22

<210> SEQ ID NO 61
<211> LENGTH: 16
<212> TYPE: DNA
<213> ORGANISM: Artificial Sequence
<220> FEATURE:
<223> OTHER INFORMATION: Synthetic construct

<400> SEQUENCE: 61
gcagggccag cattgc                                                 16

<210> SEQ ID NO 62
<211> LENGTH: 17
<212> TYPE: DNA
<213> ORGANISM: Artificial Sequence
<220> FEATURE:
<223> OTHER INFORMATION: Synthetic construct

<400> SEQUENCE: 62
caacctttgc actccac                                                17

<210> SEQ ID NO 63
<211> LENGTH: 24
<212> TYPE: DNA
<213> ORGANISM: Artificial Sequence
<220> FEATURE:
<223> OTHER INFORMATION: Synthetic construct

<400> SEQUENCE: 63
tgtccatttt tttggctact ctga                                        24

<210> SEQ ID NO 64
<211> LENGTH: 19
<212> TYPE: DNA
<213> ORGANISM: Artificial Sequence
<220> FEATURE:
<223> OTHER INFORMATION: Synthetic construct

<400> SEQUENCE: 64
cccaaacacc caggctctt                                              19

<210> SEQ ID NO 65
<211> LENGTH: 15
<212> TYPE: DNA
<213> ORGANISM: Artificial Sequence
<220> FEATURE:
<223> OTHER INFORMATION: Synthetic construct

<400> SEQUENCE: 65
cagtgtggaa caatg                                                  15

<210> SEQ ID NO 66
<211> LENGTH: 19
<212> TYPE: DNA
<213> ORGANISM: Artificial Sequence
<220> FEATURE:
<223> OTHER INFORMATION: Synthetic construct

<400> SEQUENCE: 66
gctccagtgc cccaagatt                                              19

<210> SEQ ID NO 67
<211> LENGTH: 18
<212> TYPE: DNA
<213> ORGANISM: Artificial Sequence

```
<220> FEATURE:
<223> OTHER INFORMATION: Synthetic construct

<400> SEQUENCE: 67
cgacggatcg cctctgaa                                                    18

<210> SEQ ID NO 68
<211> LENGTH: 21
<212> TYPE: DNA
<213> ORGANISM: Artificial Sequence
<220> FEATURE:
<223> OTHER INFORMATION: Synthetic construct

<400> SEQUENCE: 68
aaactgtgga tatcagcatg a                                                21

<210> SEQ ID NO 69
<211> LENGTH: 23
<212> TYPE: DNA
<213> ORGANISM: Artificial Sequence
<220> FEATURE:
<223> OTHER INFORMATION: Synthetic construct

<400> SEQUENCE: 69
tgggcaactc agaaatactt cga                                              23

<210> SEQ ID NO 70
<211> LENGTH: 21
<212> TYPE: DNA
<213> ORGANISM: Artificial Sequence
<220> FEATURE:
<223> OTHER INFORMATION: Synthetic construct

<400> SEQUENCE: 70
acgtcaatag gcacgtttgc t                                                21

<210> SEQ ID NO 71
<211> LENGTH: 19
<212> TYPE: DNA
<213> ORGANISM: Artificial Sequence
<220> FEATURE:
<223> OTHER INFORMATION: Synthetic construct

<400> SEQUENCE: 71
ctcccaagat ataagaggc                                                   19

<210> SEQ ID NO 72
<211> LENGTH: 20
<212> TYPE: DNA
<213> ORGANISM: Artificial Sequence
<220> FEATURE:
<223> OTHER INFORMATION: Synthetic construct

<400> SEQUENCE: 72
gtccaccctc tcccctttct                                                  20

<210> SEQ ID NO 73
<211> LENGTH: 26
<212> TYPE: DNA
<213> ORGANISM: Artificial Sequence
<220> FEATURE:
<223> OTHER INFORMATION: Synthetic construct

<400> SEQUENCE: 73
cacgcactct agtacaaagc ataaga                                           26
```

<210> SEQ ID NO 74
<211> LENGTH: 15
<212> TYPE: DNA
<213> ORGANISM: Artificial Sequence
<220> FEATURE:
<223> OTHER INFORMATION: Synthetic construct

<400> SEQUENCE: 74
ctcactccaa gaaac                                                      15

<210> SEQ ID NO 75
<211> LENGTH: 22
<212> TYPE: DNA
<213> ORGANISM: Artificial Sequence
<220> FEATURE:
<223> OTHER INFORMATION: Synthetic construct

<400> SEQUENCE: 75
cccaaaccga atcaccttaa ga                                              22

<210> SEQ ID NO 76
<211> LENGTH: 18
<212> TYPE: DNA
<213> ORGANISM: Artificial Sequence
<220> FEATURE:
<223> OTHER INFORMATION: Synthetic construct

<400> SEQUENCE: 76
caggagggtg gccatcct                                                   18

<210> SEQ ID NO 77
<211> LENGTH: 15
<212> TYPE: DNA
<213> ORGANISM: Artificial Sequence
<220> FEATURE:
<223> OTHER INFORMATION: Synthetic construct

<400> SEQUENCE: 77
acagggctag ggcat                                                      15

<210> SEQ ID NO 78
<211> LENGTH: 21
<212> TYPE: DNA
<213> ORGANISM: Artificial Sequence
<220> FEATURE:
<223> OTHER INFORMATION: Synthetic construct

<400> SEQUENCE: 78
tctccatggc atcttcgtct t                                               21

<210> SEQ ID NO 79
<211> LENGTH: 20
<212> TYPE: DNA
<213> ORGANISM: Artificial Sequence
<220> FEATURE:
<223> OTHER INFORMATION: Synthetic construct

<400> SEQUENCE: 79
atcccttacc ccaccctcaa                                                 20

<210> SEQ ID NO 80
<211> LENGTH: 17
<212> TYPE: DNA
<213> ORGANISM: Artificial Sequence
<220> FEATURE:
<223> OTHER INFORMATION: Synthetic construct

<400> SEQUENCE: 80
actcttaggc actttgg                                                          17

<210> SEQ ID NO 81
<211> LENGTH: 18
<212> TYPE: DNA
<213> ORGANISM: Artificial Sequence
<220> FEATURE:
<223> OTHER INFORMATION: Synthetic construct

<400> SEQUENCE: 81
cggcctcagg cacaagaa                                                         18

<210> SEQ ID NO 82
<211> LENGTH: 20
<212> TYPE: DNA
<213> ORGANISM: Artificial Sequence
<220> FEATURE:
<223> OTHER INFORMATION: Synthetic construct

<400> SEQUENCE: 82
gcagcccatc cagtgtcaat                                                       20

<210> SEQ ID NO 83
<211> LENGTH: 19
<212> TYPE: DNA
<213> ORGANISM: Artificial Sequence
<220> FEATURE:
<223> OTHER INFORMATION: Synthetic construct

<400> SEQUENCE: 83
atgtggacta tgtgatcct                                                        19

<210> SEQ ID NO 84
<211> LENGTH: 27
<212> TYPE: DNA
<213> ORGANISM: Artificial Sequence
<220> FEATURE:
<223> OTHER INFORMATION: Synthetic construct

<400> SEQUENCE: 84
catggtacat gagtggctat catactg                                               27

<210> SEQ ID NO 85
<211> LENGTH: 23
<212> TYPE: DNA
<213> ORGANISM: Artificial Sequence
<220> FEATURE:
<223> OTHER INFORMATION: Synthetic construct

<400> SEQUENCE: 85
gtgagcacct tccttctttt tga                                                   23

<210> SEQ ID NO 86
<211> LENGTH: 23
<212> TYPE: DNA
<213> ORGANISM: Artificial Sequence
<220> FEATURE:
<223> OTHER INFORMATION: Synthetic construct

<400> SEQUENCE: 86
ctattatatg ggtttcagac aaa                                                   23

<210> SEQ ID NO 87

```
<211> LENGTH: 27
<212> TYPE: DNA
<213> ORGANISM: Artificial Sequence
<220> FEATURE:
<223> OTHER INFORMATION: Synthetic construct

<400> SEQUENCE: 87
gactattgtc tcctaaaccc aggacta                                          27

<210> SEQ ID NO 88
<211> LENGTH: 22
<212> TYPE: DNA
<213> ORGANISM: Artificial Sequence
<220> FEATURE:
<223> OTHER INFORMATION: Synthetic construct

<400> SEQUENCE: 88
cccagtgcat ttaatgacca aa                                               22

<210> SEQ ID NO 89
<211> LENGTH: 17
<212> TYPE: DNA
<213> ORGANISM: Artificial Sequence
<220> FEATURE:
<223> OTHER INFORMATION: Synthetic construct

<400> SEQUENCE: 89
agttccctcg tactgtc                                                     17

<210> SEQ ID NO 90
<211> LENGTH: 22
<212> TYPE: DNA
<213> ORGANISM: Artificial Sequence
<220> FEATURE:
<223> OTHER INFORMATION: Synthetic construct

<400> SEQUENCE: 90
atcaattttc ccgacgatct tc                                               22

<210> SEQ ID NO 91
<211> LENGTH: 21
<212> TYPE: DNA
<213> ORGANISM: Artificial Sequence
<220> FEATURE:
<223> OTHER INFORMATION: Synthetic construct

<400> SEQUENCE: 91
cggttggcat ccatgtaaag t                                                21

<210> SEQ ID NO 92
<211> LENGTH: 14
<212> TYPE: DNA
<213> ORGANISM: Artificial Sequence
<220> FEATURE:
<223> OTHER INFORMATION: Synthetic construct

<400> SEQUENCE: 92
tggctccaac actg                                                        14

<210> SEQ ID NO 93
<211> LENGTH: 21
<212> TYPE: DNA
<213> ORGANISM: Artificial Sequence
<220> FEATURE:
<223> OTHER INFORMATION: Synthetic construct

<400> SEQUENCE: 93
```
aggtccaccg tgatcaacat c					21

<210> SEQ ID NO 94
<211> LENGTH: 20
<212> TYPE: DNA
<213> ORGANISM: Artificial Sequence
<220> FEATURE:
<223> OTHER INFORMATION: Synthetic construct

<400> SEQUENCE: 94
cagggaccag acgacatggt					20

<210> SEQ ID NO 95
<211> LENGTH: 16
<212> TYPE: DNA
<213> ORGANISM: Artificial Sequence
<220> FEATURE:
<223> OTHER INFORMATION: Synthetic construct

<400> SEQUENCE: 95
acagcgagac ctccgt					16

<210> SEQ ID NO 96
<211> LENGTH: 20
<212> TYPE: DNA
<213> ORGANISM: Artificial Sequence
<220> FEATURE:
<223> OTHER INFORMATION: Synthetic construct

<400> SEQUENCE: 96
caacttgtgg acggccagta					20

<210> SEQ ID NO 97
<211> LENGTH: 22
<212> TYPE: DNA
<213> ORGANISM: Artificial Sequence
<220> FEATURE:
<223> OTHER INFORMATION: Synthetic construct

<400> SEQUENCE: 97
gtgccactga gggagaacat tt					22

<210> SEQ ID NO 98
<211> LENGTH: 19
<212> TYPE: DNA
<213> ORGANISM: Artificial Sequence
<220> FEATURE:
<223> OTHER INFORMATION: Synthetic construct

<400> SEQUENCE: 98
aaactgcttc tacaagatt					19

<210> SEQ ID NO 99
<211> LENGTH: 21
<212> TYPE: DNA
<213> ORGANISM: Artificial Sequence
<220> FEATURE:
<223> OTHER INFORMATION: Synthetic construct

<400> SEQUENCE: 99
cagcagagac cctgaaggaa a					21

<210> SEQ ID NO 100
<211> LENGTH: 20
<212> TYPE: DNA

```
<213> ORGANISM: Artificial Sequence
<220> FEATURE:
<223> OTHER INFORMATION: Synthetic construct

<400> SEQUENCE: 100
caagccatga gttgccatca                                              20

<210> SEQ ID NO 101
<211> LENGTH: 18
<212> TYPE: DNA
<213> ORGANISM: Artificial Sequence
<220> FEATURE:
<223> OTHER INFORMATION: Synthetic construct

<400> SEQUENCE: 101
aggtgcatat aagatctt                                                18

<210> SEQ ID NO 102
<211> LENGTH: 19
<212> TYPE: DNA
<213> ORGANISM: Artificial Sequence
<220> FEATURE:
<223> OTHER INFORMATION: Synthetic construct

<400> SEQUENCE: 102
cccattctgc gtcatgctt                                               19

<210> SEQ ID NO 103
<211> LENGTH: 24
<212> TYPE: DNA
<213> ORGANISM: Artificial Sequence
<220> FEATURE:
<223> OTHER INFORMATION: Synthetic construct

<400> SEQUENCE: 103
aatgcagttt agacacagcc aaac                                         24

<210> SEQ ID NO 104
<211> LENGTH: 23
<212> TYPE: DNA
<213> ORGANISM: Artificial Sequence
<220> FEATURE:
<223> OTHER INFORMATION: Synthetic construct

<400> SEQUENCE: 104
tgttataact actccggaga cag                                          23

<210> SEQ ID NO 105
<211> LENGTH: 21
<212> TYPE: DNA
<213> ORGANISM: Artificial Sequence
<220> FEATURE:
<223> OTHER INFORMATION: Synthetic construct

<400> SEQUENCE: 105
agttcagccc agatggaagg t                                            21

<210> SEQ ID NO 106
<211> LENGTH: 20
<212> TYPE: DNA
<213> ORGANISM: Artificial Sequence
<220> FEATURE:
<223> OTHER INFORMATION: Synthetic construct

<400> SEQUENCE: 106
gcggcatcgc taaataagga                                              20
```

<210> SEQ ID NO 107
<211> LENGTH: 17
<212> TYPE: DNA
<213> ORGANISM: Artificial Sequence
<220> FEATURE:
<223> OTHER INFORMATION: Synthetic construct

<400> SEQUENCE: 107
ttcagggaaa ggtgggc                                                    17

<210> SEQ ID NO 108
<211> LENGTH: 29
<212> TYPE: DNA
<213> ORGANISM: Artificial Sequence
<220> FEATURE:
<223> OTHER INFORMATION: Synthetic construct

<400> SEQUENCE: 108
cacagggact tgaagttgtt actaactaa                                       29

<210> SEQ ID NO 109
<211> LENGTH: 20
<212> TYPE: DNA
<213> ORGANISM: Artificial Sequence
<220> FEATURE:
<223> OTHER INFORMATION: Synthetic construct

<400> SEQUENCE: 109
tgacgcagaa tgggatgaga                                                 20

<210> SEQ ID NO 110
<211> LENGTH: 17
<212> TYPE: DNA
<213> ORGANISM: Artificial Sequence
<220> FEATURE:
<223> OTHER INFORMATION: Synthetic construct

<400> SEQUENCE: 110
ctctctttgg gaatgtt                                                    17

<210> SEQ ID NO 111
<211> LENGTH: 21
<212> TYPE: DNA
<213> ORGANISM: Artificial Sequence
<220> FEATURE:
<223> OTHER INFORMATION: Synthetic construct

<400> SEQUENCE: 111
caaagcagcc agacgttgaa c                                               21

<210> SEQ ID NO 112
<211> LENGTH: 20
<212> TYPE: DNA
<213> ORGANISM: Artificial Sequence
<220> FEATURE:
<223> OTHER INFORMATION: Synthetic construct

<400> SEQUENCE: 112
cacaccagat ccggaagaca                                                 20

<210> SEQ ID NO 113
<211> LENGTH: 16
<212> TYPE: DNA
<213> ORGANISM: Artificial Sequence
<220> FEATURE:

<223> OTHER INFORMATION: Synthetic construct

<400> SEQUENCE: 113
tttccctggg cgcagg                                                         16

<210> SEQ ID NO 114
<211> LENGTH: 23
<212> TYPE: DNA
<213> ORGANISM: Artificial Sequence
<220> FEATURE:
<223> OTHER INFORMATION: Synthetic construct

<400> SEQUENCE: 114
gggattccta ccccagattt cta                                                 23

<210> SEQ ID NO 115
<211> LENGTH: 25
<212> TYPE: DNA
<213> ORGANISM: Artificial Sequence
<220> FEATURE:
<223> OTHER INFORMATION: Synthetic construct

<400> SEQUENCE: 115
cagaaactgt tgttggactg catag                                               25

<210> SEQ ID NO 116
<211> LENGTH: 20
<212> TYPE: DNA
<213> ORGANISM: Artificial Sequence
<220> FEATURE:
<223> OTHER INFORMATION: Synthetic construct

<400> SEQUENCE: 116
agtcagaaat gtaccaaaaa                                                     20

<210> SEQ ID NO 117
<211> LENGTH: 24
<212> TYPE: DNA
<213> ORGANISM: Artificial Sequence
<220> FEATURE:
<223> OTHER INFORMATION: Synthetic construct

<400> SEQUENCE: 117
tgagctgtag ctgcgtaagt acct                                                24

<210> SEQ ID NO 118
<211> LENGTH: 20
<212> TYPE: DNA
<213> ORGANISM: Artificial Sequence
<220> FEATURE:
<223> OTHER INFORMATION: Synthetic construct

<400> SEQUENCE: 118
ggccttgtgc ctttcagaag                                                     20

<210> SEQ ID NO 119
<211> LENGTH: 16
<212> TYPE: DNA
<213> ORGANISM: Artificial Sequence
<220> FEATURE:
<223> OTHER INFORMATION: Synthetic construct

<400> SEQUENCE: 119
cttgatgcct gtcggc                                                         16

```
<210> SEQ ID NO 120
<211> LENGTH: 19
<212> TYPE: DNA
<213> ORGANISM: Artificial Sequence
<220> FEATURE:
<223> OTHER INFORMATION: Synthetic construct

<400> SEQUENCE: 120
tggctgccct acacatgct                                                    19

<210> SEQ ID NO 121
<211> LENGTH: 22
<212> TYPE: DNA
<213> ORGANISM: Artificial Sequence
<220> FEATURE:
<223> OTHER INFORMATION: Synthetic construct

<400> SEQUENCE: 121
caggatcccc tctaccactt tg                                                22

<210> SEQ ID NO 122
<211> LENGTH: 18
<212> TYPE: DNA
<213> ORGANISM: Artificial Sequence
<220> FEATURE:
<223> OTHER INFORMATION: Synthetic construct

<400> SEQUENCE: 122
cctgctctat ctgcattt                                                     18

<210> SEQ ID NO 123
<211> LENGTH: 22
<212> TYPE: DNA
<213> ORGANISM: Artificial Sequence
<220> FEATURE:
<223> OTHER INFORMATION: Synthetic construct

<400> SEQUENCE: 123
gaggctcagc tgtgattgac at                                                22

<210> SEQ ID NO 124
<211> LENGTH: 23
<212> TYPE: DNA
<213> ORGANISM: Artificial Sequence
<220> FEATURE:
<223> OTHER INFORMATION: Synthetic construct

<400> SEQUENCE: 124
cacccatatc ctcgaagcta gag                                               23

<210> SEQ ID NO 125
<211> LENGTH: 19
<212> TYPE: DNA
<213> ORGANISM: Artificial Sequence
<220> FEATURE:
<223> OTHER INFORMATION: Synthetic construct

<400> SEQUENCE: 125
agaacatgga tgatacctc                                                    19

<210> SEQ ID NO 126
<211> LENGTH: 20
<212> TYPE: DNA
<213> ORGANISM: Artificial Sequence
<220> FEATURE:
<223> OTHER INFORMATION: Synthetic construct
```

<400> SEQUENCE: 126
tccagccaca gtcccctaga                                                   20

<210> SEQ ID NO 127
<211> LENGTH: 27
<212> TYPE: DNA
<213> ORGANISM: Artificial Sequence
<220> FEATURE:
<223> OTHER INFORMATION: Synthetic construct

<400> SEQUENCE: 127
tcctgaatgt tcctgatgat agtctct                                           27

<210> SEQ ID NO 128
<211> LENGTH: 23
<212> TYPE: DNA
<213> ORGANISM: Artificial Sequence
<220> FEATURE:
<223> OTHER INFORMATION: Synthetic construct

<400> SEQUENCE: 128
agattaacat tgacagttcg aca                                               23

<210> SEQ ID NO 129
<211> LENGTH: 19
<212> TYPE: DNA
<213> ORGANISM: Artificial Sequence
<220> FEATURE:
<223> OTHER INFORMATION: Synthetic construct

<400> SEQUENCE: 129
cgagaggaag gcgctgatc                                                    19

<210> SEQ ID NO 130
<211> LENGTH: 26
<212> TYPE: DNA
<213> ORGANISM: Artificial Sequence
<220> FEATURE:
<223> OTHER INFORMATION: Synthetic construct

<400> SEQUENCE: 130
acatcactcc atccttatac agcaaa                                            26

<210> SEQ ID NO 131
<211> LENGTH: 17
<212> TYPE: DNA
<213> ORGANISM: Artificial Sequence
<220> FEATURE:
<223> OTHER INFORMATION: Synthetic construct

<400> SEQUENCE: 131
cctgcaagag attattt                                                      17

<210> SEQ ID NO 132
<211> LENGTH: 23
<212> TYPE: DNA
<213> ORGANISM: Artificial Sequence
<220> FEATURE:
<223> OTHER INFORMATION: Synthetic construct

<400> SEQUENCE: 132
ggatcctctt gacattcctc aaa                                               23

<210> SEQ ID NO 133
<211> LENGTH: 14

```
<212> TYPE: DNA
<213> ORGANISM: Artificial Sequence
<220> FEATURE:
<223> OTHER INFORMATION: Synthetic construct

<400> SEQUENCE: 133
ggccccccga tgga                                                      14

<210> SEQ ID NO 134
<211> LENGTH: 17
<212> TYPE: DNA
<213> ORGANISM: Artificial Sequence
<220> FEATURE:
<223> OTHER INFORMATION: Synthetic construct

<400> SEQUENCE: 134
ctccaccttt gaagacc                                                   17

<210> SEQ ID NO 135
<211> LENGTH: 19
<212> TYPE: DNA
<213> ORGANISM: Artificial Sequence
<220> FEATURE:
<223> OTHER INFORMATION: Synthetic construct

<400> SEQUENCE: 135
cgagggtgtg gccatatga                                                 19

<210> SEQ ID NO 136
<211> LENGTH: 25
<212> TYPE: DNA
<213> ORGANISM: Artificial Sequence
<220> FEATURE:
<223> OTHER INFORMATION: Synthetic construct

<400> SEQUENCE: 136
gaacaggcat tagaaatacc caaag                                          25

<210> SEQ ID NO 137
<211> LENGTH: 19
<212> TYPE: DNA
<213> ORGANISM: Artificial Sequence
<220> FEATURE:
<223> OTHER INFORMATION: Synthetic construct

<400> SEQUENCE: 137
tgactagatg gctaatatg                                                 19

<210> SEQ ID NO 138
<211> LENGTH: 22
<212> TYPE: DNA
<213> ORGANISM: Artificial Sequence
<220> FEATURE:
<223> OTHER INFORMATION: Synthetic construct

<400> SEQUENCE: 138
ctactgcaag gcatgctttg at                                             22

<210> SEQ ID NO 139
<211> LENGTH: 16
<212> TYPE: DNA
<213> ORGANISM: Artificial Sequence
<220> FEATURE:
<223> OTHER INFORMATION: Synthetic construct

<400> SEQUENCE: 139
``` tggcccoctg cattga                                                16

<210> SEQ ID NO 140
<211> LENGTH: 17
<212> TYPE: DNA
<213> ORGANISM: Artificial Sequence
<220> FEATURE:
<223> OTHER INFORMATION: Synthetic construct

<400> SEQUENCE: 140
tcccttcatc attgctg                                               17

<210> SEQ ID NO 141
<211> LENGTH: 19
<212> TYPE: DNA
<213> ORGANISM: Artificial Sequence
<220> FEATURE:
<223> OTHER INFORMATION: Synthetic construct

<400> SEQUENCE: 141
dccggtgcag ttacacgtt                                             19

<210> SEQ ID NO 142
<211> LENGTH: 18
<212> TYPE: DNA
<213> ORGANISM: Artificial Sequence
<220> FEATURE:
<223> OTHER INFORMATION: Synthetic construct

<400> SEQUENCE: 142
ccccaaaccc gtgacaac                                              18

<210> SEQ ID NO 143
<211> LENGTH: 15
<212> TYPE: DNA
<213> ORGANISM: Artificial Sequence
<220> FEATURE:
<223> OTHER INFORMATION: Synthetic construct

<400> SEQUENCE: 143
cctccaagga gcctc                                                 15

<210> SEQ ID NO 144
<211> LENGTH: 20
<212> TYPE: DNA
<213> ORGANISM: Artificial Sequence
<220> FEATURE:
<223> OTHER INFORMATION: Synthetic construct

<400> SEQUENCE: 144
caaggccctc aacacattca                                            20

<210> SEQ ID NO 145
<211> LENGTH: 23
<212> TYPE: DNA
<213> ORGANISM: Artificial Sequence
<220> FEATURE:
<223> OTHER INFORMATION: Synthetic construct

<400> SEQUENCE: 145
ggtacataac gggcatcttg atg                                        23

<210> SEQ ID NO 146
<211> LENGTH: 15
<212> TYPE: DNA
<213> ORGANISM: Artificial Sequence

```
<220> FEATURE:
<223> OTHER INFORMATION: Synthetic construct

<400> SEQUENCE: 146
acctgttcgc ctttg                                                    15

<210> SEQ ID NO 147
<211> LENGTH: 26
<212> TYPE: DNA
<213> ORGANISM: Artificial Sequence
<220> FEATURE:
<223> OTHER INFORMATION: Synthetic construct

<400> SEQUENCE: 147
cctatgctgg agaaggatta gaaagt                                        26

<210> SEQ ID NO 148
<211> LENGTH: 22
<212> TYPE: DNA
<213> ORGANISM: Artificial Sequence
<220> FEATURE:
<223> OTHER INFORMATION: Synthetic construct

<400> SEQUENCE: 148
cgatgattag aggtgcatgg aa                                            22

<210> SEQ ID NO 149
<211> LENGTH: 15
<212> TYPE: DNA
<213> ORGANISM: Artificial Sequence
<220> FEATURE:
<223> OTHER INFORMATION: Synthetic construct

<400> SEQUENCE: 149
atgtggcaga taaag                                                    15

<210> SEQ ID NO 150
<211> LENGTH: 18
<212> TYPE: DNA
<213> ORGANISM: Artificial Sequence
<220> FEATURE:
<223> OTHER INFORMATION: Synthetic construct

<400> SEQUENCE: 150
tctcgccacc ctcaccat                                                 18

<210> SEQ ID NO 151
<211> LENGTH: 24
<212> TYPE: DNA
<213> ORGANISM: Artificial Sequence
<220> FEATURE:
<223> OTHER INFORMATION: Synthetic construct

<400> SEQUENCE: 151
gctgacagaa gtagatgcca ttgt                                          24

<210> SEQ ID NO 152
<211> LENGTH: 16
<212> TYPE: DNA
<213> ORGANISM: Artificial Sequence
<220> FEATURE:
<223> OTHER INFORMATION: Synthetic construct

<400> SEQUENCE: 152
caaggcatcc ggtttg                                                   16
```

<210> SEQ ID NO 153
<211> LENGTH: 20
<212> TYPE: DNA
<213> ORGANISM: Artificial Sequence
<220> FEATURE:
<223> OTHER INFORMATION: Synthetic construct

<400> SEQUENCE: 153
aagtcgccct ggaacttcct                                            20

<210> SEQ ID NO 154
<211> LENGTH: 20
<212> TYPE: DNA
<213> ORGANISM: Artificial Sequence
<220> FEATURE:
<223> OTHER INFORMATION: Synthetic construct

<400> SEQUENCE: 154
caccgagtcc tgctcctcat                                            20

<210> SEQ ID NO 155
<211> LENGTH: 19
<212> TYPE: DNA
<213> ORGANISM: Artificial Sequence
<220> FEATURE:
<223> OTHER INFORMATION: Synthetic construct

<400> SEQUENCE: 155
atgagttgta cgagcagtc                                             19

<210> SEQ ID NO 156
<211> LENGTH: 25
<212> TYPE: DNA
<213> ORGANISM: Artificial Sequence
<220> FEATURE:
<223> OTHER INFORMATION: Synthetic construct

<400> SEQUENCE: 156
catgagctgg tgaaaatgg tattt                                       25

<210> SEQ ID NO 157
<211> LENGTH: 23
<212> TYPE: DNA
<213> ORGANISM: Artificial Sequence
<220> FEATURE:
<223> OTHER INFORMATION: Synthetic construct

<400> SEQUENCE: 157
aaagctattc ctatcgtggc aaa                                        23

<210> SEQ ID NO 158
<211> LENGTH: 18
<212> TYPE: DNA
<213> ORGANISM: Artificial Sequence
<220> FEATURE:
<223> OTHER INFORMATION: Synthetic construct

<400> SEQUENCE: 158
aaccagatac caagtttt                                              18

<210> SEQ ID NO 159
<211> LENGTH: 19
<212> TYPE: DNA
<213> ORGANISM: Artificial Sequence
<220> FEATURE:
<223> OTHER INFORMATION: Synthetic construct

```
<400> SEQUENCE: 159
tccccagctc ttgccaaag                                                   19

<210> SEQ ID NO 160
<211> LENGTH: 23
<212> TYPE: DNA
<213> ORGANISM: Artificial Sequence
<220> FEATURE:
<223> OTHER INFORMATION: Synthetic construct

<400> SEQUENCE: 160
cagagaactc cctccaagtt gct                                              23

<210> SEQ ID NO 161
<211> LENGTH: 20
<212> TYPE: DNA
<213> ORGANISM: Artificial Sequence
<220> FEATURE:
<223> OTHER INFORMATION: Synthetic construct

<400> SEQUENCE: 161
ctggagtaga aggacaacag                                                  20

<210> SEQ ID NO 162
<211> LENGTH: 17
<212> TYPE: DNA
<213> ORGANISM: Artificial Sequence
<220> FEATURE:
<223> OTHER INFORMATION: Synthetic construct

<400> SEQUENCE: 162
ggcaggccag ggtttgt                                                     17

<210> SEQ ID NO 163
<211> LENGTH: 21
<212> TYPE: DNA
<213> ORGANISM: Artificial Sequence
<220> FEATURE:
<223> OTHER INFORMATION: Synthetic construct

<400> SEQUENCE: 163
cgagatggct ggaaacacag a                                                21

<210> SEQ ID NO 164
<211> LENGTH: 14
<212> TYPE: DNA
<213> ORGANISM: Artificial Sequence
<220> FEATURE:
<223> OTHER INFORMATION: Synthetic construct

<400> SEQUENCE: 164
aggcgctgtc tgtc                                                        14

<210> SEQ ID NO 165
<211> LENGTH: 20
<212> TYPE: DNA
<213> ORGANISM: Artificial Sequence
<220> FEATURE:
<223> OTHER INFORMATION: Synthetic construct

<400> SEQUENCE: 165
gactcagcct ctgggatgga                                                  20

<210> SEQ ID NO 166
```

<210> SEQ ID NO 166
<211> LENGTH: 21
<212> TYPE: DNA
<213> ORGANISM: Artificial Sequence
<220> FEATURE:
<223> OTHER INFORMATION: Synthetic construct

<400> SEQUENCE: 166
ggatccggaa gtagccattc t                                              21

<210> SEQ ID NO 167
<211> LENGTH: 21
<212> TYPE: DNA
<213> ORGANISM: Artificial Sequence
<220> FEATURE:
<223> OTHER INFORMATION: Synthetic construct

<400> SEQUENCE: 167
tggattgtta aaaacagctg g                                              21

<210> SEQ ID NO 168
<211> LENGTH: 18
<212> TYPE: DNA
<213> ORGANISM: Artificial Sequence
<220> FEATURE:
<223> OTHER INFORMATION: Synthetic construct

<400> SEQUENCE: 168
aggcggcttc ccatacct                                                  18

<210> SEQ ID NO 169
<211> LENGTH: 20
<212> TYPE: DNA
<213> ORGANISM: Artificial Sequence
<220> FEATURE:
<223> OTHER INFORMATION: Synthetic construct

<400> SEQUENCE: 169
cttcttccac cagcccaaaa                                                20

<210> SEQ ID NO 170
<211> LENGTH: 18
<212> TYPE: DNA
<213> ORGANISM: Artificial Sequence
<220> FEATURE:
<223> OTHER INFORMATION: Synthetic construct

<400> SEQUENCE: 170
attgcaggaa agtacgcc                                                  18

<210> SEQ ID NO 171
<211> LENGTH: 19
<212> TYPE: DNA
<213> ORGANISM: Artificial Sequence
<220> FEATURE:
<223> OTHER INFORMATION: Synthetic construct

<400> SEQUENCE: 171
cccaaacctg caccactga                                                 19

<210> SEQ ID NO 172
<211> LENGTH: 21
<212> TYPE: DNA
<213> ORGANISM: Artificial Sequence
<220> FEATURE:
<223> OTHER INFORMATION: Synthetic construct

<400> SEQUENCE: 172
caagatgttg gcaaatgcaa a                                            21

<210> SEQ ID NO 173
<211> LENGTH: 18
<212> TYPE: DNA
<213> ORGANISM: Artificial Sequence
<220> FEATURE:
<223> OTHER INFORMATION: Synthetic construct

<400> SEQUENCE: 173
ctgaaataca gcaaaaga                                                18

<210> SEQ ID NO 174
<211> LENGTH: 24
<212> TYPE: DNA
<213> ORGANISM: Artificial Sequence
<220> FEATURE:
<223> OTHER INFORMATION: Synthetic construct

<400> SEQUENCE: 174
cctttgtggc atttattcat cagt                                         24

<210> SEQ ID NO 175
<211> LENGTH: 23
<212> TYPE: DNA
<213> ORGANISM: Artificial Sequence
<220> FEATURE:
<223> OTHER INFORMATION: Synthetic construct

<400> SEQUENCE: 175
gcttctatga caagcagcct ttg                                          23

<210> SEQ ID NO 176
<211> LENGTH: 15
<212> TYPE: DNA
<213> ORGANISM: Artificial Sequence
<220> FEATURE:
<223> OTHER INFORMATION: Synthetic construct

<400> SEQUENCE: 176
agggtgtccg attgg                                                   15

<210> SEQ ID NO 177
<211> LENGTH: 22
<212> TYPE: DNA
<213> ORGANISM: Artificial Sequence
<220> FEATURE:
<223> OTHER INFORMATION: Synthetic construct

<400> SEQUENCE: 177
ctctgtagca caggctggat tg                                           22

<210> SEQ ID NO 178
<211> LENGTH: 20
<212> TYPE: DNA
<213> ORGANISM: Artificial Sequence
<220> FEATURE:
<223> OTHER INFORMATION: Synthetic construct

<400> SEQUENCE: 178
aggctgcagt gcaagattga                                              20

<210> SEQ ID NO 179
<211> LENGTH: 17
<212> TYPE: DNA

```
<213> ORGANISM: Artificial Sequence
<220> FEATURE:
<223> OTHER INFORMATION: Synthetic construct

<400> SEQUENCE: 179
agtgcaatcc tgcaatt                                                      17

<210> SEQ ID NO 180
<211> LENGTH: 20
<212> TYPE: DNA
<213> ORGANISM: Artificial Sequence
<220> FEATURE:
<223> OTHER INFORMATION: Synthetic construct

<400> SEQUENCE: 180
ccacttggag gcctttcatc                                                   20

<210> SEQ ID NO 181
<211> LENGTH: 21
<212> TYPE: DNA
<213> ORGANISM: Artificial Sequence
<220> FEATURE:
<223> OTHER INFORMATION: Synthetic construct

<400> SEQUENCE: 181
aggttggcga tcaggaatac a                                                 21

<210> SEQ ID NO 182
<211> LENGTH: 16
<212> TYPE: DNA
<213> ORGANISM: Artificial Sequence
<220> FEATURE:
<223> OTHER INFORMATION: Synthetic construct

<400> SEQUENCE: 182
tcgggtgtgc tatgga                                                       16

<210> SEQ ID NO 183
<211> LENGTH: 20
<212> TYPE: DNA
<213> ORGANISM: Artificial Sequence
<220> FEATURE:
<223> OTHER INFORMATION: Synthetic construct

<400> SEQUENCE: 183
ccttgcctgg tttcgatgtt                                                   20

<210> SEQ ID NO 184
<211> LENGTH: 23
<212> TYPE: DNA
<213> ORGANISM: Artificial Sequence
<220> FEATURE:
<223> OTHER INFORMATION: Synthetic construct

<400> SEQUENCE: 184
gagcatttcc ctgtaggctt ctt                                               23

<210> SEQ ID NO 185
<211> LENGTH: 16
<212> TYPE: DNA
<213> ORGANISM: Artificial Sequence
<220> FEATURE:
<223> OTHER INFORMATION: Synthetic construct

<400> SEQUENCE: 185
cccaaagcat aaaatt                                                       16
```

```
<210> SEQ ID NO 186
<211> LENGTH: 23
<212> TYPE: DNA
<213> ORGANISM: Artificial Sequence
<220> FEATURE:
<223> OTHER INFORMATION: Synthetic construct

<400> SEQUENCE: 186
caaccgttgg aaacataacc att                                          23

<210> SEQ ID NO 187
<211> LENGTH: 25
<212> TYPE: DNA
<213> ORGANISM: Artificial Sequence
<220> FEATURE:
<223> OTHER INFORMATION: Synthetic construct

<400> SEQUENCE: 187
aacaatcagt agcacattgc atctg                                        25

<210> SEQ ID NO 188
<211> LENGTH: 16
<212> TYPE: DNA
<213> ORGANISM: Artificial Sequence
<220> FEATURE:
<223> OTHER INFORMATION: Synthetic construct

<400> SEQUENCE: 188
agggagctgg gacact                                                  16

<210> SEQ ID NO 189
<211> LENGTH: 22
<212> TYPE: DNA
<213> ORGANISM: Artificial Sequence
<220> FEATURE:
<223> OTHER INFORMATION: Synthetic construct

<400> SEQUENCE: 189
tggactcact gaggctgacg ta                                           22

<210> SEQ ID NO 190
<211> LENGTH: 21
<212> TYPE: DNA
<213> ORGANISM: Artificial Sequence
<220> FEATURE:
<223> OTHER INFORMATION: Synthetic construct

<400> SEQUENCE: 190
gattcccgag aacccttgat g                                            21

<210> SEQ ID NO 191
<211> LENGTH: 19
<212> TYPE: DNA
<213> ORGANISM: Artificial Sequence
<220> FEATURE:
<223> OTHER INFORMATION: Synthetic construct

<400> SEQUENCE: 191
tcaccaagtt tgtgagttc                                               19

<210> SEQ ID NO 192
<211> LENGTH: 21
<212> TYPE: DNA
<213> ORGANISM: Artificial Sequence
<220> FEATURE:
```

```
<223> OTHER INFORMATION: Synthetic construct

<400> SEQUENCE: 192
gctgccaatt ttgagcagtt t                                              21

<210> SEQ ID NO 193
<211> LENGTH: 20
<212> TYPE: DNA
<213> ORGANISM: Artificial Sequence
<220> FEATURE:
<223> OTHER INFORMATION: Synthetic construct

<400> SEQUENCE: 193
gttcccagct tttccgttca                                                20

<210> SEQ ID NO 194
<211> LENGTH: 17
<212> TYPE: DNA
<213> ORGANISM: Artificial Sequence
<220> FEATURE:
<223> OTHER INFORMATION: Synthetic construct

<400> SEQUENCE: 194
tgcaagaaag gatcaaa                                                   17

<210> SEQ ID NO 195
<211> LENGTH: 19
<212> TYPE: DNA
<213> ORGANISM: Artificial Sequence
<220> FEATURE:
<223> OTHER INFORMATION: Synthetic construct

<400> SEQUENCE: 195
tcttgcctgc cctgtgttg                                                 19

<210> SEQ ID NO 196
<211> LENGTH: 21
<212> TYPE: DNA
<213> ORGANISM: Artificial Sequence
<220> FEATURE:
<223> OTHER INFORMATION: Synthetic construct

<400> SEQUENCE: 196
tgccttcccc ttaataatgc a                                              21

<210> SEQ ID NO 197
<211> LENGTH: 16
<212> TYPE: DNA
<213> ORGANISM: Artificial Sequence
<220> FEATURE:
<223> OTHER INFORMATION: Synthetic construct

<400> SEQUENCE: 197
aaaatgcggg tccctt                                                    16

<210> SEQ ID NO 198
<211> LENGTH: 24
<212> TYPE: DNA
<213> ORGANISM: Artificial Sequence
<220> FEATURE:
<223> OTHER INFORMATION: Synthetic construct

<400> SEQUENCE: 198
ctcccgctac acagaagtaa caaa                                           24
```

```
<210> SEQ ID NO 199
<211> LENGTH: 25
<212> TYPE: DNA
<213> ORGANISM: Artificial Sequence
<220> FEATURE:
<223> OTHER INFORMATION: Synthetic construct

<400> SEQUENCE: 199
aaaacatccc tgctaccaat acatt                                          25

<210> SEQ ID NO 200
<211> LENGTH: 23
<212> TYPE: DNA
<213> ORGANISM: Artificial Sequence
<220> FEATURE:
<223> OTHER INFORMATION: Synthetic construct

<400> SEQUENCE: 200
atggtagtca gttttgtatt tag                                            23

<210> SEQ ID NO 201
<211> LENGTH: 24
<212> TYPE: DNA
<213> ORGANISM: Artificial Sequence
<220> FEATURE:
<223> OTHER INFORMATION: Synthetic construct

<400> SEQUENCE: 201
tccgttacaa gatgaggtct gtgt                                           24

<210> SEQ ID NO 202
<211> LENGTH: 24
<212> TYPE: DNA
<213> ORGANISM: Artificial Sequence
<220> FEATURE:
<223> OTHER INFORMATION: Synthetic construct

<400> SEQUENCE: 202
dattctcctg gataacaacg ttga                                           24

<210> SEQ ID NO 203
<211> LENGTH: 13
<212> TYPE: DNA
<213> ORGANISM: Artificial Sequence
<220> FEATURE:
<223> OTHER INFORMATION: Synthetic construct

<400> SEQUENCE: 203
tgctcacttc ccc                                                       13

<210> SEQ ID NO 204
<211> LENGTH: 20
<212> TYPE: DNA
<213> ORGANISM: Artificial Sequence
<220> FEATURE:
<223> OTHER INFORMATION: Synthetic construct

<400> SEQUENCE: 204 tccatcccttt gacggttctg                                               20

<210> SEQ ID NO 205
<211> LENGTH: 23
<212> TYPE: DNA
<213> ORGANISM: Artificial Sequence
<220> FEATURE:
<223> OTHER INFORMATION: Synthetic construct
```

```
<400> SEQUENCE: 205
agcccaagag gaatcaaaag atc                                          23

<210> SEQ ID NO 206
<211> LENGTH: 17
<212> TYPE: DNA
<213> ORGANISM: Artificial Sequence
<220> FEATURE:
<223> OTHER INFORMATION: Synthetic construct

<400> SEQUENCE: 206
ccttcccaaa ctgcttt                                                 17

<210> SEQ ID NO 207
<211> LENGTH: 27
<212> TYPE: DNA
<213> ORGANISM: Artificial Sequence
<220> FEATURE:
<223> OTHER INFORMATION: Synthetic construct

<400> SEQUENCE: 207
gagtcatcac tgaggaagag aagaatt                                      27

<210> SEQ ID NO 208
<211> LENGTH: 16
<212> TYPE: DNA
<213> ORGANISM: Artificial Sequence
<220> FEATURE:
<223> OTHER INFORMATION: Synthetic construct

<400> SEQUENCE: 208
tggcacgggc catacg                                                  16

<210> SEQ ID NO 209
<211> LENGTH: 17
<212> TYPE: DNA
<213> ORGANISM: Artificial Sequence
<220> FEATURE:
<223> OTHER INFORMATION: Synthetic construct

<400> SEQUENCE: 209
caaagccttc gctagtc                                                 17

<210> SEQ ID NO 210
<211> LENGTH: 23
<212> TYPE: DNA
<213> ORGANISM: Artificial Sequence
<220> FEATURE:
<223> OTHER INFORMATION: Synthetic construct

<400> SEQUENCE: 210
cctacacccc ttatccccat act                                          23

<210> SEQ ID NO 211
<211> LENGTH: 21
<212> TYPE: DNA
<213> ORGANISM: Artificial Sequence
<220> FEATURE:
<223> OTHER INFORMATION: Synthetic construct

<400> SEQUENCE: 211
ccagggctat tggttgaatg a                                            21

<210> SEQ ID NO 212
<211> LENGTH: 21
```

<212> TYPE: DNA
<213> ORGANISM: Artificial Sequence
<220> FEATURE:
<223> OTHER INFORMATION: Synthetic construct

<400> SEQUENCE: 212
ttattatcga aaccatcagc c                                             21

<210> SEQ ID NO 213
<211> LENGTH: 20
<212> TYPE: DNA
<213> ORGANISM: Artificial Sequence
<220> FEATURE:
<223> OTHER INFORMATION: Synthetic construct

<400> SEQUENCE: 213
cgacctgcga gactcacaag                                               20

<210> SEQ ID NO 214
<211> LENGTH: 19
<212> TYPE: DNA
<213> ORGANISM: Artificial Sequence
<220> FEATURE:
<223> OTHER INFORMATION: Synthetic construct

<400> SEQUENCE: 214
ggcacagcac tccgtctgt                                                19

<210> SEQ ID NO 215
<211> LENGTH: 17
<212> TYPE: DNA
<213> ORGANISM: Artificial Sequence
<220> FEATURE:
<223> OTHER INFORMATION: Synthetic construct

<400> SEQUENCE: 215
aagctgacag agatacc                                                  17

<210> SEQ ID NO 216
<211> LENGTH: 24
<212> TYPE: DNA
<213> ORGANISM: Artificial Sequence
<220> FEATURE:
<223> OTHER INFORMATION: Synthetic construct

<400> SEQUENCE: 216
tctggctgtc cttttttataa tgca                                         24

<210> SEQ ID NO 217
<211> LENGTH: 23
<212> TYPE: DNA
<213> ORGANISM: Artificial Sequence
<220> FEATURE:
<223> OTHER INFORMATION: Synthetic construct

<400> SEQUENCE: 217
cttggcaata gaacctggac aac                                           23

<210> SEQ ID NO 218
<211> LENGTH: 15
<212> TYPE: DNA
<213> ORGANISM: Artificial Sequence
<220> FEATURE:
<223> OTHER INFORMATION: Synthetic construct

<400> SEQUENCE: 218
agtgagaact ttccc                                                    15

<210> SEQ ID NO 219
<211> LENGTH: 22
<212> TYPE: DNA
<213> ORGANISM: Artificial Sequence
<220> FEATURE:
<223> OTHER INFORMATION: Synthetic construct

<400> SEQUENCE: 219
gcaagaagaa gccactgaaa ca                                            22

<210> SEQ ID NO 220
<211> LENGTH: 24
<212> TYPE: DNA
<213> ORGANISM: Artificial Sequence
<220> FEATURE:
<223> OTHER INFORMATION: Synthetic construct

<400> SEQUENCE: 220
gaaagcctta tcttcctcgt ccat                                          24

<210> SEQ ID NO 221
<211> LENGTH: 16
<212> TYPE: DNA
<213> ORGANISM: Artificial Sequence
<220> FEATURE:
<223> OTHER INFORMATION: Synthetic construct

<400> SEQUENCE: 221
cccaagaagc aggcca                                                   16

<210> SEQ ID NO 222
<211> LENGTH: 21
<212> TYPE: DNA
<213> ORGANISM: Artificial Sequence
<220> FEATURE:
<223> OTHER INFORMATION: Synthetic construct

<400> SEQUENCE: 222
ggctgaaaat ggtggaaaag g                                             21

<210> SEQ ID NO 223
<211> LENGTH: 23
<212> TYPE: DNA
<213> ORGANISM: Artificial Sequence
<220> FEATURE:
<223> OTHER INFORMATION: Synthetic construct

<400> SEQUENCE: 223
ctttgtccct gaggtgtcag ttt                                           23

<210> SEQ ID NO 224
<211> LENGTH: 15
<212> TYPE: DNA
<213> ORGANISM: Artificial Sequence
<220> FEATURE:
<223> OTHER INFORMATION: Synthetic construct

<400> SEQUENCE: 224
ccaagatggc ggccg                                                    15

<210> SEQ ID NO 225
<211> LENGTH: 21
<212> TYPE: DNA
<213> ORGANISM: Artificial Sequence

```
<220> FEATURE:
<223> OTHER INFORMATION: Synthetic construct

<400> SEQUENCE: 225
tgtggatgag gcttccaaga a                                              21

<210> SEQ ID NO 226
<211> LENGTH: 20
<212> TYPE: DNA
<213> ORGANISM: Artificial Sequence
<220> FEATURE:
<223> OTHER INFORMATION: Synthetic construct

<400> SEQUENCE: 226
cagcagggtc cggtcatact                                                20

<210> SEQ ID NO 227
<211> LENGTH: 20
<212> TYPE: DNA
<213> ORGANISM: Artificial Sequence
<220> FEATURE:
<223> OTHER INFORMATION: Synthetic construct

<400> SEQUENCE: 227
agatcaaaga catcctcatc                                                20

<210> SEQ ID NO 228
<211> LENGTH: 23
<212> TYPE: DNA
<213> ORGANISM: Artificial Sequence
<220> FEATURE:
<223> OTHER INFORMATION: Synthetic construct

<400> SEQUENCE: 228
ggcaggtgga ctacgagtca tac                                            23

<210> SEQ ID NO 229
<211> LENGTH: 19
<212> TYPE: DNA
<213> ORGANISM: Artificial Sequence
<220> FEATURE:
<223> OTHER INFORMATION: Synthetic construct

<400> SEQUENCE: 229
gtctcctcgc tgccaggat                                                 19

<210> SEQ ID NO 230
<211> LENGTH: 14
<212> TYPE: DNA
<213> ORGANISM: Artificial Sequence
<220> FEATURE:
<223> OTHER INFORMATION: Synthetic construct

<400> SEQUENCE: 230
catggcggaa actg                                                      14

<210> SEQ ID NO 231
<211> LENGTH: 21
<212> TYPE: DNA
<213> ORGANISM: Artificial Sequence
<220> FEATURE:
<223> OTHER INFORMATION: Synthetic construct

<400> SEQUENCE: 231
ccggaacatt aagaccattg c                                              21
```

```
<210> SEQ ID NO 232
<211> LENGTH: 19
<212> TYPE: DNA
<213> ORGANISM: Artificial Sequence
<220> FEATURE:
<223> OTHER INFORMATION: Synthetic construct

<400> SEQUENCE: 232
cccttggcag cattgatga                                                   19

<210> SEQ ID NO 233
<211> LENGTH: 15
<212> TYPE: DNA
<213> ORGANISM: Artificial Sequence
<220> FEATURE:
<223> OTHER INFORMATION: Synthetic construct

<400> SEQUENCE: 233
agtgcctggc agatg                                                       15

<210> SEQ ID NO 234
<211> LENGTH: 21
<212> TYPE: DNA
<213> ORGANISM: Artificial Sequence
<220> FEATURE:
<223> OTHER INFORMATION: Synthetic construct

<400> SEQUENCE: 234
ctgccacccc actcttaatc a                                                21

<210> SEQ ID NO 235
<211> LENGTH: 23
<212> TYPE: DNA
<213> ORGANISM: Artificial Sequence
<220> FEATURE:
<223> OTHER INFORMATION: Synthetic construct

<400> SEQUENCE: 235
ggccaattga aacaaacagt tct                                              23

<210> SEQ ID NO 236
<211> LENGTH: 16
<212> TYPE: DNA
<213> ORGANISM: Artificial Sequence
<220> FEATURE:
<223> OTHER INFORMATION: Synthetic construct

<400> SEQUENCE: 236
tggtggaaga acggtc                                                      16

<210> SEQ ID NO 237
<211> LENGTH: 20
<212> TYPE: DNA
<213> ORGANISM: Artificial Sequence
<220> FEATURE:
<223> OTHER INFORMATION: Synthetic construct

<400> SEQUENCE: 237
ggaagcctgc cacctcctat                                                  20

<210> SEQ ID NO 238
<211> LENGTH: 17
<212> TYPE: DNA
<213> ORGANISM: Artificial Sequence
<220> FEATURE:
<223> OTHER INFORMATION: Synthetic construct
```

<400> SEQUENCE: 238
tggcgcgagc attcttg                                                      17

<210> SEQ ID NO 239
<211> LENGTH: 14
<212> TYPE: DNA
<213> ORGANISM: Artificial Sequence
<220> FEATURE:
<223> OTHER INFORMATION: Synthetic construct

<400> SEQUENCE: 239
tgcggaccac catc                                                         14

<210> SEQ ID NO 240
<211> LENGTH: 27
<212> TYPE: DNA
<213> ORGANISM: Artificial Sequence
<220> FEATURE:
<223> OTHER INFORMATION: Synthetic construct

<400> SEQUENCE: 240
tgtccttgaa gcttgtatct gatatca                                           27

<210> SEQ ID NO 241
<211> LENGTH: 25
<212> TYPE: DNA
<213> ORGANISM: Artificial Sequence
<220> FEATURE:
<223> OTHER INFORMATION: Synthetic construct

<400> SEQUENCE: 241
ttcaatacaa ggtcaaaatc agcaa                                             25

<210> SEQ ID NO 242
<211> LENGTH: 18
<212> TYPE: DNA
<213> ORGANISM: Artificial Sequence
<220> FEATURE:
<223> OTHER INFORMATION: Synthetic construct

<400> SEQUENCE: 242
cactggattg tagaactt                                                     18

<210> SEQ ID NO 243
<211> LENGTH: 24
<212> TYPE: DNA
<213> ORGANISM: Artificial Sequence
<220> FEATURE:
<223> OTHER INFORMATION: Synthetic construct

<400> SEQUENCE: 243
agcctcagat gaaagaaaca atca                                              24

<210> SEQ ID NO 244
<211> LENGTH: 20
<212> TYPE: DNA
<213> ORGANISM: Artificial Sequence
<220> FEATURE:
<223> OTHER INFORMATION: Synthetic construct

<400> SEQUENCE: 244
cacttgtgcc tgcagtttgg                                                   20

<210> SEQ ID NO 245

```
<211> LENGTH: 15
<212> TYPE: DNA
<213> ORGANISM: Artificial Sequence
<220> FEATURE:
<223> OTHER INFORMATION: Synthetic construct

<400> SEQUENCE: 245
aaccaggaaa aactc                                                    15

<210> SEQ ID NO 246
<211> LENGTH: 21
<212> TYPE: DNA
<213> ORGANISM: Artificial Sequence
<220> FEATURE:
<223> OTHER INFORMATION: Synthetic construct

<400> SEQUENCE: 246
aagcaggcga atcgtaatga g                                             21

<210> SEQ ID NO 247
<211> LENGTH: 23
<212> TYPE: DNA
<213> ORGANISM: Artificial Sequence
<220> FEATURE:
<223> OTHER INFORMATION: Synthetic construct

<400> SEQUENCE: 247
tgcttgtgga atgtacagtg cat                                           23

<210> SEQ ID NO 248
<211> LENGTH: 13
<212> TYPE: DNA
<213> ORGANISM: Artificial Sequence
<220> FEATURE:
<223> OTHER INFORMATION: Synthetic construct

<400> SEQUENCE: 248
cgtgcgccgc caa                                                      13

<210> SEQ ID NO 249
<211> LENGTH: 21
<212> TYPE: DNA
<213> ORGANISM: Artificial Sequence
<220> FEATURE:
<223> OTHER INFORMATION: Synthetic construct

<400> SEQUENCE: 249 ccctttctg ggtttgaagc t                                              21

<210> SEQ ID NO 250
<211> LENGTH: 26
<212> TYPE: DNA
<213> ORGANISM: Artificial Sequence
<220> FEATURE:
<223> OTHER INFORMATION: Synthetic construct

<400> SEQUENCE: 250
ctgactgata caaagcacaa ttgaga                                        26

<210> SEQ ID NO 251
<211> LENGTH: 17
<212> TYPE: DNA
<213> ORGANISM: Artificial Sequence
<220> FEATURE:
<223> OTHER INFORMATION: Synthetic construct

<400> SEQUENCE: 251
```

-continued

```
ctgtctctag aagtgcc                                              17

<210> SEQ ID NO 252
<211> LENGTH: 24
<212> TYPE: DNA
<213> ORGANISM: Artificial Sequence
<220> FEATURE:
<223> OTHER INFORMATION: Synthetic construct

<400> SEQUENCE: 252
gctgtgaaag caacataaat ggat                                      24

<210> SEQ ID NO 253
<211> LENGTH: 23
<212> TYPE: DNA
<213> ORGANISM: Artificial Sequence
<220> FEATURE:
<223> OTHER INFORMATION: Synthetic construct

<400> SEQUENCE: 253
ggcatgggaa cttaacagat gag                                       23

<210> SEQ ID NO 254
<211> LENGTH: 20
<212> TYPE: DNA
<213> ORGANISM: Artificial Sequence
<220> FEATURE:
<223> OTHER INFORMATION: Synthetic construct

<400> SEQUENCE: 254
ttaaactgtc tacggttctt                                           20

<210> SEQ ID NO 255
<211> LENGTH: 22
<212> TYPE: DNA
<213> ORGANISM: Artificial Sequence
<220> FEATURE:
<223> OTHER INFORMATION: Synthetic construct

<400> SEQUENCE: 255
cgctatccag aacctccact ct                                        22

<210> SEQ ID NO 256
<211> LENGTH: 22
<212> TYPE: DNA
<213> ORGANISM: Artificial Sequence
<220> FEATURE:
<223> OTHER INFORMATION: Synthetic construct

<400> SEQUENCE: 256
caggtcatca cccttacttg ca                                        22

<210> SEQ ID NO 257
<211> LENGTH: 15
<212> TYPE: DNA
<213> ORGANISM: Artificial Sequence
<220> FEATURE:
<223> OTHER INFORMATION: Synthetic construct

<400> SEQUENCE: 257 tcgaccccett tgctg                                               15

<210> SEQ ID NO 258
<211> LENGTH: 2034
<212> TYPE: DNA
```

<213> ORGANISM: Homo sapiens

<400> SEQUENCE: 258

```
aaaccttggc catggtcact tcctcttttc caatctctgt ggcagttttt gccctaataa      60
ccctgcaggt tggtactcag gacagtttta tagctgcagt gtatgaacat gctgtcattt     120
tgccaaataa aacagaaaca ccagtttctc aggaggatgc cttgaatctc atgaacgaga     180
atatagacat tctggagaca gcgatcaagc aggcagctga gcagggtgct cgaatcattg     240
tgactccaga agatgcactt tatggatgga aatttaccag ggaaactgtt ttcccttatc     300
tggaggatat cccagaccct caggtgaact ggattccgtg tcaagacccc cacagatttg     360
gtcacacacc agtacaagca agactcagct gcctggccaa ggacaactct atctatgtct     420
tggcaaattt gggggacaaa aagccatgta attcccgtga ctccacatgt cctcctaatg     480
gctactttca atacaatacc aatgtggtgt ataatacaga aggaaaactc gtggcacgtt     540
accataagta ccacctgtac tctgagcctc agtttaatgt ccctgaaaag ccggagttgg     600
tgactttcaa caccgcattt ggaaggtttg gcattttcac gtgctttgat atattcttct     660
atgatcctgg tgttaccctg gtgaaagatt ccatgtgga caccatactg tttcccacag     720
cttgatgaa cgttttgccc cttttgacag ctattgaatt ccattcagct tgggcaatgg     780
gaatgggagt taatcttctt gtggccaaca cacatcatgt cagcctaaat atgacaggaa     840
gtggtattta tgcaccaaat ggtcccaaag tgtatcatta tgacatgaag acagagttgg     900
gaaaacttct cctttcagag gtggattcac atcccctatc ctcgcttgcc tacccaacag     960
ctgttaattg gaatgcctac gccaccacca tcaaaccatt tccagtacag aaaaacactt    1020
tcagggatt tatttccagg gatgggttca acttcacaga acttttgaa aatgcaggaa     1080
acttacagt ctgtcaaaag gagctttgct gtcatttaag ctacagaatg ttacaaaaag     1140
aagagaatga agtatacgtt ctaggagctt ttacaggatt acatggccga aggagaagag    1200
agtactggca ggtctgcaca atgctgaagt gcaaaactac taatttgaca acttgtggac    1260
ggccagtaga aactgcttct acaagatttg aaatgttctc cctcagtggc acatttggaa    1320
cagagtatgt ttttcctgaa gtgctactta ccgaaattca tctgtcacct ggaaaatttg    1380
aggtgctgaa agatgggcgt ttggtaaaca agaatggatc atctgggcct atactaacag    1440
tgtcactctt tggaggtgg tacacaaagg actcacttta cagctcatgt gggaccagca    1500
attcagcaat aacttacctg ctaatattca tattattaat gatcatagct ttgcaaaata    1560
ttgtaatgtt atagggcgtc tctttatcac tcagcttctg catcatatgc ttggctgaat    1620
gtgtttatcg gcttcccaag tttactaaga aactttgaag ggctatttca gtagtataga    1680
ccagtgagtc ctaaatattt ttctctcatca ataattattt tttaagtatt atgataatgt    1740
tgtccattt tttggctact ctgaaatgtt gcagtgtgga acaatggaaa gagcctgggt    1800
gtttgggtca gataaatgaa gatcaaactc cagctccagc ctcatttgct tgagactttg    1860
tgtgtatggg ggacttgtat gtatgggagt gaggagtttc agggccattg caaacatagc    1920
tgtgcccttg aagagaatag taatgatggg aatttagagg tttatgactg aattcccttt    1980
gacattaaag actatttgaa ttcaaaaaaa aaaaaaaaaa aaaaaaaaaa aaaa          2034
```

<210> SEQ ID NO 259
<211> LENGTH: 1498
<212> TYPE: DNA
<213> ORGANISM: Homo sapiens

<400> SEQUENCE: 259

| | |
|---|---:|
| gaggccagag tgccatcgaa ggtaattata gagacagtaa aatccttttta ctctgggaaa | 60 |
| aataaaatgc tgggtgtctc acaaaatttc agaacctgat ttcaaacgga tcataacaaa | 120 |
| gaggagatca aatttagcat ggtggactgc tcgacaggat atatttgtca atggaatgtt | 180 |
| tccacatatt ataccaccaa catgagaaaa aaatgatcat tgtttatttg aagcttgatg | 240 |
| atattctaac gctgcctttt ctcttctcat tttagagaaa aatgagcagg cggaattgtt | 300 |
| ggatttgtaa gatgtgcaga gatgaatcta agaggccccc ttcaaacctt actttggagg | 360 |
| aagtattaca gtgggcccag tcttttgaaa atttaatggc tacaaaatat ggtccagtag | 420 |
| tctatgcagc atatttaaaa atggagcaca gtgacgagaa tattcaattc tggatggcat | 480 |
| gtgaaaccta taagaaaatt gcctcacggt ggagcagaat ttctagggca agaagctttt | 540 |
| ataagattta catccagcca cagtcccta gagagattaa cattgacagt tcgacaagag | 600 |
| agactatcat caggaacatt caggaaccca ctgaaacatg ttttgaagaa gctcagaaaa | 660 |
| tagtctatat gcatatggaa agggattcct accccagatt tctaaagtca gaaatgtacc | 720 |
| aaaaactttt gaaaactatg cagtccaaca acagtttctg actacaactc aaaagtttaa | 780 |
| atagaaaaca gtatattgaa agtggtgggt ttgatctttt tatttagaaa cccacaaaat | 840 |
| cagaaacaca gtacaaataa aacagaaatc aaactataag ttgactttta gttcctaaaa | 900 |
| agaaacatat ttcaaaagca atggaatcta gaattcttat aacatgaata acaaaatgta | 960 |
| cagcaagcct atgtagttca attaatatat aaggaaaagg aaggtctttc ttcatgatac | 1020 |
| aagcattata aagttttttac tgtagtagtc aattaatgga tatttccttg ttaataaaat | 1080 |
| tttgtgtcat aatttacaaa ttagttcttt aaaaattgtt gttatatgaa ttgtgtttct | 1140 |
| agcatgaatg ttctatagag tactctaaat aacttgaatt tatagacaaa tgctactcac | 1200 |
| agtacaatca attgtattat accatgagaa aatcaaaaag gtgttcttca gagacatttt | 1260 |
| atctataaaa ttttcctact attatgttca ttaacaaact tctttatcac atgtatcttc | 1320 |
| tacatgtaaa acatttctga tgatttttta acaaaaaata tatgaatttc ttcatttgct | 1380 |
| cttgcatcta cattgctata aggatataaa atgtggtttc tatattttga gatgtttttt | 1440 |
| ccttacaatg tgaactcatc gtgatcttgg aaatcaataa agtcaaatat caactaaa | 1498 |

<210> SEQ ID NO 260
<211> LENGTH: 3260
<212> TYPE: DNA
<213> ORGANISM: Homo sapiens

<400> SEQUENCE: 260

| | |
|---|---:|
| ccatcccata gtgagggaag acacgcggaa acaggcttgc acccagacac gacaccatgc | 60 |
| atctcctcgg ccctggctc ctgctcctgg ttctagaata cttggctttc tctgactcaa | 120 |
| gtaaatgggt ttttgagcac cctgaaaccc tctacgcctg gaggggggcc tgcgtctgga | 180 |
| tccctgcac ctacagagcc ctagatggtg acctggaaag cttcatcctg ttccacaatc | 240 |
| ctgagtataa caagaacacc tcgaagtttg atgggacaag actctatgaa agcacaaagg | 300 |
| atgggaaggt tccttctgag cagaaaaggg tgcaattcct gggagacaag aataagaact | 360 |
| gcacactgag tatccacccg gtgcacctca atgcagtgg tcagctgggg ctgaggatgg | 420 |
| agtccaagac tgagaaatgg atggaacgaa tacacctcaa tgtctctgaa aggccttttc | 480 |
| cacctcatat ccagctccct ccagaaattc aagagtccca ggaagtcact ctgacctgct | 540 |
| tgctgaattt ctcctgctat gggtatccga tccaattgca gtggctccta gagggggtc | 600 |

```
caatgaggca ggctgctgtc acctcgacct ccttgaccat caagtctgtc ttcacccgga    660
gcgagctcaa gttctcccca cagtggagtc accatgggaa gattgtgacc tgccagcttc    720
aggatgcaga tgggaagttc ctctccaatg acacggtgca gctgaacgtg aagcacaccc    780
cgaagttgga gatcaaggtc actcccagtg atgccatagt gagggagggg gactctgtga    840
ccatgacctg cgaggtcagc agcagcaacc cggagtacac gacggtatcc tggctcaagg    900
atgggacctc gctgaagaag cagaatacat tcacgctaaa cctgcgcgaa gtgaccaagg    960
accagagtgg gaagtactgc tgtcaggtct ccaatgacgt gggcccggga aggtcggaag   1020
aagtgttcct gcaagtgcag tatgcccccgg aaccttccac ggttcagatc ctccactcac   1080
cggctgtgga gggaagtcaa gtcgagtttc tttgcatgtc actggccaat cctcttccaa   1140
caaattacac gtggtaccac aatgggaaag aaatgcaggg aaggacagag gagaaagtcc   1200
acatcccaaa gatcctcccc tggcacgctg ggacttattc ctgtgtggca gaaaacattc   1260
ttggtactgg acagaggggc cgggagctg agctggatgt ccagtatcct cccaagaagg   1320
tgaccacagt gattcaaaac cccatgccga ttcgagaagg agacacagtg acccctttcct  1380 gtaactacaa ttccagtaac cccagtgtta cccggtatga atggaaaccc catggcgcct   1440
gggaggagcc atcgcttggg gtgctgaaga tccaaaacgt tggctgggac aacacaacca   1500
tcgcctgcgc acgttgtaat agttggtgct cgtgggcctc ccctgtcgcc ctgaatgtcc   1560
agtatgcccc ccgagacgtg agggtccgga aaatcaagcc cctttccgag attcactctg   1620
gaaactcggt cagcctccaa tgtgacttct caagcagcca ccccaaagaa gtccagttct   1680
tctgggagaa aaatggcagg cttctgggga agaaagcca gctgaatttt gactccatct   1740
ccccagaaga tgctgggagt tacagctgct gggtgaacaa ctccatagga cagacagcgt   1800
ccaaggcctg gacacttgaa gtgctgtatg cacccaggag gctgcgtgtg tccatgagcc   1860
cgggggacca agtgatggag gggaagagtg caaccctgac ctgtgagagt gacgccaacc   1920
ctcccgtctc ccactacacc tggtttgact ggaataacca aagcctcccc caccacagcc   1980
agaagctgag attggagccg gtgaaggtcc agcactcggg tgcctactgg tgcagggga   2040 ccaacagtgt gggcaagggc cgttcgcctc tcagcaccct tactgtctac tatagcccgg   2100
agaccatcgg caggcgagtg gctgtgggac tcgggtcctg cctcgccatc ctcatcctgg   2160
caatctgtgg gctcaagctc cagcgacgtt ggaagaggac acagagccag caggggcttc   2220
aggagaattc cagcggccag agcttctttg tgaggaataa aaaggttaga agggcccccc   2280
tctctgaagg cccccactcc ctgggatgct acaatccaat gatggaagat ggcattagct   2340
acaccaccct gcgctttccc gagatgaaca taccacgaac tggagatgca gagtcctcag   2400
agatgcagag acctcccccgg acctgcgatg acacggtcac ttattcagca ttgcacaagc   2460
gccaagtggg cgactatgag aacgtcattc cagattttcc agaagatgag gggattcatt   2520
actcagagct gatccagttt ggggtcgggg agcggcctca ggcacaagaa aatgtggact   2580
atgtgatcct caaacattga cactggatgg gctgcagcag aggcactggg ggcagcgggg   2640
gccagggaag tccccgagtt tccccagaca ccgccacatg gcttcctcct gcgtgcatgt   2700
gcgcacacac acacacacac gcacacacac acacacacac tcactgcgga gaaccttgtg   2760
cctggctcag agccagtctt tttggtgagg gtaacccccaa acctccaaaa ctcctgcccc   2820
tgttctcttc cactctcctt gctacccaga aatcatctaa atacctgccc tgacatgcac   2880
acctcccctg ccccaccagc ccactggcca tctccacccg gagctgctgt gtcctctgga   2940
tctgctcgtc attttccttc ccttctccat ctctctggcc ctctacccct gatctgacat   3000
```

```
ccccactcac gaatattatg cccagtttct gcctctgagg aaagcccag aaaaggacag    3060 aaacgaagta gaaagggggcc cagtcctggc ctggcttctc ctttggaagt gaggcattgc   3120
acggggagac gtacgtatca gcggcccctt gactctgggg actccgggtt tgagatggac   3180
acactggtgt ggattaacct gccagggaga cagagctcac aataaaaatg gctcagatgc   3240
cacttcaaag aaaaaaaaaa                                                3260

<210> SEQ ID NO 261
<211> LENGTH: 2433
<212> TYPE: DNA
<213> ORGANISM: Homo sapiens

<400> SEQUENCE: 261
atgattccgg tgacagagct ccgctacttt gcggacacgc agccagcata ccggatcctg     60
aagccgtggt gggatgtgtt cacagactac atctctatcg tcatgctgat gattgccgtc    120
ttcgggggga cgctgcaggt cacccaagac aagatgatct gcctgccttg taagtgggtc    180
accaaggact cctgcaatga ttcgttccgg ggctgggcag cccctggccc ggagcccacc    240 tacccccaact ccaccattct gccgacccct gacacgggcc ccacaggcat caagtatgac    300
ctggaccggc accagtacaa ctacgtggac gctgtgtgct atgagaaccg actgcactgg    360
tttgccaagt acttcccccta cctggtgctt ctgcacacgc tcatcttcct ggcctgcagc    420
aacttctggt tcaaattccc gcgcaccagc tcgaagctgg agcactttgt gtctatcctg    480
ctgaagtgct tcgactcgcc ctggaccacg agggccctgt cggagacagt ggtggaggag    540
agcgacccca gccggccctt cagcaagatg aatgggtcca tggacaaaaa gtcatcgacc    600
gtcagtgagg acgtggaggc caccgtgccc atgctgcagc ggaccaagtc acggatcgag    660
cagggtatcg tggaccgctc agagacgggc gtgctggaca agaaggaggg ggagcaagcc    720
aaggcgctgt ttgagaaggt gaagaagttc cggacccatg tggaggaggg ggacattgtg    780
taccgcctct acatgcggca gaccatcatc aaggtgatca agttcatcct catcatctgc    840
tacaccgtct actacgtgca caacatcaag ttcgacgtgg actgcaccgt ggacattgag    900
agcctgacgg gctaccgcac ctaccgctgt gcccaccccc tggccacact cttcaagatc    960
ctggcgtcct tctacatcag cctagtcatc ttctacggcc tcatctgcat gtatacactg   1020
tggtggatgc tacggcgctc cctcaagaag tactcgtttg agtcgatccg tgaggagagc   1080
agctacagcg acatccccga cgtcaagaac gacttcgcct tcatgctgca cctcattgac   1140
caatacgacc cgctctactc caagcgcttc gccgtcttcc tgtcggaggt gagtgagaac   1200
aagctgcggc agctgaacct caacaacgag tggacgctgg acaagctccg gcagcggctc   1260
accaagaacg cgcaggacaa gctggagctg cacctgttca tgctcagtgg catccctgac   1320
actgtgtttg acctggtgga gctggaggtc tcaagctgg agctgatccc cgacgtgacc   1380
atcccgccca gcattgccca gctcacgggc tcaaggagc tgtggctcta ccacacagcg   1440
gccaagattg aagcgcccgc gctggccttc ctgcgcgaga acctgcgggc gctgcacatc   1500
aagttcaccg acatcaagga gatcccgctg tggatctata gcctgaagac actggaggag   1560
ctgcacctga cgggcaacct gagcgcggag aacaaccgct acatcgtcat cgacgggctg   1620
cgggagctca aacgcctcaa ggtgctgcgg ctcaagagca acctaagcaa gctgccacag   1680
gtggtcacag atgtgggcgt gcacctgcag aagctgtcca tcaacaatga gggcaccaag   1740
ctcatcgtcc tcaacagcct caagaagatg gcgaacctga ctgagctgga gctgatccgc   1800
```

| | |
|---|---|
| tgtgacctgg agcgcatccc ccactccatc ttcagcctcc acaacctgca ggagattgac | 1860 |
| ctcaaggaca caacctcaa gaccatcgag gagatcatca gcttccagca cctgcaccgc | 1920 |
| ctcacctgcc ttaagctgtg gtacaaccac atcgcctaca tccccatcca gatcggcaac | 1980 |
| ctcaccaacc tggagcgcct ctacctgaac cgcaacaaga tcgagaagat ccccacccag | 2040 |
| ctcttctact gccgcaagct gcgctacctg gacctcagcc acaacaacct gaccttcctc | 2100 |
| cctgccgaca tcggcctcct gcagaacctc cagaacctag ccatcacggc caaccggatc | 2160 |
| gagacgctcc ctccggagct cttccagtgc cggaagctgc gggccctgca cctgggcaac | 2220 |
| aacgtgctgc agtcactgcc ctccagggtg ggcgagctga ccaacctgac gcagatcgag | 2280 |
| ctgcggggca accggctgga gtgcctgcct gtggagctgg gcgagtgccc actgctcaag | 2340 |
| cgcagcggct tggtggtgga ggaggacctg ttcaacacac tgccacccga ggtgaaggag | 2400 |
| cggctgtgga gggctgacaa ggagcaggcc tga | 2433 |

<210> SEQ ID NO 262
<211> LENGTH: 1616
<212> TYPE: DNA
<213> ORGANISM: Homo sapiens

<400> SEQUENCE: 262

| | |
|---|---|
| gccaaggctg gggcagggga gtcagcagag gcctcgctcg ggcgcccagt ggtcctgccg | 60 |
| cctggtctca cctcgctatg gttcgtctgc ctctgcagtg cgtcctctgg ggctgcttgc | 120 |
| tgaccgctgt ccatccagaa ccacccactg catgcagaga aaacagtac ctaataaaca | 180 |
| gtcagtgctg ttctttgtgc cagccaggac agaaactggt gagtgactgc acagagttca | 240 |
| ctgaaacgga atgccttcct tgcggtgaaa gcgaattcct agacacctgg aacagagaga | 300 |
| cacactgcca ccagcacaaa tactgcgacc ccaacctagg gcttcgggtc cagcagaagg | 360 |
| gcacctcaga aacagacacc atctgcacct gtgaagaagg ctggcactgt acgagtgagg | 420 |
| cctgtgagag ctgtgtcctg caccgctcat gctcgcccgg cttttgggtc aagcagattg | 480 |
| ctacaggggt ttctgatacc atctgcgagc cctgcccagt cggcttcttc tccaatgtgt | 540 |
| catctgcttt cgaaaaatgt caccccttgga caagctgtga gaccaaagac ctggttgtgc | 600 |
| aacaggcagg cacaaacaag actgatgttg tctgtggtcc ccaggatcgg ctgagagccc | 660 |
| tggtggtgat cccatcatc ttcgggatcc tgtttgccat cctctcttgtg ctggtcttta | 720 |
| tcaaaaaggt ggccaagaag ccaaccaata aggcccccca ccccaagcag gaaccccagg | 780 |
| agatcaattt tcccgacgat cttcctggct ccaacactgc tgctccagtg caggagactt | 840 |
| tacatggatg ccaaccggtc acccaggagg atggcaaaga gagtcgcatc tcagtgcagg | 900 |
| agagacagtg aggctgcacc cacccaggag tgtggccacg tgggcaaaca ggcagttggc | 960 |
| cagagagcct ggtgctgctg ctgctgtggc gtgagggtga ggggctggca ctgactgggc | 1020 |
| atagctcccc gcttctgcct gcaccctgc agtttgagac aggagacctg gcactggatg | 1080 |
| cagaaacagt tcaccttgaa gaacctctca cttcaccctg gagcccatcc agtctcccaa | 1140 |
| cttgtattaa agacagaggc agaagtttgg tggtggtggt gttggggtat ggtttagtaa | 1200 |
| tatccaccag accttccgat ccagcagttt ggtgcccaga gaggcatcat ggtggcttcc | 1260 |
| ctgcgcccag gaagccatat acacagatgc ccattgcagc attgtttgtg atagtgaaca | 1320 |
| actggaagct gcttaactgt ccatcagcag gagactggct aaataaaatt agaatatatt | 1380 |
| tatacaacag aatctcaaaa acactgttga gtaaggaaaa aaaggcatgc tgctgaatga | 1440 |
| tgggtatgga acttttttaaa aaagtacatg cttttatgta tgtatattgc ctatggatat | 1500 |

| | |
|---|---|
| atgtataaat acaatatgca tcatatattg atataacaag ggttctggaa gggtacacag | 1560 |
| aaaacccaca gctcgaagag tggtgacgtc tggggtgggg aagaagggtc tgggggg | 1616 |

<210> SEQ ID NO 263
<211> LENGTH: 733
<212> TYPE: DNA
<213> ORGANISM: Homo sapiens

<400> SEQUENCE: 263

| | |
|---|---|
| aaacagcagg aaatagaaac ttaagagaaa tacacacttc tgagaaactg aaacgacagg | 60 |
| ggaaaggagg tctcactgag caccgtccca gcatccggac accacagcgg cccttcgctc | 120 |
| cacgcagaaa accacacttc tcaaaccttc actcaacact tccttcccca agccagaag | 180 |
| atgcacaagg aggaacatga ggtggctgtg ctggggcac cccccagcac catccttcca | 240 |
| aggtccaccg tgatcaacat ccacagcgag acctccgtgc ccgaccatgt cgtctggtcc | 300 |
| ctgttcaaca ccctcttctt gaactggtgc tgtctgggct tcatagcatt cgcctactcc | 360 |
| gtgaagtcta gggacaggaa gatggttggc gacgtgaccg ggcccaggc ctatgcctcc | 420 |
| accgccaagt gcctgaacat ctgggccctg attctgggca tcctcatgac cattggattc | 480 |
| atcctgttac tggtattcgg ctctgtgaca gtctaccata ttatgttaca gataatacag | 540 |
| gaaaaacggg gttactagta gccgcccata gcctgcaacc tttgcactcc actgtgcaat | 600 |
| gctggccctg cacgctgggg ctgttgcccc tgccccttg gtcctgcccc tagatacagc | 660 |
| agtttatacc cacacacctg tctacagtgt cattcaataa agtgcacgtg cttgtgaaaa | 720 |
| aaaaaaaaaa aaa | 733 |

<210> SEQ ID NO 264
<211> LENGTH: 8787
<212> TYPE: DNA
<213> ORGANISM: Homo sapiens

<400> SEQUENCE: 264

| | |
|---|---|
| ggccgcagct ccccggcgga ggcaagaggt ggttgggggg gaccatggct gacgttttcc | 60 |
| cgggcaacga ctccacggcg tctcaggacg tggccaaccg cttcgcccgc aaaggggcgc | 120 |
| tgaggcagaa gaacgtgcac gaggtgaagg accacaaatt catcgcgcgc ttcttcaagc | 180 |
| agcccaccct ctgcagccac tgcaccgact tcatctgggg gtttgggaaa caaggcttcc | 240 |
| agtgccaagt ttgctgtttt gtggtccaca agaggtgcca tgaatttgtt acttttttctt | 300 |
| gtccgggtgc ggataaggga cccgacactg atgaccccag gagcaagcac aagttcaaaa | 360 |
| tccacactta cggaagcccc accttctgcg atcactgtgg gtcactgctc tatggactta | 420 |
| tccatcaagg gatgaaatgt gacacctgcg atatgaacgt tcacaagcaa tgcgtcatca | 480 |
| atgtccccag cctctgcgga atggatcaca ctgagaagag ggggcggatt tacctaaagg | 540 |
| ctgaggttgc tgatgaaaag ctccatgtca cagtacgaga tgcaaaaaat ctaatcccta | 600 |
| tggatccaaa cgggctttca gatccttatg tgaagctgaa acttattcct gatcccaaga | 660 |
| atgaaagcaa gcaaaaaacc aaaaccatcc gctccacact aaatccgcag tggaatgagt | 720 |
| cctttacatt caaattgaaa ccttcagaca agaccgacg actgtctgta gaaatctggg | 780 |
| actgggatcg aacaacaagg aatgacttca tgggatccct ttcctttgga gtttcggagc | 840 |
| tgatgaagat gccggccagt ggatggtaca agttgcttaa ccaagaagaa ggtgagtact | 900 |
| acaacgtacc cattccggaa ggggacgagg aaggaaacat ggaactcagg cagaaattcg | 960 |

```
agaaagccaa acttggccct gctggcaaca aagtcatcag tccctctgaa gacaggaaac    1020
aaccttccaa caaccttgac cgagtgaaac tcacggactt caatttcctc atggtgttgg    1080
gaaaggggag ttttggaaag gtgatgcttg ccgacaggaa gggcacagaa gaactgtatg    1140
caatcaaaat cctgaagaag gatgtggtga ttcaggatga tgacgtggag tgcaccatgg    1200
tagaaaagcg agtcttggcc ctgcttgaca aacccccgtt cttgacgcag ctgcactcct    1260
gcttccagac agtggatcgg ctgtacttcg tcatggaata tgtcaacggt ggggacctca    1320
tgtaccacat tcagcaagta ggaaaattta aggaaccaca agcagtattc tatgcggcag    1380
agatttccat cggattgttc tttcttcata aaagaggaat catttatagg gatctgaagt    1440
tagataacgt catgttggat tcagaaggac atatcaaaat tgctgacttt gggatgtgca    1500
aggaacacat gatggatgga gtcacgacca ggaccttctg tgggactcca gattatatcg    1560
ccccagagat aatcgcttat cagccgtatg gaaaatctgt ggactggtgg gcctatggcg    1620
tcctgttgta tgaaatgctt gccgggcagc ctccatttga tggtgaagat gaagacgagc    1680
tatttcagtc tatcatggag cacaacgttt cctatccaaa atccttgtcc aaggaggctg    1740
tttctatctg caaaggactg atgaccaaac acccagccaa gcggctgggc tgtgggcctg    1800 aggggagag ggacgtgaga gagcatgcct tcttccggag gatcgactgg gaaaaactgg    1860
agaacaggga gatccagcca ccattcaagc ccaaagtgtg tggcaaagga gcagagaact    1920
ttgacaagtt cttcacacga ggacagcccg tcttaacacc acctgatcag ctggttattg    1980
ctaacataga ccagtctgat tttgaagggt tctcgtatgt caaccccag tttgtgcacc    2040 ccatcttaca gagtgcagta tgaaactcac cagcgagaac aaaacacctcc ccagccccca    2100 gccctccccg cagtgggaag tgaatcctta accctaaaat tttaaggcca cggccttgtg    2160
tctgattcca tatggaggcc tgaaaattgt agggttatta gtccaaatgt gatcaactgt    2220
tcagggtctc tctcttacaa ccaagaacat tatcttagtg aagatggta cgtcatgctc    2280 agtgtccagt ttaattctgt agaagttacg tctggctcta ggttaaccct tcctagaaag    2340
caagcagact gttgccccat tttgggtaca atttgatata cttcccatac cctccatctg    2400
tggatttttc agcattggaa tcccccaacc agagatgtta aagtgagcct gtcccaggaa    2460
acatctccac ccaagacgtc tttggaatcc aagaacagga agccaagaga gtgagcaggg    2520
agggattggg ggtgggggag gcctcaaaat accgactgcg tccattctct gcctccatgg    2580
aaacagcccc tagaatctga aaggccggga taaacctaat cactgttccc aaacattgac    2640
aaatcctaac ccaaccatgg tccagcagtt accagtttaa acaaaaaaac ctcagatgag    2700
tgttgggtga atctgtcatc tggtaccctc cttggttgat aactgtcttg atactttca    2760 ttctttgtaa gaggccaaat cgtctaagga cgttgctgaa caagcgtgtg aaatcatttc    2820
agatcaagga taagccagtg tgtacatatg ttcattttaa tctctgggag attattttc    2880 catccagggt gccatcagta atcatgccac tactcaccag tgttgttcgc caacacccac    2940
ccccacacac accaacattt tgctgcctac cttgttatcc ttctcaagaa gctgaagtgt    3000
acgccctctc cccttttgtg cttatttatt taataggctg cagtgtcgct tatgaaagta    3060
cgatgtacag taacttaatg gaagtgctga ctctagcatc agcctctacc gattgatttt    3120
cctcccttct ctagccctgg atgtccactt agggataaaa agaatatggt tttggttccc    3180
atttctagtt cacgttgaat gacaggcctg gagctgtaga atcaggaaac ccggatgcct    3240
aacagctcaa agatgttttg ttaatagaag gattttaata cgttttgcaa atgcatcatg    3300
caatgaattt tgcatgttta ataaaaccct taataacaag tgaatctata ttattgatat    3360
```

```
aatcgtatca agtataaaga gagtattata ataatttat aagacacaat tgtgctctat    3420
ttgtgcaggt tcttgtttct aatcctcttt tctaattaag ttttagctga atcccttgct    3480
tctgtgctttt ccctccctgc acatgggcac tgtatcagat agattacttt ttaaatgtag    3540
ataaaatttc aaaaatgaat ggctagttta cgtgatagat taggctctta ctacatatgt    3600
gtgtgtatat atatgtattt gattctacct gcaaacaaat ttttattggt gaggactatt    3660
tttgagctga cactccctct tagtttcttc atgtcacctt tcgtcctggt tcctccgcca    3720
ctcttcctct tggggacaac aggaagtgtc tgattccagt ctgcctagta cgttggtaca    3780
cacgtggcat tgccgcagca cctgggctga cctttgtgtg tgcgtgtgtg tgtgtttcct    3840
tcttcccttc agcctgtgac tgttgctgac tccaggggtg ggagggatgg ggagactccc    3900
ctcttgctgt gtgtactgga cacgcaggaa gcatgctgtc ttgctgcctc tgcaacgacc    3960
tgtcgtttgc tccagcatgc acaaacttcg tgagaccaac acagccgtgc cctgcaggca    4020
ccagcacgtg cttttcagag gctgcggact ttcttccagc cattgtggca ttggcctttc    4080
cagtcttggg aggagcgcgc tgctttggtg agacaccccc atgcaaggtc ctcagagtag    4140
ccgggttcta ccacaaacag aaacagaatg aaagtagctg tcagtccttg tagagagccg    4200
ctctgtttcc tcccagaagc atctcccagc taagctcgca ttattttct cctctggctg    4260
tttgcctgaa gttcacagaa cacacaacca tgaaaggctt tttgaggtga gaggcccagg    4320
tggtcctggc aaccctgagt agaaggagag acggggtagg gaacgggccc ggccagaaaa    4380
gaaccatttc ttctgccatc ttttatgcac catagacatc gagactccag ggggtcctgg    4440
ctcccctgtc cctgcagccc tgcaggtcag tgcatgatct gggttcgtgt cctgaccagg    4500
tgctcctcct ttgatccgag gggaaaggga ctggtttata gaaagagcct aggagacaaa    4560
agggccagtc ccctgccca gaatggagca gcagcaggac agaccccac gaggcccccc    4620
agagaggagg aagatcccac ggaggaacac atgaggttag ggacccttgt tcagcacccc    4680
aaacagcctg cctgtttaaa gcaggcagca ggcttaggcc ttccctgcaa ccccaacacc    4740
cacaagtttg tttctctagg aaacacattc actgtctcag ctggctgtta ctctctcaga    4800
ccatatggca aagttttcca agaaaatgcc ccgacagggg tgcccagcac actgcctgag    4860
ggacaacaga catcagaaca aaccccagaa gagaaacagt caaaatcagg gcccggtgca    4920
gtgttgtcat gtggaacctg ctttatccat tgctgagtgt tgaatgtggg taatggttag    4980
ggctttccag atctcagcag ccaaagacag ttattgttgg aagactgtca tgtagataac    5040
catgagcaat ggctcgcctc agaatcagtt cataaaattc tatggtactg gcccccttcgt    5100
gggtattgtg tgaaatgaga tggtggcgag gggtgcgctg tggaactgcc gcagccacgc    5160
aggaggtccc tggggggatgc tttgggaagt ccttgcccct gagcactgcc tgattgccag    5220
ggcctgtgga ggtctaggcc gcctggcaga atctagcacc gtccgaatcc ccgcaggacc    5280
catggagcta tgaccacacc aggccattca aatggctctg cattatcttc ccttggaagg    5340
tggccactcc tcggtggcag ggcctttccc tgaggctgca ggccgtgggc tggcagcccg    5400
tctcttggca tttcaattga aggtcaccag gtgctgggtt tgaaaggaag tcactggagt    5460
gctgccaggg gccgccctcc aaggttaatg agaggcccac atccaggcaa gaactaattc    5520
aaaaggcaga tcagaaacca caggagtcaa aattattgct ccggcagtgc ttcccttcct    5580
ttcatccact ggcctcgtgt ggtccatgca gggccactgt ctgcccttc tgatgccacg    5640
tattaggctt tcttactcag aattttgata gaaaaccatg gggccaagag ctctggaagc    5700
```

```
ctggccggaa agaccaaggt tcatgcagcc aacaaatga ttgttgagca cctctcggag      5760
ccaaagtcct taggcgagtg tggtgacttc ctggaaggag gatgcagact tccagagagc      5820
cccccaacg gacgtgctga agggagag ggaggcgggg gctgtagtca ggaaggagcc      5880
agagaagaac agggtttggg tgcatccaga aatatgcctg cagtaggagg gagaggaagg      5940
ggtgccaccg tcaacggctt cccatcggag gtggttggtg cagatggaag tttctgtctg      6000
ctggccctca agagagtgtt ttgccaggga cacagtctgt tcctcctcag aaaacacccc      6060
ccaaatgcta caacatccc caccagctgc tagaagcccc tttcccctcc ccaccttgaa      6120
gtagctcata gttctctggg cagagccaga ccatccagtg taccccagag gccagtaggt      6180
tcctgcccat tttcctctct ggcttcctgc caagaattat ggcagctgag gatgaatgga      6240
gaagtaaaaa caactaacac cgcacaacta acaactaaca ccgcagttcc cacctgggtt      6300
ccacttagca ggagacattt cggagggttt ttttttgtttt tgttcctgtt ttttttttt      6360
ttgctggaat tgttttctc agtactgaaa agagaaaaag tgacaatctt gtatttttaa      6420
aagcctcgga aaggtgatac catctgacag tcatttctc acgttggtct tctaaagtca      6480
cctatttctt gtgtgtgcac atcacaccat ttcctgtttc tttataaccc gacaagggta      6540
ggagtgcctg tttcccctgc tgggcacacc agacaatcgt aatcacaaaa cagacactga      6600
gccaggggcc caaagggtgt gatcatgaga gttaccggga cagcagtagg catgacagtc      6660
accaggaagg acaagggtgc tctgttgtta gtggccacac accaatttga caaggagtgt      6720
tgcgaaattt ttatttattt atttatttat tttgagatgg agtttcactc ttgttgccca      6780
ggctggagtg cggtggtaca atctcggctc actgcaacct ccacctccca ggttcaagcg      6840
attctcctgc ctcagcctcc caagtacctg ggactacagg tgcgtgccac cacacccagc      6900
taaattttgt gttttttagta gagatggggt ttcaccatgt tggccaggat ggtcttgaac      6960
ccctgacctc atgatctgcc tgcctcggcc tcccaaagtg ctgggattac aggcatgagc      7020
caccacgccc agccaaaata tttttttaaa gtcattttcc ttaagctgct tgggctacat      7080
gtgaaataca ctggacggtc aacattcctg tctcctccca tttgggctga tgcagcagat      7140
ccagggaatt ttacctgttt ctgctgctag aagatccagg aaattgggaa ggttacctga      7200
cgcacacatg gatgaaggcc atcatctaga aatgggtca accacaattg tgttaattcc      7260
gtagtgtcag ggattcttcg ggaaggtcaa cagtatgaag gattctgacc cctgtgcctc      7320
ccatttatgt gatcaggtga cagttaataa ccgtggaggt cacactcagc catccaacag      7380
ccttacagtg accctacaca aaagccccca aattccaaag acttttttctt aacctaaagg      7440
aagaaattat ttgttaattc cagtagagca actgaatata ctgggctatt tgtactttt      7500
tatagagaac tttaataata attctttaaa aatgagtttt tagaacaaag caactgacga      7560
tttcctaaga ttccaatgcc ctggagcttg taggaggact tagcctgggt cagctggagc      7620
accccgacc tgatctccca ctgccagatt ttcccatgct cctagggtat ggagtccacg      7680
tgggaatgac tgcaagttca ggtggaactt ggccgactga tgctctgcga gttttttaata      7740
gacactgggg acaactgctt aaggtttaga aacttccaaa ccacaggaaa gacatttta      7800
gtgtccccca tccagaggca gccctggaat aggattccca ggggtttctg ggacccctt      7860
ccttgctccg tgaggctctg tggccatctt ttggcaggag gaggatgctt ccttggctct      7920
gtgcccagac ccgcctggtc cccaggtctc tcaccttggg tgaagattca gagatgccct      7980
gtaaggattt tgcccactgg gcaactcaga aatacttcga tctcccaaga tataagaggc      8040
agcagcaaac gtgcctattg acgtctgttt catagttacc acttacgcga gtagacagaa      8100
```

```
ctcggctttt cagaaaatag gtgtcaagtc cactttataa gaaccttttt ttctaaaata    8160
agataaaagg tggctttgca ttttctgatt aaacgactgt gtctttgtca cctctgctta    8220
actttaggag tatccattcc tgtgattgta gacttttgtt gatattcttc ctggaagaat    8280
atcattcttt tcttgaaggg ttggtttact agaatattca aaatcaatca tgaaggcagt    8340
tactattttg agtctaaagg ttttctaaaa attaacctca catcccttct gttagggtct    8400
ttcagaatat cttttataaa cagaagcatt tgaagtcatt gcttttgcta catgatttgt    8460
gtgtgtgaag gacataccac gtttaaatca ttaattgaaa aacatcatat aagccccaac    8520
tttgtttgga ggaagagacg gaggttgagg ttttccttc tgtataagca cctactgaca    8580
aaatgtagag gccattcaac cgtcaaacac catttggtta tatcgcagag gagacggatg    8640
tgtaaattac tgcattgctt tttttttcag tttgtataac ctctaatctc cgtttgcatg    8700
atacgctttg ttagaaacat taattgtagt ttggaagcaa gtgtgtatga ataaagataa    8760
tgatcattcc aaaaaaaaaa aaaaaaa                                        8787

<210> SEQ ID NO 265
<211> LENGTH: 3537
<212> TYPE: DNA
<213> ORGANISM: Homo sapiens

<400> SEQUENCE: 265
ggcccctcga gcctcgaacc ggaacctcca aatccgagac gctctgctta tgaggacctc      60
gaaatatgcc ggccagtgaa aaaatcttgt ggctttgagg gcttttggtt ggccaggggc     120
agtaaaaatc tcggagagct gacaccaagt cctcccctgc cacgtagcag tggtaaagtc     180
cgaagctcaa attccgagaa ttgagctctg ttgattctta gaactggggt tcttagaagt     240
ggtgatgcaa gaagtttcta ggaaaggccg gacaccaggt tttgagcaaa attttggact     300
gtgaagcaag gcattggtga agacaaaatg gcctcgccgg ctgacagctg tatccagttc     360
acccgccatg ccagtgatgt tcttctcaac cttaatcgtc tccggagtcg agacatcttg     420
actgatgttg tcattgttgt gagccgtgag cagtttagag cccataaaac ggtcctcatg     480
gcctgcagtg gcctgttcta tagcatcttt acagaccagt tgaaatgcaa ccttagtgtg     540
atcaatctag atcctgagat caaccctgag ggattctgca tcctcctgga cttcatgtac     600
acatctcggc tcaatttgcg ggagggcaac atcatggctg tgatggccac ggctatgtac     660
ctgcagatgg agcatgttgt ggacacttgc cggaagttta ttaaggccag tgaagcagag     720
atggtttctg ccatcaagcc tcctcgtgaa gagttcctca acagccggat gctgatgccc     780
caagacatca tggcctatcg gggtcgtgag gtggtggaga caacctgcc actgaggagc     840
gcccctgggt gtgagagcag agcctttgcc cccagcctgt acagtggcct gtccacaccg     900
ccagcctctt attccatgta cagccacctc cctgtcagca gcctcctctt ctccgatgag     960
gagtttcggg atgtccggat gcctgtggcc aaccccttcc ccaaggagcg ggcactccca    1020
tgtgatagtg ccaggccagt ccctggtgag tacagccggc cgactttgga ggtgtccccc    1080
aatgtgtgcc acagcaatat ctattccaccc aaggaaacaa tcccagaaga ggcacgaagt    1140
gatatgcact acagtgtggc tgagggcctc aaacctgctg ccccctcagc ccgaaatgcc    1200
ccctacttcc cttgtgacaa ggccagcaaa gaagaagaga gaccctcctc ggaagatgag    1260
attgccctgc atttcgagcc ccccaatgca cccctgaacc ggaagggtct ggttagtcca    1320
cagagccccc agaaatctga ctgccagccc aactcgccca cagagtcctg cagcagtaag    1380
```

```
aatgcctgca tcctccaggc ttctggctcc cctccagcca agagccccac tgaccccaaa    1440
gcctgcaact ggaagaaata caagttcatc gtgctcaaca gcctcaacca gaatgccaaa    1500
ccagaggggc ctgagcaggc tgagctgggc cgccttccc cacgagccta cacggcccca    1560
cctgcctgcc agccacccat ggagcctgag aaccttgacc tccagtcccc aaccaagctg    1620
agtgccagcg gggaggactc caccatccca caagccagcc ggctcaataa catcgttaac    1680
aggtccatga cgggctctcc ccgcagcagc agcgagagcc actcaccact ctacatgcac    1740
cccccgaagt gcacgtcctg cggctctcag tccccacagc atgcagagat gtgcctccac    1800
accgctggcc ccacgttccc tgaggagatg ggagagaccc agtctgagta ctcagattct    1860
agctgtgaga cggggccttt cttctgcaat gagtgtgact gccgcttctc tgaggaggcc    1920
tcactcaaga ggcacacgct gcagacccac agtgacaaac cctacaagtg tgaccgctgc    1980
caggcctcct tccgctacaa gggcaacctc gccagccaca agaccgtcca taccggtgag    2040 aaacccatc gttgcaacat ctgtgggggcc cagttcaacc ggccagccaa cctgaaaacc    2100
cacactcgaa ttcactctgg agagaagccc tacaaatgcg aaacctgcgg agccagattt    2160
gtacaggtgg cccacctccg tgcccatgtg cttatccaca ctggtgagaa gccctatccc    2220
tgtgaaatct gtggcacccg tttccggcac cttcagactc tgaagagcca cctgcgaatc    2280
cacacaggag agaaaccta ccattgtgag aagtgtaacc tgcatttccg tcacaaaagc    2340
cagctgcgac ttcacttgcg ccagaagcat ggcgccatca ccaacaccaa ggtgcaatac    2400
cgcgtgtcag ccactgacct gcctccggag ctccccaaag cctgctgaag catggagtgt    2460
tgatgctttc gtctccagcc ccttctcaga atctacccaa aggatactgt aacactttac    2520
aatgttcatc ccatgatgta gtgcctcttt catccactag tgcaaatcat agctgggggt    2580 tggggggtggt gggggtcggg gcctggggga ctggagccg cagcagctcc ccctccccca    2640
ctgccataaa acattaagaa aatcatattg cttcttctcc tatgtgtaag gtgaaccatg    2700
tcagcaaaaa gcaaaatcat tttatatgtc aaagcagggg agtatgcaaa agttctgact    2760
tgactttagt ctgcaaaatg aggaatgtat atgttttgtg ggaacagatg tttcttttgt    2820
atgtaaatgt gcattctttt aaaagacaag acttcagtat gttgtcaaag agagggcttt    2880 aatttttta accaaggtg aaggaatata tggcagagtt gtaaatatat aaatatatat    2940
atatataaaa taaatatata taaacctaac aaagatatat taaaaatata aaactgcgtt    3000
aaaggctcga ttttgtatct gcaggcagac acggatctga aatctttat tgagaaagag    3060 cacttaagag aatattttaa gtattgcatc tgtataagta agaaaatatt ttgtctaaaa    3120
tgcctcagtg tatttgtatt tttttgcaag tgaaggttta caatttacaa agtgtgtatt    3180
aaaaaaaaca aaaagaacaa aaaaatctgc agaaggaaaa atgtgtaatt ttgttctagt    3240
tttcagtttg tatatacccg tacaacgtgt cctcacggtg cctttttca cggaagtttt    3300 caatgatggg cgagcgtgca ccatcccttt ttgaagtgta ggcagacaca gggacttgaa    3360
gttgttacta actaaactct ctttgggaat gtttgtctca tcccattctg cgtcatgctt    3420
gtgttataac tactccggag acagggtttg gctgtgtcta aactgcatta ccgcgttgta    3480
aaatatagct gtacaaatat aagaataaaa tgttgaaaag tcaaactgga aaaaaa        3537
```

<210> SEQ ID NO 266
<211> LENGTH: 2613
<212> TYPE: DNA
<213> ORGANISM: Homo sapiens

<400> SEQUENCE: 266

```
tcccccctct taaaacacga tgcctcccag gatgctagtg gcaccactgc cactgcattt      60
cctgttggca gcagtgagca gtgaaaaccg aagcggcaga aggcagtggc agcaggcagt    120
ggcagcaggc agtggcccag gcagaaatag ctcccgcgcg attcactgga gccttccccg    180
ggccctggtc ccggctaccg ggactcgcgc gtccggatct caaaagcggc agaggccacc    240
gaagggacag gaagcacttt ggtccagacc acactcccgg cacagtgcgg aaagagccgg    300
cgggagccac tctgatcccg gacgcctcag cgccccttg gcttgggct tgccctcggg      360
ccggggaagg ctgaccgcga tgccaggacg cgctcccctc cgcaccgtcc cgggcgccct    420
gggtgcctgg ctgctgggcg gcctctgggc ctggaccctg tgcggcctgt gcagcctggg    480
ggcggtggga ccccgcgcc cgtgccaggc gccgcagcag tgggaggggc gccaggttat     540
gtaccagcaa agtagcgggc gcaacagccg cgccctgctc tcctacgacg ggctcaacca    600
gcgcgtgcgg gtgctggacg agaggaaggc gctgatcccc tgcaagagat tatttgaata    660
tatttgctg tataaggatg gagtgatgtt tcagattgac caagccacca agcagtgctc      720
aaagatgacc ctgacacagc cctgggatcc tcttgacatt cctcaaaact ccacctttga    780
agaccagtac tccatcgggg ggcctcagga gcagatcacc gtccaggagt ggtcggacag    840
aaagtcagct agatcctatg aaacctggat tggcatctat acagtcaagg attgctatcc    900
tgtccaggaa acctttacca taaactacag tgtgatattg tctacgcggt ttttgacat     960
ccagctgggt attaaagacc cctcggtgtt taccctcca agcacgtgcc agatggccca   1020
actggagaag atgagcgaag actgctcctg gtgagcctgt gcatagggaa gcggcagcat   1080
cggatgtcag ccccctgcgg ccccagctgg agatggatat gagactagtc aagatgtgaa   1140
tgctaattgg agagaaatat aattttagga agatgcacat tgatgtgggg ttttgatgtg   1200
tctgattttg actactcaag ctctgtttac agaagaaaat tgaatggcga gggtgtggcc   1260
atatgaactg actagatggc taatatggac actttgggta tttctaatgc ctgttcaggg   1320
ctggttttct gcatgcacgg gtatacacat aatgcagtgc catgcacata gggaagggtc   1380
agtaagagaa gtttgccttg gcagcaagta tttattgttg acattattca gaattagtga   1440
taataaaaag cagagtgatt ttggtcaatt ttattattaa ttcttaaatt ccctgcagag   1500
aatgccccct ttattgctgc accagggttg gcattgctcc cactgagccc tactccaccc   1560
tgtccctgca ctcccttggt tgccaaaaaa atgataactt aaatcccttc cagacttaag   1620
aattttatgg catggcccaa ttgatataaa catttagaag gaaatgaaaa gctaaaatag   1680
gaagtaatta ttcctctaaa gaaacatttt gagcaaggca gtttagagaa tcctaatgtc   1740
tacactggca tagcacgagc catgtaagct tcttttttt ctatgcaaga gtattgatgt    1800
atgtgctgaa tcttcacaga cttgtcaata cacaggcagt attctaaaat agcactgaac   1860
agggagtcag gagactattg tctcctaaac ccaggactag agttccctcg tactgtcact   1920
cctttggtca ttaaatgcac tgggcttgcc cgcactttgg ccttcctaga acactgcttc   1980
ataacctctc tgtctgactt ctgcatctcc ttccaggtca gctcattcac aagagttgct   2040
cccaagcctg gatgagttgc accttgcatc ttgagcatgc atttctcaca ataattatta   2100
agctgtgtga taatttctgc tttcaggaca ctcatccatt atcttggctg tgagctcctt   2160
gggtacgggt accttgtatg tttacttta tatccctagc acaaagcaag tgcctggcac   2220
atagtcagtg ccctaagtat tcgtagagtg aagaatgcca gcctctcttg tccctggttt   2280
ccttatgtgt tgaatgtggt tgagtttgtc cattgctagg gagagacttc cagtaataaa   2340
```

| | |
|---|---|
| atttactatt ctagatgctt ctactgttat gttttatctg cccatttatc tttcttagtt | 2400 |
| accaggagaa atgtgtgaca cctatattat aatgaaaaca atctcattac ttatagttta | 2460 |
| tctatattaa acaaatttaa ttgcatttta aagcattctt tgatactgtt gcttttgcaa | 2520 |
| taaatatgga taatcttggt tataagggag ttaaaacaat gctgtaataa ataaagtgct | 2580 |
| tcatgtgatc aaaatcaaaa aaaaaaaaaa aaa | 2613 |

<210> SEQ ID NO 267
<211> LENGTH: 1890
<212> TYPE: DNA
<213> ORGANISM: Homo sapiens

<400> SEQUENCE: 267

| | |
|---|---|
| ctagagaggc cgccaggaga cccggcgctt tcttccttct gcagctgagg ctgcggcggg | 60 |
| gccggggctg gggtcggggc caggaggaat tttgttgtca gagaataaaa ggaggttgtc | 120 |
| cataattgac tttaagcagc aatcagtaaa acattgagct cttcagctcc gcctttcttg | 180 |
| ctctgaaaat tggaaaacca agaaggtttt gatgttttgt gtgacgccac ctgaattaga | 240 |
| aaccaagatg aacataacca aaggtggtct ggtgttgttt tcagcaaact cgaattcatc | 300 |
| atgtatggag ctatcaaaga aaattgcaga gcggctaggg gtggagatgg gcaaagtgca | 360 |
| ggtttaccag gaacctaaca gagaaacaag agtacaaatt caagagtctg tgagggaaa | 420 |
| agatgttttc atcatccaaa ctgtttcgaa ggacgtgaac accaccatca tggagctcct | 480 |
| gatcatggtg tatgcatgta agacctcttg tgccaagagc atcattggcg tgataccta | 540 |
| ctttccttac agcaagcagt gcaagatgag aaaaagaggc tccattgtct ctaaattgct | 600 |
| ggcttccatg atgtgcaaag ctggtctaac tcatcttatt actatggatt tacaccagaa | 660 |
| ggaaattcag ggcttcttca atattcctgt tgacaattta agagcatctc ccttcttatt | 720 |
| acagtatatt caagaagaga tcccagatta caggaatgca gtaatcgtgg ccaagtctcc | 780 |
| agcctcggcg aagagggcac agtcttttgc tgagcgcctg cgcctgggaa ttgcagtgat | 840 |
| tcatggagag gcgcaggatg ccgagtcgga cttggtggat ggacggcatt ccccacccat | 900 |
| ggtcagaagt gtggctgcca tccaccccag cctgagatcc ccatgctga ttcctaaaga | 960 |
| aaagccccca atcacggttg tgggtgatgt tggaggaagg attgccatca tcgtggatga | 1020 |
| catcattgat gatgttgaca gctttcttgc tgcagcagag accctgaagg aaagaggtgc | 1080 |
| atataagatc tttgtgatgg caactcatgg cttgttgtct tctgacgccc ccggcggat | 1140 |
| tgaagagtct gccattgatg aggtggtggt caccaataca attccacatg aagtccagaa | 1200 |
| gctccagtgc cccaagatta aaactgtgga tatcagcatg atcctttcag aggcgatccg | 1260 |
| tcggatccac aatgggggagt ccatgtccta ccttttcaga aacataggct agatgactg | 1320 |
| agttttcctt taggaaaact cccgagggcc aaactggaaa cataagagtg actgctcggt | 1380 |
| gggatggatt tcacaggaac cgtcatgctt gttcctccct ctcccctgta acctcacttc | 1440 |
| ttattgattc ctaagaagat agaccaactt tttatgtcgg tttgggtgtt tgtgagtttg | 1500 |
| gggagcaatt tttataaaag aaaaacttta ttctcctctt tgaaaaggt aagacctcgt | 1560 |
| tttagttgta actgtttaaa aataacact tggaataaga tttgtaagct cacaaagcct | 1620 |
| tcttccaaag ttgcttgagc caagtgctta aaaagttaat aaaataaaat gatctgtatg | 1680 |
| atacctgcaa ttgaaaagcc gaaaagatta tactgtcaag tccagtaaat gacatttta | 1740 |
| gagatgcttt tgtagacaag catatggaat atgtgattgt atttattttc tgcaactaaa | 1800 |
| aaaggaataa aaacttgtgt tgtgtgtttt ttctaaaact ttgtgttttg gcaatcgttt | 1860 | tataactaaa ataaaatgaa agctaaatct               1890

<210> SEQ ID NO 268
<211> LENGTH: 11242
<212> TYPE: DNA
<213> ORGANISM: Homo sapiens

<400> SEQUENCE: 268

```
tttttttttt ttttttttga gaaagggaa tttcatccca aataaaagga atgaagtctg      60
gctccggagg agggtccccg acctcgctgt gggggctcct gtttctctcc gccgcgctct     120
cgctctggcc gacgagtgga gaaatctgcg ggccaggcat cgacatccgc aacgactatc     180
agcagctgaa gcgcctggag aactgcacgg tgatcgaggg ctacctccac atcctgctca     240
tctccaaggc cgaggactac cgcagctacc gcttccccaa gctcacggtc attaccgagt     300
acttgctgct gttccgagtg gctggcctcg agagcctcgg agacctcttc cccaacctca     360
cggtcatccg cggctggaaa ctcttctaca actacgccct ggtcatcttc gagatgacca     420
atctcaagga tattgggctt tacaacctga ggaacattac tcgggggcc atcaggattg     480
agaaaaatgc tgacctctgt tacctctcca ctgtggactg gtccctgatc ctggatgcgg     540
tgtccaataa ctacattgtg gggaataagc ccccaaagga atgtggggac ctgtgtccag     600
ggaccatgga ggagaagccg atgtgtgaga agaccaccat caacaatgag tacaactacc     660
gctgctggac cacaaaccgc tgccagaaaa tgtgcccaag cacgtgtggg aagcgggcgt     720
gcaccgagaa caatgagtgc tgccaccccg agtgcctggg cagctgcagc gcgcctgaca     780
acgacacggc ctgtgtagct tgccgccact actactatgc cggtgtctgt gtgcctgcct     840
gcccgcccaa cacctacagg tttgagggct ggcgctgtgt ggaccgtgac ttctgcgcca     900
acatcctcag cgccgagagc agcgactccg aggggtttgt gatccacgac ggcgagtgca     960
tgcaggagtg cccctcgggc ttcatccgca acggcagcca gagcatgtac tgcatcccct    1020
gtgaaggtcc ttgcccgaag gtctgtgagg aagaaaagaa aacaaagacc attgattctg    1080
ttacttctgc tcagatgctc caaggatgca ccatcttcaa gggcaatttg ctcattaaca    1140
tccgacgggg gaataacatt gcttcagagc tggagaactt catggggctc atcgaggtgg    1200
tgacgggcta cgtgaagatc cgccattctc atgccttggt ctccttgtcc ttcctaaaaa    1260
accttcgcct catcctagga gaggagcagc tagaaggaa ttactccttc tacgtcctcg    1320
acaaccagaa cttgcagcaa ctgtgggact gggaccaccg caacctgacc atcaaagcag    1380
ggaaaatgta ctttgctttc aatcccaaat tatgtgtttc cgaaatttac cgcatggagg    1440
aagtgacggg gactaagggg cgccaaagca aggggacat aaacaccagg aacaacgggg    1500
agagagcctc ctgtgaaagt gacgtcctgc atttcacctc caccaccacg tcgaagaatc    1560
gcatcatcat aacctggcac cggtaccggc cccctgacta cagggatctc atcagcttca    1620
ccgtttacta caaggaagca cccttaagaa atgtcacaga gtatgatggg caggatgcct    1680
gcggctccaa cagctggaac atggtggacg tggacctccc gcccaacaag acgtggagc    1740
ccggcatctt actacatggg ctgaagccct ggactcagta cgccgtttac gtcaaggctg    1800
tgaccctcac catggtggag aacgaccata tccgtgggc caagagtgag atcttgtaca    1860
ttcgcaccaa tgcttcagtt ccttccattc ccttggacgt tctttcagca tcgaactcct    1920
cttctcagtt aatcgtgaag tggaaccctc cctctctgcc caacggcaac ctgagttact    1980
acattgtgcg ctggcagcgg cagcctcagg acggctacct ttaccggcac aattactgct    2040
```

```
ccaaagacaa aatccccatc aggaagtatg ccgacggcac catcgacatt gaggaggtca    2100
cagagaaccc caagactgag gtgtgtggtg gggagaaagg gccttgctgc gcctgcccca    2160
aaactgaagc cgagaagcag gccgagaagg aggaggctga ataccgcaaa gtctttgaga    2220
atttcctgca caactccatc ttcgtgccca gacctgaaag gaagcggaga gatgtcatgc    2280
aagtggccaa caccaccatg tccagccgaa gcaggaacac cacggccgca gacacctaca    2340
acatcaccga cccggaagag ctggagacag agtacccttt ctttgagagc agagtggata    2400
acaaggagag aactgtcatt tctaaccttc ggcctttcac attgtaccgc atcgatatcc    2460
acagctgcaa ccacgaggct gagaagctgg gctgcagcgc ctccaacttc gtctttgcaa    2520
ggactatgcc cgcagaagga gcagatgaca ttcctgggcc agtgacctgg gagccaaggc    2580
ctgaaaactc catcttttta aagtggccgg aacctgagaa tcccaatgga ttgattctaa    2640
tgtatgaaat aaaatacgga tcacaagttg aggatcagcg agaatgtgtg tccagacagg    2700
aatacaggaa gtatggaggg gccaagctaa accggctaaa cccggggaac tacacagccc    2760
ggattcaggc cacatctctc tctgggaatg ggtcgtggac agatcctgtg ttcttctatg    2820
tccaggccaa aacaggatat gaaaacttca tccatctgat catcgctctg cccgtcgctg    2880
tcctgttgat cgtgggaggg ttggtgatta tgctgtacgt cttccataga aagagaaata    2940
acagcaggct ggggaatgga gtgctgtatg cctctgtgaa cccggagtac ttcagcgctg    3000
ctgatgtgta cgttcctgat gagtggggag tggctcggga agatcacc atgagccggg    3060
aacttgggca ggggtcgttt gggatggtct atgaaggagt tgccaagggt gtggtgaaag    3120
atgaacctga aaccagagtg gccattaaaa cagtgaacga ggccgcaagc atgcgtgaga    3180
ggattgagtt tctcaacgaa gcttctgtga tgaaggagtt caattgtcac catgtggtgc    3240
gattgctggg tgtggtgtcc caaggccagc caacactggt catcatggaa ctgatgacac    3300
ggggcgatct caaaagttat ctccggtctc tgaggccaga aatggagaat aatccagtcc    3360
tagcacctcc aagcctgagc aagatgattc agatggccgg agagattgca gacggcatgg    3420
catacctcaa cgccaataag ttcgtccaca gagaccttgc tgcccggaat tgcatggtag    3480
ccgaagattt cacagtcaaa atcggagatt ttggtatgac gcgagatatc tatgagacag    3540
actattaccg gaaggagggg aaagggctgc tgcccgtgcg ctggatgtct cctgagtccc    3600
tcaaggatgg agtcttcacc acttactcgg acgtctggtc cttcggggtc gtcctctggg    3660
agatcgccac actggccgag cagccctacc agggcttgtc caacgagcaa gtccttcgct    3720
tcgtcatgga gggcggcctt ctggacaagc cagacaactg tcctgacatg ctgtttgaac    3780
tgatgcgcat gtgctggcag tataaccccc agatgaggcc ttccttcctg agatcatca    3840
gcagcatcaa agaggagatg gagcctggct tccgggaggt ctccttctac tacagcgagg    3900
agaacaagct gcccgagccg gaggagctgg acctggagcc agaaaacatg gagagcgtcc    3960
ccctggaccc ctcggcctcc tcgtcctccc tgccactgcc cgacagacac tcaggacaca    4020
aggccgagaa cggccccggc cctggggtgc tggtcctccg cgccagcttc gacgagagac    4080
agccttacgc ccacatgaac gggggccgca agaacgagcg ggccttgccg ctgccccagt    4140
cttcgacctg ctgatccttg gatcctgaat ctgtgcaaac agtaacgtgt gcgcacgcgc    4200
agcggggtgg gggggagag agagttttaa caatccattc acaagcctcc tgtacctcag    4260
tggatcttca gaactgccct tgctgccgcg gggagacagc ttctctgcag taaaacacat    4320
ttgggatgtt cctttttca atatgcaagc agctttttat tccctgccca aacccttaac    4380
tgacatgggc ctttaagaac cttaatgaca acacttaata gcaacagagc acttgagaac    4440
```

```
cagtctcctc actctgtccc tgtccttccc tgttctccct ttctctctcc tctctgcttc    4500
ataacggaaa aataattgcc acaagtccag ctgggaagcc cttttttatca gtttgaggaa    4560 gtggctgtcc ctgtggcccc atccaaccac tgtacacacc cgcctgacac cgtgggtcat    4620
tacaaaaaaa cacgtggaga tggaaatttt tacctttatc tttcaccttt ctagggacat    4680
gaaatttaca aagggccatc gttcatccaa ggctgttacc attttaacgc tgcctaattt    4740
tgccaaaatc ctgaactttc tccctcatcg gcccggcgct gattcctcgt gtccggaggc    4800
atgggtgagc atggcagctg gttgctccat ttgagagaca cgctggcgac acactccgtc    4860
catccgactg cccctgctgt gctgctcaag gccacaggca cacaggtctc attgcttctg    4920
actagattat tatttggggg aactggacac aataggtctt tctctcagtg aaggtgggga    4980
gaagctgaac cggcttccct gcctgcctc cccagccccc tgcccaaccc caagaatct    5040 ggtggccatg ggccccgaag cagcctggcg gacaggcttg gagtcaaggg gccccatgcc    5100
tgcttctctc ccagccccag ctcccccgcc cgccccaag gacacagatg ggaaggggtt    5160
tccagggact cagccccact gttgatgcag gtttgcaagg aaagaaattc aaacaccaca    5220
acagcagtaa aagaaaaagc agtcaatgga ttcaagcatt ctaagctttg ttgacatttt    5280
ctctgttcct aggacttctt catgggtctt acagttctat gttagaccat gaaacatttg    5340
catacacatc gtctttaatg tcacttttat aactttttta cggttcagat attcatctat    5400
acgtctgtac agaaaaaaaa aagctgctat tttttttgtt cttgatcttt gtggatttaa    5460
tctatgaaaa ccttcaggtc caccctctcc cctttctgct cactccaaga aacttcttat    5520
gctttgtact agagtgcgtg actttcttcc tcttttcccg gtaatggata cttctatcac    5580
ataatttgcc atgaactgtt ggatgccttt ttataaatac atcccccatc cctgctccca    5640
cctgcccctt tagttgtttt ctaacccgta ggctctctgg gcacgaggca gaaagcaggc    5700
cgggcaccca tcctgagagg gccgcgctcc tctccccagc ctgccctcac agcattggag    5760
cctgttacag tgcaagacat gatacaaact caggtcagaa aaacaaaggt taaatatttc    5820
acacgtcttt gttcagtgtt tccactcacc gtggttgaga agcctcaccc tctctttccc    5880
ttgcctttgc ttaggttgtg acacacatat atatatattt ttttaattct tgggtacaac    5940
agcagtgtta accgcagaca ctaggcattt ggattactat ttttcttaat ggctatttaa    6000
tccttccatc ccacgaaaaa cagctgctga gtccaaggga gcagcagagc gtggtccggc    6060
agggcctgtt gtggccctcg ccacccccct caccggaccg actgacctgt ctttggaacc    6120
agaacatccc aagggaactc cttcgcactg gcgttgagtg ggaccccggg atccaggctg    6180
gcccagggcg gcaccctcag ggctgtgccc gctggagtgc taggtggagg cagcacagac    6240
gccacggtgg cccaagagcc cctttgcttc ttgctggggg accagggctg tggtgctggc    6300
ccactttccc tcggccagga atccaggtcc ttggggccca ggggtcttgt cttgtttcat    6360
ttttagcact tctcaccaga gagatgacag cacaagagtt gcttctggga tagaaatgtt    6420
taggagtaag aacaaagctg ggatacggtg attgctagtt gtgactgaag attcaacaca    6480
gaaaagaaag tttatacggc tttttttgctg gtcagcagtt tgtcccactg ctttctctag    6540
tctctatccc atagcgtgtt ccctttaaaa aaaaaaaaa ggtattatat gtaggagttt    6600
tcttttaatt tattttgtga taaattacca gtttcaatca ctgtagaaaa gccccattat    6660
gaatttaaat ttcaaggaaa gggtgtgtgt gtgtgtatgt gtggggtgtg tgtgtgtgag    6720
agtgatggga cagttcttga ttttttgggt ttttttttccc ccaaacattt atctacctca    6780
```

```
ctcttatttt ttatatgtgt atatagacaa agaatacat ctcacctttc tcagcacctg    6840
acaataggcc gttgatactg gtaacctcat ccacgccaca ggcgccacac ccaggtgatg    6900 caggggaag ccaggctgta ttccggggtc aaagcaacac taactcacct ctctgctcat    6960
ttcagacagc ttgccttttt ctgagatgtc ctgttttgtg ttgcttttt tgttttgttt    7020 tctatcttgg tttccaccaa ggtgttagat ttctcctcct cctagccagg tggccctgtg    7080
aggccaacga gggcaccaga gcacacctgg gggagccacc aggctgtccc tggctggttg    7140
tctttggaac aaactgcttc tgtgcagatg gaatgaccaa cacatttcgt ccttaagaga    7200
gcagtggttc ctcaggttct gaggagagga aggtgtccag gcagcaccat ctctgtgcga    7260
atccccaggg taaaggcgtg gggcattggg tttgctcccc ttgctgctgc tccatccctg    7320
caggaggctc gcgctgaggc aggaccgtgc ggccatggct gctgcattca ttgagcacaa    7380
aggtgcagct gcagcagcag ctggagagca agagtcaccc agcctgtgcg ccagaatgca    7440
gaggctcctg acctcacagc cagtccctga tagaacacac gcaggagcag agtcccctcc    7500
ccctccaggc tgccctctca acttctccct cacctccttc cctaggggta gacagagatg    7560
taccaaacct tccggctgga aagcccagtg gccggcgccg aggctcgtgg cgtcacgccc    7620
cccccgccag ggctgtacct ccgtctccct ggtcctgctg ctcacaggac agacggctcg    7680 ctccccctctt ccagcagctg ctcttacagg cactgatgat ttcgctggga agtgtggcgg    7740
gcagctttgc ctaagcgtgg atggctcctc ggcaattcca gcctaagtga aggcgctcag    7800
gagcctcctg ctggaacgcg acccatctct cccaggaccc cggggatctt aaggtcattg    7860
agaaatactg ttggatcagg gttttgttct tccacactgt aggtgacccc ttggaataac    7920
ggcctctcct ctcgtgcaca tacctaccgg tttccacaac tggatttcta cagatcattc    7980
agctggttat aagggttttg tttaaactgt ccgagttact gatgtcattt tgttttgtt    8040 ttatgtaggt agcttttaag tagaaaacac taacagtgta gtgcccatca tagcaaatgc    8100
ttcagaaaca cctcaataaa agagaaaact tggcttgtgt gatggtgcag tcactttact    8160
ggaccaaccc acccaccttg actataccaa ggcatcatct atccacagtt ctagcctaac    8220
ttcatgctga tttctctgcc tcttgatttt tctctgtgtg ttccaaataa tcttaagctg    8280
agttgtggca ttttccatgc aacctccttc tgccagcagc tcacactgct tgaagtcata    8340
tgaaccactg aggcacatca tggaattgat gtgagcatta agacgttctc ccacacagcc    8400
cttccctgag gcagcaggag ctggtgtgta ctggagacac tgttgaactt gatcaagacc    8460
cagaccaccc caggtctcct tcgtgggatg tcatgacgtt tgacatacct ttggaacgag    8520
cctcctcctt ggaagatgga agaccgtgtt cgtggccgac ctggcctctc ctggcctgtt    8580
tcttaagatg cggagtcaca tttcaatggt acgaaaagtg gcttcgtaaa atagaagagc    8640
agtcactgtg gaactaccaa atggcgagat gctcggtgca cattggggtg ctttgggata    8700
aaagatttat gagccaacta ttctctggca ccagattcta ggccagtttg ttccactgaa    8760
gcttttccca cagcagtcca cctctgcagg ctggcagccg aatggcttgc cagtggctct    8820
gtggcaagat cacactgaga tcgatgggtg agaaggctag gatgcttgtc tagtgttctt    8880
agctgtcacg ttggctcctt ccagggtggc cagacggtgt tggccactcc cttctaaaac    8940
acaggcgccc tcctggtgac agtgacccgc cgtggtatgc cttggcccat tccagcagtc    9000
ccagttatgc atttcaagtt tgggggtttgt tcttttcgtt aatgttcctc tgtgttgtca    9060
gctgtcttca tttcctgggc taagcagcat tgggagatgg ggaccagaga tccactcctt    9120
aagaaccagt ggcgaaagac actttctttc ttcactctga agtagctggt ggtacaaatg    9180
```

```
agaacttcaa gagaggatgt tatttagact gaacctctgt tgccagagat gctgaagata    9240
cagaccttgg acaggtcaga gggtttcatt tttggccttc atcttagatg actggttgcg    9300
tcatttggag aagtgagtgc tccttgatgg tggaatgacc gggtggtggg tacagaacca    9360
ttgtcacagg gatcctggca cagagaagag ttacgagcag cagggtgcag gcttggaag    9420 gaatgtgggc aaggttttga acttgattgt tcttgaagct atcagaccac atcgaggctc    9480
agcagtcatc cgtgggcatt tggtttcaac aaagaaacct aacatcctac tctgaaaact    9540
gatctcggag ttaaggcgaa ttgttcaaga acacaaacta catcgcactc gtcagttgtc    9600
agttctgggg catgacttta gcgttttgtt tctgcgagaa cataacgatc actcattttt    9660
atgtcccacg tgtgtgtgtc cgcatctttc tggtcaacat tgttttaact agtcactcat    9720
tagcgttttc aatagggctc ttaagtccag tagattacgg gtagtcagtt gacgaagatc    9780
tggtttacaa gaactaatta aatgtttcat tgcattttg taagaacaga ataattttat    9840
aaaatgtttg tagtttataa ttgccgaaaa taatttaaag cactttttt tttctctgtg    9900 tgtgcaaatg tgtgtttgtg atccattttt tttttttttt tttaggacac ctgtttacta    9960
gctagcttta caatatgcca aaaaaggatt tctccctgac cccatccgtg gttcaccctc    10020 ttttccccc atgcttttg ccctagttta taacaaagga atgatgatga tttaaaaagt    10080
agttctgtat cttcagtatc ttggtcttcc agaaccctct ggttgggaag gggatcattt    10140
tttactggtc atttcccttt ggagtgtagc tactttaaca gatggaaaga acctcattgg    10200
ccatggaaac agccgaggtg ttggagccca gcagtgcatg gcaccgttcg gcatctggct    10260
tgattggtct ggctgccgtc attgtcagca cagtgccatg gacatgggaa gacttgactg    10320
cacagccaat ggttttcatg atgattacag catacacagt gatcacataa acgatgacag    10380 ctatgggca cacaggccat ttgcttacat gcctcgtatc atgactgatt actgctttgt    10440
tagaacacag aagagaccct atttatttta aggcagaacc ccgaagatac gtatttccaa    10500
tacagaaaag aatttttaat aaaaactata acatacacaa aaattggttt taaagttgac    10560
tccacttcct ctaactccag tggattgttg gccatgtctc cccaactcca caatatctct    10620
atcatgggaa acacctgggg ttttgcgct acataggaga aagatctgga aactatttgg    10680 gttttgttt caacttttca tttggatgtt tggcgttgca cacacacatc caccggtgga    10740
agagacgccc ggtgaaaaca cctgtctgct ttctaagcca gtgaggttga ggtgagaggt    10800
ttgccagagt ttgtctacct ctgggtatcc ctttgtctgg gataaaaaaa atcaaaccag    10860
aaggcgggat ggaatggatg caccgcaaat aatgcatttt ctgagttttc ttgttaaaaa    10920 aaaattttt taagtaagaa aaaaaaggt aataacatgg ccaatttgtt acataaaatg    10980
actttctgtg tataaattat tcctaaaaaa tcctgtttat ataaaaaatc agtagatgaa    11040
aaaaatttca aaatgttttt gtatattctg ttgtaagaat ttattcctgt tattgcgata    11100
tactctggat tctttacata atggaaaaaa gaaactgtct attttgaatg gctgaagcta    11160
aggcaacgtt agtttctctt actctgcttt tttctagtaa agtactacat ggtttaagtt    11220
aaataaaata attctgtatg ca                                             11242
```

<210> SEQ ID NO 269
<211> LENGTH: 2718
<212> TYPE: DNA
<213> ORGANISM: Homo sapiens

<400> SEQUENCE: 269

-continued

```
cagggtaacg ctgtcttgtg gacccgcact tcccacccga gacctctcac tgagcccgag      60
ccgcgcgcga catgagccac gggaagggaa ccgacatgct cccggagatc gccgccgccg     120
tgggcttcct ctccagcctc ctgaggaccc ggggctgcgt gagcgagcag aggcttaagg     180
tcttcagcgg ggcgctccag gaggcactca cagagcacta caaacaccac tggtttcccg     240
aaaagccgtc caagggctcc ggctaccgct gcattcgcat caaccacaag atggacccca     300
tcatcagcag ggtggccagc cagatcggac tcagccagcc ccagctgcac cagctgctgc     360
ccagcgagct gaccctgtgg gtggacccct atgaggtgtc ctaccgcatt ggggaggacg     420
gctccatctg cgtcttgtac gaggaggccc cactggccgc ctcctgtggg ctcctcacct     480
gcaagaacca agtgctgctg ggccggagca gcccctccaa gaactacgtg atggcagtct     540
ccagctaggc ccttccgccc ccgccctggg cgccgccgtg tcatgctgcc cgtgacaaca     600
ggccaccaca tacctcaacc tggggaactg tattttaaa tgaagagcta tttatatata     660
ttattttttt ttaagaaagg aggaaaagaa accaaaagtt ttttttaaga aaaaaaatcc     720 ttcagggag ctgcttggaa gtggcctccc caggtgcctt tggagagaac tgttgcgtgc     780
ttgagtctgt gagccagtgt ctgcctatag agggggagc tgttagggg tagacctagc     840 caaggagaag tgggagacgt ttggctagca ccccaggaag atgtgagagg gagcaagcaa     900
ggttagcaac tgtgaacaga gaggtcggga tttgccctgg gggaggaaga gaggccaagt     960
tcagagctct ctgtctcccc cagcagaca cctgcatccc tggctcctct attactcagg    1020
ggcattcatg cctggactta aacaatacta tgttatcttt tcttttattt ttctaatgag    1080
gtcctgggca gagagtgaaa aggcctctcc tgattcctac tgtcctaagc tgcttttctt    1140
gaaatcatga cttgtttcta attctacccct cagggcctg tagatgttgc tttccagcca    1200
ggaatctaaa gctttgggtt ttctgagggg gggaggagg gaactggagg ttattggggt    1260
taggatggaa gggaactctg cacaaaacct ttgctttgct agtgctgctt tgtgtgtatg    1320
tgtggcaaat aatttggggg tgatttgcaa tgaaattttg ggacccaaag agtatccact    1380
ggggatgttt tttggccaaa actcttcctt ttggaaccac atgaaagtct tgatgctgct    1440
gccatgatcc ctttgagagg tggctcaaaa gctacaggga actccaggtc ctttattact    1500
gccttctttt caaaagcaca actctcctct aaccctcccc tcccccttcc cttctggtcg    1560
ggtcatagag ctaccgtatt ttctaggaca agagttctca gtcactgtgc aatatgcccc    1620
ctgggtccca ggagggtctg gaggaaaact ggctatcaga acctcctgat gccctggtgg    1680
gcttagggaa ccatctctcc tgctctcctt gggatgatgg ctggctagtc agccttgcat    1740
gtattccttg gctgaatggg agagtgcccc atgttctgca agactacttg gtattcttgt    1800
agggccgaca ctaaataaaa gccaaacctt gggcactgtt tttctcccct ggtgctcaga    1860
gcacctgtgg gaaaggttgc tgtctgtctc agtacaatcc aaatttgtcg tagacttgtg    1920
caatatatac tgttgtgggt tggagaaaag tggaaagcta cactgggaag aaactccctt    1980
ccttcaattt ctcagtgaca ttgatgaggg gtcctcaaaa gacctcgagt ttcccaaacc    2040
gaatcacctt aagaaggaca gggctagggc atttggccag gatggccacc ctcctgctgt    2100 tgcccccttag tgaggaatct tcaccccact tcctctaccc caggttctc ctccccacag    2160 ccagtcccct ttcctggatt tctaaactgc tcaatttga ctcaaggtg ctatttacca    2220 aacactctcc ctaccattc ctgccagctc tgcctccttt tcaactctcc acattttgta    2280
ttgccttccc agacctgctt ccagtcttta ttgctttaaa gttcactttg ggcccacaga    2340
cccaagagct aattttctgg tttgtgggtt gaaacaaagc tgtgaatcac tgcaggctgt    2400
```

```
gttcttgcat cttgtctgca aacaggtccc tgcctttta gaagcagcct catggtctca      2460
tgcttaatct tgtctctctt ctcttcttta tgatgttcac tttaaaaaca acaaaacccc      2520
tgagctggac tgttgagcag gcctgtctct cctattaagt aaaaataaat agtagtagta      2580
tgtttgtaag ctattctgac agaaaagaca aaggttacta attgtatgat agtgttttta      2640
tatggaagaa tgtacagctt atggacaaat gtacacctt ttgttacttt aataaaaatg      2700
tagtaggata aaaaaaaa                                                    2718

<210> SEQ ID NO 270
<211> LENGTH: 2304
<212> TYPE: DNA
<213> ORGANISM: Homo sapiens

<400> SEQUENCE: 270
gaattcgtcc aaactgagga tcacaagtct ccacattctg agtaggagga tgagggtctg        60
agttaggatt tgggtcctgc agggcttgct aaggaatccc ctgatggcct aggattccac       120
gcagagcaca tctggtgtga gagagctcgc tgcaagggtg aaggctccgc cctatcagat       180
agacaaccag gccaccaaga ggcccagccc tccaaacct ggatttgcaa catcctcaaa       240
gaacagcaac gggccttgag cagaattgag aaggaaatac ccccacctgc cctcagccgt       300
taagtgggct ttgctattca caagggcctc tgggtgtcct ggcagagagg ggagatggca       360
caggcaccag gtgctagggt gccagggcct cccgagaagg aacaggtgca aagcaggcaa       420
ttagcccaga aggtatccgt ggggcaggca gcctagatct gatgggggaa gccaccagga       480
ttacatcatc tgctgtaaca actgctctga aaagaagata ttttcaacc tgaacttgca       540 gtagctagtg gagaggcagg aaaaaggaaa tgaaacagag acagagggaa gcctgagcca       600
aaatagacct tcccgagaga ggaggaagcc cggagagaga cgcacggtcc cctcccgcc       660 cctaggccgc cgccccctct ctgccctcgg cggcgagcag ggcgccgcga cccggggccg       720
gaaaggtgcc aggggctccg gcggccgggg cgggcgcaca ccatccccgc gggcggcgcg       780
gagccggcga cagcgcgcga gagggaccgg gcggtggcgg cggcgggacc gggatggaag       840
ggagcgcggt gactgtcctt gagcgcggag gggcgagctc gccggcggag gccgagcaag       900
cggaggcagg agcggcggcg acggcggcg cggcggcggc gccgagcac ccgagggggt       960 ccgagccccg gcagccggcc agccccgcgc acaaaggga gcgcccccgc cgcccggcac      1020
cccgcctccc tccccaatgt cctcggccat cgaaaggaag agcctggacc cttcagagga      1080
accagtggat gaggtgctgc agatccccc atccctgctg acatgcggcg gctgccagca      1140
gaacatcggg gaccgctact tcctgaaggc catcgaccag tactggcacg aggactgcct      1200
gagctgcgac ctctgtggct gccggctggg tgaggtgggg cggcgcctct actacaaact      1260
gggccggaag ctctgccgga gagactatct caggcttttt gggcaagacg gtctctgcgc      1320
atcctgtgac aagcggattc gtgcctatga tgacaatg cgggtgaaag acaaagtgta      1380
tcacctggaa tgtttcaagt gcgccgcctg tcagaagcat ttctgtgtag gtgacagata      1440
cctcctcatc aactctgaca tagtgtgcga acaggacatc tacgagtgga ctaagatcaa      1500
tgggatgata taggcccgag tccccgggca tctttgggga ggtgttcact gaagacgccg      1560
tctccatggc atcttcgtct tcactcttag gcactttggg ggtttgaggg tggggtaagg      1620
gatttcttag gggatggtag acctttattg ggtatcaaga catagcatcc aagtggcata      1680
attcaggggc tgacacttca aggtgacaga aggaccagcc cttgagggag aacttatggc      1740
```

| | |
|---|---|
| cacagcccat ccatagtaac tgacatgatt agcagaagaa aggaacattt aggggcaagc | 1800 |
| aggcgctgtg ctatcatgat ggaatttcat atctacagat agagagttgt tgtgtacaga | 1860 |
| cttgttgtga cttttgacgct tgcgaactag agatgtgcaa ttgatttctt ttcttcctgg | 1920 |
| ctttttaact cccctgtttc aatcactgtc ctccacacaa gggaaggaca gaaaggagag | 1980 |
| tggccattct tttttcttg gccccctccc caaggcctta agctttggac ccaagggaaa | 2040 |
| actgcatgga gacgcatttc ggttgagaat ggaaaccaca acttttaacc aaacaattat | 2100 |
| ttaaagcaat gctgatgaat cactgttttt agacaccttc attttgaggg gaggagttcc | 2160 |
| acagattgtt tctatacaaa tataaatctt aaaaagttgt tcaactatttt tattatccta | 2220 |
| gattatatca aagtatttgt cgtgtgtaga aaaaaaaaac agctctgcag gcttaataaa | 2280 |
| aatgacagac tgaaaaaaaa aaaa | 2304 |

<210> SEQ ID NO 271
<211> LENGTH: 1554
<212> TYPE: DNA
<213> ORGANISM: Homo sapiens

<400> SEQUENCE: 271

| | |
|---|---|
| gcttctcctt tttgtgttcc ggccgatccc acctctcctc gaccctggac gtctaccttc | 60 |
| cggaggccca catcttgccc actccgcgcg cggggctagc gcgggtttca gcgacgggag | 120 |
| ccctcaaggg acatggcaac tacagcgcg ccggcgggcg cgcccgaaa tggagctggc | 180 |
| ccggaatggg gagggttcga agaaaacatc cagggcggag gctcagctgt gattgacatg | 240 |
| gagaacatga tgatacctc aggctctagc ttcgaggata tgggtgagct gcatcagcgc | 300 |
| ctgcgcgagg aagaagtaga cgctgatgca gctgatgcag ctgctgctga agaggaggat | 360 |
| ggagagttcc tgggcatgaa gggctttaag ggacagctga gccggcaggt ggcagatcag | 420 |
| atgtggcagg ctgggaaaag acaagcctcc agggccttca gcttgtacgc caacatcgac | 480 |
| atcctcagac cctactttga tgtggagcct gctcaggtgc gaagcaggct cctgagtcc | 540 |
| atgatcccta tcaagatggt caacttcccc cagaaaattg caggtgaact ctatggacct | 600 |
| ctcatgctgg tcttcactct ggttgctatc ctactccatg ggatgaagac gtctgacact | 660 |
| attatccggg agggcaccct gatgggcaca gccattggca cctgcttcgg ctactggctg | 720 |
| ggagtctcat ccttcatta cttccttgcc tacctgtgca acgcccagat caccatgctg | 780 |
| cagatgttgg cactgctggg ctatggcctc tttgggcatt gcattgtcct gttcatcacc | 840 |
| tataatatcc acctccacgc cctcttctac ctcttctggc tgttggtggg tggactgtcc | 900 |
| acactgcgca tggtagcagt gttggtgtct cggaccgtgg gccccacaca gcggctgctc | 960 |
| ctctgtggca ccctggctgc cctacacatg ctccttcctgc tctatctgca ttttgcctac | 1020 |
| cacaaagtgg tagagggat cctggacaca ctggagggcc caacatccc gcccatccag | 1080 |
| agggtcccca gagacatccc tgccatgctc cctgctgctc ggcttccac caccgtcctc | 1140 |
| aacgccacag ccaaagctgt tgcggtgacc ctgcagtcac actgacccca cctgaaattc | 1200 |
| ttggccagtc ctcttttcccg cagctgcaga gaggaggaag actattaaag gacagtcctg | 1260 |
| atgacatgtt tcgtagatgg ggtttgcagc tgccactgag ctgtagctgc gtaagtacct | 1320 |
| ccttgatgcc tgtcggcact tctgaaaggc acaaggccaa gaactcctgg ccaggactgc | 1380 |
| aaggctctgc agccaatgca gaaaatgggt cagctccttt gagaaccct ccccacctac | 1440 |
| cccttccttc ctctttatct ctcccacatt gtcttgctaa atatagactt ggtaattaaa | 1500 |
| atgttgattg aagtctggaa aaaaaaaaaa aaaaaaaaa aaaaaaaaa aaaa | 1554 |

<210> SEQ ID NO 272
<211> LENGTH: 1511
<212> TYPE: DNA
<213> ORGANISM: Homo sapiens

<400> SEQUENCE: 272

```
ggggacccgc gggtttgcta tggcgatgag cagcggcggc agtggtggcg gcgtcccgga      60
gcaggaggat tccgtgctgt tccggcgcgg cacaggccag agcgatgatt ctgacatttg     120
ggatgataca gcactgataa agcatatgat aaagctgtg gcttcattta agcatgctct     180
aaagaatggt gacatttgtg aaacttcggg taaaccaaaa accacaccta aagaaaacc     240
tgctaagaag aataaaagcc aaagaagaa tactgcagct tccttacaac agtggaaagt     300
tggggacaaa tgttctgcca tttggtcaga gacggttgc atttacccag ctaccattgc     360
ttcaattgat tttaagagag aaacctgtgt tgtggtttac actggatatg aaatagaga     420
ggagcaaaat ctgtccgatc tactttcccc aatctgtgaa gtagctaata atatagaaca     480
aaatgctcaa gagaatgaaa atgaaagcca agtttcaaca gatgaaagtg agaactccag     540
gtctcctgga aataaatcag ataacatcaa gcccaaatct gctccatgga actcttttct     600
ccctccacca ccccccatgc cagggccaag actgggacca ggaaagccag gtctaaaatt     660
caatggccca ccaccgccac cgccaccacc accaccccac ttactatcat gctggctgcc     720
tccatttcct tctggaccac caataattcc cccaccacct cccatatgtc cagattctct     780
tgatgatgct gatgctttgg gaagtatgtt aatttcatgg tacatgagtg ctatcatac     840
tggctattat atgggtttca gacaaaatca aaagaagga aggtgctcac attccttaaa     900
ttaaggagaa atgctggcat agagcagcac taaatgacac cactaaagaa acgatcagac     960
agatctggaa tgtgaagcgt tatagaagat aactggcctc atttcttcaa aatatcaagt    1020
gttgggaaag aaaaaaggaa gtggaatggg taactcttct tgattaaaag ttatgtaata    1080
accaaatgca atgtgaaata ttttactgga ctctatttg aaaaccatc tgtaaaagac    1140
tggggtgggg gtgggaggcc agcacggtgg tgaggcagtt gagaaaattt gaatgtggat    1200
tagattttga atgatattgg ataattattg gtaattttta tgagctgtga aagggtgtt    1260
gtagtttata aaagactgtc ttaatttgca tacttaagca tttaggaatg aagtgttaga    1320
gtgtcttaaa atgtttcaaa tggtttaaca aaatgtatgt gaggcgtatg tggcaaaatg    1380
ttacagaatc taactggtgg acatggctgt tcattgtact gttttttct atcttctata    1440
tgtttaaaag tatataataa aaatatttaa tttttttta aaaaaaaaaa aaaaaaaaca    1500
aaaaaaaaa a                                                         1511
```

<210> SEQ ID NO 273
<211> LENGTH: 1300
<212> TYPE: DNA
<213> ORGANISM: Homo sapiens

<400> SEQUENCE: 273

```
ctgcagccgg tgcagttaca cgttttcctc caaggagcct cggacgttgt cacgggtttg      60
gggtcgggga cagagcggtg accatggcca ggctggcgtt gtctcctgtg cccagccact     120
ggatggtggc gttgctgctg ctgctctcag ctgagccagt accagcagcc agatcggagg     180
accggtaccg gaatcccaaa ggtagtgctt gttcgcggat ctggcagagc ccacgtttca     240
tagccaggaa acggggcttc acggtgaaaa tgcactgcta catgaacagc gcctccggca     300
```

```
atgtgagctg gctctggaag caggagatgg acgagaatcc ccagcagctg aagctggaaa      360
agggccgcat ggaagagtcc cagaacgaat ctctcgccac cctcaccatc caaggcatcc      420
ggtttgagga caatggcatc tacttctgtc agcagaagtg caacaacacc tcggaggtct      480
accagggctg cggcacagag ctgcgagtca tgggattcag caccttggca cagctgaagc      540
agaggaacac gctgaaggat ggtatcatca tgatccagac gctgctgatc atcctcttca      600
tcatcgtgcc tatcttcctg ctgctggaca aggatgacag caaggctggc atggaggaag      660
atcacaccta cgagggcctg acattgacc agacagccac ctatgaggac atagtgacgc      720
tgcggacagg ggaagtgaag tggtctgtag gtgagcaccc aggccaggag tgagagccag      780 gtcgcccat gacctgggtg caggctccct ggcctcagtg actgcttcgg agctgcctgg      840
ctcatggccc aaccccttc ctggaccccc agctggcct ctgaagctgg cccaccagag      900
ctgccatttg tctccagccc ctggtcccca gctcttgcca aagggcctgg agtagaagga      960
caacagggca gcaacttgga gggagttctc tggggatgga cgggacccag ccttctgggg     1020
gtgctatgag gtgatccgtc cccacacatg ggatggggga ggcagagact ggtccagagc     1080
ccgcaaatgg actcggagcc gagggcctcc cagcagagct tgggaagggc catggaccca     1140
actgggcccc agaagagcca caggaacatc attcctctcc cgcaaccact cccacccag     1200 ggaggccctg gcctccagtg ccttcccccg tggaataaac ggtgtgtcct gagaaaccac     1260
aaaaaaaaaa aaaaaaaaa aaaaaaaaaa aaaaaaaaa                            1300
```

<210> SEQ ID NO 274
<211> LENGTH: 5748
<212> TYPE: DNA
<213> ORGANISM: Homo sapiens

<400> SEQUENCE: 274

```
gagaagaaag ccagtgcgtc tctgggcgca ggggccagtg gggctcggag gcacaggcac       60
cccgcgacac tccaggttcc ccgacccacg tccctggcag cccgattat ttacagcctc      120 agcagagcac ggggcggggg cagaggggcc cgcccgggag ggctgctact tcttaaaacc      180
tctgcgggct gcttagtcac agcccccctt gcttgggtgt gtccttcgct cgctccctcc      240
ctccgtctta ggtcactgtt ttcaacctcg aataaaaact gcagccaact tccgaggcag      300
cctcattgcc cagcggaccc cagcctctgc caggttcggt ccgccatcct cgtcccgtcc      360
tccgccggcc cctgccccgc gcccagggat cctccagctc ctttcgcccg cgccctccgt      420
tcgctccgga caccatggac aagttttggt ggcacgcagc ctgggactc tgcctcgtgc      480 cgctgagcct ggcgcagatc gatttgaata taacctgccg ctttgcaggt gtattccacg      540
tggagaaaaa tggtcgctac agcatctctc ggacggaggc cgctgacctc tgcaaggctt      600
tcaatagcac cttgcccaca atggcccaga tggagaaagc tctgagcatc ggatttgaga      660
cctgcaggta tgggttcata gaagggcacg tggtgattcc ccggatccac cccaactcca      720
tctgtgcagc aaacaacaca ggggtgtaca tcctcacatc caacacctcc agtatgaca      780 catattgctt caatgcttca gctccacctg aagaagattg tacatcagtc acagacctgc      840
ccaatgcctt tgatggacca attaccataa ctattgttaa ccgtgatggc accgctatg      900 tccagaaagg agaatacaga acgaatcctg aagcatctca cccagcaac cctactgatg      960 atgacgtgag cagcggctcc tccagtgaaa ggagcagcac ttcaggaggt tacatctttt     1020 acacctttc tactgtacac cccatcccag acgaagacag tcctggatc accgacagca     1080 cagacagaat ccctgctacc actttgatga gcactagtgc tacagcaact gagacagcaa     1140
```

```
ccaagaggca agaaacctgg gattggtttt catggttgtt tctaccatca gagtcaaaga    1200
atcatcttca cacaacaaca caaatggctg gtacgtcttc aaataccatc tcagcaggct    1260
gggagccaaa tgaagaaaat gaagatgaaa gagacagaca cctcagtttt tctggatcag    1320
gcattgatga tgatgaagat tttatctcca gcaccatttc aaccacacca cgggcttttg    1380
accacacaaa acagaaccag gactggaccc agtggaaccc aagccattca aatccggaag    1440
tgctacttca gacaaccaca aggatgactg atgtagacag aaatggcacc actgcttatg    1500
aaggaaactg gaacccagaa gcacaccctc ccctcattca ccatgagcat catgaggaag    1560
aagagacccc acattctaca agcacaatcc aggcaactcc tagtagtaca acggaagaaa    1620
cagctaccca gaaggaacag tggtttggca acagatggca tgagggatat cgccaaacac    1680
ccaaagaaga ctcccattcg acaacaggga cagctgcagc ctcagctcat accagccatc    1740
caatgcaagg aaggacaaca ccaagcccag aggacagttc ctggactgat ttcttcaacc    1800
caatctcaca ccccatggga cgaggtcatc aagcaggaag aaggatggat atggactcca    1860
gtcatagtat aacgcttcag cctactgcaa atccaaacac aggtttggtg aagatttgg     1920 acaggacagg acctctttca atgacaacgc agcagagtaa ttctcagagc ttctctacat    1980
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattacccac acacgaagga agcaggacc ttcatcccag      2160 tgacctcagc taagactggg tcctttggag ttactgcagt tactgttgga gattccaact    2220
ctaatgtcaa tcgttcctta tcaggagacc aagacacatt ccaccccagt gggggggtccc   2280 ataccactca tggatctgaa tcagatggac actcacatgg gagtcaagaa ggtggagcaa    2340
acacaacctc tggtcctata aggacacccc aaattccaga atggctgatc atcttggcat    2400
ccctcttggc cttggctttg attcttgcag tttgcattgc agtcaacagt cgaagaaggt    2460
gtgggcagaa gaaaaagcta gtgatcaaca gtggcaatgg agctgtggag gacagaaagc    2520
caagtggact caacggagag gccagcaagt ctcaggaaat ggtgcatttg gtgaacaagg    2580
agtcgtcaga aactccagac cagtttatga cagctgatga gacaaggaac ctgcagaatg    2640
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat cttttttagc ataaaatttt ctactctttt tgtttttgt gttttgttct     2820 ttaaagtcag gtccaatttg taaaaacagc attgctttct gaaattaggg cccaattaat    2880
aatcagcaag aatttgatcg ttccagttcc cacttggagg cctttcatcc ctcgggtgtg    2940
ctatggatgc cttctaacaa aaactacaca tatgtattcc tgatcgccaa cctttccccc    3000
accagctaag gacatttccc agggttaata gggcctggtc cctgggagga aatttgaatg    3060
ggtccatttt gcccttccat agcctaatcc ctgggcattg ctttccactg aggttggggg    3120
ttggggtgta ctagttacac atcttcaaca gacccctct agaaattttt cagatgcttc     3180
tgggagacac ccaaagggtg aagctattta tctgtagtaa actatttatc tgtgttttg     3240 aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
```

```
cactcagacc cactcagcca aatctcatgg aagaccaagg agggcagcac tgttttttgtt    3540 ttttgttttt tgttttttttt ttttgacact gtccaaaggt tttccatcct gtcctggaat    3600
cagagttgga agctgaggag cttcagcctc ttttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg cctttttgatg   3780 tcttacaata agagaagaag ccaatggaaa tgaaagagat tggcaaaggg aaggatgat    3840 gccatgtaga tcctgtttga catttttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc ccttggcaa gtcctttgtg    4080 gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc attttcagtg gtctggattt    4500
ctttttattt tcttttcaac ttgaaagaaa ctggacatta ggccactatg tgttgttact    4560
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aatttttattt tggaattaaa tactttttc cctttattac tgttgtagtc    4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcatt    5100 aaactgggtc tttataaaag taaaaggcca acatttaatt attttgcaaa gcaacctaag    5160
agctaaagat gtaatttttc ttgcaattgt aaatcttttg tgtctcctga agacttccct    5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga    5400
gtaggagaga ggaaacattt gacttatctg gaaaagcaaa atgtacttaa gaataagaat    5460
aacatggtcc attcacccttt atgttataga tatgtctttg tgtaaatcat tgttttttgag   5520 ttttcaaaga atagcccatt gttcattctt gtgctgtaca atgaccactg ttattgttac    5580
tttgactttt cagagcacac ccttcctctg gtttttgtat atttattgat ggatcaataa    5640
taatgaggaa agcatgatat gtatattgct gagttgaaag cacttattgg aaaatattaa    5700
aaggctaaca ttaaaagact aaaggaaaca gaaaaaaaaa aaaaaaa               5748
```

<210> SEQ ID NO 275
<211> LENGTH: 1924

```
<212> TYPE: DNA
<213> ORGANISM: Homo sapiens

<400> SEQUENCE: 275
cgtagctatt tcaaggcgcg cgcctcgtgg tggactcacc gctagccgc agcgctcggc      60
ttcctggtaa ttcttcacct cttttctcag ctccctgcag catgggtgct gggccctcct    120
tgctgctcgc cgccctcctg ctgcttctct ccggcgacgg cgccgtgcgc tgcgacacac    180
ctgccaactg cacctatctt gacctgctgg gcacctgggt cttccaggtg ggctccagcg    240
gttcccagcg cgatgtcaac tgctcggtta tgggaccaca agaaaaaaaa gtagtggtgt    300
accttcagaa gctggataca gcatatgatg accttggcaa ttctggccat ttcaccatca    360
tttacaacca aggctttgag attgtgttga atgactacaa gtggtttgcc ttttttaagt    420
ataaagaaga gggcagcaag gtgaccactt actgcaacga acaatgact gggtgggtgc     480
atgatgtgtt gggccggaac tgggcttgtt tcaccggaaa aaggtggga actgcctctg     540
agaatgtgta tgtcaacata gcacacctta agaattctca ggaaaagtat tctaataggc    600
tctacaagta tgatcacaac tttgtgaaag ctatcaatgc cattcagaag tcttggactg    660
caactacata catggaatat gagactctta ccctgggaga tatgattagg agaagtggtg    720
gccacagtcg aaaaatccca aggcccaaac ctgcaccact gactgctgaa atacagcaaa    780
agattttgca tttgccaaca tcttgggact ggagaaatgt tcatggtatc aattttgtca    840
gtcctgttcg aaaccaagca tcctgtggca gctgctactc atttgcttct atgggtatgc    900
tagaagcgag aatccgtata ctaaccaaca attctcagac cccaatccta agccctcagg    960
aggttgtgtc ttgtagccag tatgctcaag gctgtgaagg cggcttccca taccttattg   1020
caggaaagta cgcccaagat tttgggctgg tggaagaagc ttgcttcccc tacacaggca   1080
ctgattctcc atgcaaaatg aaggaagact gctttcgtta ttactcctct gagtaccact   1140
atgtaggagg tttctatgga ggctgcaatg aagccctgat gaagcttgag ttggtccatc   1200
atgggcccat ggcagttgct tttgaagtat atgatgactt cctccactac aaaaagggga   1260
tctaccacca cactggtcta agagacccctt caaccccctt tgagctgact aatcatgctg   1320
ttctgcttgt gggctatggc actgactcag cctctgggat ggattactgg attgttaaaa   1380
acagctgggg caccggctgg ggtgagaatg gctacttccg gatccgcaga ggaactgatg   1440
agtgtgcaat tgagagcata gcagtggcag ccacaccaat tcctaaattg tagggtatgc   1500
cttccagtat ttcataatga tctgcatcag ttgtaaaggg gaattggtat attcacagac   1560
tgtagacttt cagcagcaat ctcagaagct tacaaataga tttccatgaa gatatttgtc   1620
ttcagaatta aaactgccct taattttaat atacctttca atcggccact ggccattttt   1680
ttctaagtat tcaattaagt gggaattttc tggaagatgg tcagctatga agtaatagag   1740
tttgcttaat catttgtaat tcaaacatgc tatattttt aaaatcaatg tgaaaacata    1800
gacttatttt taaattgtac caatcacaag aaaataatgg caataattat caaaactttt   1860
aaaatagatg ctcatatttt taaaataaag ttttaaaaat aactgcaaaa aaaaaaaaaa   1920
aaaa                                                                1924

<210> SEQ ID NO 276
<211> LENGTH: 2344
<212> TYPE: DNA
<213> ORGANISM: Homo sapiens

<400> SEQUENCE: 276
```

```
cggccgcctc cgcgtccgcg tcgtcgtctg tgctcccggc gctgacgtgt ctgggcggtc    60
ggcttccact ccttcaggcg tcggcagcca ctagtcgtgg cgagaggggc ggggtggccg   120
gggctggcgc tccacttggc ccccgctccc ggcccgcccc gccgccgcgg cccccccggat  180
gagggtatat attcggagcg agcgcgggac gccgatgagt ggccgcgcgg aaggagctgg   240
agacggtcgt agctgcggtc gcgccgagaa aggtttacag gtacatacat tacacccta   300
tttctacaaa gcttggctat tagagcatta tgaacattaa tgacctcaaa ctcacgttgt   360
ccaaagctgg gcaagagcac ctactacgtt tctggaatga gcttgaagaa gcccaacagg   420
tagaacttta tgcagagctc caggccatga actttgagga gctgaacttc ttttttccaaa   480
aggccattga aggttttaac cagtcttctc accaaaagaa tgtggatgca cgaatggaac   540
ctgtgcctcg agaggtatta ggcagtgcta caagggatca agatcagctc caggcctggg   600
aaagtgaagg acttttccag atttctcaga ataaagtagc agttcttctt ctagctggtg   660
ggcaggggac aagactcggc gttgcatatc ctaaggggat gtatgatgtt ggtttgccat   720
cccgtaagac acttttttcag attcaagcag agcgtatcct gaagctacag caggttgctg   780
aaaaatatta tggcaacaaa tgcattattc catggtatat aatgaccagt ggcagaacaa   840
tggaatctac aaaggagttc ttccaccaagc acaagtactt tggtttaaaa aaagagaatg   900
taatcttttt tcagcaagga atgctccccg ccatgagttt tgatgggaaa attattttgg   960
aagagaagaa caaagtttct atggctccag atggaatgg tggtctttat cgggcacttg   1020
cagcccagaa tattgtggag gatatggagc aaagaggcat ttggagcatt catgtctatt   1080
gtgttgacaa catattagta aaagtggcag acccacggtt cattggattt tgcattcaga   1140
aaggagcaga ctgtggagca aaggtggtag agaaaacgaa ccctacagaa ccagttggag   1200
tggtttgccg agtggatgga gtttaccagg tggtagaata tagtgagatt tccctggcaa   1260
cagctcaaaa acgaagctca gacggacgac tgctgttcaa tgcgggaac attgccaacc    1320
atttcttcac tgtaccattt ctgagagatg ttgtcaatgt ttatgaacct cagttgcagc   1380
accatgtggc tcaaaagaag attccttatg tggataccca aggacagtta attaagccag   1440
acaaacccaa tggaataaag atggaaaaat ttgtctttga catcttccag tttgcaaaga   1500
agtttgtggt atatgaagta ttgcgagaag atgagttttc cccactaaag aatgctgata   1560
gtcagaatgg gaaagacaac cctactactg caaggcatgc tttgatgtcc cttcatcatt   1620
gctgggtcct caatgcaggg ggccatttca tagatgaaaa tggctctcgc cttccagcaa   1680
ttccccgctt gaaggatgcc aatgatgtac caatccaatg tgaaatctct cctcttatct   1740
cctatgctgg agaaggatta gaaagttatg tggcagataa agaattccat gcacctctaa   1800
tcatcgatga aatggagtt catgagctgg tgaaaaatgg tatttgaacc agataccaag   1860
ttttgtttgc cacgatagga atagctttta tttttgatag accaactgtg aacctacaag   1920
acgtcttgga caactgaagt ttaaatatcc acagggtttt attttgcttg ttgaactctt   1980
agagctattg caaacttccc aagatccaga tgactgaatt tcagatagca ttttatgat   2040
tcccaactca ttgaaggtct tatttatata atttttttcca agccaaggag accattggcc   2100
atccaggaaa tttcgtacag ctgaaatata ggcaggatgt tcaacatcag tttacttgca   2160
gctggaagca tttgtttttg aagttgtaca tagtaataat atgtcattgt acatgttgaa   2220
aggtttctat ggtactaaaa gtttgttttta ttttatcaaa cattaagctt ttttaagaaa   2280
ataattgggc agtgaaataa atgtatcttc ttgtctctgg agtgtcaaaa aaaaaaaaaa   2340
aaaa                                                                2344
```

<210> SEQ ID NO 277
<211> LENGTH: 3484
<212> TYPE: DNA
<213> ORGANISM: Homo sapiens

<400> SEQUENCE: 277

```
gtgcgagccc ggccgccggt gagtcggctg gagcgcatct ggtcctccgc gcggaaagcg      60
ctgcttttgc ctggccgccc tagccgctgg ctcatccaag tggccttcgc cgctctcttg     120
cgtcccaacc agagcgctgg ccacctcgcc gcccagctca cgccgcgccc gcgctcccag     180
gctccgggtt ttcttaaatg ttttcttgga gccttaaaga tggagatgac agaaatgact     240
ggtgtgtcgc tgaaacgtgg ggcactggtt gtcgaagata atgacagtgg agtcccagtt     300
gaagagacaa aaaacagaa gctgtcggaa tgcagtctaa ccaaaggtca agatgggcta     360
cagaatgact ttctgtccat cagtgaagac gtgcctcggc ctcctgacac tgtcagtact     420
gggaaaggtg gaaagaattc tgaggctcag ttggaagatg aggaagaaga ggaggaagat     480
ggactttcag aggagtgcga ggaggaggaa tcagagagtt ttgcagacat gatgaagcat     540
ggactcactg aggctgacgt aggcatcacc aagtttgtga ttctcatca agggttctcg     600
ggaatcttaa agaaagata ctccgacttc gttgttcatg aaataggaaa agatggacgg     660
atcagccatt tgaatgactt gtccattcca gtggatgagg aggacccttc agaagacata     720
tttacagttt tgacagctga agaaaagcag cgattggaag agctccagct gttcaaaaat     780
aaggaaacca gtgttgccat tgaggttatc gaggacacca agagaaaag aaccatcatc     840
catcaggcta tcaaatctct gtttccagga ttagagacaa aaacagagga tagggagggg     900
aagaaataca ttgtagccta ccacgcagct gggaaaaagg ctttggcaaa tccaagaaaa     960
cattcttggc caaatctag gggaagttac tgccacttcg tactatataa ggaaaacaaa    1020
gacaccatgg atgctattaa tgtactctcc aaatacttaa gagtcaagcc aaatatattc    1080
tcctacatgg gaaccaaaga taaagggct ataacagttc aagaaattgc tgttctcaaa    1140
ataactgcac aaagacttgc ccacctgaat aagtgcttga tgaactttaa gctagggaat    1200
ttcagctatc aaaaaaaccc actgaaattg ggagagcttc aaggaaacca cttcactgtt    1260
gttctcagaa atataacagg aactgatgac caagtacagc aagctatgaa ctctctcaag    1320
gagattggat ttattaacta ctatggaatg caaagatttg gaaccacagc tgtccctacg    1380
tatcaggttg gaagagctat actacaaaat tcctggacag aagtcatgga tttaatattg    1440
aaacccgct ctggagctga aaagggctac ttggttaaat gcagagaaga atgggcaaag    1500
accaaagacc caactgctgc cctcagaaaa ctacctgtca aaggtgtgt ggaagggcag    1560
ctgcttcgag actttcaaa atatggaatg aagaatatag tctctgcatt tggcataata    1620
cccagaaata atcgcttaat gtatattcat agctaccaaa gctatgtgtg gaataacatg    1680
gtaagcaaga ggatagaaga ctatggacta aaacctgttc caggggacct cgttctcaaa    1740
ggagccacag ccacctatat tgaggaagat gatgttaata attactctat ccatgatgtg    1800
gtaatgccct tgcctggttt cgatgttatc tacccaaagc ataaaattca agaagcctac    1860
agggaaatgc tcacagctga caatcttgat attgacaaca tgacacaa attcgagat    1920
tattccttgt caggggccta ccgaaagatc attattcgtc ctcagaatgt tagctgggaa    1980
gtcgttgcat atgatgatcc caaaattcca cttttcaaca cagatgtgga caacctagaa    2040
gggaagacac caccagtttt tgcttctgaa ggcaaataca gggctctgaa aatggatttt    2100
```

```
tctctacccc cttctactta cgccaccatg gccattcgag aagtgctaaa aatggatacc    2160
agtatcaaga accagacgca gctgaataca acctggcttc gctgagcagt accttgtcca    2220
cagattagaa aacgtacaca agtgtttgct tcctggctcc ctgtgcattt ttgtcttagt    2280
tcagactcat atatggattt caaatctttg taataaaaat tatttgtatt tttaagtttt    2340
tattagctta aagaaataat ttgcaatatt tgtacatgta cacaaatcct gaggttctta    2400
attttagctc agaatataaa ttagtcaaaa tacacttcag gtgcttaaat cagagtaaaa    2460
tgtcagcttt acaataataa aaaaaggact ttggtttaaa gtagcaggtt taggttttgc    2520
tacattctca aaagacagca ggagtatttg acacatctgt gatggagtat acaacaatgc    2580
attttaagag caaatgcaac aaaacaaatc tggactatgg ataaataatt tgagagctgc    2640
cacccacaaa tataaataca gtactcatgc tgactgaaat aataagacat ctacaaattt    2700
ataaacaaaa agtgattgtc attatcctgc ttatgtacta gattcaggca agcattatag    2760 acttttggt  tgcggtggct tttgcattta tattatcaat gccttgcagg aacgttgcat    2820
tgataggccc attttatttt tttatttttt ttttcgagac aggatctcac tctgtagcac    2880
aggctggatt gcagtgcaat cctgcaattc tcaatcttgc actgcagcct cgacctccca    2940
ggctccagtg actctcccac ctcagcctcc taagtagctg ggagtacagg cgcgcaccac    3000
cacgcctagc tgattttgt  attttttgt  agagacgggg gtttggccat gttgccgagg    3060
ctaactcctg ggattacagg catgagctgt gctggccggg tttttttttc ttgatgtaaa    3120
cgtgtacagc tgttttatta gttaaggtct aattttttact ctaggtgcct tttatgttca    3180
gaactctttc cactggactg gtatttgctc aaaaataaat aatggtagag aagaaaacta    3240
taaaaatgga caaggctttc ttctatcagt agcgtttacc ctttgtcacc agtggctttg    3300
gtatttccat gtctggcatt gcataaactt ctctggtgtg aaaggataaa tatgcctttc    3360
taaagttgta tatcaaaatt gtatcaattt ttatttctta tgatttctag aaacaaatgt    3420
aataaatatt tttaaaatct cctttctact ggttatgtaa ataaatcaaa taaatatatc    3480
aaaa                                                                 3484

<210> SEQ ID NO 278
<211> LENGTH: 1498
<212> TYPE: DNA
<213> ORGANISM: Homo sapiens

<400> SEQUENCE: 278
gaggccagag tgccatcgaa ggtaattata gagacagtaa aatcctttta ctctgggaaa      60
aataaaatgc tgggtgtctc acaaaatttc agaacctgat ttcaaacgga tcataacaaa     120
gaggagatca aatttagcat ggtggactgc tcgacaggat atatttgtca atggaatgtt     180
tccacatatt ataccaccaa catgagaaaa aaatgatcat tgtttatttg aagcttgatg     240
atattctaac gctgcctttt ctcttctcat tttagagaaa aatgagcagg cggaattgtt     300
ggatttgtaa gatgtgcaga gatgaatcta agaggccccc ttcaaacctt actttggagg     360
aagtattaca gtgggcccag tcttttgaaa atttaatggc tacaaaatat ggtccagtag     420
tctatgcagc atatttaaaa atggagcaca gtgacgagaa tattcaattc tggatggcat     480
gtgaaaccta agaaaaatt  gcctcacggt ggagcagaat ttctagggca aagaagcttt     540
ataagattta catccagcca cagtccccta gagagattaa cattgacagt tcgacaagag     600
agactatcat caggaacatt caggaaccca ctgaaacatg ttttgaagaa gctcagaaaa     660
tagtctatat gcatatggaa agggattcct accccagatt tctaaagtca gaaatgtacc     720
```

```
aaaaacttttt gaaaactatg cagtccaaca acagtttctg actacaactc aaaagtttaa      780
atagaaaaca gtatattgaa agtggtgggt ttgatctttt tatttagaaa cccacaaaat      840
cagaaacaca gtacaaataa aacagaaatc aaactataag ttgactttta gttcctaaaa      900
agaaacatat ttcaaaagca atggaatcta gaattcttat aacatgaata acaaaatgta      960
cagcaagcct atgtagttca attaatatat aaggaaaagg aaggtctttc ttcatgatac     1020
aagcattata aagttttttac tgtagtagtc aattaatgga tatttccttg ttaataaaat     1080
tttgtgtcat aatttacaaa ttagttcttt aaaaattgtt gttatatgaa ttgtgtttct     1140
agcatgaatg ttctatagag tactctaaat aacttgaatt tatagacaaa tgctactcac     1200
agtacaatca attgtattat accatgagaa aatcaaaaag gtgttcttca gagacatttt     1260
atctataaaa ttttcctact attatgttca ttaacaaact tctttatcac atgtatcttc     1320
tacatgtaaa acatttctga tgatttttta acaaaaaata tatgaatttc ttcatttgct     1380
cttgcatcta cattgctata aggatataaa atgtggtttc tatattttga gatgtttttt     1440
ccttacaatg tgaactcatc gtgatcttgg aaatcaataa agtcaaatat caactaaa      1498

<210> SEQ ID NO 279
<211> LENGTH: 3293
<212> TYPE: DNA
<213> ORGANISM: Homo sapiens

<400> SEQUENCE: 279
cttttgctct cagatgctgc cagggtccct gaagagggaa gacacgcgga aacaggcttg       60
cacccagaca cgacaccatg catctcctcg gcccctggct cctgctcctg gttctagaat      120
acttggcttt ctctgactca agtaaatggg tttttgagca ccctgaaacc ctctacgcct      180 gggaggggggc ctgcgtctgg atcccctgca cctacagagc cctagatggt gacctggaaa     240
gcttcatcct gttccacaat cctgagtata acaagaacac ctcgaagttt gatgggacaa      300
gactctatga aagcacaaag gatgggaagg ttccttctga gcagaaaagg gtgcaattcc      360
tgggagacaa gaataagaac tgcacactga gtatccaccc ggtgcacctc aatgacagtg      420
gtcagctggg gctgaggatg gagtccaaga ctgagaaatg gatggaacga atacacctca      480
atgtctctga aaggccttttt ccacctcata tccagctccc tccagaaatt caagagtccc      540
aggaagtcac tctgacctgc ttgctgaatt tctcctgcta tgggtatccg atccaattgc      600
agtggctcct agagggggtt ccaatgaggc aggctgctgt cacctcgacc tccttgacca      660
tcaagtctgt cttcacccgg agcgagctca gttctcccc acagtggagt caccatggga      720
agattgtgac ctgccagctt caggatgcag atgggaagtt cctctccaat gacacggtgc      780
agctgaacgt gaagcacacc ccgaagttgg agatcaaggt cactcccagt gatgccatag      840
tgagggaggg ggactctgtg accatgacct gcgaggtcag cagcagcaac ccggagtaca      900
cgacggtatc ctggctcaag gatgggacct cgctgaagaa gcagaataca ttcacgctaa      960
acctgcgcga agtgaccaag gaccagagtg ggaagtactg ctgtcaggtc tccaatgacg     1020
tgggcccggg aaggtcggaa gaagtgttcc tgcaagtgca gtatgccccg gaaccttcca     1080
cggttcagat cctccactca ccggctgtgg agggaagtca agtcgagttt ctttgcatgt     1140
cactggccaa tcctctcttc ca acaaattaca cgtggtacca caatgggaaa gaaatgcagg     1200
gaaggacaga ggagaaagtc cacatcccaa agatcctccc ctggcacgct gggacttatt     1260
cctgtgtggc agaaaacatt cttggtactg gacagagggg cccgggagct gagctggatg     1320
```

```
tccagtatcc tcccaagaag gtgaccacag tgattcaaaa ccccatgccg attcgagaag    1380
gagacacagt gacccttttcc tgtaactaca attccagtaa ccccagtgtt acccggtatg    1440
aatggaaacc ccatggcgcc tgggaggagc catcgcttgg ggtgctgaag atccaaaacg    1500
ttggctggga caacacaacc atcgcctgcg cagcttgtaa tagttggtgc tcgtgggcct    1560
cccctgtcgc cctgaatgtc cagtatgccc cccgagacgt gagggtccgg aaaatcaagc    1620
ccctttccga gattcactct ggaaactcgg tcagcctcca atgtgacttc tcaagcagcc    1680
accccaaaga agtccagttc ttctgggaga aaaatggcag gcttctgggg aagaaagcc     1740 agctgaattt tgactccatc tccccagaag atgctgggag ttacagctgc tgggtgaaca    1800
actccatagg acagacagcg tccaaggcct ggacacttga agtgctgtat gcacccagga    1860
ggctgcgtgt gtccatgagc ccgggggacc aagtgatgga ggggaagagt gcaaccctga    1920
cctgtgagag cgacgccaac cctcccgtct cccactacac ctggtttgac tggaataacc    1980
aaagcctccc ctaccacagc cagaagctga gattggagcc ggtgaaggtc cagcactcgg    2040
gtgcctactg gtgccagggg accaacagtg tgggcaaggg ccgttcgcct ctcagcaccc    2100
tcaccgtcta ctatagcccg gagaccatcg gcaggcgagt ggctgtggga ctcgggtcct    2160
gcctcgccat cctcatcctg gcaatctgtg ggctcaagct ccagcgacgt ggaagagga    2220 cacagagcca gcagggcttt caggagaatt ccagcggcca gagcttcttt gtgaggaata    2280 aaaggttag aagggccccc ctctctgaag gcccccactc cctgggatgc tacaatccaa     2340
tgatggaaga tggcattagc tacaccaccc tgcgctttcc cgagatgaac ataccacgaa    2400
ctggagatgc agagtcctca gagatgcaga gacctccccc ggactgcgat gacacggtca    2460
cttattcagc attgcacaag cgccaagtgg gcgactatga aacgtcatt ccagatttc     2520 cagaagatga ggggattcat tactcagagc tgatccagtt tggggtcggg gagcggcctc    2580
aggcacaaga aaatgtggac tatgtgatcc tcaaacattg acactggatg ggctgcagca    2640
gaggcactgg gggcagcggg ggccagggaa gtccccgagt ttcccagac accgccacat     2700 ggcttcctcc tgcgcgcatg tgcgcacaca cacacacaca cgcacacaca cacacacaca    2760
ctcactgcgg agaaccttgt gcctggctca gagccagtct ttttggtgag ggtaaccca     2820 aacctccaaa actcctgccc ctgttctctt ccactctcct tgctacccag aaatccatct    2880
aaatacctgc cctgacatgc acacctcccc ctgcccccac cacggccact ggccatctcc    2940 accccagct gcttgtgtcc ctcctgggat ctgctcgtca tcatttttcc ttccccttctc     3000 catctctctg gccctctacc cctgatctga catccccact cacgaatatt atgcccagtt    3060
tctgcctctg agggaaagcc cagaaaagga cagaaacgaa gtagaagggg gcccagtcct    3120
ggcctggctt ctccttttgga agtgaggcat tgcacgggga gacgtacgta tcagcggccc    3180
cttgactctg gggactccgg gtttgagatg gacacactgg tgtggattaa cctgccaggg    3240
agacagagct cacaataaaa atggctcaga tgccacttca agaaaaaaa aaa           3293

<210> SEQ ID NO 280
<211> LENGTH: 1621
<212> TYPE: DNA
<213> ORGANISM: Homo sapiens

<400> SEQUENCE: 280
ccacaaatgt gggagggcga taaccactcg tagaaagcgt gagaagttac tacaagcggt     60
cctcccggcc accgtactgt tccgctccca gaagccccgg gcggcggaag tcgtcactct    120
taagaaggga cggggcccca cgctgcgcac ccgcgggttt gctatggcga tgagcagcgg    180
```

```
cggcagtggt ggcggcgtcc cggagcagga ggattccgtg ctgttccggc gcggcacagg      240
ccagagcgat gattctgaca tttgggatga tacagcactg ataaaagcat atgataaagc      300
tgtggcttca tttaagcatg ctctaaagaa tggtgacatt tgtgaaactt cgggtaaacc      360
aaaaaccaca cctaaaagaa aacctgctaa gaagaataaa agccaaaaga gaatactgc       420 agcttcctta caacagtgga aagttgggga caaatgttct gccatttggt cagaagacgg      480
ttgcatttac ccagctacca ttgcttcaat tgatttaag agagaaacct gtgttgtggt       540
ttacactgga tatggaaata gagaggagca aaatctgtcc gatctacttt ccccaatctg      600
tgaagtagct aataatatag aacagaatgc tcaagagaat gaaaatgaaa gccaagtttc      660
aacagatgaa agtgagaact ccaggtctcc tggaaataaa tcagataaca tcaagcccaa      720
atctgctcca tggaactctt ttctccctcc accacccccc atgccagggc caagactggg      780
accaggaaag ccaggtctaa aattcaatgg cccaccaccg ccaccgccac caccaccacc      840
ccacttacta tcatgctggc tgcctccatt tccttctgga ccaccaataa ttcccccacc      900
acctcccata tgtccagatt ctcttgatga tgctgatgct ttgggaagta tgttaatttc      960
atggtacatg agtggctatc atactggcta ttatatgggt ttcagacaaa atcaaaaaga     1020
aggaaggtgc tcacattcct taaattaagg agaaatgctg gcatagagca gcactaaatg     1080
acaccactaa agaacgatc agacagatct ggaatgtgaa gcgttataga agataactgg      1140
cctcatttct tcaaaatatc aagtgttggg aaagaaaaaa ggaagtggaa tgggtaactc     1200
ttcttgatta aaagttatgt aataaccaaa tgcaatgtga atatttttac tggactcttt     1260
tgaaaaacca tctgtaaaag actggggtgg gggtgggagg ccagcacggt ggtgaggcag     1320
ttgagaaaat ttgaatgtgg attagatttt gaatgatatt ggataattat tggtaatttt     1380
atggcctgtg agaagggtgt tgtagtttat aaaagactgt cttaatttgc atacttaagc     1440
atttaggaat gaagtgttag agtgtcttaa aatgtttcaa atggtttaac aaaatgtatg     1500
tgaggcgtat gtggcaaaat gttacagaat ctaactggtg gacatggctg ttcattgtac     1560 tgttttttc tatcttctat atgtttaaaa gtatataata aaaatattta atttttttt       1620 a                                                                    1621
```

<210> SEQ ID NO 281
<211> LENGTH: 1572
<212> TYPE: DNA
<213> ORGANISM: Homo sapiens

<400> SEQUENCE: 281

```
aagttgcttt tgtccaaaca tccgggcttc tccttttgt gttccggccg atcccacctc        60
tcctcgaccc tggacgtcta ccttccggag gcccacatct tgcccactcc gcgcgcgggg     120
ctagcgcggg tttcagcgac gggagccctc aagggacatg gcaactacag cggcgccggc     180
gggcggcgcc cgaaatggag ctggcccgga atggggagtt tcgaagaaa acatccaggg     240 cggaggctca gctgtgattg acatggagaa catggatgat acctcaggct ctagcttcga     300
ggatatgggt gagctgcatc agcgcctgcg cgaggaagaa gtagacgctg atgcagctga      360
tgcagctgct gctgaagagg aggatggaga gttcctgggc atgaagggct taagggaca     420 gctgagccgg caggtggcag atcagatgtg gcaggctggg aaaagacaag cctccagggc     480
cttcagcttg tacgccaaca tcgacatcct cagaccctac tttgatgtgg agcctgctca     540
ggtgcgaagc aggctcctgg agtccatgat ccctatcaag atggtcaact tccccagaa      600
```

-continued

```
aattgcaggt gaactctatg gacctctcat gctggtcttc actctggttg ctatcctact    660
ccatgggatg aagacgtctg acactattat ccgggagggc accctgatgg gcacagccat    720
tggcacctgc ttcggctact ggctgggagt ctcatccttc atttacttcc ttgcctacct    780
gtgcaacgcc cagatcacca tgctgcagat gttggcactg ctgggctatg gcctctttgg    840
gcattgcatt gtcctgttca tcacctataa tatccacctc cacgccctct tctacctctt    900
ctggctgttg gtgggtggac tgtccacact gcgcatggta gcagtgttgg tgtctcggac    960
cgtgggcccc acacagcggc tgctcctctg tggcaccctg gctgccctac acatgctctt   1020
cctgctctat ctgcattttg cctaccacaa agtggtagag gggatcctgg acacactgga   1080 gggcccaac atcccgccca tccagagggt ccccagagac atccctgcca tgctccctgc    1140
tgctcggctt cccaccaccg tcctcaacgc cacagccaaa gctgttgcgg tgaccctgca   1200
gtcacactga ccccacctga aattcttggc cagtcctctt tcccgcagct gcagagagga   1260
ggaagactat taaaggacag tcctgatgac atgtttcgta gatggggttt gcagctgcca   1320
ctgagctgta gctgcgtaag tacctccttg atgcctgtcg gcacttctga aaggcacaag   1380
gccaagaact cctggccagg actgcaaggc tctgcagcca atgcagaaaa tgggtcagct   1440
cctttgagaa cccctcccca cctacccctt ccttcctctt tatctctccc acattgtctt   1500
gctaaatata gacttggtaa ttaaaatgtt gattgaagtc tggaactgca aaaaaaaaa    1560 aaaccaaaaa aa                                                      1572
```